United States Patent
Pugliese et al.

(10) Patent No.: US 11,447,505 B1
(45) Date of Patent: Sep. 20, 2022

(54) PYRROLO[2,3-B]PYRIDINE COMPOUNDS AND THEIR USE IN THE TREATMENT OF CANCER

(71) Applicant: Cancer Research Technology Limited, London (GB)

(72) Inventors: Angelo Pugliese, Glasgow (GB); Stuart Francis, Glasgow (GB); Duncan McArthur, Glasgow (GB); Mairi Sime, Glasgow (GB); Justin Bower, Glasgow (GB); Simone Belshaw, Glasgow (GB)

(73) Assignee: Cancer Research Technology Limited, London (GB)

( * ) Notice: Subject to any disclaimer, the term of this patent is extended or adjusted under 35 U.S.C. 154(b) by 10 days.

(21) Appl. No.: 16/640,034

(22) PCT Filed: Aug. 17, 2018

(86) PCT No.: PCT/GB2018/052338
§ 371 (c)(1),
(2) Date: Feb. 18, 2020

(87) PCT Pub. No.: WO2019/034890
PCT Pub. Date: Feb. 21, 2019

(30) Foreign Application Priority Data

Aug. 18, 2017 (GB) .................................... 1713319
Apr. 12, 2018 (GB) .................................... 1806050

(51) Int. Cl.
*C07D 471/04* (2006.01)
*C07D 519/00* (2006.01)
*A61P 35/04* (2006.01)

(52) U.S. Cl.
CPC ............ *C07D 519/00* (2013.01); *A61P 35/04* (2018.01); *C07D 471/04* (2013.01)

(58) Field of Classification Search
CPC ...... C07D 471/04; C07D 519/00; A61P 35/04
USPC ..................................................... 514/210.16
See application file for complete search history.

(56) References Cited

U.S. PATENT DOCUMENTS

2010/0184790 A1   7/2010   Meijer et al.
2011/0201599 A1*  8/2011   Bahceci .................. A61P 19/02
                                                       514/217.06

FOREIGN PATENT DOCUMENTS

WO   WO-2010/003133 A2   1/2010
WO      2015092592    *  6/2015
WO   WO-2015/092592 A1   6/2015

OTHER PUBLICATIONS

Fang et al., "Generation and validation of the first predictive pharmacophore model for cyclin-dependent kinase 9 inhibitors," Journal of Molecular Graphics and Modelling, 29(6):800-808 (2011).
Unbekandt et al., "A novel small-molecule MRCK inhibitor blocks cancer cell invasion," Cell Communication and Signaling, 12(1):54 (2014).

* cited by examiner

*Primary Examiner* — Niloofar Rahmani
(74) *Attorney, Agent, or Firm* — Foley Hoag LLP; David P. Halstead; Lawrence P. Tardibono

(57) ABSTRACT

The present application relates to a compound of Formula I, or a salt, hydrate or solvate thereof, as defined herein. The present compounds are found to have pharmacological effects, particularly at MRCK. Further provided are pharmaceutical compositions comprising said compounds. The present invention also relates to the use of these compounds as therapeutic agents, in particular, for the treatment and/or prevention of proliferative diseases, such as cancer.

15 Claims, 14 Drawing Sheets

Figure 1A:
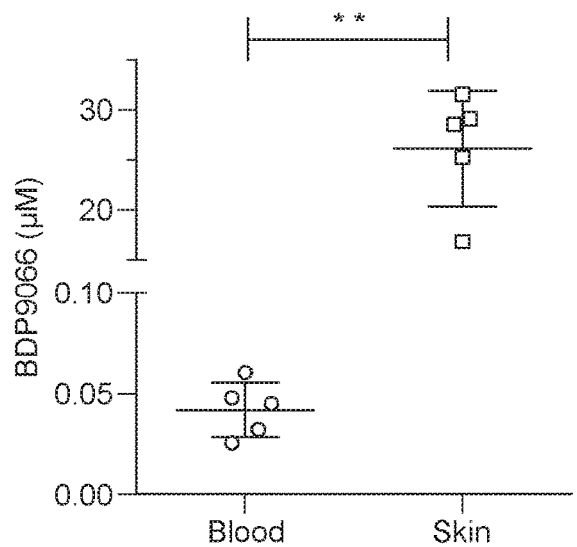

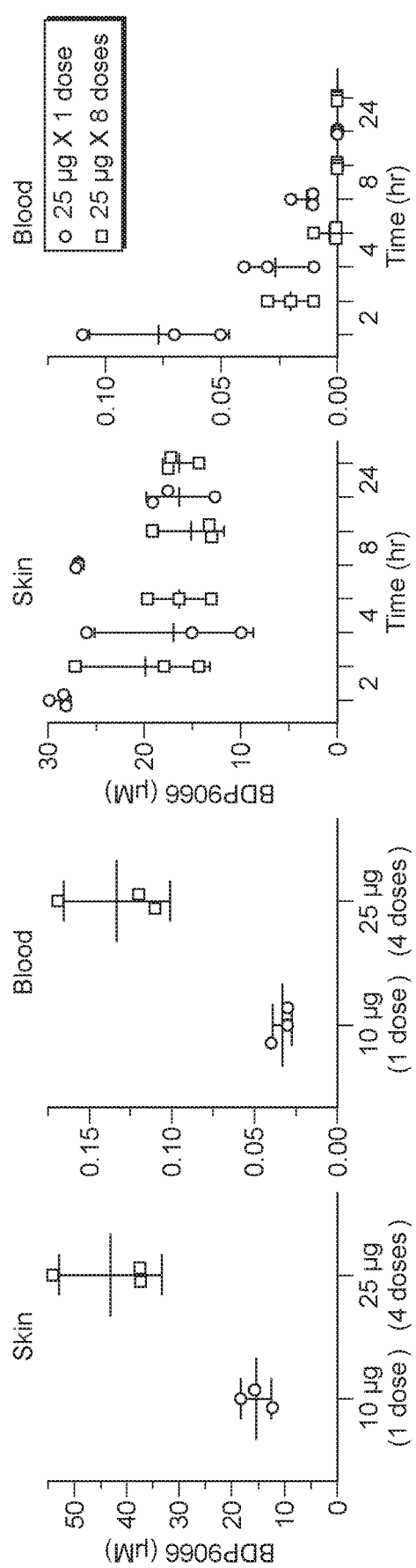
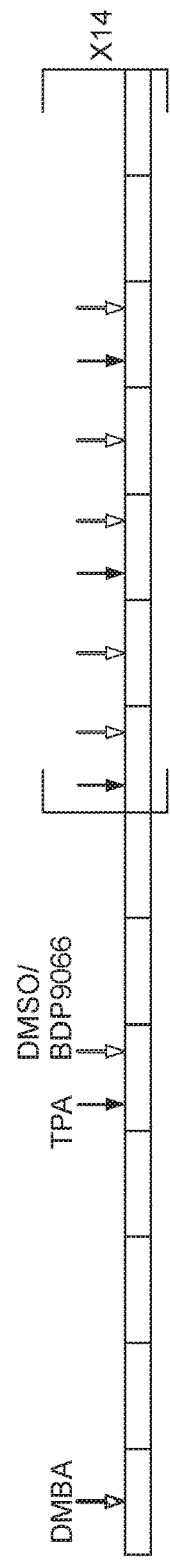
FIG. 1C
FIG. 1D
FIG. 1E

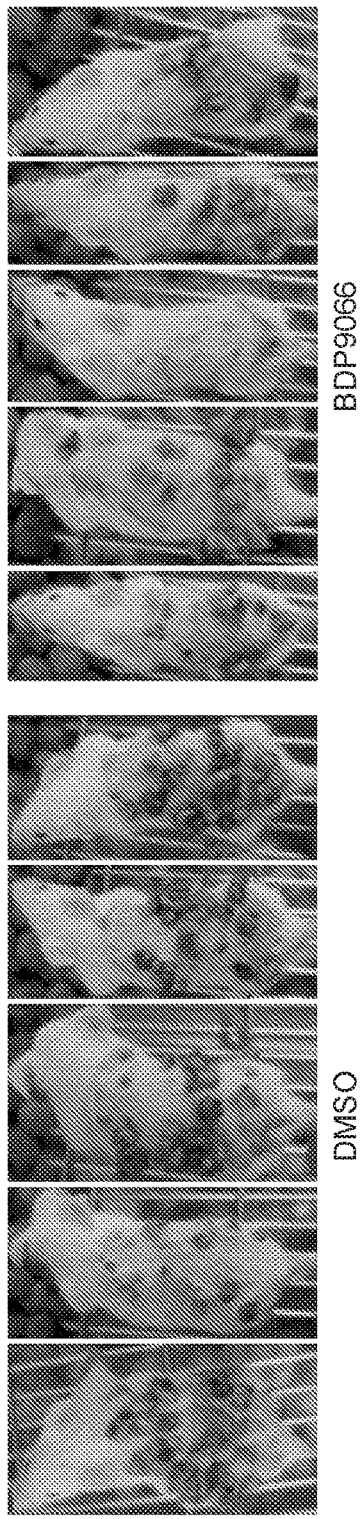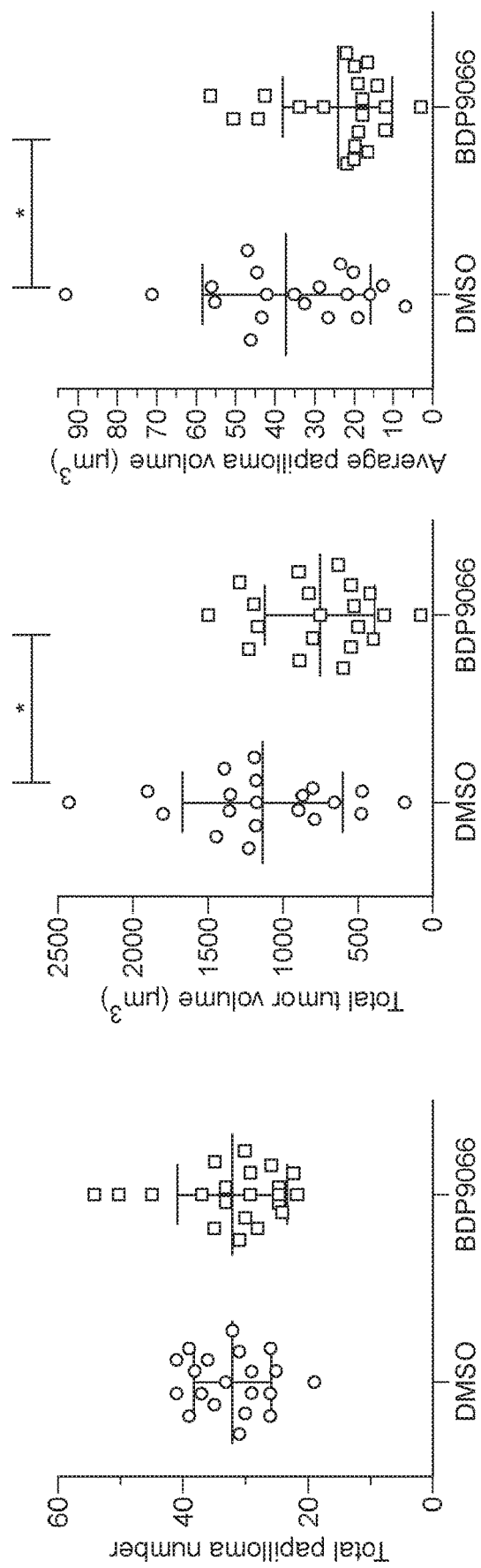
FIG. 1F
FIG. 1H
FIG. 1G

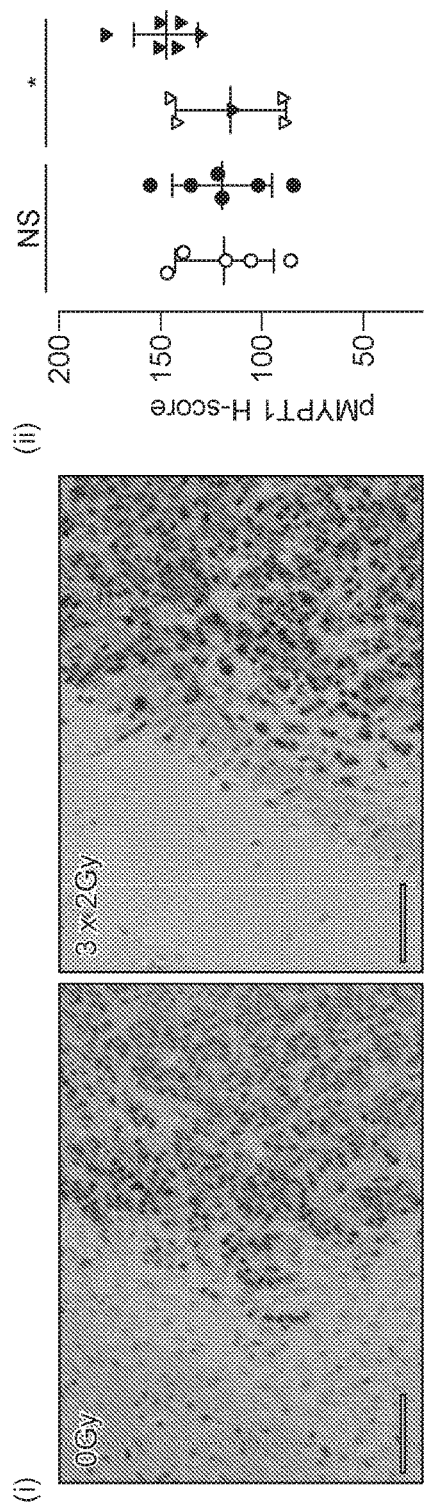
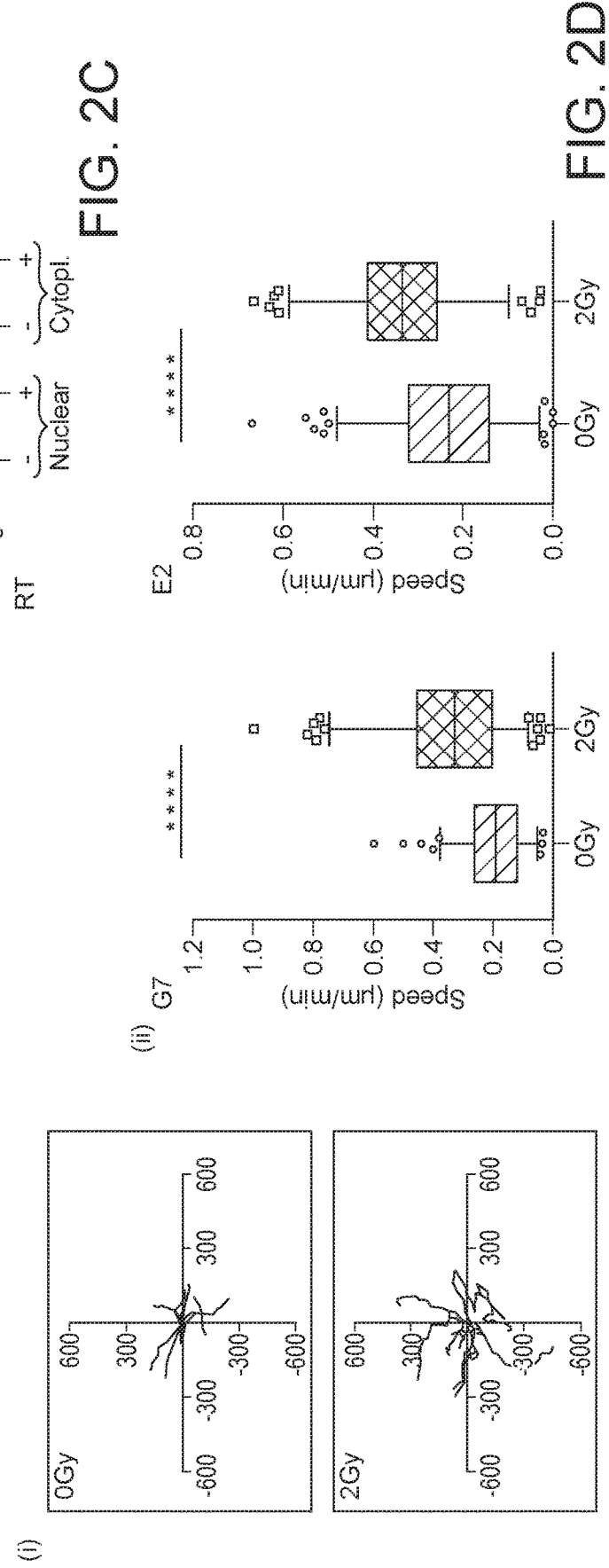
FIG. 2C
FIG. 2D (i)

(ii)

PYRROLO[2,3-B]PYRIDINE COMPOUNDS AND THEIR USE IN THE TREATMENT OF CANCER

RELATED APPLICATIONS

This application is a U.S. national stage of International Patent Application No. PCT/GB2018/052338, filed Aug. 17, 2018, which claims priority to Applications GB 1806050.9 filed on Apr. 12, 2018 and GB 1713319.0 filed on Aug. 18, 2017.

INTRODUCTION

The present invention relates to compounds that inhibit myotonic dystrophy kinase-related Cdc42-binding kinase (MRCK). In particular, the present invention relates to these compounds and their use as therapeutic agents, for instance in the treatment and/or prevention of proliferative diseases, such as cancer. Disclosed herein are also pharmaceutical compositions and combinations comprising the claimed compounds.

BACKGROUND OF THE INVENTION

Tumour cell invasion is a defining hallmark of malignancy [1]. For most types of solid tumours, patient mortality and much morbidity is attributable to metastatic disease, of which invasion is an obligatory component process. Current anticancer drugs mainly target tumour growth, and their clinical benefits at all stages of the disease typically are modest. By subduing cancer cell invasion, particularly in an adjuvant setting, molecularly-targeted inhibitors that block key invasion drivers would be expected to provide clinical benefit to a significant range of cancer patients with solid tumours at various stages.

Metastasis is a multi-step process powered by dynamic reorganization of the actin-myosin cytoskeleton and remodelling of the extracellular matrix, allowing cells to invade their local environment, cross tissue boundaries and spread via blood and lymphatic vessels to distal regions of the body [2]. Contraction of actin-myosin cytoskeletal structures generates the mechanical force required for cell motility and invasion [2]. A key element of the cytoskeletal contractile machinery is myosin II, which is regulated by phosphorylation of myosin II light chain proteins (MLC) at two key sites (Thr18 and Ser19) [3].

Members of the RhoGTPase family are central regulators of the actin-myosin cytoskeleton and have been shown to contribute to multiple processes associated with invasion and metastasis [2]. Cdc42 signals through effector proteins including the myotonic dystrophy kinase-related Cdc42-binding kinases α and β (MRCKβ and MRCKβ), which are 190 kDa multi-domain proteins with ~80% amino acid identity across their kinase domains, that are expressed in a wide range of tissues [4]. MRCK and the Rho-regulated ROCK kinases belong to the AGC kinase family [5], and share ~45-50% amino acid identity in their N-terminal kinase domains, which is reflected in their shared abilities to phosphorylate a similar set of substrates including MLC and the inhibitory phosphorylation of the myosin binding subunit (MYPT1) of the MLC phosphatase complex [6]. However, MRCK and ROCK kinases may phosphorylate substrates, such as MLC, at different subcellular localizations due to their specific interactions with targeting proteins and/or lipids [7]-[10].

Importantly, it has been observed that the actin-myosin contractility required for the invasion of three-dimensional extracellular protein matrices by MDA-MB-231 breast cancer cells [6],[11] and for the collective invasion of squamous cell carcinoma (SCC) cells through three dimensional collagen matrices in an organotypic model [12] were dependent on MRCK signalling. Elevated MRCKβ expression was reported to contribute to Ras oncogene-driven SCC development in genetically-modified mice following repression of the Notch1 tumour suppressor [13]. In addition, gene expression analysis identified MRCKβ as part of a breast cancer gene expression signature linked to poor patient prognosis and increased incidence of metastasis under five years [14]. These observations indicate that MRCK contributes to tumour cell invasiveness and may be an important driver of metastasis.

A small molecular inhibitor of MRCK has recently been described [15], however, there is a need in the art for alternative and/or improved MRCK inhibitors as a means of blocking cancer cell invasion for instance.

SUMMARY OF THE INVENTION

In one aspect, the present invention provides a compound of Formula I as defined herein, and/or a salt or solvate thereof.

In another aspect, the present invention provides a pharmaceutical composition which comprises a compound of Formula I as defined herein, or a pharmaceutically acceptable salt or solvate thereof, and one or more pharmaceutically acceptable excipients.

In another aspect, the present invention provides a compound of Formula I as defined herein, or a pharmaceutically acceptable salt or solvate thereof, or a pharmaceutical composition as defined herein, for use in therapy.

In another aspect, the present invention provides a compound of Formula I as defined herein, or a pharmaceutically acceptable salt or solvate thereof, or a pharmaceutical composition as defined herein, for use in the treatment or prevention of a proliferative disorder.

In another aspect, the present invention provides a compound of Formula I as defined herein, or a pharmaceutically acceptable salt or solvate thereof, or a pharmaceutical composition as defined herein, for use in inhibiting MRCK.

In another aspect, the present invention provides a compound of Formula I as defined herein, or a pharmaceutically acceptable salt or solvate thereof, or a pharmaceutical composition as defined herein, for use in the treatment or prevention of cancer cell invasion.

In another aspect, the present invention provides the use of a compound of Formula I as defined herein, or a pharmaceutically acceptable salt or solvate thereof, in the manufacture of a medicament for the treatment or prevention of a proliferative disorder.

In another aspect, the present invention provides the use of a compound of Formula I as defined herein, or a pharmaceutically acceptable salt or solvate thereof, in the manufacture of a medicament for inhibiting MRCK.

In another aspect, the present invention provides the use of a compound of Formula I as defined herein, or a pharmaceutically acceptable salt or solvate thereof, in the manufacture of a medicament for the treatment or prevention of cancer cell invasion.

In another aspect, the present invention provides a method of treating or preventing a proliferative disorder, said method comprising administering to a subject in need thereof an effective amount of a compound of Formula I as defined herein, or a pharmaceutically acceptable salt or solvate thereof.

In another aspect, the present invention provides a method of inhibiting MRCK in vitro or in vivo, said method comprising contacting a cell with an effective amount of a compound of Formula I as defined herein, or a pharmaceutically acceptable salt or solvate thereof.

In another aspect, the present invention provides a method of treating or preventing cancer cell invasion, said method comprising administering to a subject in need thereof a therapeutically effective amount of a compound of Formula I as defined herein, or a pharmaceutically acceptable salt or solvate thereof, or a pharmaceutical composition as defined herein.

In another aspect, the present invention provides a combination comprising a compound of Formula I, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and include any and all compounds described by and/or with reference to Formula I. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, either by themselves or in combination with additional agents.

Similarly, references to the various sub formulae of formula I (e.g. formula Ia, Ib, Ic etc.) encompass isomers of the described compounds as listed above, unless specifically described to the contrary.

The various hydrocarbon-containing moieties provided herein may be described using a prefix designating the minimum and maximum number of carbon atoms in the moiety, e.g. "$(C_{a-b})$" or "$C_a$-$C_b$" or "(a-b)C". For example, $(C_{a-b})$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_2$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene (—$C_6H_4$—) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2$—). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$CI=CH_2$, —$C≡C$—$CF_3$, —$CHFCH_2CH_3$ and —$CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, —$OCF_3$, —$OCHF_2$, —$OCH_2F$, —$OCF_2CF_3$, —$OCHFCF_3$, —$OCH_2CF_3$, —$OCF_2CH_3$, —$OCHFCH_3$, —$OCF_2CF_2CF_3$, —$OCF_2CH_2CH_3$, —$OCF=CF_2$, —$OCCl=CH_2$, —$OCBr=CH_2$, —$OCHFCH_2CH_3$ and —$OCHFCH_2CF_3$. Haloalkoxy groups can be substituted or unsubstituted. Suitably, a haloalkyoxy group is selected from —$OCHF_2$ and —$OCF_3$, suitably —$OCF_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro- 7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers are provided, e.g. ($C_{n-m}$)alkylheteroaryl, the range refers to the whole group. Suitably, the constituent alkyl group has 1-6 carbons, suitably 1-3 carbon, and the heteroaryl group is 5 or 6 membered.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroyocloalkyl groups can be substituted or unsubstituted. Where carbon numbers are provided, e.g. ($C_{n-m}$)alkylheterocycloalkyl, the range refers to the whole group. Suitably, the constituent alkyl group has 1-6 carbons, suitably 1-3 carbons, and the hetereocycloalkyl group is 3-7 membered, suitably 5 or 6 membered.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —$CF_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by themselves or in conjunction with another term or terms, "subject(s)" and "patient(s)", suitably refer to mammals, in particular humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

A dashed bond ( ---- ) is used herein to show a point of attachment. For instance, when $R^4$ is formula II, the dashed bond indicates that $R^4$ is attached to the bicyclic core via the nitrogen atom.

Compounds

The compounds of the present invention will now be further described by way of the following numbered paragraphs:

1. A compound of Formula I, or a salt, hydrate or solvate thereof;

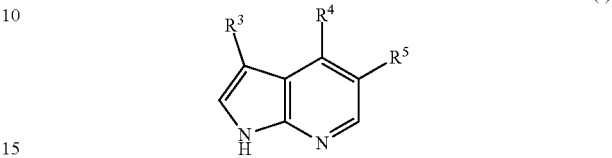

(I)

wherein, $R^5$ is selected from hydrogen, halogen, hydroxyl, $NH_2$, $NH(C_{1-6}$ alkyl), $N(C_{1-6}$ alkyl$)_2$, $C_{1-6}$ alkyl, O—$C_{1-6}$ alkyl, $C_{1-6}$ haloalkyl, O—$C_{1-6}$ haloalkyl, $C_{3-6}$ cycloalkyl, phenyl and CN.

$R^3$ is selected from CN and 5-15 membered heteroaryl, where said 5-15 membered heteroaryl is optionally substituted by one or more $R^b$;

each $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, phenyl, and 3-7 membered heterocycloalkyl; wherein said $C_{1-6}$ alkyl and 3-7 membered heterocycloalkyl are optionally substituted with one or more groups selected from hydroxyl, halogen, =O, $NR^cR^d$, $C_{1-6}$ alkyl, O—$C_{1-6}$ alkyl, and phenyl;

each $R^c$ is independently selected from hydrogen and $C_{1-6}$ alkyl;

each $R^d$ is independently selected from hydrogen, CN, $C_{1-6}$ haloalkyl, O—$C_{1-6}$ haloalkyl, 3-7 membered heterocycloalkyl, 5-6 membered heteroaryl, $C_{3-6}$ cycloalkyl, $C_{1-6}$ alkyl, O—$C_{1-6}$ alkyl and phenyl, wherein said $C_{1-6}$ alkyl, phenyl, 5-6 membered heteroaryl, 3-7 membered heterocycloalkyl and $C_{3-6}$ cycloalkyl are optionally substituted with one or more groups selected from hydroxyl, halogen, CN, $NH_2$, $NH(C_{1-6}$alkyl), $N(C_{1-6}$alkyl$)_2$, $C_{1-6}$ haloalkyl, $C_{3-6}$ cycloalkyl, phenyl, 3-7 membered heterocycloalkyl, $C_{3-10}$alkylheterocycloalkyl, $C_{1-6}$ alkyl and O—$C_{1-6}$ alkyl; or $R^c$ and $R^d$, when attached to the same atom, together with the atom to which they are attached form a 3-7 membered heterocycloalkyl ring optionally substituted by one or more groups selected from hydroxyl, halogen, CN, $NH_2$, $NH(C_{1-6}$alkyl), $N(C_{1-6}$ alkyl$)_2$, $C_{1-6}$ haloalkyl, O—$C_{1-6}$ haloalkyl, $C_{3-6}$ cycloalkyl, phenyl, 3-7 membered heterocycloalkyl, $C_{1-6}$ alkyl and O—$C_{1-6}$ alkyl;

$R^4$ is selected from $OR^6$, $SR^6$, $NHR^6$, $NR^7R^8$ and a group of formula II:

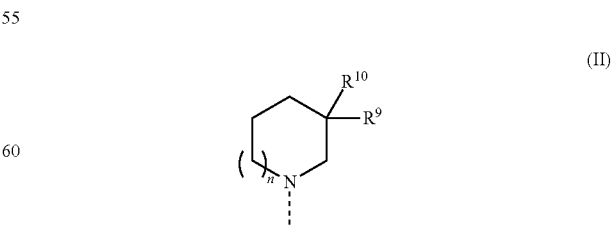

(II)

$R^6$ is independently selected from $C_{1-6}$ alkyl, 3-7 membered heterocycloalkyl and alkylheterocycloalkyl, each optionally substituted by one or more $R^f$;

$R^f$ is selected from hydroxyl, halogen, CN, $C_{1-6}$ alkyl, $C_{3-6}$ cycloalkyl, $C_{1-6}$ haloalkyl and $OR^a$; where $R^a$ is selected from hydrogen, $C_{1-6}$ alkyl, $C_{1-6}$ haloalkyl, phenyl and $C_{3-6}$ cycloalkyl;

$R^7$ and $R^8$ are independently selected from hydrogen, $C_{1-6}$ alkyl optionally substituted by one or more $R^g$, $C_{6-11}$ aryl optionally substituted by one or more $R^g$, alkylaryl optionally substituted by one or more $R^g$, $C_{3-11}$ cycloalkyl optionally substituted by one or more $R^g$, alkylcycloalkyl optionally substituted by one or more $R^g$, 3-15 membered heterocycloalkyl optionally substituted by one or more $R^g$, alkylheterocycloalkyl optionally substituted by one or more $R^g$, 5-15 membered heteroaryl optionally substituted by one or more $R^g$, and alkylheteroaryl optionally substituted by one or more $R^g$, with the proviso that both $R^7$ and $R^8$ cannot be hydrogen; or $R^7$ and $R^8$ together with the nitrogen atom to which they are attached form a 3-15 membered heterocycloalkyl optionally substituted by one or more $R^j$;

each $R^g$ is independently selected from hydroxyl, halogen, CN, $C_{1-6}$ alkyl, $C_{3-6}$ cycloalkyl, $C_{1-6}$ haloalkyl, and $OR^a$; where $R^a$ is defined above;

$R^j$ is selected from halogen, hydroxyl, CN, $NH_2$, $NH(C_{1-6}$alkyl), $N(C_{1-6}$alkyl$)_2$, $NR^cR^d$, $C(=O)NR^cR^d$, $C_{1-6}$ alkyl, $O-C_{1-6}$ alkyl, $C_{1-6}$haloalkyl, $C_{1-6}$haloalkoxy, $C_{3-6}$ cycloalkyl and phenyl, wherein said $C_{1-6}$ alkyl is optionally substituted with one or more groups selected from hydroxyl, $NH_2$, $NH(C_{1-6}$alkyl), $N(C_{1-6}$ alkyl$)_2$, phenyl, $OR^a$, where each of $R^a$, $R^c$ and $R^d$ are defined above;

$R^9$ and $R^{10}$ are independently selected from hydrogen, hydroxyl, $C_{1-6}$ alkyl, $O-C_{1-6}$ alkyl, $C_{1-6}$haloalkyl, $C_{1-6}$haloalkoxy, $NH_2$, $NH(C_{1-6}$alkyl), $N(C_{1-6}$alkyl$)_2$, $NR^cR^d$, $NR^cC(=O)R^d$, $C(O)NR^cR^d$, phenyl, and 3-7 membered heterocycloalkyl, where said $C_{1-6}$ alkyl, phenyl and 3-7 membered heterocycloalkyl are optionally substituted with one or more groups selected from halogen, hydroxyl, CN, $NH_2$, $NH(C_{1-6}$alkyl), $N(C_{1-6}$alkyl$)_2$, $C_{1-6}$ alkyl, $O-C_{1-6}$ alkyl, $C_{1-6}$haloalkyl, $C_{1-6}$haloalkoxy, $C_{3-6}$ cycloalkyl and phenyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

$R^m$ is selected from hydroxyl, halogen, CN, $C_{1-6}$ alkyl, $C_{3-6}$ cycloalkyl, $C_{1-6}$ haloalkyl, and $OR^a$; where $R^a$ is defined above; and n is a number selected from 0 and 1.

2. A compound according to paragraph 1, or a salt, hydrate or solvate thereof, wherein $R^5$ is selected from hydrogen, halogen, hydroxyl, $C_{1-6}$ alkyl, $O-C_{1-6}$ alkyl, $C_{1-6}$ haloalkyl, $O-C_{1-6}$ haloalkyl, $C_{3-6}$ cycloalkyl, phenyl and CN.

3. A compound according to any one of preceding paragraphs 1 and 2, or a salt, hydrate or solvate thereof, wherein $R^5$ is selected from hydrogen, halogen, hydroxyl, $C_{1-6}$ alkyl, $O-C_{1-6}$ alkyl, $C_{1-6}$ haloalkyl, $O-C_{1-6}$ haloalkyl and CN.

4. A compound according to any one of the preceding paragraphs, or a salt, hydrate or solvate thereof, $R^5$ is selected from hydrogen, halogen and $C_{1-6}$ alkyl.

5. A compound according to any one of the preceding paragraphs, or a salt, hydrate or solvate thereof, $R^5$ is selected from hydrogen and halogen.

6. A compound according to any one of the preceding paragraphs, or a salt, hydrate or solvate thereof, $R^5$ is hydrogen.

7. A compound according to paragraph 1, or a salt, hydrate or solvate thereof, of sub-formula Ia:

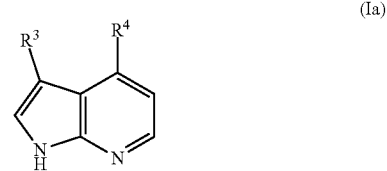

(Ia)

wherein
$R^3$ and $R^4$ are as defined in paragraph 1.

8. A compound according to any one of the preceding paragraphs, or a salt, hydrate or solvate thereof, wherein $R^3$ is selected from 5-6 membered heteroaryl and CN, where said 5-6 membered heteroaryl is optionally substituted by one or more $R^b$.

9. A compound according to any one of the paragraphs 1 to 7, or a salt, hydrate or solvate thereof, wherein $R^3$ is selected from a 5-15 membered heteroaryl optionally substituted by one or more $R^b$.

10. A compound according to any one of the preceding paragraphs, or a salt, hydrate or solvate thereof, wherein $R^3$ is selected from a 5-6 membered heteroaryl optionally substituted by one or more $R^b$.

11. A compound according paragraph 1, or a salt, hydrate or solvate thereof, of sub-formula Ib:

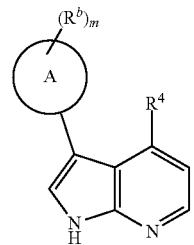

(Ib)

wherein
ring A is a 5-6 membered heteroaryl ring;
m is a number selected from 0, 1 and 2; and
$R^b$ and $R^4$ are as defined in paragraph 1.

12. A compound according to any one of the preceding paragraphs, or a salt, hydrate or solvate thereof, wherein $R^4$ is selected from $OR^6$, $NHR^6$, $NR^7R^8$ and a group of formula II.

13. A compound according to any one of the preceding paragraphs, or a salt, hydrate or solvate thereof, wherein $R^4$ is selected from $OR^6$, $NHR^6$ and a group of formula II.

14. A compound according to any one of the preceding paragraphs, or a salt, hydrate or solvate thereof, wherein $R^4$ is selected from $NHR^6$, $NR^7R^8$ and a group of formula II.

15. A compound according to any one of the preceding paragraphs, or a salt, hydrate or solvate thereof, wherein $R^4$ is selected from $NHR^6$ and a group of formula II.

16. A compound according to any one of the preceding paragraphs, or a salt, hydrate or solvate thereof, wherein $R^6$ is selected from 3-7 membered heterocycloalkyl and $C_3$-$C_{10}$ alkylheterocycloalkyl, each optionally substituted by one or more $R^f$.

17. A compound according to any one of the preceding paragraphs, or a salt, hydrate or solvate thereof, wherein $R^6$ is selected from 3-7 membered heterocycloalkyl and $C_3$-$C_7$ alkylheterocycloalkyl, each optionally substituted by one or more $R^f$.

18. A compound according to any one of the preceding paragraphs, or a salt, hydrate or solvate thereof, wherein $R^6$ is selected from 5-7 membered heterocycloalkyl and $C_5$-$C_7$ alkylheterocycloalkyl, each optionally substituted by one or more $R^f$.

19. A compound according to any one of the preceding paragraphs, or a salt, hydrate or solvate thereof, wherein $R^6$ is selected from 5-6 membered heterocycloalkyl and $C_5$-$C_6$ alkylheterocycloalkyl, each optionally substituted by one or more $R^f$.

20. A compound according to any one of the preceding paragraphs, or a salt, hydrate or solvate thereof, wherein each $R^f$ is independently selected from hydroxyl, halogen, CN, $C_{1-6}$ alkyl, $C_{1-6}$ haloalkyl and $OR^a$.

21. A compound according to any one of the preceding paragraphs, or a salt, hydrate or solvate thereof, wherein each $R^f$ is independently selected from halogen, CN, $C_{1-6}$ alkyl and $OR^a$.

22. A compound according to any one of the preceding paragraphs, or a salt, hydrate or solvate thereof, wherein each $R^f$ is independently selected from halogen and $C_{1-3}$ alkyl.

23. A compound according to any one of the preceding paragraphs, or a salt, hydrate or solvate thereof, wherein each $R^f$ is independently a $C_{1-3}$ alkyl.

24. A compound according to any one of the preceding paragraphs or a salt, hydrate or solvate thereof, wherein $R^6$ is selected from:

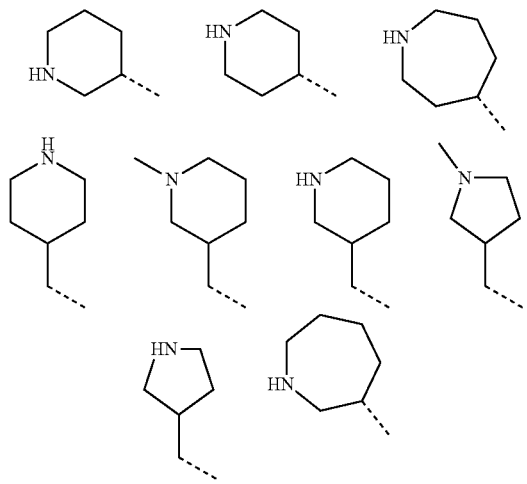

where the dashed line indicates the point of attachment to the remainder of the molecule.

25. A compound according to any one of the preceding paragraphs, or a salt, hydrate or solvate thereof, wherein $R^4$ is selected from $NR^7R^8$ and a group of formula II.

26. A compound according to any one of the preceding paragraphs, or a salt, hydrate or solvate thereof, wherein $R^7$ and $R^8$ are independently selected from hydrogen, $C_{1-6}$ alkyl optionally substituted by one or more $R^g$, $C_{3-11}$ cycloalkyl optionally substituted by one or more $R^g$, $(C_{4-17})$ alkylcycloalkyl optionally substituted by one or more $R^g$, 3-15 membered heterocycloalkyl optionally substituted by one or more $R^g$, $C_3$-$C_{10}$ alkylheterocycloalkyl optionally substituted by one or more $R^g$, with the proviso that both $R^7$ and $R^8$ cannot be hydrogen; or $R^7$ and $R^8$ together with the nitrogen atom to which they are attached form a 3-15 membered heterocycloalkyl optionally substituted by one or more $R^j$;

27. A compound according to any one of the preceding paragraphs, or a salt, hydrate or solvate thereof, wherein $R^7$ and $R^8$ are independently selected from hydrogen, $C_{1-6}$ alkyl optionally substituted by one or more $R^g$, $C_{3-7}$cycloalkyl optionally substituted by one or more $R^g$, $(C_{4-11})$ alkylcycloalkyl optionally substituted by one or more $R^g$, 3-7 membered heterocycloalkyl optionally substituted by one or more $R^g$, $C_3$-$C_{10}$ alkylheterocycloalkyl optionally substituted by one or more $R^g$, with the proviso that both $R^7$ and $R^8$ cannot be hydrogen; or $R^7$ and $R^8$ together with the nitrogen atom to which they are attached form a 3-15 membered heterocycloalkyl optionally substituted by one or more $R^j$;

28. A compound according to any one of the preceding paragraphs, or a salt, hydrate or solvate thereof, wherein $R^7$ and $R^8$ are independently selected from hydrogen, $C_{1-6}$ alkyl optionally substituted by one or more $R^g$, $C_{3-7}$cycloalkyl optionally substituted by one or more $R^g$, $(C_{4-11})$ alkylcycloalkyl optionally substituted by one or more $R^g$, 3-7 membered heterocycloalkyl optionally substituted by one or more $R^g$, $C_3$-$C_{10}$ alkylheterocycloalkyl optionally substituted by one or more $R^g$, with the proviso that both $R^7$ and $R^8$ cannot be hydrogen; or $R^7$ and $R^8$ together with the nitrogen atom to which they are attached form a 3-12 membered heterocycloalkyl optionally substituted by one or more $R^j$:

29. A compound according to any one of the preceding paragraphs, or a salt, hydrate or solvate thereof, wherein $R^7$ and $R^8$ are independently selected from hydrogen, $C_{1-6}$ alkyl optionally substituted by one or more $R^g$, 3-7 membered heterocycloalkyl optionally substituted by one or more $R^g$, $C_3$-$C_{10}$ alkylheterocycloalkyl optionally substituted by one or more $R^g$, with the proviso that both $R^7$ and $R^8$ cannot be hydrogen; or $R^7$ and $R^8$ together with the nitrogen atom to which they are attached form a 3-12 membered heterocycloalkyl optionally substituted by one or more $R^j$;

30. A compound according to any one of the preceding paragraphs, or a salt, hydrate or solvate thereof, wherein $R^7$ and $R^8$ are independently selected from hydrogen, $C_{1-3}$ alkyl optionally substituted by one or more $R^g$, 3-7 membered heterocycloalkyl optionally substituted by one or more $R^g$, $C_3$-$C_7$ alkylheterocycloalkyl optionally substituted by one or more $R^g$, with the proviso that both $R^7$ and $R^8$ cannot be hydrogen; or $R^7$ and $R^8$ together with the nitrogen atom to which they are attached form a 3-12 membered heterocycloalkyl optionally substituted by one or more $R^j$;

31. A compound according to any one of the preceding paragraphs, or a salt, hydrate or solvate thereof, wherein $R^7$ is selected from hydrogen and $C_{1-3}$ alkyl optionally substituted by one or more $R^g$.

32. A compound according to any one of the preceding paragraphs, or a salt, hydrate or solvate thereof, wherein $R^7$ is hydrogen.

33. A compound according to any one of the preceding paragraphs, or a salt, hydrate or solvate thereof, wherein $R^8$ is selected from 3-7 membered heterocycloalkyl optionally substituted by one or more $R^g$, and $C_3$-$C_7$ alkylheterocycloalkyl optionally substituted by one or more $R^g$.

34. A compound according to any one of the preceding paragraphs, or a salt, hydrate or solvate thereof, wherein $R^g$ is selected from hydroxyl, halogen, CN, and $C_{1-6}$ alkyl.

35. A compound according to any one of the preceding paragraphs, or a salt, hydrate or solvate thereof, wherein $R^g$ is selected from halogen and $C_{1-6}$ alkyl.

36. A compound according to any one of the preceding paragraphs, or a salt, hydrate or solvate thereof, wherein $R^g$ is selected from halogen and $C_{1-3}$ alkyl.

37. A compound according to any one of the preceding paragraphs, or a salt, hydrate or solvate thereof, wherein $R^g$ is selected from $C_{1-3}$ alkyl.

38. A compound according to any one of paragraphs 1 to 30, or a salt, hydrate or solvate thereof, wherein $R^7$ and $R^8$ together with the nitrogen atom to which they are attached form a 3-12 membered heterocycloalkyl optionally substituted by one or more $R^j$;

39. A compound according to paragraph 38, or a salt, hydrate or solvate thereof, wherein $R^7$ and $R^8$ together with the nitrogen atom to which they are attached form a 5-12 membered heterocycloalkyl optionally substituted by one or more $R^j$;

40. A compound according to any one of the preceding paragraphs, or a salt, hydrate or solvate thereof, wherein $R^j$ is selected from halogen, hydroxyl, CN, $NH_2$, $NH(C_{1-6}alkyl)$, $N(C_{1-6}\ alkyl)_2$, $NR^cR^d$, $C(=O)NR^cR^d$, $C_{1-6}$ alkyl, $O-C_{1-6}$ alkyl, $C_{1-6}$haloalkyl, $C_{1-6}$haloalkoxy, wherein said $C_{1-6}$ alkyl is optionally substituted with one or more groups selected from hydroxyl, $NH_2$, $NH(C_{1-6}alkyl)$, $N(C_{1-6}\ alkyl)_2$, phenyl and $OR^a$.

41. A compound according to any one of the preceding paragraphs, or a salt, hydrate or solvate thereof, wherein $R^j$ is selected from halogen, hydroxyl, CN, $NH_2$, $NH(C_{1-6}alkyl)$, $N(C_{1-6}\ alkyl)_2$, $NR^cR^d$, $C_{1-6}$ alkyl, wherein said $C_{1-6}$ alkyl is optionally substituted with one or more groups selected from hydroxyl, $NH_2$, $NH(C_{1-6}alkyl)$, $N(C_{1-6}\ alkyl)_2$, phenyl and $OR^a$.

42. A compound according to any one of the preceding paragraphs, or a salt, hydrate or solvate thereof, wherein $R^j$ is selected from $C_{1-4}$ alkyl, suitably $C_{1-3}$ alkyl.

43. A compound according to any one of the preceding paragraphs, or a salt, hydrate or solvate thereof, wherein $R^4$ or $NR^7R^8$ is selected from

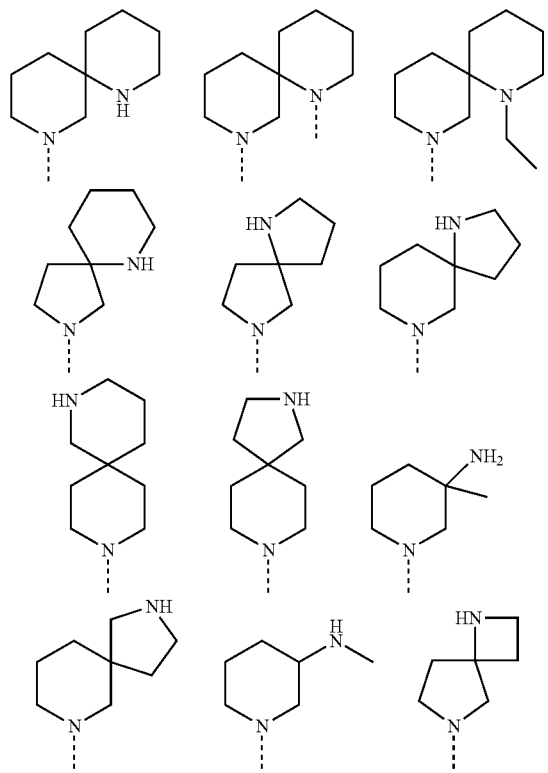

where the dashed line indicates the point of attachment to the remainder of the molecule, and wherein each is optionally substituted on a carbon atom by one or more $R^j$, wherein $R^j$ is selected from halogen, $C_{1-6}$ alkyl, hydroxyl and $O-C_{1-6}$ alkyl with the proviso that $R^j$ is selected from halogen and $C_{1-6}$ alkyl when bonded to a carbon adjacent to N.

44. A compound according to any one of the preceding paragraphs, or a salt, hydrate or solvate thereof, wherein $R^4$ or $NR^7R^8$ is selected from

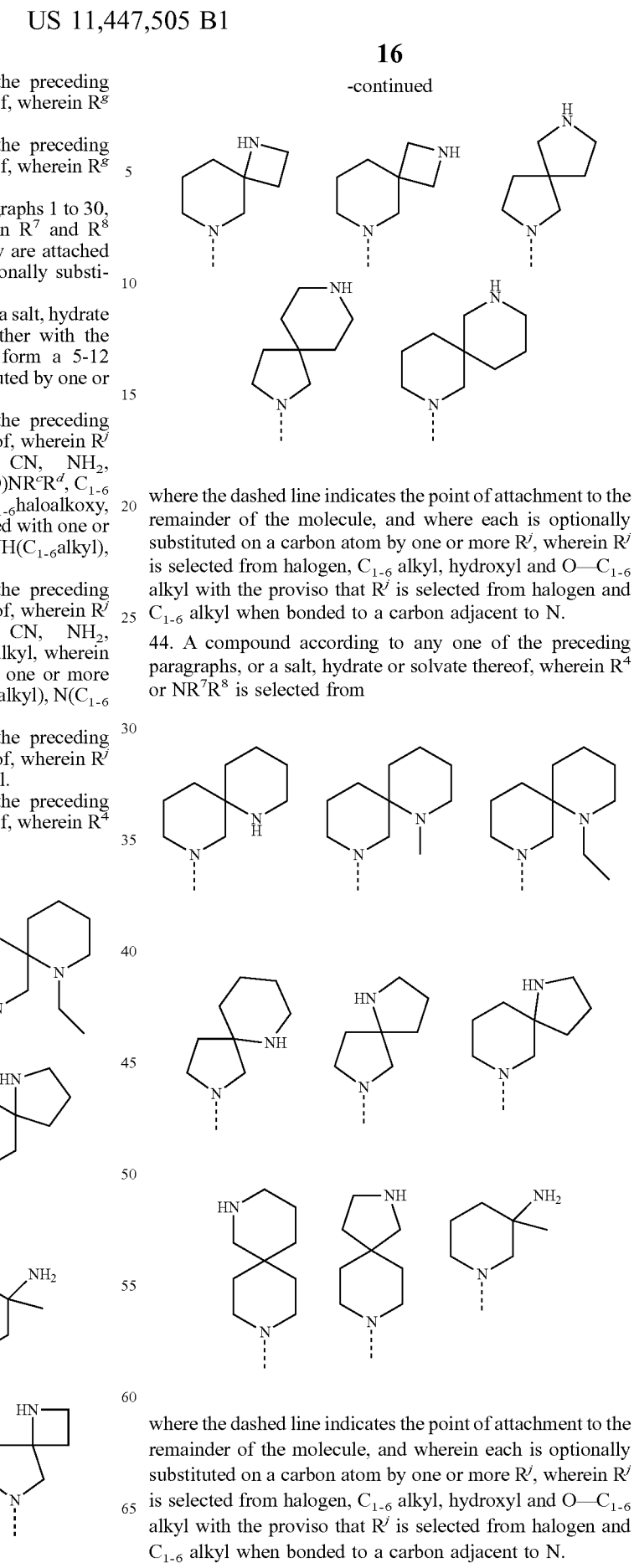

where the dashed line indicates the point of attachment to the remainder of the molecule, and where each is optionally substituted on a carbon atom by one or more $R^j$, wherein $R^j$ is selected from halogen, $C_{1-6}$ alkyl, hydroxyl and $O-C_{1-6}$ alkyl with the proviso that $R^j$ is selected from halogen and $C_{1-6}$ alkyl when bonded to a carbon adjacent to N.

45. A compound according to any one of the preceding paragraphs, or a salt, hydrate or solvate thereof, wherein $R^4$ or $NR^7R^8$ is selected from

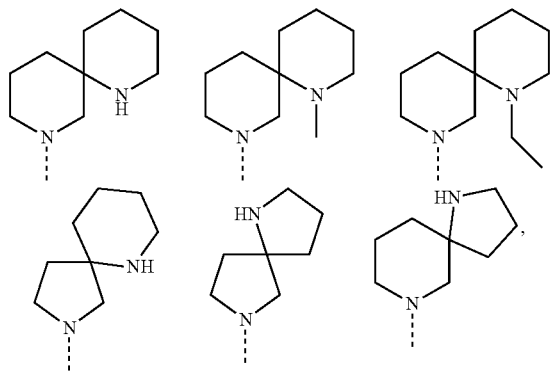

where the dashed line indicates the point of attachment to the remainder of the molecule, and wherein each is optionally substituted on a carbon atom by one or more $R^j$, wherein $R^j$ is selected from halogen, $C_{1-6}$ alkyl, hydroxyl and $O-C_{1-6}$ alkyl with the proviso that $R^j$ is selected from halogen and $C_{1-6}$ alkyl when bonded to a carbon adjacent to N.

46. A compound according to any one of the preceding paragraphs, or a salt, hydrate or solvate thereof, wherein $R^4$ or $NR^7R^8$ is selected from

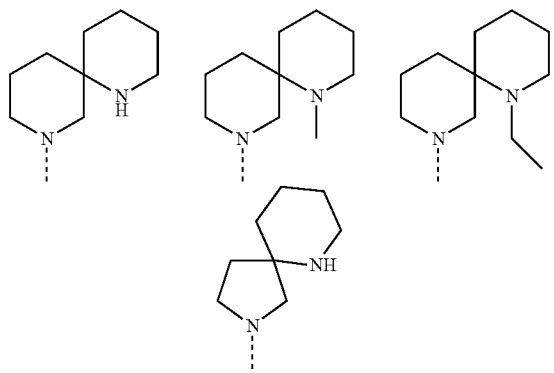

where the dashed line indicates the point of attachment to the remainder of the molecule, and wherein each is optionally substituted on a carbon atom by one or more $R^j$, wherein $R^j$ is selected from halogen, $C_{1-6}$ alkyl, hydroxyl and $O-C_{1-6}$ alkyl with the proviso that $R^j$ is selected from halogen and $C_{1-6}$ alkyl when bonded to a carbon adjacent to N.

47. A compound according to any one of the preceding paragraphs, or a salt, hydrate or solvate thereof, wherein $R^4$ or $NR^7R^8$ is selected from

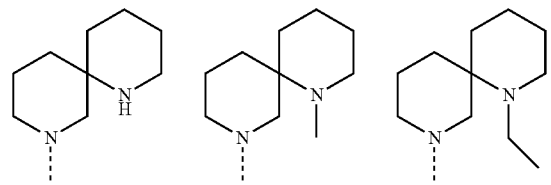

where the dashed line indicates the point of attachment to the remainder of the molecule, and wherein each is optionally substituted on a carbon atom by one or more $R^j$, wherein $R^j$ is selected from halogen, $C_{1-6}$ alkyl, hydroxyl and $O-C_{1-6}$ alkyl with the proviso that $R^j$ is selected from halogen and $C_{1-6}$ alkyl when bonded to a carbon adjacent to N.

48. A compound according to paragraph 1, or a salt, hydrate or solvate thereof, of sub-formula Ic:

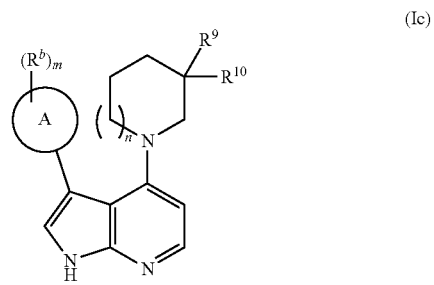

(Ic)

wherein
ring A is a 5-6 membered heteroaryl ring;
m is a number selected from 0, 1 and 2; and
n, $R^9$ and $R^{10}$ are as defined in paragraph 1.

49. A compound according to any one of the preceding paragraphs, or a salt, hydrate or solvate thereof, wherein $R^3$ or ring A is selected from thiadiazole, isothiazole, pyrimidine, thiazole, pyridazine, pyridine, pyrazine and pyrazole, each optionally substituted by one or two $R^b$ groups.

50. A compound according to any one of the preceding paragraphs, or a salt, hydrate or solvate thereof, wherein $R^3$ or ring A is selected from thiadiazole, isothiazole, pyrimidine, thiazole, and pyridazine, each optionally substituted by one or two $R^b$ groups.

51. A compound according to any one of the preceding paragraphs, or a salt, hydrate or solvate thereof, wherein $R^3$ or ring A is selected from thiazole and pyrimidine, each optionally substituted by one or two $R^b$ groups.

52. A compound according to any one of the preceding paragraphs, or a salt, hydrate or solvate thereof, wherein $R^3$ or ring A is selected from

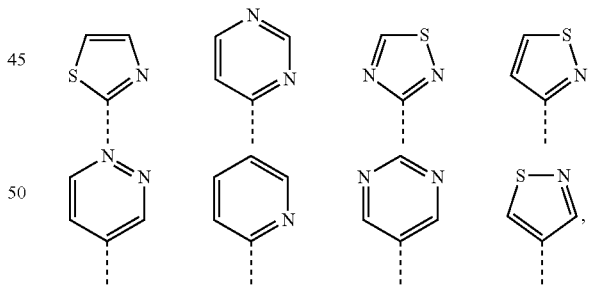

each optionally substituted by one or two $R^b$ groups.

53. A compound according to any one of the preceding paragraphs, or a salt, hydrate or solvate thereof, wherein $R^3$ or ring A is selected from

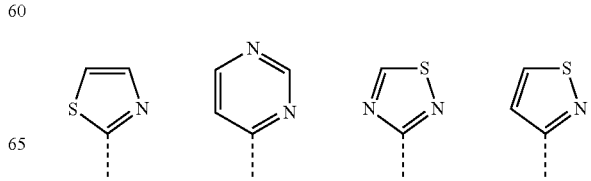

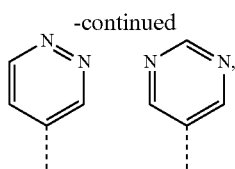

each optionally substituted by one or two $R^b$ groups.

54. A compound according to any one of the preceding paragraphs, or a salt, hydrate or solvate thereof, wherein $R^3$ or ring A is selected from

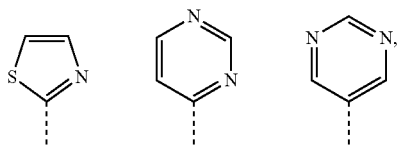

each optionally substituted by one or two $R^b$ groups.

55. A compound according to any one of the preceding paragraphs, or a salt, hydrate or solvate thereof, wherein $R^3$ or ring A is

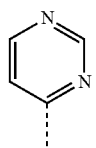

optionally substituted by one or two $R^b$ groups.

56. A compound according to any one of the preceding paragraphs, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$, $NR^cC(=O)R^d$, $C(O)NR^cR^d$, phenyl, and 3-7 membered heterocycloalkyl, where said $C_{1-6}$ alkyl, phenyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$, $C_{1-6}$ alkyl, O—$C_{1-6}$ alkyl, $C_{1-6}$haloalkyl, $C_{1-6}$haloalkoxy, $C_{3-6}$ cycloalkyl and phenyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

57. A compound according to any one of the preceding paragraphs, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$ and 3-7 membered heterocycloalkyl, where said $C_{1-6}$ alkyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$, $C_{1-6}$ alkyl, O—$C_{1-6}$alkyl, $C_{1-6}$haloalkyl, $C_{1-6}$haloalkoxy, $C_{3-6}$ cycloalkyl and phenyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$.

58. A compound according to any one of the preceding paragraphs, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$ and 3-7 membered heterocycloalkyl, where said $C_{1-6}$ alkyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$ and $C_{1-6}$ alkyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

59. A compound according to any one of the preceding paragraphs, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$ and $N(C_{1-6}alkyl)_2$, where said $C_{1-6}$ alkyl is optionally substituted with one or more groups selected from halogen, hydroxyl, CN, $NH_2$, $NH(C_{1-6}alkyl)$, $N(C_{1-6}$ alkyl$)_2$ and $C_{1-6}$alkyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

60. A compound according to any one of the preceding paragraphs, or a salt, hydrate or solvate thereof, wherein $R^9$ is selected from hydrogen and $C_{1-6}$ alkyl.

61. A compound according to any one of the preceding paragraphs, or a salt, hydrate or solvate thereof, wherein $R^9$ is selected from hydrogen and $C_{1-3}$ alkyl.

62. A compound according to any one of the preceding paragraphs, or a salt, hydrate or solvate thereof, wherein $R^{10}$ is selected from $NH_2$, $NH(C_{1-6}alkyl)$ and $N(C_{1-6}alkyl)_2$.

63. A compound according to any one of the preceding paragraphs, or a salt, hydrate or solvate thereof, wherein $R^{10}$ is selected from $NH_2$, $NH(C_{1-3}alkyl)$ and $N(C_{1-3}alkyl)_2$.

64. A compound according to any one of paragraphs 1 to 59, or a salt, hydrate or solvate thereof, wherein $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$.

65. A compound according to paragraph 64, or a salt, hydrate or solvate thereof, wherein $R^9$ and $R^{10}$ together with the carbon atom to which they are attached form a 4-6 membered heterocycloalkyl ring comprising at least one nitrogen atom, where said heterocycloalkyl ring is optionally substituted with one or more $R^m$.

66. A compound according to paragraph 64, or a salt, hydrate or solvate thereof, wherein $R^9$ and $R^{10}$ together with the carbon atom to which they are attached form a 4-6 membered heterocycloalkyl ring comprising one nitrogen atom, where said heterocycloalkyl ring is optionally substituted with one or more $R^m$.

67. A compound according to paragraph 64, or a salt, hydrate or solvate thereof, wherein $R^9$ and $R^{10}$ together with the carbon atom to which they are attached form a 5-6 membered heterocycloalkyl ring comprising one nitrogen atom, where said heterocycloalkyl ring is optionally substituted with one or more $R^m$.

68. A compound according to any one of the preceding paragraphs, or a salt, hydrate or solvate thereof, wherein $R^m$ is selected from halogen, CN, $C_{1-6}$ alkyl, and $OR^a$.

69. A compound according to any one of the preceding paragraphs, or a salt, hydrate or solvate thereof, wherein $R^m$ is selected from halogen and $C_{1-6}$ alkyl.

70. A compound according to any one of the preceding paragraphs, or a salt, hydrate or solvate thereof, wherein $R^m$ is selected from $C_{1-3}$ alkyl.

71. A compound according to any one of the preceding paragraphs, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen, =O, $NR^cR^d$, $C_{1-6}$ alkyl, O—$C_{1-6}$ alkyl, and phenyl;

72. A compound according to any one of the preceding paragraphs, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen, =O, $NR^cR^d$ and O—$C_{1-5}$ alkyl.

73. A compound according to any one of the preceding paragraphs, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen and $NR^cR^d$.

74. A compound according to any one of the preceding paragraphs, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more halogens.

75. A compound according to any one of the preceding paragraphs, or a salt, hydrate or solvate thereof, wherein $R^b$ is selected from hydrogen, hydroxyl, halogen, CN, $C_{1-6}$ alkyl and O—$C_{1-6}$ alkyl.

76. A compound according to any one of the preceding paragraphs, or a salt, hydrate or solvate thereof, wherein $R^b$ is selected from hydrogen, halogen, CN and $C_{1-6}$ alkyl.

77. A compound according to any one of the preceding paragraphs, or a salt, hydrate or solvate thereof, wherein $R^b$ is selected from hydrogen, halogen, CN and $C_{1-3}$ alkyl.

78. A compound according to any one of the preceding paragraphs, or a salt, hydrate or solvate thereof, wherein $R^b$ is selected from hydrogen and $C_{1-3}$ alkyl, suitably hydrogen.

79. A compound according to any one of paragraphs 11 to 78, or a salt, hydrate or solvate thereof, wherein m is selected from 0 and 1.

80. A compound according to any one of paragraphs 11 to 78, or a salt, hydrate or solvate thereof, wherein m is 0.

81. A compound according to any one of the preceding paragraphs, or a salt, hydrate or solvate thereof, wherein n is 1.

82. A compound according to any one of the preceding paragraphs, or a salt, hydrate or solvate thereof, wherein n is 0.

83. A compound according to any one of the preceding paragraphs, or a salt, hydrate or solvate thereof, wherein $R^a$ is selected from hydrogen and $C_{1-6}$ alkyl.

84. A compound according to any one of the preceding paragraphs, or a salt, hydrate or solvate thereof, wherein $R^a$ is selected from hydrogen and $C_{1-3}$ alkyl.

85. A compound according to any one of the preceding paragraphs, or a salt, hydrate or solvate thereof, wherein $R^c$ is selected from hydrogen and $C_{1-3}$ alkyl.

86. A compound according to any one of the preceding paragraphs, or a salt, hydrate or solvate thereof, wherein $R^d$ is selected from hydrogen, 5-6 membered heteroaryl, $C_{3-6}$ cycloalkyl, $C_{1-6}$ alkyl, wherein said $C_{1-6}$ alkyl and 5-6 membered heteroaryl are optionally substituted with one or more groups selected from hydroxyl, halogen, CN, $NH_2$, $NH(C_{1-6}$ alkyl), $N(C_{1-6}$alkyl$)_2$, $C_{1-6}$ haloalkyl, $C_{3-6}$ cycloalkyl, phenyl, 3-7 membered heterocycloalkyl, $C_{3-10}$alkylheterocycloalkyl, $C_{1-6}$ alkyl and O—$C_{1-6}$ alkyl.

87. A compound according to any one of the preceding paragraphs, or a salt, hydrate or solvate thereof, wherein $R^d$ is selected from hydrogen, 5-6 membered heteroaryl, $C_{3-6}$ cycloalkyl, $C_{1-6}$ alkyl, wherein said $C_{1-6}$ alkyl and 5-6 membered heteroaryl are optionally substituted with one or more groups selected from hydroxyl, halogen, phenyl, 3-7 membered heterocycloalkyl, $C_{3-10}$alkylheterocycloalkyl, $C_{1-6}$ alkyl and O—$C_{1-6}$ alkyl.

88. A compound according to any one of the preceding paragraphs, or a salt, hydrate or solvate thereof, wherein $R^d$ is selected from hydrogen, 5-6 membered heteroaryl, $C_{3-10}$ cycloalkyl, $C_{1-6}$ alkyl, wherein said $C_{1-6}$ alkyl and 5-6 membered heteroaryl are optionally substituted with one or more groups selected from hydroxyl, halogen, phenyl, $C_{3-10}$alkylheterocycloalkyl, O—$C_{1-6}$ alkyl.

89. A compound according to any one of the preceding paragraphs, or a salt, hydrate or solvate thereof, wherein $R^d$ is selected from hydrogen, $C_{3-6}$ cycloalkyl, $C_{1-6}$ alkyl, wherein said $C_{1-6}$ alkyl is optionally substituted with one or more groups selected from hydroxyl, halogen, phenyl, $C_{3-10}$alkylheterocycloalkyl, O—$C_{1-6}$ alkyl.

90. A compound according to any one of the preceding paragraphs, or a salt, hydrate or solvate thereof, wherein $R^d$ is selected from $C_{3-6}$ cycloalkyl, $C_{1-6}$ alkyl, wherein said $C_{1-6}$ alkyl is optionally substituted with one or more groups selected from hydroxyl, halogen, phenyl, $C_{3-10}$alkylheterocycloalkyl, O—$C_{1-6}$ alkyl.

91. A compound according to any one of the preceding paragraphs, or a salt, hydrate or solvate thereof, wherein $R^d$ is selected from $C_{1-3}$ alkyl.

92. A compound according to any one of paragraphs 1 to 84, or a salt, hydrate or solvate thereof, wherein $R^c$ and $R^d$, when attached to the same atom, together with the atom to which they are attached form a 3-7 membered heterocycloalkyl ring optionally substituted by one or more $C_{1-6}$ alkyl.

93. A compound according to any one of paragraphs 1 to 84, or a salt, hydrate or solvate thereof, wherein $R^c$ and $R^d$, when attached to the same atom, together with the atom to which they are attached form a 3-6 membered heterocycloalkyl ring optionally substituted by one or more $C_{1-3}$ alkyl.

94. A compound according to paragraph 1, or a salt, hydrate or solvate thereof, of sub-formula Ic':

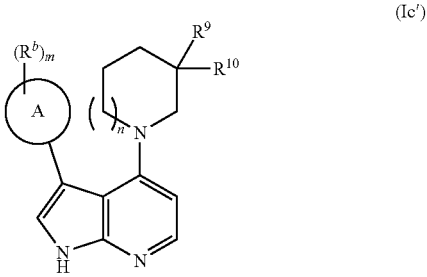

(Ic')

wherein
  ring A is a heteroaryl group selected from a pyrimidine, thiazole, thiadiazole, isothiazole, pyridazine, pyridine and pyrazine, each optionally substituted by one or two $R^b$ groups;
  m is a number selected from 0, 1 and 2; and
  n, $R^9$ and $R^{10}$ are as defined in paragraph 1.

95. A compound according to paragraph 94, or a salt, hydrate or solvate thereof, wherein ring A is selected from thiadiazole, isothiazole, pyrimidine, thiazole, and pyridazine, each optionally substituted by one or two $R^b$ groups.

96. A compound according to any one of paragraphs 94 and 95, or a salt, hydrate or solvate thereof, wherein ring A is selected from thiazole and pyrimidine, each optionally substituted by one or two $R^b$ groups.

97. A compound according to any one of paragraphs 94 to 96, or a salt, hydrate or solvate thereof, wherein ring A is selected from

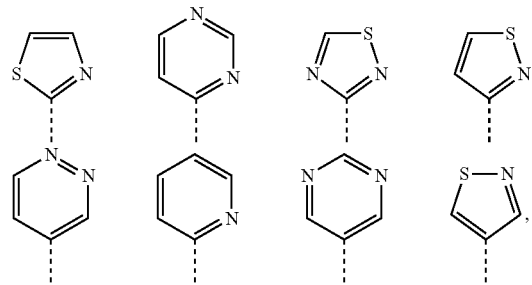

each optionally substituted by one or two $R^b$ groups.

98. A compound according to any one of paragraphs 94 to 97, or a salt, hydrate or solvate thereof, wherein $R^3$ or ring A is selected from

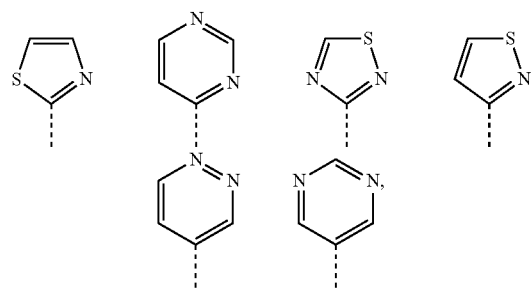

each optionally substituted by one or two $R^b$ groups.

99. A compound according to any one of paragraphs 94 to 98, or a salt, hydrate or solvate thereof, wherein A is selected from

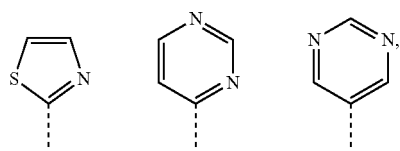

each optionally substituted by one or two $R^b$ groups.

100. A compound according to any one of paragraphs 94 to 99, or a salt, hydrate or solvate thereof, wherein $R^3$ or ring A is

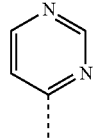

optionally substituted by one or two $R^b$ groups.

101. A compound according to any one of paragraphs 94 to 100, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$, $NR^cC(=O)R^d$, $C(O)NR^cR^d$, phenyl, and 3-7 membered heterocycloalkyl, where said $C_{1-6}$ alkyl, phenyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$, $C_{1-6}$ alkyl, $O—C_{1-6}$ alkyl, $C_{1-6}$haloalkyl, $C_{1-6}$haloalkoxy, $C_{3-6}$ cycloalkyl and phenyl; or
  $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

102. A compound according to any one of paragraphs 94 to 101, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$ and 3-7 membered heterocycloalkyl, where said $C_{1-6}$ alkyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$, $C_{1-6}$ alkyl, $O—C_{1-6}$ alkyl, $C_{1-6}$haloalkyl, $C_{1-6}$haloalkoxy, $C_{3-6}$ cycloalkyl and phenyl; or $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$.

103. A compound according to any one of paragraphs 94 to 102, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$, $N(C_{1-6}alkyl)_2$, $NR^cR^d$ and 3-7 membered heterocycloalkyl, where said $C_{1-6}$ alkyl and 3-7 membered heterocycloalkyl are optionally substituted with one or more groups selected from halogen, hydroxyl, CN, $NH_2$, $NH(C_{1-6}alkyl)$, $N(C_{1-6}alkyl)_2$ and $C_{1-6}$ alkyl; or
  $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

104. A compound according to any one paragraphs 94 to 103, or a salt, hydrate or solvate thereof, wherein $R^9$ and $R^{10}$ are independently selected from hydrogen, hydroxyl, $C_{1-6}$ alkyl, $NH_2$, $NH(C_{1-6}alkyl)$ and $N(C_{1-6}alkyl)_2$, where said $C_{1-6}$ alkyl is optionally substituted with one or more groups selected from halogen, hydroxyl, CN, $NH_2$, $NH(C_{1-6}alkyl)$, $N(C_{1-6}alkyl)_2$ and $C_{1-6}$ alkyl; or
  $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$;

105. A compound according to any one of paragraphs 94 to 104, or a salt, hydrate or solvate thereof, wherein $R^9$ is selected from hydrogen and $C_{1-6}$ alkyl.

106. A compound according to any one of paragraphs 94 to 105, or a salt, hydrate or solvate thereof, wherein $R^9$ is selected from hydrogen and $C_{1-3}$ alkyl.

107. A compound according to any one of paragraphs 94 to 106, or a salt, hydrate or solvate thereof, wherein $R^{10}$ is selected from $NH_2$, $NH(C_{1-6}alkyl)$ and $N(C_{1-6}alkyl)_2$.

108. A compound according to any one of paragraphs 94 to 107, or a salt, hydrate or solvate thereof, wherein $R^{10}$ is selected from $NH_2$, $NH(C_{1-3}alkyl)$ and $N(C_{1-3}alkyl)_2$.

109. A compound according to any one of paragraphs 94 to 104, or a salt, hydrate or solvate thereof, wherein $R^9$ and $R^{10}$ together with the carbon atom to which they are attached form a 4-6 membered heterocycloalkyl ring comprising at least one heteroatom selected from O, N and S, where said heterocycloalkyl ring is optionally substituted with one or more $R^m$.

110. A compound according to paragraph 109, or a salt, hydrate or solvate thereof, wherein $R^9$ and $R^{10}$ together with the carbon atom to which they are attached form a 4-6 membered heterocycloalkyl ring comprising at least one nitrogen atom, where said heterocycloalkyl ring is optionally substituted with one or more $R^m$.

111. A compound according to paragraph 109, or a salt, hydrate or solvate thereof, wherein $R^9$ and $R^{10}$ together with the carbon atom to which they are attached form a 4-6 membered heterocycloalkyl ring comprising one nitrogen atom, where said heterocycloalkyl ring is optionally substituted with one or more $R^m$.

112. A compound according to paragraph 109, or a salt, hydrate or solvate thereof, wherein $R^9$ and $R^{10}$ together with the carbon atom to which they are attached form a 5-6 membered heterocycloalkyl ring comprising one nitrogen atom, where said heterocycloalkyl ring is optionally substituted with one or more $R^m$.

113. A compound according to any one of the preceding paragraphs, or a salt, hydrate or solvate thereof, wherein $R^m$ is selected from halogen, CN, $C_{1-6}$ alkyl, O—$C_{1-6}$ alkyl and OH.

114. A compound according to any one of paragraphs 94 to 113, or a salt, hydrate or solvate thereof, wherein $R^m$ is selected from halogen and $C_{1-6}$ alkyl.

115. A compound according to any one of paragraphs 94 to 114, or a salt, hydrate or solvate thereof, wherein $R^m$ is selected from $C_{1-3}$ alkyl.

116. A compound according to any one of paragraphs 94 to 100, or a salt, hydrate or solvate thereof, wherein $R^9$ and $R^{10}$ together form a ring selected from (wherein the • indicates the point of attachment to the remainder of the compound):

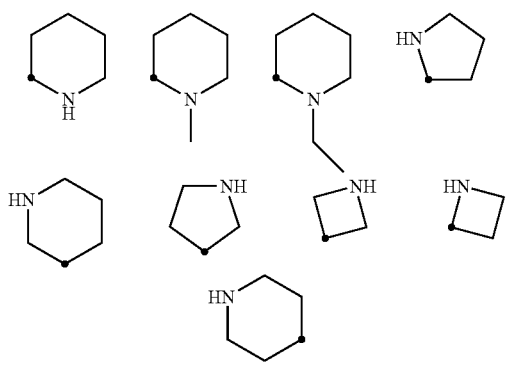

117. A compound according to any one of paragraphs 94 to 116, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen, =O, $NR^cR^d$, $C_{1-6}$ alkyl, O—$C_{1-6}$ alkyl, and phenyl;

118. A compound according to any one of paragraphs 94 to 117, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen, =O, $NR^cR^d$ and O—$C_{1-6}$ alkyl.

119. A compound according to any one of paragraphs 94 to 118, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more groups selected from hydroxyl, halogen and $NR^cR^d$.

120. A compound according to any one of paragraphs 94 to 119, or a salt, hydrate or solvate thereof, wherein $R^b$ is selected from hydrogen, hydroxyl, halogen, CN, $C_{1-6}$ alkyl, O—$C_{1-6}$ alkyl, $NH_2$, $NR^cR^d$, $C(O)NR^cR^d$, wherein said $C_{1-6}$ alkyl is optionally substituted with one or more halogens.

121. A compound according to any one of paragraphs 94 to 120, or a salt, hydrate or solvate thereof, wherein $R^b$ is selected from hydrogen, hydroxyl, halogen, CN, $C_{1-6}$ alkyl and O—$C_{1-6}$ alkyl.

122. A compound according to any one of paragraphs 94 to 121, or a salt, hydrate or solvate thereof, wherein $R^b$ is selected from hydrogen, halogen, CN and $C_{1-6}$ alkyl.

123. A compound according to any one of paragraphs 94 to 122, or a salt, hydrate or solvate thereof, wherein $R^b$ is selected from hydrogen, halogen, CN and $C_{1-3}$ alkyl.

124. A compound according to any one of paragraphs 94 to 123, or a salt, hydrate or solvate thereof, wherein $R^b$ is selected from hydrogen and $C_{1-3}$ alkyl, suitably hydrogen.

125. A compound according to any one of paragraphs 94 to 124, or a salt, hydrate or solvate thereof, wherein m is selected from 0 and 1.

126. A compound according to any one of paragraphs 94 to 125, or a salt, hydrate or solvate thereof, wherein m is 0.

127. A compound according to any one of paragraphs 94 to 126, or a salt, hydrate or solvate thereof, wherein n is 1.

128. A compound according to any one of paragraphs 94 to 127, or a salt, hydrate or solvate thereof, wherein n is 0.

129. A compound according to any one of paragraphs 94 to 128, or a salt, hydrate or solvate thereof, wherein $R^c$ is selected from hydrogen and $C_{1-3}$ alkyl.

130. A compound according to any one of paragraphs 94 to 129, or a salt, hydrate or solvate thereof, wherein $R^d$ is selected from hydrogen, 5-6 membered heteroaryl, $C_{3-6}$ cycloalkyl, $C_{1-6}$ alkyl, wherein said $C_{1-6}$ alkyl and 5-6 membered heteroaryl are optionally substituted with one or more groups selected from hydroxyl, halogen, CN, $NH_2$, $NH(C_{1-6}$ alkyl), $N(C_{1-6}alkyl)_2$, $C_{1-6}$ haloalkyl, $C_{3-6}$ cycloalkyl, phenyl, 3-7 membered heterocycloalkyl, $C_{3-10}$alkylheterocycloalkyl, $C_{1-6}$ alkyl and O—$C_{1-6}$ alkyl.

131. A compound according to any one of paragraphs 94 to 130, or a salt, hydrate or solvate thereof, wherein $R^d$ is selected from hydrogen, 5-6 membered heteroaryl, $C_{3-6}$ cycloalkyl, $C_{1-6}$ alkyl, wherein said $C_{1-6}$ alkyl and 5-6 membered heteroaryl are optionally substituted with one or more groups selected from hydroxyl, halogen, phenyl, 3-7 membered heterocycloalkyl, $C_{3-10}$alkylheterocycloalkyl, $C_{1-6}$ alkyl and O—$C_{1-6}$ alkyl.

132. A compound according to any one of paragraphs 94 to 131, or a salt, hydrate or solvate thereof, wherein $R^d$ is selected from hydrogen, 5-6 membered heteroaryl, $C_{3-6}$cycloalkyl, $C_{1-6}$ alkyl, wherein said $C_{1-6}$ alkyl and 5-6 membered heteroaryl are optionally substituted with one or more groups selected from hydroxyl, halogen, phenyl, $C_{3-10}$alkylheterocycloalkyl, O—$C_{1-6}$ alkyl.

133. A compound according to any one of paragraphs 94 to 132, or a salt, hydrate or solvate thereof, wherein $R^d$ is selected from hydrogen, $C_{3-6}$ cycloalkyl, $C_{1-6}$ alkyl, wherein said $C_{1-6}$ alkyl is optionally substituted with one or more groups selected from hydroxyl, halogen, phenyl, $C_{3-10}$alkylheterocycloalkyl, O—$C_{1-6}$ alkyl.

134. A compound according to any one of paragraphs 94 to 133 or a salt, hydrate or solvate thereof, wherein $R^d$ is selected from $C_{3-6}$ cycloalkyl, $C_{1-6}$ alkyl, wherein said $C_{1-6}$ alkyl is optionally substituted with one or more groups selected from hydroxyl, halogen, phenyl, $C_{3-10}$alkylheterocycloalkyl, O—$C_{1-6}$ alkyl.

135. A compound according to any one of paragraphs 94 to 134, or a salt, hydrate or solvate thereof, wherein $R^d$ is selected from $C_{1-3}$ alkyl.

136. A compound according to any one of paragraphs 94 to 128, or a salt, hydrate or solvate thereof, wherein R and $R^d$, when attached to the same atom, together with the atom to which they are attached form a 3-7 membered heterocycloalkyl ring optionally substituted by one or more $C_{1-6}$ alkyl.

137. A compound according to any one of paragraphs 94 to 128, or a salt, hydrate or solvate thereof, wherein RC and $R^d$, when attached to the same atom, together with the atom to which they are attached form a 3-6 membered heterocycloalkyl ring optionally substituted by one or more $C_{1-3}$alkyl.

138. A compound, or a salt, hydrate or solvate thereof, selected from:

| | |
|---|---|
| E1 | 5-methyl-4-(1-piperidyl)-3-pyrimidin-5-yl-1H-pyrrolo[2,3-b]pyridine |
| E2 | 5-methyl-4-(1-piperidyl)-3-(1H-pyrazol-4-yl)-1H-pyrrolo[2,3-b]pyridine |
| E3 | 6-[4-(1-piperidyl)-1H-pyrrolo[2,3-b]pyridin-3-yl]pyridin-2-amine |
| E4 | 4-(1-piperidyl)-3-pyrimidin-4-yl-1H-pyrrolo[2,3-b]pyridine |
| E5 | N-methyl-4-[4-(l-piperidyl)-1H-pyrrolo[2,3-b]pyridin-3-yl]pyridin-2-amine |
| E6 | 5-[4-(1-piperidyl)-1H-pyrrolo[2,3-b]pyridin-3-yl]pyridin-3-amine |
| E7 | 2-amino-5-[4-(1-piperidyl)-1H-pyrrolo[2,3-b]pyridin-3-yl]pyridine-3-carbonitrile |
| E8 | 5-[4-(1-piperidyl)-1H-pyrrolo[2,3-b]pyridin-3-yl]pyridine-3-carbonitrile |
| E9 | 4-[4-(1-piperidyl)-1H-pyrrolo[2,3-b]pyridin-3-yl]pyridin-2-amine |
| E10 | 5-[4-(1-piperidyl)-1H-pyrrolo[2,3-b]pyridin-3-yl]pyridin-2-amine |
| E11 | 3-(5-fluoro-3-pyridyl)-4-(1-piperidyl)-1H-pyrrolo[2,3-b]pyridine |
| E12 | 3-(5-chloro-3-pyridyl)-4-(1-piperidyl)-1H-pyrrolo[2,3-b]pyridine |
| E13 | N-methyl-544-(1-piperidyl)-1H-pyrrolo[2,3-b]pyridin-3-yl]pyridine-3-carboxamide |
| E14 | 4-(1-piperidyl)-3-pyridazin-4-yl-1H-pyrrolo[2,3-b]pyridine |
| E15 | 4-(1-piperidyl)-3-pyridazin-3-yl-1H-pyrrolo[2,3-b]pyridine |
| E16 | 4-(1-piperidyl)-3-pyrazin-2-yl-1H-pyrrolo[2,3-b]pyridine |
| E17 | 3-(1H-indazol-3-yl)-4-(1-piperidyl)-1H-pyrrolo[2,3-b]pyridine |
| E18 | 3-(2-methylpyrazol-3-yl)-4-(1-piperidyl)-1H-pyrrolo[2,3-b]pyridine |
| E19 | 3-(1H-indazol-5-yl)-4-(1-piperidyl)-1H-pyrrolo[2,3-b]pyridine |
| E20 | 4-(1-piperidyl)-3-pyrimidin-5-yl-1H-pyrrolo[2,3-b]pyridine |
| E21 | 3-(1-ethylpyrazol-4-yl)-4-(1-piperidyl)-1H-pyrrolo[2,3-b]pyridine |
| E22 | 3-(1-methylpyrazol-3-yl)-4-(1-piperidyl)-1H-pyrrolo[2,3-b]pyridine |
| E23 | 4-(1-piperidyl)-3-(2-pyridyl)-1H-pyrrolo[2,3-b]pyridine |
| E24 | 3-(1-methylpyrazol-4-yl)-4-(1-piperidyl)-1H-pyrrolo[2,3-b]pyridine |
| E25 | 4-(azetidin-1-yl)-3-(2-pyridyl)-1H-pyrrolo[2,3-b]pyridine |
| E26 | 4-(azetidin-1-yl)-3-(3-pyridyl)-1H-pyrrolo[2,3-b]pyridine |
| E27 | 4-(azetidin-1-yl)-3-(1H-pyrazol-4-yl)-1H-pyrrolo[2,3-b]pyridine |
| E28 | 4-(azetidin-1-yl)-3-(1H-pyrazol-3-yl)-1H-pyrrolo[2,3-b]pyridine |
| E30 | 4-(4-methyl-1,4-diazepan-l-yl)-1H-pyrrolo[2,3-b]pyridine-3-carbonitrile |
| E31 | 4-(dimethylamino)-1H-pyrrolo[2,3-b]pyridine-3-carbonitrile |
| E32 | 4-(4-methylpiperazin-1-yl)-1H-pyrrolo[2,3-b]pyridine-3-carbonitrile |
| E33 | 4-morpholino-1H-pyrrolo[2,3-b]pyridine-3-carbonitrile |
| E34 | 4-piperazin-1-yl-1H-pyrrolo[2,3-b]pyridine-3-carbonitrile |
| E35 | 4-(1-piperidyl)-1H-pyrrolo[2,3-b]pyridine-3-carbonitrile |
| E36 | 4-pyrrolidin-1-yl-1H-pyrrolo[2,3-b]pyridine-3-carbonitrile |
| E37 | 4-(methylamino)-1H-pyrrolo[2,3-b]pyridine-3-carbonitrile |
| E38 | 4-[(2S)-2-(hydroxymethyl)pyrrolidin-1-yl]-1H-pyrrolo[2,3-b]pyridine-3-carbonitrile |
| E39 | 4-[(2R)-2-(hydroxymethyl)pyrrolidin-1-yl]-1H-pyrrolo[2,3-b]pyridine-3-carbonitrile |
| E40 | 4-[(2S)-2-(phenoxymethyl)pyrrolidin-1-yl]-1H-pyrrolo[2,3-b]pyridine-3-carbonitrile |
| E41 | (3S)-N-cyclopropyl-1-(3-pyrimidin-4-yl-1H-pyrrolo[2,3-b]pyridin-4-yl)piperidin-3-amine |
| E42 | 4-fluoro-1-(3-pyrimidin-4-yl-1H-pyrrolo[2,3-b]pyridin-4-yl)piperidin-3-amine |
| E43 | 4-(1,4-diazepan-1-yl)-3-pyridazin-4-yl-1H-pyrrolo[2,3-b]pyridine |
| E44 | 4-(1,4-diazepan-1-yl)-3-pyrimidin-5-yl-1H-pyrrolo[2,3-b]pyridine |
| E45 | (3S)-N-cyclopropyl-1-(3-pyridazin-3-yl-1H-pyrrolo[2,3-b]pyridin-4-yl)piperidin-3-amine |
| E46 | (3S)-N-cyclopropyl-1-(3-pyridazin-4-yl-1H-pyrrolo[2,3-b]pyridin-4-yl)piperidin-3-amine |
| E47 | (3S)-N-methyl-1-(3-thiazol-2-yl-1H-pyrrolo[2,3-b]pyridin-4-yl)piperidin-3-amine |
| E48 | (3S)-1-[3-(3-fluoro-2-pyridyl)-1H-pyrrolo[2,3-b]pyridin-4-yl]-N-methylpiperidin-3-amine |

| | -continued |
|---|---|
| E49 | (3S)-N-methyl-1-[3-(2-pyridyl)-1H-pyrrolo[2,3-b]pyridin-4-yl]piperidin-3-amine |
| E50 | (3S)-1-[3-(5-fluoro-3-pyridyl)-1H-pyrrolo[2,3-b]pyridin-4-yl]-N-methyl-piperidin-3-amine |
| E51 | (3S)-1-[3-(5-fluoro-2-pyridyl)-1H-pyrrolo[2,3-b]pyridin-4-yl]-N-methyl-piperidin-3-amine |
| E52 | (3S)-N-methyl-1-(3-pyridazin-3-yl-1H-pyrrolo[2,3-b]pyridin-4-yl)piperidin-3-amine |
| E53 | (3S)-N-methyl-1-[3-(3-pyridyl)-1H-pyrrolo[2,3-b]pyridin-4-yl]piperidin-3-amine |
| E54 | (3S)-N-methyl-1-(3-pyridazin-4-yl-1H-pyrrolo[2,3-b]pyridin-4-yl)piperidin-3-amine |
| E55 | (3S)-N-methyl-1-[3-(1-methylpyrazol-4-yl)-1H-pyrrolo[2,3-b]pyridin-4-yl]piperidin-3-amine |
| E56 | 2-[[(3S)-1-(3-pyrimidin-5-yl-1H-pyrrolo[2,3-b]pyridin-4-yl)-3-piperidyl]amino]ethanol |
| E57 | (3S)-N-methyl-1-(3-pyrimidin-5-yl-1H-pyrrolo[2,3-b]pyridin-4-yl)piperidin-3-amine |
| E58 | (3S)-1-(3-pyrimidin-5-yl-1H-pyrrolo[2,3-b]pyridin-4-yl)pyrrolidin-3-amine |
| E59 | 1-(3-pyrimidin-5-yl-1H-pyrrolo[2,3-b]pyridin-4-yl)piperidin-3-amine |
| E60 | N,N-dimethyl-1-(3-pyrimidin-5-yl-1H-pyrrolo[2,3-b]pyridin-4-yl)piperidin-3-amine |
| E61 | (3S)-1-[3-(5-methyl-1H-pyrazol-4-yl)-1H-pyrrolo[2,3-b]pyridin-4-yl]piperidin-3-amine |
| E62 | N-methyl-1-(3-pyrimidin-5-yl-1H-pyrrolo[2,3-b]pyridin-4-yl)piperidin-3-amine |
| E63 | N-methyl-1-(3-pyrimidin-5-yl-1H-pyrrolo[2,3-b]pyridin-4-yl)piperidin-4-amine |
| E64 | (3R)-1-(3-pyrimidin-5-yl-1H-pyrrolo[2,3-b]pyridin-4-yl)piperidin-3-amine |
| E65 | 1-(3-pyrimidin-5-yl-1H-pyrrolo[2,3-b]pyridin-4-yl)piperidin-4-amine |
| E66 | (3S)-N-methyl-1-(3-pyrimidin-4-yl-1H-pyrrolo[2,3-b]pyridin-4-yl)piperidin-3-amine |
| E67 | (3S)-1-(3-isothiazol-4-yl-1H-pyrrolo[2,3-b]pyridin-4-yl)-N-methyl-piperidin-3-amine |
| E68 | N-methyl-1-(3-pyrimidin-5-yl-1H-pyrrolo[2,3-b]pyridin-4-yl)azepan-4-amine |
| E69 | (3S)-1-(3-pyrimidin-5-yl-1H-pyrrolo[2,3-b]pyridin-4-yl)piperidin-3-amine |
| E70 | 5-bromo-4-(1-piperidyl)-3-(1H-pyrazol-3-yl)-1H-pyrrolo[2,3-b]pyridine |
| E71 | (3S)-N-ethyl-1-(3-pyridazin-4-yl-1H-pyrrolo[2,3-b]pyridin-4-yl)piperidin-3-amine |
| E72 | (3S)-N-methyl-1-(3-pyrazin-2-yl-1H-pyrrolo[2,3-b]pyridin-4-yl)piperidin-3-amine |
| E73 | (3S)-N-(2-methoxyethyl)-1-(3-pyrimidin-5-yl-1H-pyrrolo[2,3-b]pyridin-4-yl)piperidin-3-amine |
| E74 | 4-[(3S)-3-(methylamino)-1-piperidyl]-1H-pyrrolo[2,3-b]pyridine-3-carbonitrile |
| E75 | (3S)-N-methyl-1-[3-(2-methylpyrimidin-5-yl)-1H-pyrrolo[2,3-b]pyridin-4-yl]piperidin-3-amine |
| E76 | (3S)-N-isopropyl-1-(3-pyrimidin-5-yl-1H-pyrrolo[2,3-b]pyridin-4-yl)piperidin-3-amine |
| E77 | (3R)-N-methyl-1-(3-pyrimidin-5-yl-1H-pyrrolo[2,3-b]pyridin-4-yl)piperidin-3-amine |
| E78 | (3S)-N-ethyl-1-[3-(1-methylpyrazol-4-yl)-1H-pyrrolo[2,3-b]pyridin-4-yl]piperidin-3-amine |
| E79 | (3S)-N-ethyl-1-(3-pyrimidin-5-yl-1H-pyrrolo[2,3-b]pyridin-4-yl)piperidin-3-amine |
| E80 | ((3S)-N-cyclopropyl-N-methyl-1-(3-pyrimidin-5-yl-1H-pyrrolo[2,3-b]pyridin-4-yl)piperidin-3-amine |
| E81 | (3S)-N-cyclopropyl-1-(3-pyrimidin-5-yl-1H-pyrrolo[2,3-b]pyridin-4-yl)piperidin-3-amine |
| E82 | (3S)-N,N-dimethyl-1-(3-pyrimidin-5-yl-1H-pyrrolo[2,3-b]pyridin-4-yl)piperidin-3-amine |
| E83 | (3S)-N-methyl-1-[3-(1H-pyrazol-3-yl)-1H-pyrrolo[2,3-b]pyridin-4-yl]piperidin-3-amine |
| E84 | (3S)-N-methyl-1-[3-(1H-pyrazol-4-yl)-1H-pyrrolo[2,3-b]pyridin-4-yl]piperidin-3-amine |
| E85 | N-(azepan-3-yl)-3-pyrimidin-5-yl-1H-pyrrolo[2,3-b]pyridin-4-amine |
| E86 | [1-(3-pyrimidin-5-yl-1H-pyrrolo[2,3-b]pyridin-4-yl)-3-piperidyl]methanamine |
| E87 | N-[(3S)-3-piperidyl]-3-pyrimidin-5-yl-1H-pyrrolo[2,3-b]pyridin-4-amine |
| E88 | N-[(3R)-3-piperidyl]-3-pyrimidin-5-yl-1H-pyrrolo[2,3-b]pyridin-4-amine |
| E89 | N-(4-piperidyl)-3-pyrimidin-5-yl-1H-pyrrolo[2,3-b]pyridin-4-amine |
| E90 | N-methyl-1-[1-(3-pyrimidin-5-yl-1H-pyrrolo[2,3-b]pyridin-4-yl)-3-piperidyl]methanamine |
| E91 | 4-(3-piperazin-1-yl-1-piperidyl)-3-pyrimidin-5-yl-1H-pyrrolo[2,3-b]pyridine |
| E92 | 1-[(3S)-1-(3-pyrimidin-5-yl-1H-pyrrolo[2,3-b]pyridin-4-yl)-3-piperidyl]piperidin-4-ol |
| E93 | [(3S)-1-(3-pyrimidin-5-yl-1H-pyrrolo[2,3-b]pyridin-4-yl)-3-piperidyl]pyrrolidin-3-ol |

| | |
|---|---|
| E94 | 4-[(3S)-3-(4-fluoro-1-piperidyl)-1-piperidyl]-3-pyrimidin-5-yl-1H-pyrrolo[2,3-b]pyridine |
| E95 | 4-[(3S)-3-(3-fluoropyrrolidin-1-yl)-1-piperidyl]-3-pyrimidin-5-yl-1H-pyrrolo[2,3-b]pyridine |
| E96 | 4-[(3S)-143-pyrimidin-5-yl-1H-pyrrolo[2,3-b]pyridin-4-yl)-3-piperidyl]morpholine |
| E97 | 4-[(3S)-3-(azetidin-l-yl)-1-piperidyl]-3-pyrimidin-5-yl-1H-pyrrolo[2,3-b]pyridine |
| E98 | 4-[(3S)-341-piperidyl)-1-piperidyl]-3-pyrimidin-5-yl-1H-pyrrolo[2,3-b]pyridine |
| E99 | 3-pyrimidin-5-yl-4-[(3S)-3-pyrrolidin-l-yl-1-piperidyl]-1H-pyrrolo[2,3-b]pyridine |
| E100 | (3R)-1-(3-pyrimidin-5-yl-1H-pyrrolo[2,3-b]pyridin-4-yl)piperidin-3-ol |
| E101 | (3S)-1-(3-pyrimidin-5-yl-1H-pyrrolo[2,3-b]pyridin-4-yl)piperidin-3-ol |
| E102 | N-(4-piperidylmethyl)-3-pyrimidin-5-yl-1H-pyrrolo[2,3-b]pyridin-4-amine |
| E103 | 4(4-methyl-1,4-diazepan-l-yl)-3-pyrimidin-5-yl-1H-pyrrolo[2,3-b]pyridine |
| E104 | 3(5-methyl-1H-pyrazol-4-yl)-441-piperidyl)-1H-pyrrolo[2,3-b]pyridine |
| E105 | [1-(3-pyrimidin-5-yl-1H-pyrrolo[2,3-b]pyridin-4-yl)-4-piperidyl]methanamine |
| E106 | 4(2-benzyl-1-piperidyl)-1H-pyrrolo[2,3-b]pyridine-3-carbonitrile |
| E107 | 4-(2-benzylpyrrolidin-l-yl)-1H-pyrrolo[2,3-b]pyridine-3-carbonitrile |
| E108 | 4-[(2S)-2-(methoxymethyl)pyrrolidin-1-yl]-1H-pyrrolo[2,3-b]pyridine-3-carbonitrile |
| E110 | 4-[(2R)-2-methylpyrrolidin-1-yl]-1H-pyrrolo[2,3-b]pyridine-3-carbonitrile |
| E111 | 4-[(2S)-2-methylpyrrolidin-l-yl]-1H-pyrrolo[2,3-b]pyridine-3-carbonitrile |
| E112 | 4(3-phenyl-l-piperidyl)-1H-pyrrolo[2,3-b]pyridine-3-carbonitrile |
| E113 | 4-(2-phenylpyrrolidin-l-yl)-1H-pyrrolo[2,3-b]pyridine-3-carbonitrile |
| E114 | 4-(4-(1,8-diazaspiro[5.5]undecan-8-yl)-1H-pyrrolo[2,3-b]pyridin-3-yl]isothiazole |
| E115 | 3-[4-[(6R)-1,8-diazaspiro[5.5]undecan-8-yl]-1H-pyrrolo[2,3-b]pyridin-3-yl]-1,2,4-thiadiazole |
| E116 | 3-[4-[(6S)-1,8-diazaspiro[5.5]undecan-8-yl]-1H-pyrrolo[2,3-b]pyridin-3-yl]-1,2,4-thiadiazole |
| E117 | (6S)-8-(3-pyrimidin-4-yl-1H-pyrrolo[2,3-b]pyridin-4-yl)-1,8-diazaspiro[5.5]undecane |
| E118 | (6R)-8-(3-pyrimidin-4-yl-1H-pyrrolo[2,3-b]pyridin-4-yl)-1,8-diazaspiro[5.5]undecane |
| E119 | 3-(4-[(6R)-1,8-diazaspiro[5.5]undecan-8-yl]-1H-pyrrolo[2,3-b]pyridin-3-yl]isothiazole |
| E120 | 3-[4-[(6S)-1,8-diazaspiro[5.5]undecan-8-yl]-1H-pyrrolo[2,3-b]pyridin-3-yl]isothiazole |
| E121 | 3-[4-(1,8-diazaspiro[5.5]undecan-8-yl)-1H-pyrrolo[2,3-b]pyridin-3-yl]isothiazole |
| E122 | (6S)-8-(3-pyrimidin-5-yl-1H-pyrrolo[2,3-b]pyridin-4-yl)-1,8-diazaspiro[5.5]undecane |
| E123 | 4-[(5R)-1,7-diazaspiro[4.4]nonan-7-yl]-3-pyrimidin-5-yl-1H-pyrrolo[2,3-b]pyridine |
| E124 | 4-[(5S)-1,7-diazaspiro[4.4]nonan-7-yl]-3-pyrimidin-5-yl-1H-pyrrolo[2,3-b]pyridine |
| E125 | (5R)-2-(3-pyrimidin-5-yl-1H-pyrrolo[2,3-b]pyridin-4-yl)-2,6-diazaspiro[4.5]decane |
| E126 | (5S)-2-(3-pyrimidin-5-yl-1H-pyrrolo[2,3-b]pyridin-4-yl)-2,6-diazaspiro[4.5]decane |
| E127 | (5R)-2-(3-pyrimidin-4-yl-1H-pyrrolo[2,3-b]pyridin-4-yl)-2,6-diazaspiro[4.5]decane |
| E128 | (5S)-2-(3-pyrimidin-4-yl-1H-pyrrolo[2,3-b]pyridin-4-yl)-2,6-diazaspiro[4.5]decane |
| E129 | 3-[4-(2,6-diazaspiro[4.5]decan-2-yl)-1H-pyrrolo[2,3-b]pyridin-3-yl]-1,2,4-thiadiazole |
| E130 | 2-[4-[(5R)-2,6-diazaspiro[4.5]decan-2-yl]-1H-pyrrolo[2,3-b]pyridin-3-yl]-5-methyl-thiazole |
| E131 | 2-[4-[(5S)-2,6-diazaspiro[4.5]decan-2-yl]-1H-pyrrolo[2,3-b]pyridin-3-yl]-5-methyl-thiazole |
| E132 | 2-[4-[(5R)-2,6-diazaspiro[4.5]decan-2-yl]-1H-pyrrolo[2,3-b]pyridin-3-yl]thiazole |
| E133 | 2-[4-[(5S)-2,6-diazaspiro[4.5]decan-2-yl]-1H-pyrrolo[2,3-b]pyridin-3-yl]thiazole |
| E134 | 2-[4-[(5S)-1,7-diazaspiro[4.4]nonan-7-yl]-1H-pyrrolo[2,3-b]pyridin-3-yl]thiazole |
| E135 | 2-[4-[(5R)-1,7-diazaspiro[4.4]nonan-7-yl]-1H-pyrrolo[2,3-b]pyridin-3-yl]thiazole |
| E136 | 3-[4-(1,7-diazaspiro[4.4]nonan-7-yl)-1H-pyrrolo[2,3-b]pyridin-3-yl]isothiazole |
| E137 | 4-(1,7-diazaspiro[4.4]nonan-7-yl)-3-(2-pyridyl)-1H-pyrrolo[2,3-b]pyridine |
| E138 | 8-[3-(2-pyridyl)-1H-pyrrolo[2,3-b]pyridin-4-yl]-1,8-diazaspiro[5.5]undecane |
| E139 | (6S)-8-[3-(2-pyridyl)-1H-pyrrolo[2,3-b]pyridin-4-yl]-1,8-diazaspiro[5.5]undecane |
| E140 | (6R)-8-[3-(2-pyridyl)-1H-pyrrolo[2,3-b]pyridin-4-yl]-1,8-diazaspiro[5.5]undecane |
| E141 | 2-[3-(2-pyridyl)-1H-pyrrolo[2,3-b]pyridin-4-yl]-2,6-diazaspiro[4.5]decane |
| E142 | 3-[4-(1,8-diazaspiro[5.5]undecan-8-yl)-1H-pyrrolo[2,3-b]pyridin-3-yl]-4-methyl-isothiazole |

-continued

| | |
|---|---|
| E143 | 2-[4-(1,9-diazaspiro[4.5]decan-9-yl)-1H-pyrrolo[2,3-b]pyridin-3-yl]-5-methyl-thiazole |
| E144 | 2-[4-(2,6-diazaspiro[4.5]decan-2-yl)-1H-pyrrolo[2,3-b]pyridin-3-yl]-5-methyl-thiazole |
| E146 | 2-[4-[(6S)-1,8-diazaspiro[5.5]undecan-8-yl]-1H-pyrrolo[2,3-b]pyridin-3-yl]-5-methyl-thiazole |
| E147 | 2-[4-(1,8-diazaspiro[5.5]undecan-8-yl)-1H-pyrrolo[2,3-b]pyridin-3-yl]-5-methyl-thiazole |
| E148 | 2-[4-[(6R)-1,8-diazaspiro[5.5]undecan-8-yl]-1H-pyrrolo[2,3-b]pyridin-3-yl]-5-methyl-thiazole |
| E149 | 2-[4-(1,8-diazaspiro[5.5]undecan-8-yl)-1H-pyrrolo[2,3-b]pyridin-3-yl]thiazole |
| E150 | 2-[4-[(6S)-1,8-diazaspiro[5.5]undecan-8-yl]-1H-pyrrolo[2,3-b]pyridin-3-yl]thiazole |
| E151 | 2-[4-[(6R)-1,8-diazaspiro[5.5]undecan-8-yl]-1H-pyrrolo[2,3-b]pyridin-3-yl]thiazole |
| E152 | 2-[4-(1,7-diazaspiro[3.4]octan-7-yl)-1H-pyrrolo[2,3-b]pyridin-3-yl]-5-methyl-thiazole |
| E153 | 2-[4-(1,8-diazaspiro[3.5]nonan-8-yl)-1H-pyrrolo[2,3-b]pyridin-3-yl]-5-methyl-thiazole |
| E154 | 2-[4-(1,7-diazaspiro[4.4]nonan-7-yl)-1H-pyrrolo[2,3-b]pyridin-3-yl]thiazole |
| E155 | 2-[4-(2,6-diazaspiro[4.5]decan-2-yl)-1H-pyrrolo[2,3-b]pyridin-3-yl]thiazole |
| E156 | 4-(2,6-diazaspiro[3.5]nonan-6-yl)-3-pyridazin-4-yl-1H-pyrrolo[2,3-b]pyridine |
| E157 | 8-(3-pyrimidin-2-yl-1H-pyrrolo[2,3-b]pyridin-4-yl)-1,8-diazaspiro[5.5]undecane |
| E158 | 2-[4-(1,8-diazaspiro[5.5]undecan-8-yl)-1H-pyrrolo[2,3-b]pyridin-3-yl]-4-methyl-thiazole |
| E159 | 444-(1,8-diazaspiro[5.5]undecan-8-yl)-1H-pyrrolo[2,3-b]pyridin-3-yl]-2-methyl-thiazole |
| E160 | 8-[3-(2-methylpyrimidin-4-yl)-1H-pyrrolo[2,3-b]pyridin-4-yl]-1,8-diazaspiro[5.5]undecane |
| E161 | 4-(1,7-diazaspiro[4.4]nonan-7-yl)-3-pyridazin-4-yl-1H-pyrrolo[2,3-b]pyridine |
| E162 | 2-(3-pyridazin-4-yl-1H-pyrrolo[2,3-b]pyridin-4-yl)-2,6-diazaspiro[4.5]decane |
| E163 | 7-(3-pyridazin-4-yl-1H-pyrrolo[2,3-b]pyridin-4-yl)-2,7-diazaspiro[4.5]decane |
| E164 | 4-(2,7-diazaspiro[4.4]nonan-2-yl)-3-pyridazin-4-yl-1H-pyrrolo+2,3-b]pyridine |
| E165 | 4-(1,8-diazaspiro[5.5]undecan-8-yl)-1H-pyrrolo[2,3-b]pyridine-3-carbonitrile |
| E166 | 8-[3-(2-methylpyrimidin-5-yl)-1H-pyrrolo[2,3-b]pyridin-4-yl]-1,8-diazaspiro[5.5]undecane |
| E167 | 4-[4-(1,8-diazaspiro[5.5]undecan-8-yl)-1H-pyrrolo[2,3-b]pyridin-3-yl]-3,5-dimethyl-isoxazole |
| E168 | 8-(3-pyrimidin-4-yl-1H-pyrrolo[2,3-b]pyridin-4-yl)-1,8-diazaspiro[5.5]undecane |
| E169 | 8-[3-(3-fluoro-2-pyridyl)-1H-pyrrolo[2,3-b]pyridin-4-yl]-1,8-diazaspiro[5.5]undecane |
| E170 | 8-[3-(5-fluoro-2-pyridyl)-1H-pyrrolo[2,3-b]pyridin-4-yl]-1,8-diazaspiro[5.5]undecane |
| E171 | 8-[3-(5-fluoro-3-pyridyl)-1H-pyrrolo[2,3-b]pyridin-4-yl]-1,8-diazaspiro[5.5]undecane |
| E172 | 8-(3-pyridazin-4-yl-1H-pyrrolo[2,3-b]pyridin-4-yl)-1,8-diazaspiro[5.5]undecane |
| E173 | (6R)-8-(3-pyridazin-4-yl-1H-pyrrolo[2,3-b]pyridin-4-yl)-1,8-diazaspiro[5.5]undecane |
| E174 | (6S)-8-(3-pyridazin-4-yl-1H-pyrrolo[2,3-b]pyridin-4-yl)-1,8-diazaspiro[5.5]undecane |
| E175 | 8-(3-pyridazin-3-yl-1H-pyrrolo[2,3-b]pyridin-4-yl)-1,8-diazaspiro[5.5]undecane |
| E176 | 3-methyl-1-(3-thiazol-2-yl-1H-pyrrolo[2,3-b]pyridin-4-Apiperidin-3-amine |
| E177 | 3-ethyl-1-[3-(5-methylthiazol-2-yl)-1H-pyrrolo[2,3-b]pyridin-4-yl]piperidin-3-amine |
| E178 | 3-methyl-1-(3-pyrimidin-5-yl-1H-pyrrolo[2,3-b]pyridin-4-Apiperidin-3-amine |
| E179 | cis-N,2-dimethyl-1-(3-pyrimidin-5-yl-1H-pyrrolo[2,3-b]pyridin-4-yl)piperidin-3-amine |
| E180 | 4-[(3aR,7aR)-1-methyl-3,3a,4,5,7,7a-hexahydro-2H-pyrrolo[2,3-c]pyridin-6-yl]-3-pyrimidin-5-yl-1H-pyrrolo[2,3-b]pyridine |
| E181 | 4-(1-piperidyl)-3-(1H-pyrazol-5-yl)-1H-pyrrolo[2,3-b]pyridine |
| E182 | 4-(1-piperidyl)-3-(3-pyridyl)-1H-pyrrolo[2,3-b]pyridine |
| E183 | 4-(1-piperidyl)-3-(1H-pyrazol-4-yl)-1H-pyrrolo[2,3-b]pyridine |
| E184 | 4-(2,6-diazaspiro[4.5]decan-2-yl)-1H-pyrrolo[2,3-b]pyridine-3-carbonitrile |
| E185 | 4-(1,7-diazaspiro[4.4]nonan-7-yl)-1H-pyrrolo[2,3-b]pyridine-3-carbonitrile |
| E186 | 4-[(6R)-1,8-diazaspiro[5.5]undecan-8-yl]-1H-pyrrolo[2,3-b]pyridine-3-carbonitrile |

-continued

| | |
|---|---|
| E187 | 4-[(6S)-1,8-diazaspiro[5.5]undecan-8-yl]-1H-pyrrolo[2,3-b]pyridine-3-carbonitrile |
| E188 | 8-[3-(1-methylpyrazol-4-yl)-1H-pyrrolo[2,3-b]pyridin-4-yl]-1,8-diazaspiro[5.5]undecane |
| E189 | 8-(3-pyrazin-2-yl-1H-pyrrolo[2,3-b]pyridin-4-yl)-1,8-diazaspiro[5.5]undecane |
| E190 | 8-(3-pyrimidin-5-yl-1H-pyrrolo[2,3-b]pyridin-4-yl)-2,8-diazaspiro[4.5]decane |
| E191 | 2-(3-pyrimidin-5-yl-1H-pyrrolo[2,3-b]pyridin-4-yl)-2,8-diazaspiro[4.5]decane |
| E192 | (6R)-8-(3-pyrimidin-5-yl-1H-pyrrolo[2,3-b]pyridin-4-yl)-1,8-diazaspiro[5.5]undecane |
| E193 | 9-(3-pyrimidin-5-yl-1H-pyrrolo[2,3-b]pyridin-4-yl)-2,9-diazaspiro[5.5]undecane |
| E194 | 2-(3-pyrimidin-5-yl-1H-pyrrolo[2,3-b]pyridin-4-yl)-2,8-diazaspiro[5.5]undecane |
| E195 | 9-(3-pyrimidin-5-yl-1H-pyrrolo[2,3-b]pyridin-4-yl)-1,9-diazaspiro[4.5]decane |
| E196 | 8-(3-pyrimidin-5-yl-1H-pyrrolo[2,3-b]pyridin-4-yl)-1,8-diazaspiro[5.5]undecane |
| E197 | 4-[(3R)-3-aminopyrrolidin-1-yl]-1H-pyrrolo[2,3-b]pyridine-3-carbonitrile |
| E198 | 4-amino-N,N-dimethyl-1-(3-pyrimidin-5-yl-1H-pyrrolo[2,3-b]pyridin-4-yl)piperidine-4-carboxamide |
| E199 | 4-(2,3,3a,4,6,6a-hexahydro-1H-pyrrolo[3,4-c]pyrrol-5-yl)-3-pyrimidin-5-yl-1H-pyrrolo[2,3-b]pyridine |
| E200 | -[(3aS,7aR)-1-methyl-3,3a,4,6,7,7a-hexahydro-2H-pyrrolo[3,2-c]pyridin-5-yl]-3-pyrimidin-5-yl-1H-pyrrolo[2,3-b]pyridine |
| E201 | 4-[(2S)-2-(4-methyl-1,4-diazepane-1-carbonyl)pyrrolidin-1-yl]-1H-pyrrolo[2,3-b]pyridine-3-carbonitrile |
| E202 | 4-[(2S)-2-(morpholine-4-carbonyl)pyrrolidin-1-yl]-1H-pyrrolo[2,3-b]pyridine-3-carbonitrile |
| E203 | 4-[(2S)-2-(piperidine-l-carbonyl)pyrrolidin-1-yl]-1H-pyrrolo[2,3-b]pyridine-3-carbonitrile |
| E204 | 4-[(2S)-2-(4-methylpiperazine-1-carbonyl)pyrrolidin-1-yl]-1H-pyrrolo[2,3-b]pyridine-3-carbonitrile |
| E205 | N-[(3S)-1-(3-pyridazin-4-yl-1H-pyrrolo[2,3-b]pyridin-4-yl)-3-piperidyl]acetamide |
| E206 | (6S)-1-methyl-8-(3-pyrimidin-4-yl-1H-pyrrolo[2,3-b]pyridin-4-yl)-1,8-diazaspiro[5.5]undecane |
| E207 | (6S)-1-ethyl-8-(3-pyrimidin-4-yl-1H-pyrrolo[2,3-b]pyridin-4-yl)-1,8-diazaspiro[5.5]undecane |
| E208 | (6R)-1-ethyl-8-(3-pyrimidin-5-yl-1H-pyrrolo[2,3-b]pyridin-4-yl)-1,8-diazaspiro[5.5]undecane |
| E209 | 2-[4-(1-ethyl-1,8-diazaspiro[5.5]undecan-8-yl)-1H-pyrrolo[2,3-b]pyridin-3-yl]thiazole |
| E210 | 2-[4-(1-ethyl-1,8-diazaspiro[5.5]undecan-8-yl)-1H-pyrrolo[2,3-b]pyridin-3-yl]-5-methyl-thiazole |
| E211 | 4-(1-ethyl-1,8-diazaspiro[5.5]undecan-8-yl)-1H-pyrrolo[2,3-b]pyridine-3-carbonitrile |
| E212 | 2-[4-[[(3R)-3-piperidyl]oxy]-1H-pyrrolo[2,3-b]pyridin-3-yl]thiazole |
| E213 | 3-pyrimidin-4-yl-4-[[(3R)-3-piperidyl]oxy]-1H-pyrrolo[2,3-b]pyridine |
| E214 | 4-[[(3R)-3-piperidyl]methoxy]-3-pyrimidin-5-yl-1H-pyrrolo[2,3-b]pyridine |
| E215 | 3-pyrimidin-5-yl-4-[[(3S)-pyrrolidin-3-yl]methoxy]-1H-pyrrolo[2,3-b]pyridine |
| E216 | 4-(azepan-4-yloxy)-3-pyrimidin-5-yl-1H-pyrrolo[2,3-b]pyridine |
| E217 | 4-[[(3R)-3-piperidyl]oxy]-3-pyrimidin-5-yl-1H-pyrrolo[2,3-b]pyridine |
| E218 | 4-[[(3S)-3-piperidyl]methoxy]-3-pyrimidin-5-yl-1H-pyrrolo[2,3-b]pyridine |
| E219 | 3-pyrimidin-5-yl-4-[[(3R)-pyrrolidin-3-yl]methoxy]-1H-pyrrolo[2,3-b]pyridine |
| E220 | 4-(3-piperidylmethoxy)-3-pyrimidin-5-yl-1H-pyrrolo[2,3-b]pyridine |
| E221 | 4-(4-piperidylmethoxy)-3-pyrimidin-5-yl-1H-pyrrolo[2,3-b]pyridine |
| E222 | 4-[[(3S)-3-piperidyl]oxy]-3-pyrimidin-5-yl-1H-pyrrolo[2,3-b]pyridine |
| E223 | 4-(4-piperidyloxy)-3-pyrimidin-5-yl-1H-pyrrolo[2,3-b]pyridine |
| E224 | 4-[[(3R)-1-methyl-3-piperidyl]methoxy]-3-pyrimidin-5-yl-1H-pyrrolo[2,3-b]pyridine |
| E225 | 4-[[(3S)-1-methylpyrrolidin-3-yl]methoxy]-3-pyrimidin-5-yl-1H-pyrrolo[2,3-b]pyridine |
| E226 | 3-pyrimidin-5-yl-4-[[(3S)-1-methyl-3-piperidyl]methoxy]-1H-pyrrolo[2,3-b]pyridine |
| E236 | 3-4-[1,8-diazaspiro[5.5]undecan-8-yl]-1H-pyrrolo[2,3-b]pyridin-3-yl]-1,2,4-thiadiazole |
| E237 | 2-[4-(1,7-diazaspiro[4.4]nonan-7-yl)-1H-pyrrolo[2,3-b]pyridin-3-yl]-5-methyl-thiazole |

139. A compound according to paragraph 138, or a salt, hydrate or solvate thereof, selected from

| Example No. | Structure | IUPAC Name |
|---|---|---|
| E116 | 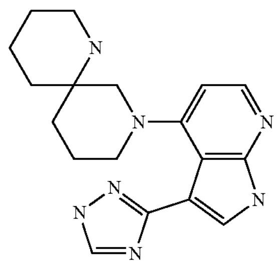 [SMILES: c1cc(N2CCCC3(CCCCN3)C2)c2c(-c3nc[nH]n3)c[nH]c2n1] | 3-[4-[(6S)-1,8-diazaspiro[5.5]undecan-8-yl]-1H-pyrrolo[2,3-b]pyridin-3-yl]-1,2,4-thiadiazole |
| E120 | 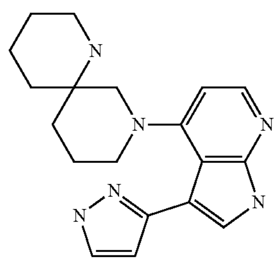 [SMILES: c1cc(N2CCCC3(CCCCN3)C2)c2c(-c3cc[nH]n3)c[nH]c2n1] | 3-[4-[(6S)-1,8-diazaspiro[5.5]undecan-8-yl]-1H-pyrrolo[2,3-b]pyridin-3-yl]isothiazole |
| E117 | 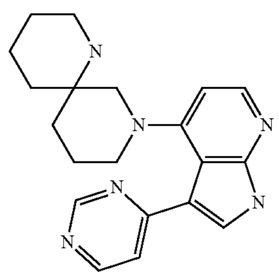 [SMILES: c1cc(-c2c[nH]c3nccc(N4CCCC5(CCCCN5)C4)c23)ncn1] | (6S)-8-(3-pyrimidin-4-yl-1H-pyrrolo[2,3-b]pyridin-4-yl)-1,8-diazaspiro[5.5]undecane |
| E150 | 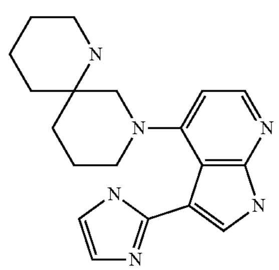 | 2-[4-[(6S)-1,8-diazaspiro[5.5]undecan-8-yl]-1H-pyrrolo[2,3-b]pyridin-3-yl]thiazole |
| E174 | 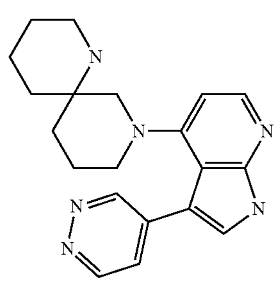 [SMILES: c1cc(-c2c[nH]c3nccc(N4CCCC5(CCCCN5)C4)c23)cnn1] | (6S)-8-(3-pyridazin-4-yl-1H-pyrrolo[2,3-b]pyridin-4-yl)-1,8-diazaspiro[5.5]undecane |

-continued

| Example No. | Structure | IUPAC Name |
|---|---|---|
| E206 | 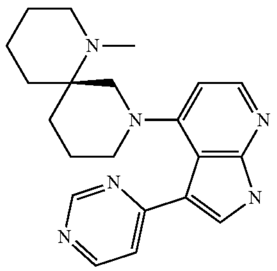 [SMILES: CN1CCCC[C@@]12CCCN(c1ccnc3[nH]cc(-c4ccncn4)c13)C2] | (6S)-1-methyl-8-(3-pyrimidin-4-yl-1H-pyrrolo[2,3-b]pyridin-4-yl)-1,8-diazaspiro[5.5]undecane |
| E133 | 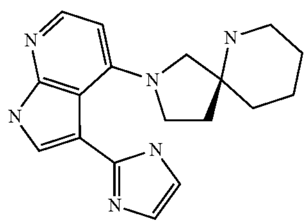 [SMILES: c1c[nH]c(-c2c[nH]c3nccc(N4CC[C@@]5(CCCCN5)C4)c23)n1] | 2-[4-[(5S)-2,6-diazaspiro[4.5]decan-2-yl]-1H-pyrrolo[2,3-b]pyridin-3-yl]thiazole |
| E209 | 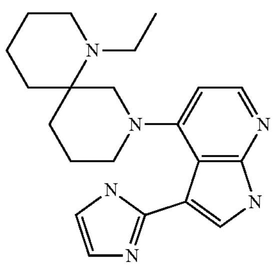 [SMILES: CCN1CCCCC12CCCN(c1ccnc3[nH]cc(-c4ncc[nH]4)c13)C2] | 2-[4-(1-ethyl-1,8-diazaspiro[5.5]undecan-8-yl)-1H-pyrrolo[2,3-b]pyridin-3-yl]thiazole |
| E139 | 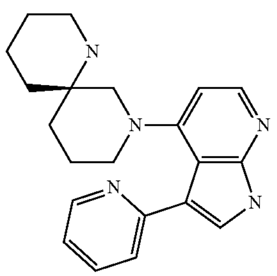 [SMILES: c1ccc(-c2c[nH]c3nccc(N4CCC[C@@]5(CCCCN5)C4)c23)nc1] | (6S)-8-[3-(2-pyridyl)-1H-pyrrolo[2,3-b]pyridin-4-yl]-1,8-diazaspiro[5.5]undecane |
| E207 | 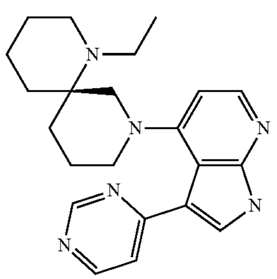 [SMILES: CCN1CCCC[C@@]12CCCN(c1ccnc3[nH]cc(-c4ccncn4)c13)C2] | (6S)-1-ethyl-8-(3-pyrimidin-4-yl-1H-pyrrolo[2,3-b]pyridin-4-yl)-1,8-diazaspiro[5.5]undecane |
| E146 | 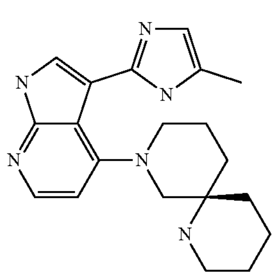 [SMILES: Cc1cnc(-c2c[nH]c3nccc(N4CCC[C@@]5(CCCCN5)C4)c23)[nH]1] | 2-[4-[(6S)-1,8-diazaspiro[5.5]undecan-8-yl]-1H-pyrrolo[2,3-b]pyridin-3-yl]-5-methyl-thiazole |

-continued

| Example No. | Structure | IUPAC Name |
|---|---|---|
| E126 | 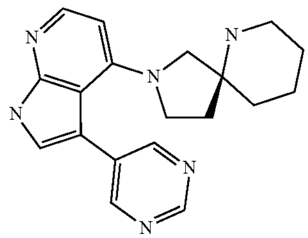 [SMILES: c1ncc(-c2c[nH]c3nccc(N4CC[C@@]5(CCCCN5)C4)c23)cn1] | (5S)-2-(3-pyrimidin-5-yl-1H-pyrrolo[2,3-b]pyridin-4-yl)-2,6-diazaspiro[4.5]decane |
| E131 | 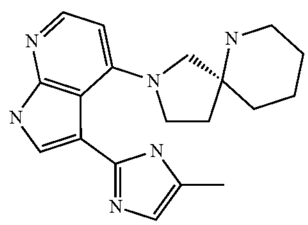 [SMILES: Cc1cnc(-c2c[nH]c3nccc(N4CC[C@@]5(CCCCN5)C4)c23)[nH]1] | 2-[4-[(5S)-2,6-diazaspiro[4.5]decan-2-yl]-1H-pyrrolo[2,3-b]pyridin-3-yl]-5-methyl-thiazole |
| E210 | 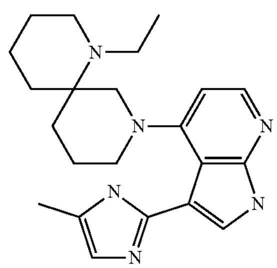 [SMILES: CCN1CCCCC12CCCN(c1ccnc3[nH]cc(-c4ncc(C)[nH]4)c13)C2] | 2-[4-(1-ethyl-1,8-diazaspiro[5.5]undecan-8-yl)-1H-pyrrolo[2,3-b]pyridin-3-yl]-5-methyl-thiazole |
| E171 | 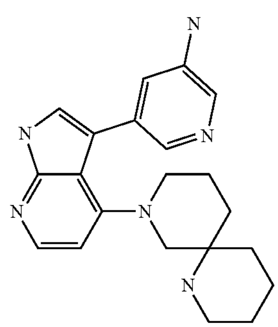 [SMILES: Nc1cncc(-c2c[nH]c3nccc(N4CCCC5(CCCCN5)C4)c23)c1] | 8-[3-(5-fluoro-3-pyridyl)-1H-pyrrolo[2,3-b]pyridin-4-yl]-1,8-diazaspiro[5.5]undecane |
| E168 | 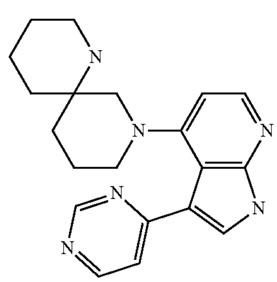 | 8-(3-pyrimidin-4-yl-1H-pyrrolo[2,3-b]pyridin-4-yl)-1,8-diazaspiro[5.5]undecane |

-continued

| Example No. | Structure | IUPAC Name |
|---|---|---|
| E128 | 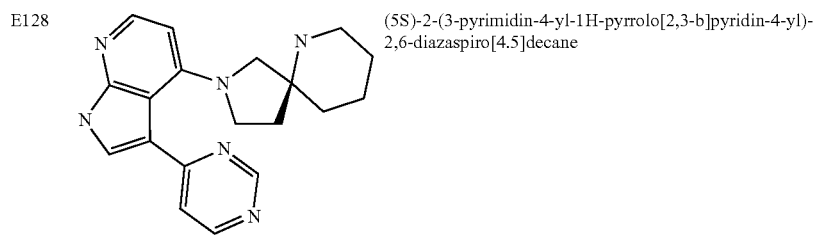 | (5S)-2-(3-pyrimidin-4-yl-1H-pyrrolo[2,3-b]pyridin-4-yl)-2,6-diazaspiro[4.5]decane |
| E114 | 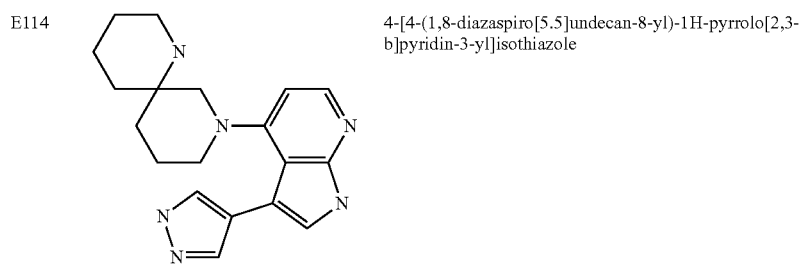 | 4-[4-(1,8-diazaspiro[5.5]undecan-8-yl)-1H-pyrrolo[2,3-b]pyridin-3-yl]isothiazole |
| E155 | 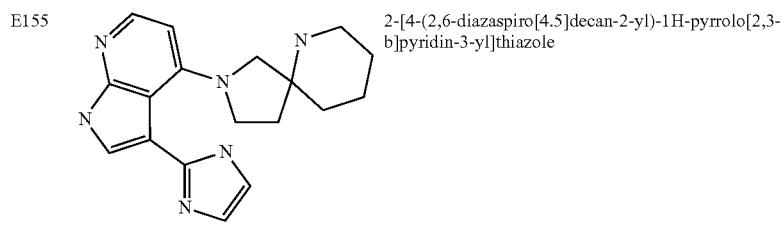 | 2-[4-(2,6-diazaspiro[4.5]decan-2-yl)-1H-pyrrolo[2,3-b]pyridin-3-yl]thiazole |
| E177 | 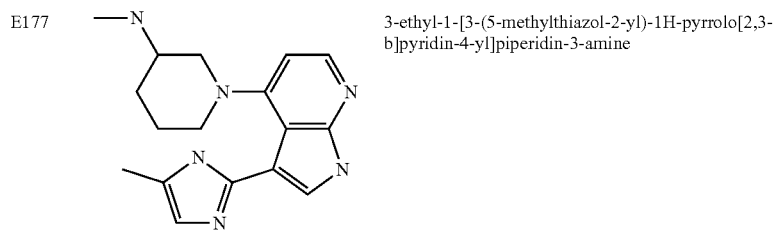 | 3-ethyl-1-[3-(5-methylthiazol-2-yl)-1H-pyrrolo[2,3-b]pyridin-4-yl]piperidin-3-amine |
| E236 | 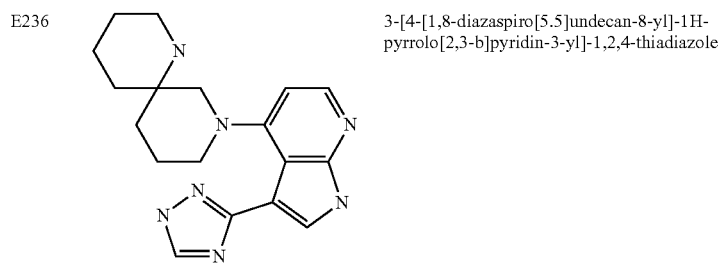 | 3-[4-[1,8-diazaspiro[5.5]undecan-8-yl]-1H-pyrrolo[2,3-b]pyridin-3-yl]-1,2,4-thiadiazole |
| E176 | 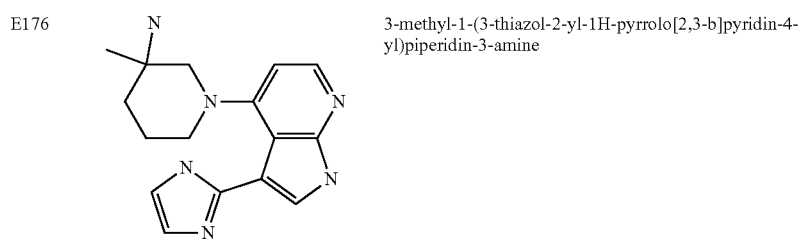 | 3-methyl-1-(3-thiazol-2-yl-1H-pyrrolo[2,3-b]pyridin-4-yl)piperidin-3-amine |

| Example No. | Structure | IUPAC Name |
|---|---|---|
| E170 | 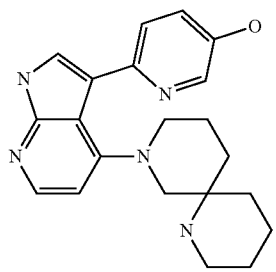 | 8-[3-(5-fluoro-2-pyridyl)-1H-pyrrolo[2,3-b]pyridin-4-yl]-1,8-diazaspiro[5.5]undecane |
| E169 | 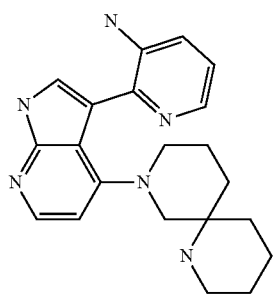 [SMILES: Nc1cccnc1-c1c[nH]c2nccc(N3CCCC4(CCCCN4)C3)c12] | 8-[3-(3-fluoro-2-pyridyl)-1H-pyrrolo[2,3-b]pyridin-4-yl]-1,8-diazaspiro[5.5]undecane |
| E136 | 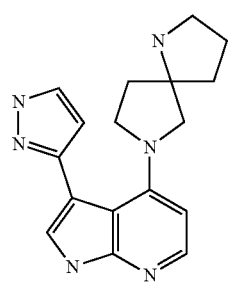 [SMILES: c1cc(N2CCC3(CCCN3)C2)c2c(-c3cc[nH]n3)c[nH]c2n1] | 3-[4-(1,7-diazaspiro[4.4]nonan-7-yl)-1H-pyrrolo[2,3-b]pyridin-3-yl]isothiazole |
| E66 | 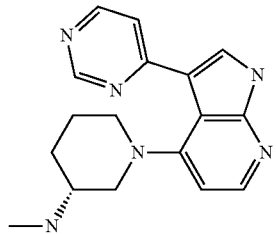 [SMILES: CN[C@@H]1CCCN(c2ccnc3[nH]cc(-c4ccncn4)c23)C1] | (3S)-N-methyl-1-(3-pyrimidin-4-yl-1H-pyrrolo[2,3-b]pyridin-4-yl)piperidin-3-amine |
| E187 | 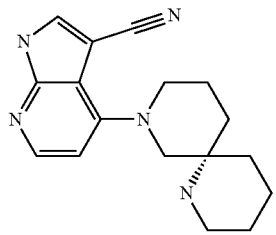 [SMILES: N#Cc1c[nH]c2nccc(N3CCC[C@@]4(CCCCN4)C3)c12] | 4-[(6S)-1,8-diazaspiro[5.5]undecan-8-yl]-1H-pyrrolo[2,3-b]pyridine-3-carbonitrile |

-continued

| Example No. | Structure | IUPAC Name |
|---|---|---|
| E178 | 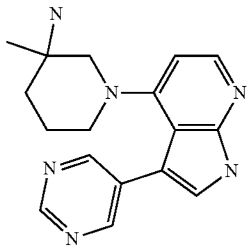 [SMILES: CC1(N)CCCN(c2ccnc3[nH]cc(-c4cncnc4)c23)C1] | 3-methyl-1-(3-pyrimidin-5-yl-1H-pyrrolo[2,3-b]pyridin-4-yl)piperidin-3-amine |
| E142 | 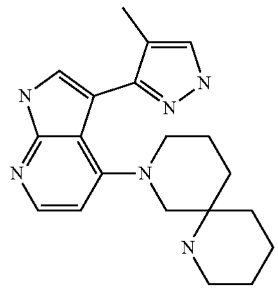 [SMILES: Cc1c[nH]nc1-c1c[nH]c2nccc(N3CCCC4(CCCCN4)C3)c12] | 3-[4-(1,8-diazaspiro[5.5]undecan-8-yl)-1H-pyrrolo[2,3-b]pyridin-3-yl]-4-methyl-isothiazole |
| E129 | 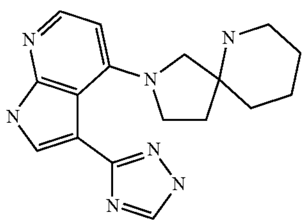 [SMILES: c1cc(N2CCC3(CCCCN3)C2)c2c(-c3nc[nH]n3)c[nH]c2n1] | 3-[4-(2,6-diazaspiro[4.5]decan-2-yl)-1H-pyrrolo[2,3-b]pyridin-3-yl]-1,2,4-thiadiazole |
| E46 | 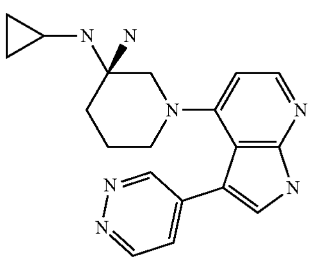 [SMILES: N[C@]1(NC2CC2)CCCN(c2ccnc3[nH]cc(-c4ccnnc4)c23)C1] | (3S)-N-cyclopropyl-1-(3-pyridazin-4-yl-1H-pyrrolo[2,3-b]pyridin-4-yl)piperidin-3-amine |
| E134 | 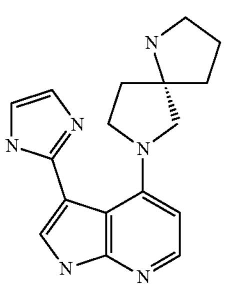 [SMILES: c1c[nH]c(-c2c[nH]c3nccc(N4CC[C@@]5(CCCN5)C4)c23)n1] | 2-[4-[(5S)-1,7-diazaspiro[4.4]nonan-7-yl]-1H-pyrrolo[2,3-b]pyridin-3-yl]thiazole |
| E47 | 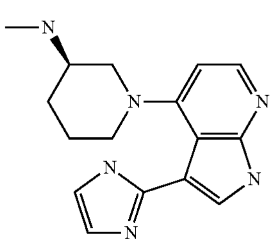 [SMILES: CN[C@@H]1CCCN(c2ccnc3[nH]cc(-c4ncc[nH]4)c23)C1] | (3S)-N-methyl-1-(3-thiazol-2-yl-1H-pyrrolo[2,3-b]pyridin-4-yl)piperidin-3-amine |

-continued

| Example No. | Structure | IUPAC Name |
|---|---|---|
| E211 | 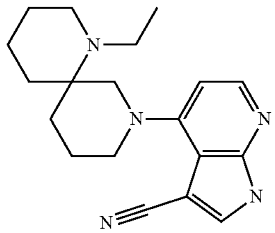 [SMILES: CCN1CCCCC12CCCN(c1ccnc3[nH]cc(C#N)c13)C2] | 4-(1-ethyl-1,8-diazaspiro[5.5]undecan-8-yl)-1H-pyrrolo[2,3-b]pyridine-3-carbonitrile |
| E122 | 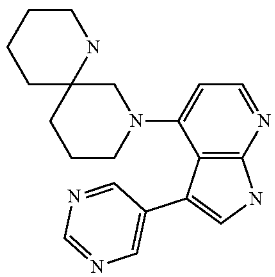 [SMILES: c1ncc(-c2c[nH]c3nccc(N4CCCC5(CCCCN5)C4)c23)cn1] | (6S)-8-(3-pyrimidin-5-yl-1H-pyrrolo[2,3-b]pyridin-4-yl)-1,8-diazaspiro[5.5]undecane |

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and sub-formulae thereof are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I and sub-formulae thereof may exist in solvated as well as unsolvated forms such as, for example, hydrated forms. It is to be understood that the invention encompasses all such solvated forms that possess the biological activity described herein.

Polymorphs

It is also to be understood that certain compounds of the Formula I and sub-formulae thereof may exhibit polymorphism, and that the invention encompasses all such forms that possess the biological activity described herein.

N-Oxides

Compounds of the Formula I and sub-formulae thereof containing an amine function may also form N-oxides. A reference herein to a compound of the Formula I and sub-formulae thereof that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I and sub-formulae thereof may exist in a number of different tautomeric forms and references to compounds of the Formula I and sub-formulae thereof include all such forms. For the avoidance of doubt, where a compound can exist in one of several tautomeric forms, and only one is specifically described or shown, all others are nevertheless embraced by Formula I and sub-formulae thereof. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

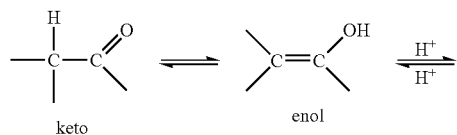

keto   enol

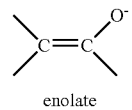

enolate

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I and sub-formulae thereof may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

It will be understood by the skilled person that $R^4$, when a group of formula II, may contain an asymmetric carbon atom, i.e. the carbon atom to which $R^9$ and $R^{10}$ are attached when $R^9$ and $R^{10}$ are different. In one embodiment, the compounds of the invention are in the R-configuration at this stereocentre. In another embodiment, the compounds of the invention are in the S-configuration at this stereocentre.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I and sub-formulae thereof may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I and sub-formulae thereof.

Accordingly, the present invention includes those compounds of the Formula I and sub-formulae thereof as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I and sub-formulae thereof may be a synthetically-produced compound or a metabolically-produced compound.

A suitable pharmaceutically acceptable pro-drug of a compound of the Formula I and sub-formulae thereof is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I and sub-formulae thereof that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$ alkoxymethyl esters such as methoxymethyl esters, $C_{1-6}$alkanoyloxymethyl esters such as pivaloyloxymethyl esters, 3-phthalidyl esters, $C_{3-8}$-cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I and sub-formulae thereof that possesses a hydroxy group is, for example, an in vivo cleavable ester or ether thereof. An in vivo cleavable ester or ether of a compound of the Formula I and sub-formulae thereof containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups.

Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I and sub-formulae thereof that possesses a carboxy group is, for example, an in vivo cleavable amide thereof, for example an amide formed with an amine such as ammonia, a $C_{1-4}$alkylamine such as methylamine, a $(C_{1-4}$alkyl)$_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I and sub-formulae thereof that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I and sub-formulae thereof may be exerted in part by one or more metabolites that are formed within the human or animal body after administration of a compound of the Formula I and sub-formulae thereof. As stated hereinbefore, the in vivo effects of a compound of the Formula I and sub-formulae thereof may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In another aspect, the present invention provides a compound of Formula I and sub-formulae thereof as defined herein, or a pharmaceutically acceptable salt or solvate thereof, or a pharmaceutical composition as defined herein, for use in therapy.

In another aspect, the present invention provides a compound of Formula I and sub-formulae thereof as defined herein, or a pharmaceutically acceptable salt or solvate thereof, or a pharmaceutical composition as defined herein, for use in the treatment of a proliferative disorder.

In another aspect, the present invention provides the use of a compound of Formula I and sub-formulae thereof as defined herein, or a pharmaceutically acceptable salt or solvate thereof, or a pharmaceutical composition as defined herein, in the manufacture of a medicament for treating a proliferative disorder.

In another aspect, the present invention provides a method of treating a proliferative disorder, said method comprising administering to a subject in need thereof an effective amount of a compound of Formula I and sub-formulae thereof as defined herein, or a pharmaceutically acceptable salt or solvate thereof, or a pharmaceutical composition as defined herein.

The terms "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g. of connective tissues), and atherosclerosis. Any type of cell may be treated, including but not limited to, lung, colon, breast, ovarian, prostate, liver, pancreas, brain, blood and skin.

In one embodiment, the proliferative disorder is cancer, suitably a cancer selected from lung, colon, breast, ovarian, prostate, liver, pancreas, brain, blood and skin cancer.

In one embodiment, the proliferative disorder is cancer, suitably a cancer selected from breast, brain, blood and skin cancer.

In one embodiment, the proliferative disorder is cancer, suitably a cancer selected from brain, blood and skin cancer.

In one embodiment, the proliferative disorder is cancer, suitably a cancer selected from brain and blood cancer.

In one embodiment, the cancer is selected from glioblastoma and squamous cell carcinoma.

The anti-proliferative effects of the compounds of the present invention have particular applications in the treatment of human cancers by virtue of their MRCK kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). Suitably, the anti-cancer effect comprises an inhibition of invasion effect and/or inhibition of metastasis.

In another aspect, the present invention provides a compound of Formula I and sub-formulae thereof as defined herein, or a pharmaceutically acceptable salt or solvate thereof, or a pharmaceutical composition as defined herein, for use in inhibiting cancer cell invasion.

In another aspect, the present invention relates to a method of inhibiting cell cell invasion, said method comprising contacting a cell with an effective amount of a compound of Formula I and sub-formulae thereof as defined herein, or a pharmaceutically acceptable salt or solvate thereof, or a pharmaceutical composition as defined herein.

In another aspect, the present invention provides the use of a compound of Formula I and sub-formulae thereof as defined herein, or a pharmaceutically acceptable salt or solvate thereof, or a pharmaceutical composition as defined herein, in the manufacture of a medicament for inhibiting cell invasion.

In the above aspects, suitably cell invasion into surrounding normal tissue is inhibited. Suitably the tissue is selected from lung, colon, breast, ovarian, prostate, liver, pancreas, brain, and skin tissue.

In one embodiment of each of the above aspects, the cell invasion is at least partly radiation-induced or radiation-enhanced cell invasion.

In one embodiment, the present invention provides for the use of a compound of Formula I and sub-formulae thereof as defined herein, or a pharmaceutically acceptable salt or solvate thereof, or a pharmaceutical composition as defined herein, in the manufacture of a medicament for the treatment of glioblastoma, wherein the glioblastoma is radiation resistant.

In another embodiment, the present invention provides for the use of a compound of Formula I and sub-formulae thereof as defined herein, or a pharmaceutically acceptable salt or solvate thereof, or a pharmaceutical composition as defined herein, in the manufacture of a medicament for the treatment of cancer, wherein the compound of Formula I and sub-formulae thereof as defined herein, or a pharmaceutically acceptable salt or solvate thereof, or a pharmaceutical composition as defined herein is for administration prior to, during and/or after radiotherapy. Suitably, the cancer is glioblastoma.

In one embodiment, the present invention provides a compound of Formula I and sub-formulae thereof as defined herein, or a pharmaceutically acceptable salt or solvate thereof, or a pharmaceutical composition as defined herein, for use in the treatment of glioblastoma, wherein the glioblastoma is radiation resistant.

In another embodiment, the present invention provides a compound of Formula I and sub-formulae thereof as defined herein, or a pharmaceutically acceptable salt or solvate thereof, or a pharmaceutical composition as defined herein, for use in the treatment of a cancer, wherein the compound of Formula I and sub-formulae thereof as defined herein, or a pharmaceutically acceptable salt or solvate thereof, or a pharmaceutical composition as defined herein is for administration prior to, during and/or after radiotherapy. Suitably, the cancer is glioblastoma.

In one embodiment, the present invention provides a method for the treatment of glioblastoma comprising administering to a subject in need thereof a compound of Formula I and sub-formulae thereof as defined herein, or a pharmaceutically acceptable salt or solvate thereof, and wherein the glioblastoma is radiation resistant.

In another embodiment, the present invention provides a method for the treatment of cancer comprising administering to a subject in need thereof a compound of Formula I and sub-formulae thereof as defined herein, or a pharmaceutically acceptable salt or solvate thereof, wherein the compound of Formula I and sub-formulae thereof as defined herein, or a pharmaceutically acceptable salt or solvate thereof, or a pharmaceutical composition as defined herein is administered to the subject prior to, during and/or after radiotherapy. Suitably, the cancer is glioblastoma.

In another aspect, the present invention relates to a method of inhibiting cell metastasis in vitro or in vivo, said method comprising contacting a cell with an effective amount of a compound of Formula I and sub-formulae thereof as defined herein, or a pharmaceutically acceptable salt or solvate thereof, or a pharmaceutical composition as defined herein.

In another aspect, the present invention provides a compound of Formula I and sub-formulae thereof as defined herein, or a pharmaceutically acceptable salt or solvate thereof, or a pharmaceutical composition as defined herein, for use in inhibiting cell metastasis.

In another aspect, the present invention provides the use of a compound of Formula I and sub-formulae thereof as defined herein, or a pharmaceutically acceptable salt or solvate thereof, or a pharmaceutical composition as defined herein, in the manufacture of a medicament for inhibiting cell metastasis.

In another aspect, the present invention relates to a method of inhibiting cell metastasis in vitro or in vivo, said method comprising contacting a cell with an effective amount of a compound of Formula I and sub-formulae thereof as defined herein, or a pharmaceutically acceptable salt or solvate thereof, or a pharmaceutical composition as defined herein.

In another aspect, the present invention provides a compound of Formula I and sub-formulae thereof as defined herein, or a pharmaceutically acceptable salt or solvate thereof, or a pharmaceutical composition as defined herein, for use in inhibiting MRCK.

In another aspect, the present invention provides the use of a compound of Formula I and sub-formulae thereof as defined herein, or a pharmaceutically acceptable salt or solvate thereof, or a pharmaceutical composition as defined herein, in the manufacture of a medicament for inhibiting MRCK.

In another aspect, the present invention provides a method of inhibiting MRCK in vitro or in vivo, said method comprising contacting a cell with an effective amount of a compound of Formula I and sub-formulae thereof as defined herein, or a pharmaceutically acceptable salt or solvate thereof, or a pharmaceutical composition as defined herein.

The compounds of the present invention are potent and selective inhibitors of MRCK. At higher doses, the compounds of the present invention may also show some activity against other targets, such as RhoA binding coiled-coil containing kinases (ROCK) and/or protein kinase C (PKC).

Thus, in each of the above aspects, in one embodiment the compounds, in addition to inhibiting MRCK, also inhibit ROCK.

In each of the above aspects, in another embodiment the compounds are selective for MRCK over ROCK. Suitably, the compounds are 30-fold or more selective over ROCK.

In each of the above aspects, in one embodiment the compounds, in addition to inhibiting MRCK, also inhibit ROCK and/or PKC.

In each of the above aspects, in another embodiment the compounds are selective for MRCK over ROCK and/or PKC. Suitably, the compounds are 30-fold or more selective over ROCK and/or PKC.

In each of the above aspects, in one embodiment, the cell is a cancer cell.

Certain compounds of the present invention (for example compound E117 (BDP9066) in the accompanying Example section) undergo rapid clearance (by deactivation and/or metabolism) in the blood [see example 236 herein and FIGS. 1A to 1K]. Such compounds are potentially suitable "soft drug" candidates (i.e. they are predictably deactivated or metabolised after exerting their pharmacological effects) for topical administration. Soft drug approaches are well known in the art [see for example, Bodor, N. & Buchwald, P. Drug targeting via retrometabolic approaches. Pharmacol. Ther. 76, 1-27 (1997); Bodor, N. & Buchwald, P. Soft drug design: general principles and recent applications. Med. Res. Rev. 20, 58-101 (2000); and Thorsteinsson, T., Loftsson, T. & Masson, M. Soft antibacterial agents. Curr. Med. Chem. 10, 1129-1136 (2003)].

Figure 1B:
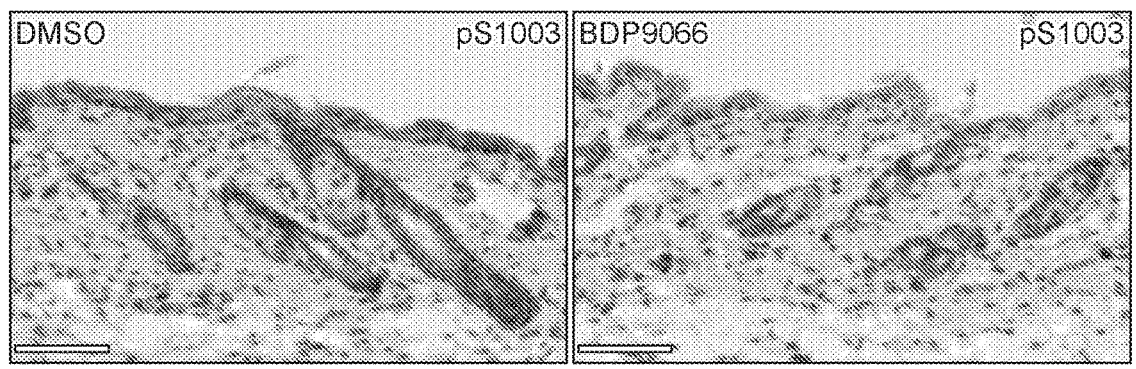
Figure 1B:
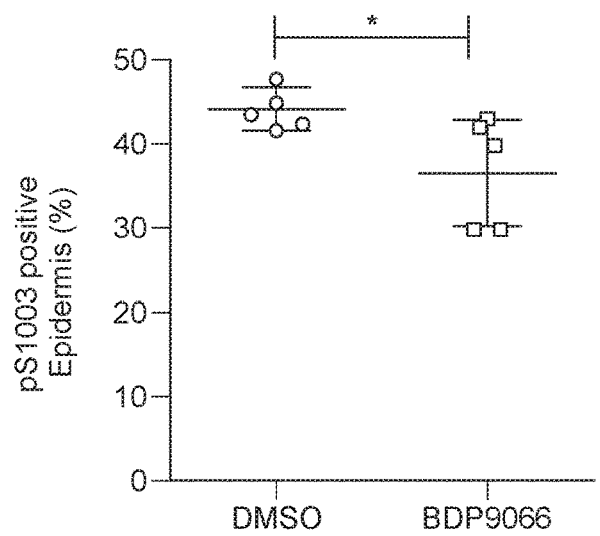
Figure 1J:
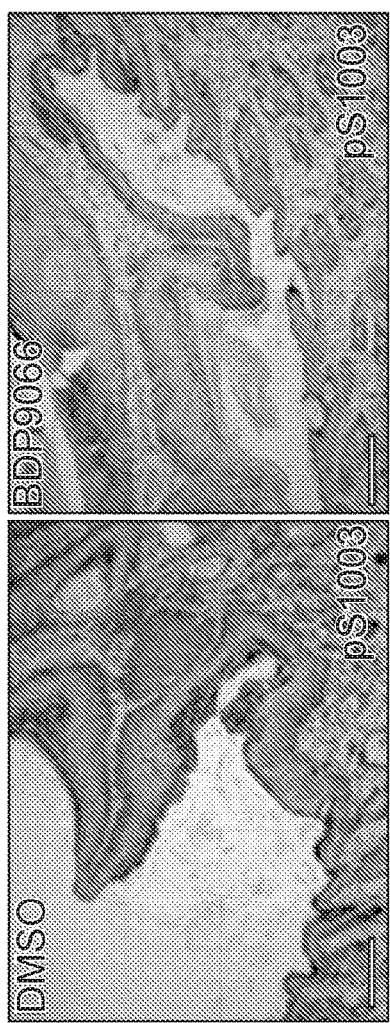
Figure 1J:
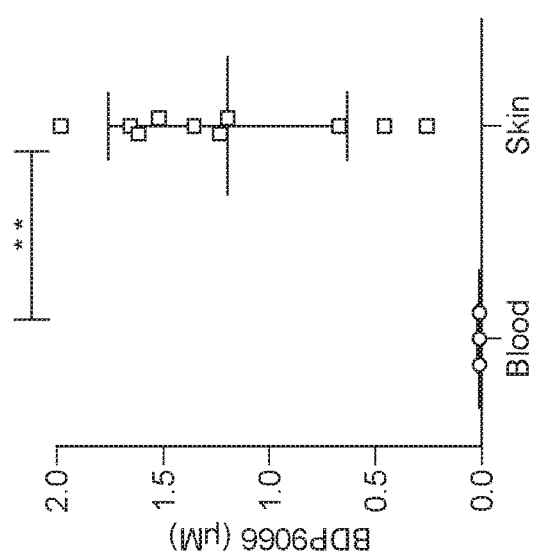
Figure 1K:
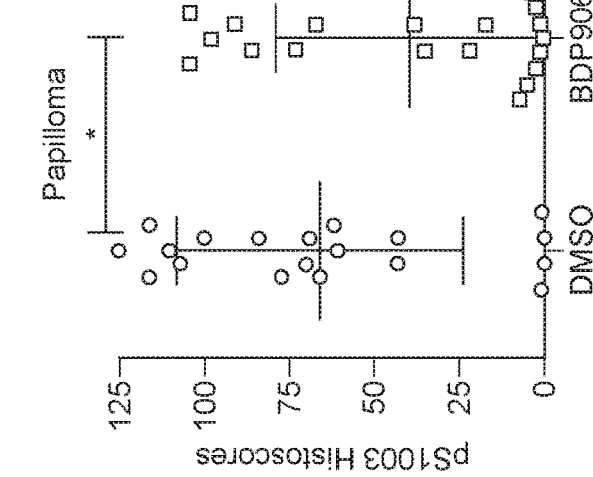
Figure 1K:
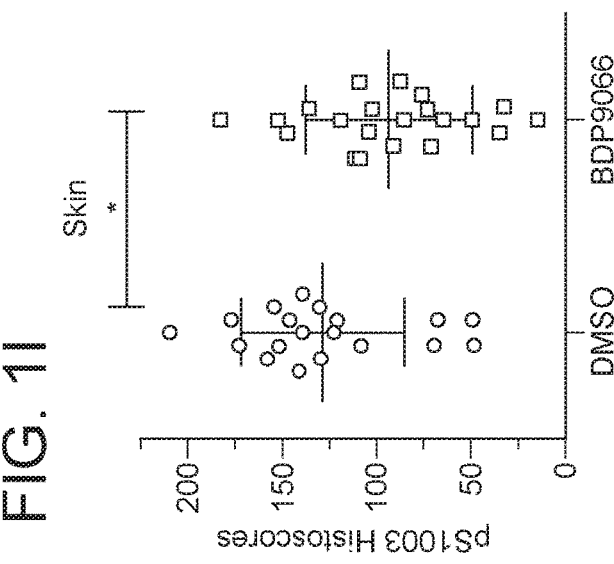

Topical administration of the example compound E117 (BDP9066) described in the accompanying example section (example 236) resulted in no detectable levels of the E117 (BDP9066) compound in the blood and mean concentrations of greater than 1 micromolar in the skin. The levels of E117 (BDP9066) observed in the skin is associated with significant decreases in MRCK-alpha (as detected by pS1003 immunohistochemistry staining (see FIG. 1J herein) and reduced histoscores in the treated skin area (see FIG. 1K, left panel) and in papillomas (FIG. 1K, right panel).

Thus, in another aspect, the present invention provides a compound of Formula I and sub-formulae thereof as defined herein, or a pharmaceutically acceptable salt or solvate thereof, or a pharmaceutical composition as defined herein, for use in the treatment of proliferative skin disorders (e.g. psoriasis and/or skin cancer).

In another aspect, the present invention provides the use of a compound of Formula I and sub-formulae thereof as defined herein, or a pharmaceutically acceptable salt or solvate thereof, or a pharmaceutical composition as defined herein, in the manufacture of a medicament for the treatment of a proliferative skin disorder (e.g. psoriasis and/or skin cancer).

In another aspect, the present invention provides a method of treating a proliferative skin disorder (e.g. psoriasis and/or skin cancer), said method comprising contacting a cell with an effective amount of a compound of Formula I and sub-formulae thereof as defined herein, or a pharmaceutically acceptable salt or solvate thereof, or a pharmaceutical composition as defined herein.

In an embodiment, the skin cancer is selected from malignant melanoma, basal cell carcinoma, squamous cell carcinoma, Merkel cell carcinoma, Kaposi's sarcoma, T-cell lymphoma of the skin and Bowen's disease.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The therapy defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ33 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(ix) herein above, in association with a pharmaceutically acceptable diluent or carrier.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

By way of example, suitable synthetic schemes by which compounds of the invention can be prepared are shown below in Schemes 1 to 6:

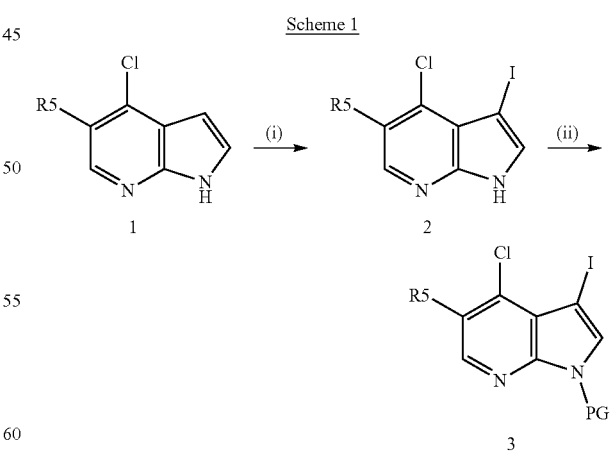

Referring to Scheme 1, the skilled person would be aware of suitable reagents and conditions to effect the above transformations. By way of example suitable reagents for (i) are I$_2$, KOH, DMF, and suitable reagents for (ii) are SEM-Cl, NaH, DMF or Ts-Cl, NaH, THF.

Scheme 2

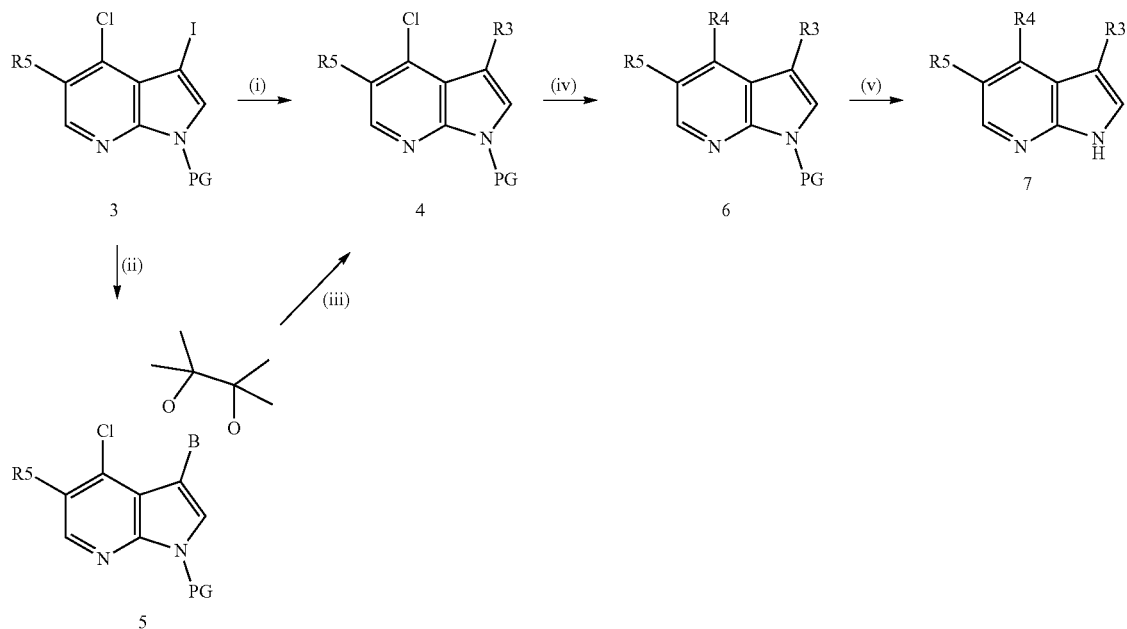

Referring to Scheme 2, the skilled person would be aware of suitable reagents and conditions to effect the above transformations. By way of example suitable reagents for step (i) are ArBPin/ArB(OH)$_2$ (wherein R$^3$=Ar), Pd$_2$(dba)$_3$, PCy$_3$, K$_3$PO$_4$, Dioxane/water or ArSnBu$_3$, CuI, CsF, dioxane, Suitable reagents for step (ii) are BuLi, THF then PinB(OiPr). Suitable reagents for step (iii) are Ar—X (wherein R$^3$=Ar), Pd$_2$(dba)$_3$, PCy$_3$, K$_3$PO$_4$, dioxane/water. Suitable reagents for step (iv) are R$^4$H, Et$_3$N, NMP or R$^4$H, NaH, DMF. Suitable reagents for step (iv) are HCl or TFA in Dioxane/THF.

Scheme 3

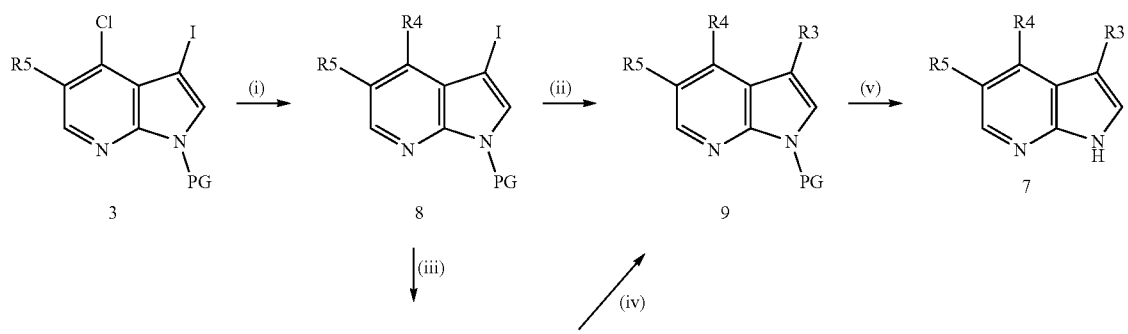

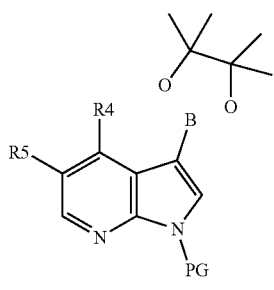

Referring to Scheme 3, the skilled person would be aware of suitable reagents and conditions to effect the above transformations. By way of example suitable reagents for step (i) are R⁴H, Et₃N, NMP. Suitable reagents for step (ii) are ArBPin/ArB(OH)₂ (wherein R³=Ar), Pd₂(dba)₃, PCy₃, K₃PO₄, Dioxane/water. Suitable reagents for step (iii) are BuLi, B2Pin2, THF. Suitable reagents for step (iv) are Ar—X (wherein R³=Ar), Pd₂(dba)₃, PCy₃, K₃PO₄, dioxane/water. Suitable reagents for step (v) are HCl or TFA in Dioxane/THF.

SEMCl, NaH, DMF. Suitable reagents for step (vi) are R⁴H, Et₃N, NMP. Suitable reagents for step (vii) are HCl/TFA in Dioxane/THF.

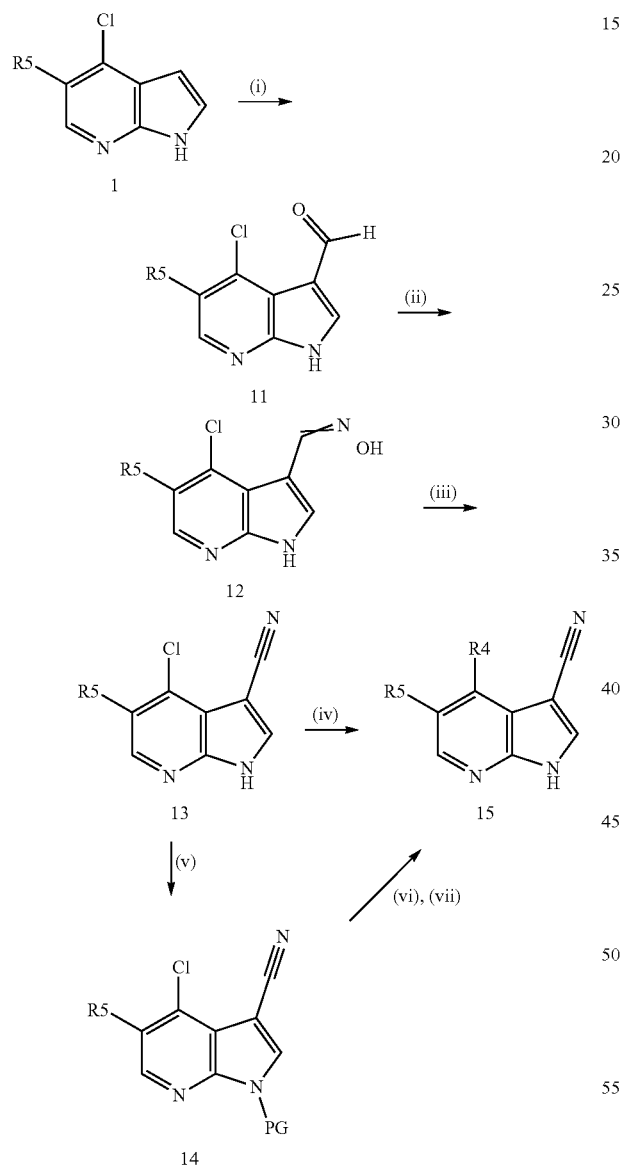

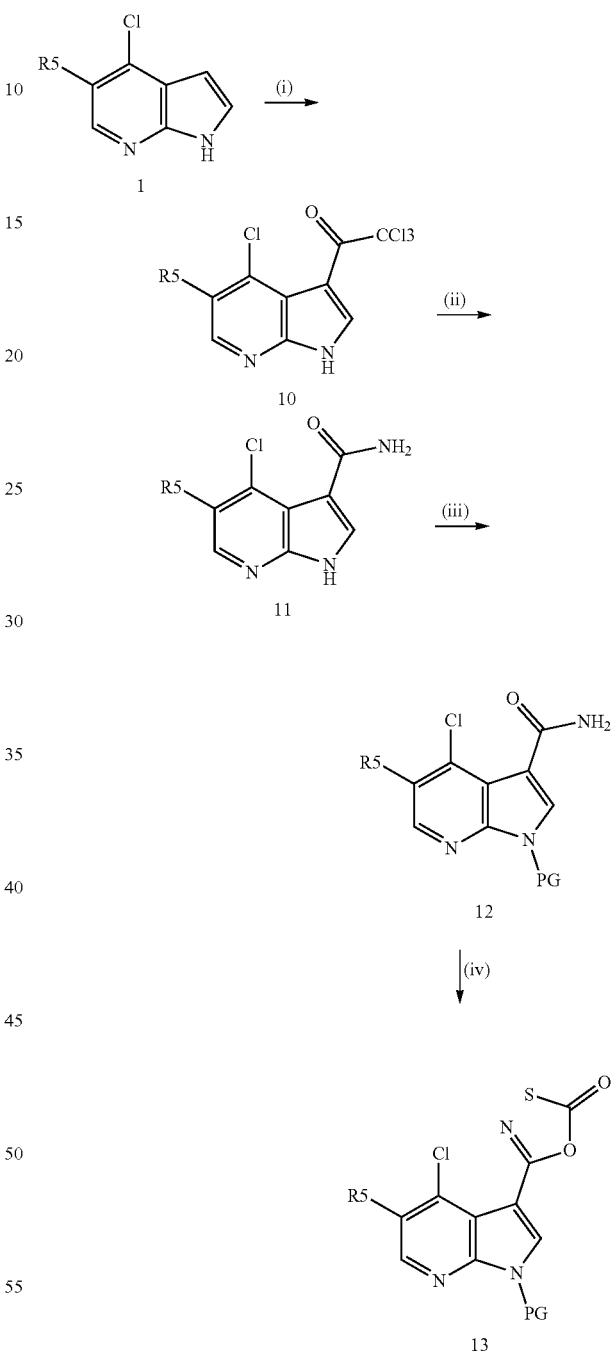

Referring to Scheme 4, the skilled person would be aware of suitable reagents and conditions to effect the above transformations. By way of example suitable reagents for step (i) are AcOH, hexamethylenetetramine, water. Suitable reagent for step (ii) are NH₂OH.HCl, EtOH. Suitable reagents for step (iii) are SOCl₂, DCM. Suitable reagents for step (iv) are R⁴H, dioxane. Suitable reagents for step (v) are Referring to Scheme 5, the skilled person would be aware of suitable reagents and conditions to effect the above transformations. By way of example suitable reagents for step (i) are COClC₃, AlCl₃, DCM. Suitable reagents for step (ii) are NH₃, dioxane. Suitable reagents for step (iii) are SEMCl, NaH, DMF. Suitable reagents for step (iv) are ClSCOCl, THF.

Scheme 6

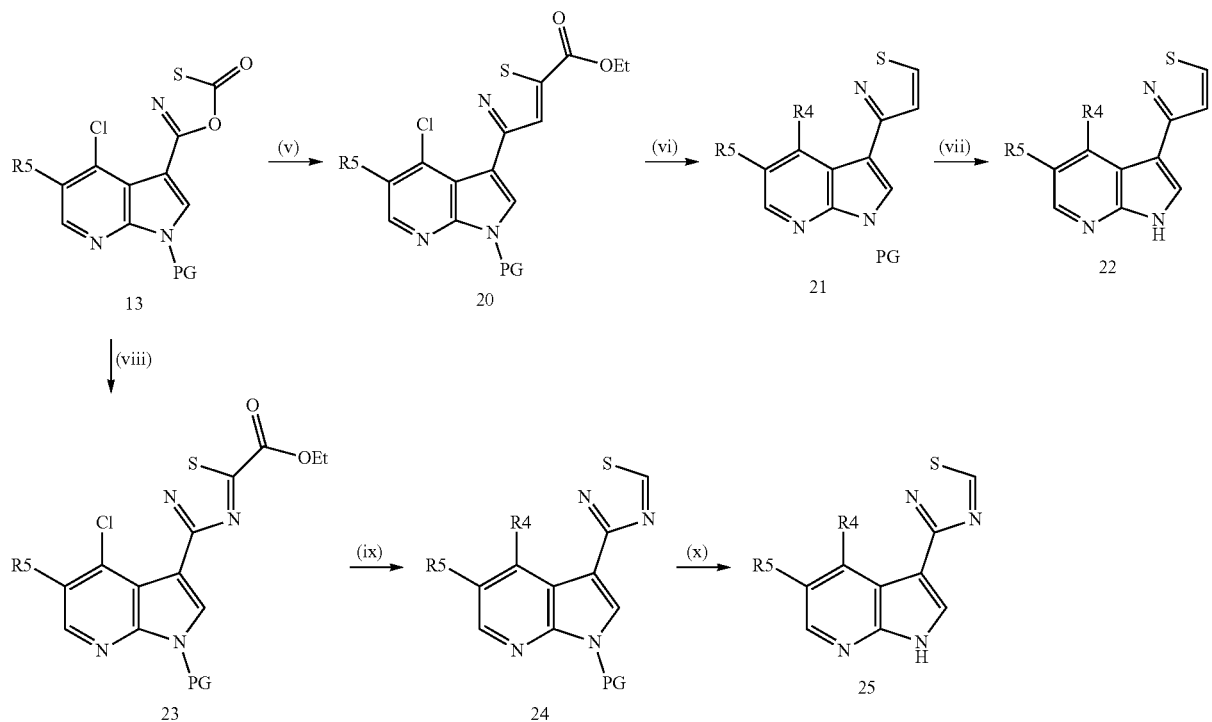

Referring to Scheme 6, the skilled person would be aware of suitable reagents and conditions to effect the above transformations. By way of example suitable reagents for step (vi) are ethyl propiolate, xylene. Suitable reagents for step (vi) are $R^4H$, $Et_3N$, NMP. Suitable reagents for step (vii) are HCl/TFA in Dioxane/THF. Suitable reagents for step (viii) are ethyl cyanoformate, xylene. Suitable reagents for step (ix) are $R^4H$, $Et_3N$, NMP. Suitable reagents for step (x) are HCl/TFA in Dioxane/THF.

SYNTHESIS AND CHARACTERISATION

Abbreviations

AcOH Acetic acid
BINAP 2,2'-bis(diphenylphosphino)-1,1'-binaphthalene
BOC tert-butyloxycarbonyl
Cbz Carboxybenzyl
CVs Column volumes
DCM Dichloromethane
DEA Diethanolamine
DIPEA N,N-Diisopropylethylamine
DMF N,N-Dimethylformamide
DMSO Dimethylsulfoxide
DMSO-d6 Deuterated dimethylsulfoxide
ES Electrospray (ionisation)
EtOAc Ethyl acetate
EtOH Ethanol
HATU 1-[Bis(dimethylamino)methylene-1H-1,2,3-triazolo[4,5-b]pyridinium-3-oxide-hexafluorophosphate
HPLC High performance liquid chromatography
LCMS Liquid chromatography mass spectrometry
MeCN Acetonitrile
MeOH Methanol
Ms Mesyl
n-BuLi n-Butyllithium
NMP N-Methyl-2-pyrrolidone
$Pd(PPh_3)_4$ Tetrakis(triphenylphosphine)palladium(0)
Pet ether Petroleum ether
Rt Retention time (minutes)
RuPhos 2-Dicyclohexylphosphino-2',6'-diisopropoxybiphenyl
SCX Strong cation exchange (column)
SEM [2-(Trimethylsilyl)ethoxy]methyl acetal
TBDPS tert-butyldiphenylsilyl
THF Tetrahydrofuran
THP Tetrahydropyran
TLC Thin layer chromatography
TRT Trityl
Ts Tosyl
w/w % weight per weight Materials and Methods Reagents were purchased from commercial sources and used as received. All solvents were of reagent grade unless otherwise stated, with anhydrous equivalents being sourced from Acros Organics. All reactions were performed under an inert atmosphere of nitrogen unless otherwise stated. Brine refers to a saturated aqueous solution of sodium chloride.

Reaction and final product mass spectrometry and UV analysis was carried out using an Acquity Ultra Performance Liquid Chromatography system. Flash Chromatography purification was carried out using one of two systems: Biotage Isolera Four, fitted with Biotage SNAP cartridges; or Teledyne Isco Combi Flash RF, fitted with Teledyne Isco Redi-Sep cartridges or Gold Redi-Sep cartridges in parallel with Macherey-Nagel aluminium backed TLC plates coated with silica gel 60. Preparative scale LCMS separations were carried out on a Waters high performance liquid chromatography system, fitted with an XBridge Prep C18 5 μm OBD column, utilising a basic gradient of 5-95% MeCN with 0.1% ammonium hydroxide in 10 mM aqueous ammonium carbonate with 0.1% ammonium hydroxide or an acidic gradient of 5-95% MeCN in water with 0.1% formic acid. Early, middle or late methods modify the % of organic solvent used in the gradient, causing different retention times to improve separation as required. Samples were prepared for injection in no greater than 100 mg ml$^{-1}$ in solutions of methanol and/or DMSO or MeCN as required.

Microwave reactions were carried out in a CEM Discover unit. Hydrogenations were carried out in a Thales Nano H-Cube Flow Reactor. Lyophilisations and high boiling point solvent removal was carried out in a Genevac EZ-2 Elite.

All $^1$H NMR spectra were obtained in solutions of chloroform-d, methanol-d$^4$ or DMSO-d$^6$ at 25° C. using a Varian 400 MHz spectrometer with chemical shifts given in parts per million (ppm).

Preparation 1 (P1)-2,2,2-trichloro-1-(4-chloro-1H-pyrrolo[2,3-b]pyridin-3-yl)ethanone

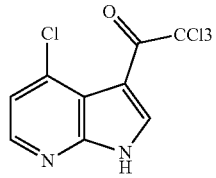

A solution of 4-chloro-1H-pyrrolo[2,3-b]pyridine (2.500 g, 16.38 mmol) in dry DCM (50 ml) was stirred at room temperature under an atmosphere of nitrogen. Trichloroalumane (6.554 g, 49.15 mmol) was added portionwise to the stirred solution and stirring was continued for 1¾ hours. After this time, a solution of trichloroacetyl chloride (2.01 ml, 18.02 mmol) in dry DCM (5 ml) was added dropwise to the stirred suspension. The resulting solution was stirred at room temperature for 48 hours. The reaction mixture was cooled to 0° C. using an ice/water bath and water (20 ml) was added dropwise to the stirred reaction mixture (CAUTION—upon addition of first couple of drops of water, no visible reaction/exotherm, after couple of minutes, bubbling and warming of reaction mixture was observed, a pale brown coloured precipitate was also observed). The reaction mixture was allowed to warm to room temperature before being filtered. The precipitate was washed with DCM (50 ml) and 2% HCl (approx. 50 ml). The precipitate was collected and dried to give a pale yellow coloured solid, 2,2,2-trichloro-1-(4-chloro-1H-pyrrolo[2,3-b]pyridin-3-yl)ethanone (P1) (3.424 g, 11.49 mmol, 70.1% yield), LCMS ES$^+$ 296 [M+H]$^+$, Rt=1.31 mins (Generic Acidic Method).

Preparation 2 (P2)-4-chloro-1H-pyrrolo[2,3-b]pyridine-3-carboxamide

A solution of 2,2,2-trichloro-1-(4-chloro-1H-pyrrolo[2,3-b]pyridin-3-yl)ethanone (P1) (2.450 g, 8.22 mmol) in ammonia in dioxane (164.46 ml, 82.23 mmol, 0.5 M) was heated to 130° C. in the microwave for a maximum of 8 hours (reaction solution split into 7 batches for reaction). A precipitate formed which was collected under vacuum filtration and washed with iso-hexane. The mother liquors from the reaction mixture were concentrated under reduced pressure and allowed to stand for 72 hours, upon which time further precipitate was formed. The precipitate was isolated to give 4-chloro-1H-pyrrolo[2,3-b]pyridine-3-carboxamide (P2) (1.398 g, 7.15 mmol, 86.9% yield), LCMS ES$^+$ 196,198 [M+H]$^+$, Rt=0.63 mins (Generic Basic Method).

Preparation 3 (P3)-4-chloro-1H-pyrrolo[2,3-b]pyridine-3-carbaldehyde

To a round bottomed flask equipped with stirrer bar was added 4-chloro-1H-pyrrolo[2,3-b]pyridine (1.089 g, 7.14 mmol) and hexamethylenetetramine (1.500 g, 10.71 mmol). The flask was charged with acetic acid (3 ml) and water (7 ml) before the resulting solution was heated to 100° C. for 18 hours (overnight). After this time a precipitate was observed. The solution was cooled to room temperature and further water (20 ml) was added. The solid was collected via filtration and dried to give 4-chloro-1H-pyrrolo[2,3-b]pyridine-3-carbaldehyde (P3) (905 mg), LCMS ES$^+$ 179, 181 [M+H]$^+$ Rt=0.91 mins (Generic Basic Method).

Preparation 4 (P4)-4-chloro-1H-pyrrolo[2,3-b]pyridine-3-carbaldehyde oxime

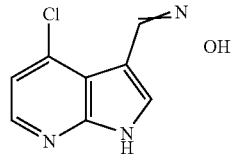

To a suspension of 4-chloro-1H-pyrrolo[2,3-b]pyridine-3-carbaldehyde (P3) (905 mg, 5.01 mmol) in ethanol (12 ml) stirring at room temperature was added hydroxylamine hydrochloride (417.9 mg, 6.01 mmol) followed by sodium hydroxide (236.5 mg, 5.91 mmol) dropwise. The reaction mixture was allowed to stir under nitrogen for 10 minutes before raising the temperature to 50° C. for 3 hours. After this time, the reaction was cooled to room temperature and allowed to stand for 18 hours. A precipitate formed which was collected via filtration, washed with water and dried to give 4-chloro-1H-pyrrolo[2,3-b]pyridine-3-carbaldehyde oxime (P4) (779 mg) (as a mixture of E and Z isomers), LCMS ES$^+$ 194, 196 [M+H]$^+$ Rt=0.88, 0.85 mins (Generic Basic Method).

Preparation 5 (P5)-4-chloro-1H-pyrrolo[2,3-b]pyridine-3-carbonitrile

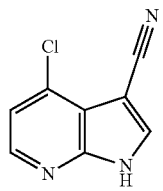 [SMILES: N#Cc1c[nH]c2nccc(Cl)c12]

To a stirred solution of 4-chloro-1H-pyrrolo[2,3-b]pyridine-3-carbaldehyde oxime (P4) (775.10 mg, 3.96 mmol) (mixture of E and Z isomers) in DCM (8 ml) under nitrogen was added thionyl chloride (4.714 g, 39.63 mmol) dropwise. The reaction mixture was allowed to stir at room temperature overnight. After this time, the mixture was concentrated in vacuo before treating with sodium bicarbonate (10 ml, sat. aq. soln.), filtering and washed with water. The solid obtained was dissolved in DCM and subsequently concentrated under reduced pressure to afford 4-chloro-1H-pyrrolo[2,3-b]pyridine-3-carbonitrile (P5) (665 mg), LCMS ES+ 176, 178 [M−H]− Rt=0.93 mins (Generic Basic Method).

Preparation 6 (P6)-4-chloro-3-iodo-1H-pyrrolo[2,3-b]pyridine

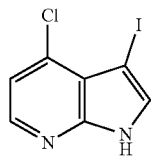 [SMILES: Clc1ccnc2[nH]cc(I)c12]

KOH (35.20 g, 0.629 mol) was added to a stirred solution of 4-chloro-1H-pyrrolo[2,3-b]pyridine (80.00 g, 0.525 mol) in DMF (800 mL) at 0° C. The resulting mixture was stirred at 0° C. for 30 min. I₂ (160.00 g, 0.629 mol) was added slowly to the stirred mixture at 0° C. The resulting mixture was allowed to warm to room temperature and stirred overnight. After this time, the reaction was quenched with Na₂S₂O₃ (aq. soln.) at 0° C. until the purple colour disappeared. The precipitate was collected by filtration and dried to afford 4-chloro-3-iodo-1H-pyrrolo[2,3-b]pyridine (P6) (140.00 g, 95.9% yield).

$^1$H NMR (400 MHz, CDCl₃): δ ppm 10.87 (br s, 1H), 8.19 (d, J=5.2 Hz, 1H), 7.51 (s, 1H), 7.14 (d, J=5.2 Hz, 1H).

Preparation 7 (P7)-5-bromo-7-oxido-1H-pyrrolo[2,3-b]pyridin-7-ium

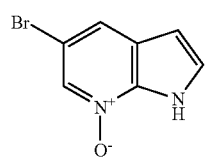 [SMILES: [O-][n+]1cc(Br)cc2cc[nH]c21]

5-Bromo-7-azaindole (25.00 g, 126.88 mmol) was suspended in DCM (500 ml) in a 50 ml flask equipped with a stirrer bar and suba-seal, and flushed with N₂. NMP (25 ml) was added dropwise and stirring continued until complete solvation of the solid occurred. 3-chlorobenzenecarboperoxoic acid (35.03 g, 203.01 mmol) was added portionwise over 10 minutes. The reaction mixture was stirred vigorously at room temperature for 1 hour after which time a thick precipitate fell out of solution. Stirring was continued for 1 hour, before the reaction mixture was filtered and the precipitate was washed with DCM (4×25 ml). The resulting material was suspended in DCM (350 ml) and NaHCO₃ (300 ml, sat. aq. soln.) added. The biphasic mixture was stirred vigorously for 2 hours, after which time the resultant grey solid was filtered and allowed to dry to yield 5-bromo-7-oxido-1H-pyrrolo[2,3-b]pyridin-7-ium (P7) (19.00 g), $^1$H NMR (400 MHz, (CD₃)₂SO): δ ppm 8.33 (br s, 1H), 7.87 (br s, 1H), 7.49 (br s, 1H), 6.50 (br s, 1H).

Preparation 8 (P8)-5-bromo-4-chloro-1H-pyrrolo[2,3-b]pyridine

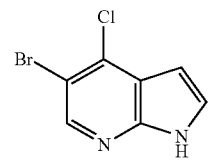 [SMILES: Clc1c(Br)cnc2[nH]ccc12]

A solution of 5-bromo-7-oxido-1H-pyrrolo[2,3-b]pyridin-7-ium (P7) (10.00 g, 46.94 mmol) in NMP (50 ml) was cooled to −20° C., under an atmosphere of N₂. Phosphorus (V) oxychloride (21.88 ml, 234.71 mmol) was added dropwise over 10 minutes, before the reaction mixture was warmed to room temperature and stirred for 4 hours. After this time, the reaction mixture was cooled to 0° C. and quenched by the addition of water (250 ml) with vigorous stirring. The resulting precipitate was filtered and washed with water (2×50 ml) to give 5-bromo-4-chloro-1H-pyrrolo[2,3-b]pyridine (P8) (9.3 g), LCMS ES+ 232 [M+H]+ Rt=1.25 mins (Generic Basic Method).

Preparation 9 (P9)-5-bromo-4-chloro-3-iodo-1H-pyrrolo[2,3-b]pyridine

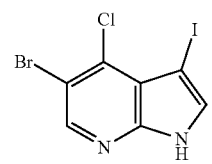

5-bromo-4-chloro-1H-pyrrolo[2,3-b]pyridine (P8) (5.00 g, 21.60 mmol) was suspended in acetone (100 ml). N-Iodosuccinimide (5.30 g, 23.54 mmol) was added and the reaction mixture was left to stir for ca 2 hours. Saturated thiosulphate solution (20 ml) and water (100 ml) were added and the resulting precipitate was filtered and dried at 40° C. in a vacuum desiccator to give 5-bromo-4-chloro-3-iodo-1H-pyrrolo[2,3-b]pyridine (P9) (7.45 g), LCMS ES+ 358 [M+H]+ Rt=0.68 mins (Late Basic Method).

Preparation 10 (P10)-4-chloro-1-(2-trimethylsilylethoxymethyl)pyrrolo[2,3-b]pyridine-3-carboxamide

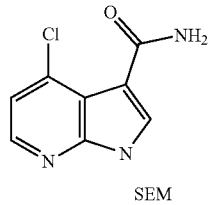 [SMILES: NC(=O)c1c[nH]c2nccc(Cl)c12 ; "SEM"]

A suspension of 4-chloro-1H-pyrrolo[2,3-b]pyridine-3-carboxamide (P2) (1.398 g, 7.15 mmol) in DMF (20 ml) under nitrogen was stirred at 0° C. Sodium hydride (400.22 mg, 10.01 mmol, 60% w/w) was added portionwise to the stirred suspension. The resulting suspension was allowed to stir at 0° C. for 30 minutes. After this time, 2-(trimethylsilyl)ethoxymethyl chloride (1.77 ml, 10.01 mmol) was added. The reaction mixture was allowed to warm to room temperature and the resulting suspension was stirred for a further 72 hours. After this time, water (15 ml) was added and the reaction mixture was diluted with EtOAc (20 ml). The reaction mixture was diluted with EtOAc (50 ml) and washed with water (50 ml). The aqueous portion was washed a further time with EtOAc (80 ml). The organics were combined and washed with LiCl (5% (aq.) soln.) and brine before passing through a hydrophobic frit. The resulting gum, 4-chloro-1-(2-trimethylsilylethoxymethyl)pyrrolo[2,3-b]pyridine-3-carboxamide (P10) was used in subsequent steps without further purification, LCMS ES$^+$ 326, 328 [M+H]$^+$, Rt=1.20 mins (Generic Basic Method).

Preparation 11 (P11)-2-[(4-chloro-3-iodo-pyrrolo[2,3-b]pyridin-1-yl)methoxy]ethyl-trimethyl-silane

NaH (24.10 g, 0.608 mol) was added portion-wise to a solution of 4-chloro-3-iodo-1H-pyrrolo[2,3-b]pyridine (P6) (140.00 g, 0.496 mol) in DMF (1000 ml) at 0° C. The resulting mixture was stirred at 0° C. for 30 min. After this time, 2-(chloromethoxy)ethyl-trimethyl-silane (116.50 g, 0.750 mol) was added slowly to the stirred solution at 0° C. The resulting mixture was allowed to warm to room temperature before being stirred for 18 hours overnight. The mixture was subsequently poured into ice water and extracted with EtOAc. The combined organics were washed with brine, dried over Na$_2$SO$_4$, filtered and concentrated under reduced pressure. The resulting residue was purified chromatographed (SiO$_2$, Pet Ether:EtOAc=10:1) to afford 2-[(4-chloro-3-iodo-pyrrolo[2,3-b]pyridin-1-yl)methoxy]ethyl-trimethyl-silane (P11) (199.00 g, 96.6% yield).

Preparation 12 (P12)-4-chloro-3-iodo-1-(p-tolylsulfonyl)pyrrolo[2,3-b]pyridine

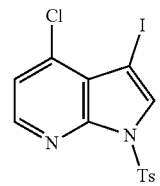 [SMILES: Cc1ccc(S(=O)(=O)n2cc(I)c3c(Cl)ccnc32)cc1]

To a stirred suspension of sodium hydride (191.97 mg, 4.8 mmol) in THF (10 ml) under nitrogen at 0° C. was added 4-chloro-3-iodo-1H-pyrrolo[2,3-b]pyridine (P6) (1.215 g, 4.36 mmol) in THF (10 ml) dropwise. The resulting suspension was allowed to stir at 0° C. for 30 minutes before a solution of p-toluenesulfonyl chloride (914.99 mg, 4.8 mmol) in THF (5 ml) was added dropwise. The reaction mixture was allowed to warm to room temperature. NaHCO$_3$ (10% aq. soln., 25 ml) was added slowly to the reaction mixture. The mixture was stirred at room temperature for 15 minutes. The mixture was extracted with EtOAc (1×60 ml, then 2×30 ml). The combined organics were washed with brine, dried over magnesium sulfate and concentrated under reduced pressure. The resulting solid was triturated with diethyl ether and methanol respectively to give 4-chloro-3-iodo-1-(p-tolylsulfonyl)pyrrolo[2,3-b]pyridine (P12) (1.720 g), LCMS ES$^+$ 433 [M+H]$^+$ Rt=1.64 mins (Generic Basic Method).

Preparation 13 (P13)-4-chloro-1-(2-trimethylsilylethoxymethyl)pyrrolo[2,3-b]pyridine-3-carbonitrile

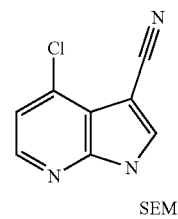

A mixture of 2-[(4-chloro-3-iodo-pyrrolo[2,3-b]pyridin-1-yl)methoxy]ethyl-trimethyl-silane (P11) (4.10 g, 10.00 mmol), zinc cyanide (0.70 g, 6.00 mmol) and Pd(PPh$_3$)$_4$ (1.10 g, 1.00 mmol) in DMF (40 ml) was stirred at 100° C. under an atmosphere of argon for 18 hours (overnight). After this time, the reaction mixture was poured onto water and the organics were extracted with EtOAc. The combined organics were washed with water, brine, dried over Na$_2$SO$_4$, filtered and concentrated under reduced pressure to give 4-chloro-1-(2-trimethylsilylethoxymethyl)pyrrolo[2,3-b]pyridine-3-carbonitrile (P13).

Preparation 14 (P14)-2-[(5-bromo-4-chloro-3-iodo-pyrrolo[2,3-b]pyridin-1-yl)methoxy]ethyl-trimethyl-silane

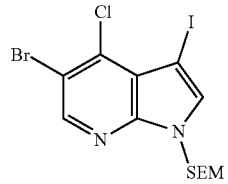 [SMILES: Clc1c(Br)cnc2[nH]cc(I)c12 ; "SEM"]

5-bromo-4-chloro-3-iodo-1H-pyrrolo[2,3-b]pyridine (P9) (7.45 g, 20.85 mmol) was dissolved in DMF (150 ml) and cooled to 0° C. Sodium hydride 60% w/w (958.53 mg, 25.02 mmol) was added portionwise and the reaction mixture was cooled to −42° C. 2-(Trimethylsilyl)ethoxymethyl chloride (4.8 ml, 27.1 mmol) was added dropwise and the reaction mixture was left to stir for ca 2 hours. The reaction was quenched with ammonium chloride (100 ml, sat. aq. soln.) and water (100 ml) before the organics were extracted into DCM. The combined organics were washed with water, dried over magnesium sulphate, filtered and the solvent removed in vacuo to give crude product. The crude product was chromatographed [SiO₂, 0-5% Ethyl Acetate:Hexane] to give 2-[(5-bromo-4-chloro-3-iodo-pyrrolo[2,3-b]pyridin-1-yl)methoxy]ethyl-trimethyl-silane (P14) (7.70 g), LCMS ES⁺ 488 [M+H]⁺ Rt=1.5 mins (Late Basic Method)

Preparation 15 (P15)-2-[[4-chloro-3-(4,4,5,5-tetramethyl-1,3,2-dioxaborolan-2-yl)pyrrolo[2,3-b]pyridin-1-yl]methoxy]ethyl-trimethyl-silane

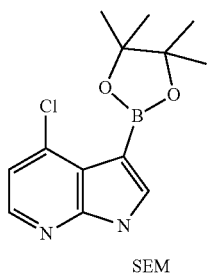 [SMILES: CC1(C)OB(c2c[nH]c3nccc(Cl)c23)OC1(C)C ; "SEM"]

A solution of 2-[(4-chloro-3-iodo-pyrrolo[2,3-b]pyridin-1-yl)methoxy]ethyl-trimethyl-silane (P11) (42.00 g, 103.00 mmol) in dry THF (400 ml) was stirred at −78° C. n-BuLi (50 mL, 124.00 mmol, 2.5 M in THF) was added dropwise to the stirred mixture and stirring was continued for 30 minutes. After this time, 2-isopropoxy-4,4,5,5-tetramethyl-1,3,2-dioxaborolane (38.00 g, 205.00 mmol) was added dropwise to the stirred solution and the resulting mixture was stirred at −78° C. for 1 hour, before being allowed to warm to room temperature and stirred for a further 18 hours (overnight). The reaction mixture was poured onto water and the organics were extracted with EtOAc. The combined organics were washed with water, brine, dried over Na₂SO₄, filtered and concentrated under reduced pressure. The residue was chromatographed [SiO₂, 0-10% EtOAc in Pet. Ether] to give 2-[[4-chloro-3-(4,4,5,5-tetramethyl-1,3,2-dioxaborolan-2-yl)pyrrolo[2,3-b]pyridin-1-yl]methoxy]ethyl-trimethyl-silane (P15) (23.50 g).

Preparation 16 (P16)-2-[(3-bromopyrazol-1-yl)methoxy]ethyl-trimethyl-silane

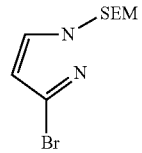

To a solution of 3-bromo-1H-pyrazole (1.16 g, 7.89 mmol) in THF (100 ml) at 0° C. was added NaH (227 mg, 9.46 mmol). The solution was stirred at 0° C. for 15 minutes. 3-(chloromethoxy)propyl-trimethyl-silane (1.44 g, 8.67 mmol) was added and stirring was continued at room temperature for 1 hour. After this time, water was added and the organics were extracted with EtOAc. The organics were combined, dried over Na₂SO₄, concentrated and chromatographed [SiO₂] to give 2-[(3-bromopyrazol-1-yl)methoxy]ethyl-trimethyl-silane (P16) (1.81 g, 83% yield).

Preparation 17 (P17)-3-bromo-1-trityl-pyrazole

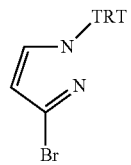

To a solution of 3-bromo-1H-pyrazole (5.39 g, 36.67 mmol) and triphenylchloromethane (10.40 g, 37.41 mmol) in DCM (300 ml) was added trimethylamine (7.41 g, 73.37 mmol). The reaction mixture was heated at 50° C. for 18 hours (overnight). After this time, the mixture was concentrated under reduced pressure and chromatographed [SiO₂] to give 3-bromo-1-trityl-pyrazole (P17) (8.97 g).

Preparation 18 (P18)-4-(4,4,5,5-tetramethyl-1,3,2-dioxaborolan-2-yl)-1-trityl-pyrazole

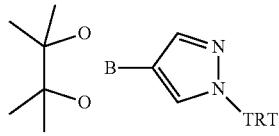

To a solution of 3-bromo-1-trityl-pyrazole (P17) (9.01 g, 23.16 mmol), 4,4,5,5-tetramethyl-2-(4,4,5,5-tetramethyl-1,3,2-dioxaborolan-2-yl)-1,3,2-dioxaborolane (7.06 g, 27.80 mmol) and potassium acetate (6.81 g, 69.49 mmol) in DMF (200 ml) was added 1,1'-bis(diphenylphosphino)ferrocene] dichloropalladium(II) (1.89 g, 2.32 mmol) under an atmosphere of nitrogen. The mixture was heated 80° c. for 18 hours (overnight). The reaction mixture was subsequently poured into water and the organics were extracted into EtOAc. The combined organics were washed with brine, dried over Na₂SO₄, concentrated under reduced pressure and chromatographed [SiO₂] to give 4-(4,4,5,5-tetramethyl-1,3,2-dioxaborolan-2-yl)-1-trityl-pyrazole (P18), (6.93 g, 68.6% yield).

Preparation 19 (P19)-5-[4-chloro-1-(2-trimethylsilylethoxymethyl)pyrrolo[2,3-b]pyridin-3-yl]-1,3,4-oxathiazol-2-one

A solution of 4-chloro-1-(2-trimethylsilylethoxymethyl)pyrrolo[2,3-b]pyridine-3-carboxamide (P10) (2.33 g, 7.15 mmol) in THF (20 ml) was stirred at 0° C. Chloro(chlorothio)oxo-methane (1.09 mL, 12.86 mmol) was added dropwise to the stirred solution. The reaction mixture was allowed to warm to room temperature and stirred for 4 hours, after which time LCMS indicated consumption of starting material. The mixture was concentrated under reduced pressure and the resulting residue was purified using flash silica chromatography eluting with 0-20% EtOAc:iso-Hexane to give 5-[4-chloro-1-(2-trimethylsilylethoxymethyl)pyrrolo[2,3-b]pyridin-3-yl]-1,3,4-oxathiazol-2-one (P19) (0.484 g, 1.21 mmol, 17.6% yield) as a white solid, LCMS ES+ 384, 386 [M+H]+, Rt=1.75 mins (Generic Basic Method).

Preparation 20 (P20)-Ethyl 3-[4-chloro-1-(2-trimethylsilylethoxymethyl)pyrrolo[2,3-b]pyridin-3-yl]-1,2,4-thiadiazole-5-carboxylate

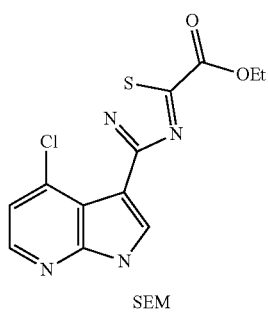 [SMILES: CCOC(=O)/C(S)=N/C(=N)c1c[nH]c2nccc(Cl)c12 ; "SEM"]

A solution of 5-[4-chloro-1-(2-trimethylsilylethoxymethyl)pyrrolo[2,3-b]pyridin-3-yl]-1,3,4-oxathiazol-2-one (P19) (400.00 mg, 1.04 mmol) and ethyl cyanoformate (2.06 mL, 20.84 mmol) in p-xylene (3 ml) was heated to 130° C. for 25 minutes. After this time, the solution was allowed to cool to room temperature. LCMS was consistent with desired product. The reaction mixture was concentrated under reduced pressure to afford the crude product ethyl 3-[4-chloro-1-(2-trimethylsilylethoxymethyl)pyrrolo[2,3-b]pyridin-3-yl]-1,2,4-thiadiazole-5-carboxylate (P20) as a yellow oil. The oil was used in subsequent steps without further purification.

Preparation 21 (P21)-ethyl 3-[4-chloro-1-(2-trimethylsilylethoxymethyl)pyrrolo[2,3-b]pyridin-3-yl]isothiazole-5-carboxylate

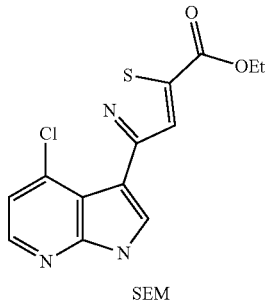 [SMILES: CCOC(=O)/C(S)=C/C(=N)c1c[nH]c2nccc(Cl)c12 ; "SEM"]

A mixture of 5-[4-chloro-1-(2-trimethylsilylethoxymethyl)pyrrolo[2,3-b]pyridin-3-yl]-1,3,4-oxathiazol-2-one (915.00 mg, 2.38 mmol) (P19), ethyl propiolate (4.83 ml, 47.66 mmol) and xylene (6 ml) was split evenly between 2 reaction vials. The reaction mixtures were heated to 160° C. for 30 minutes before being allowed to cool to room temperature. The mixtures were combined and solvent was removed under reduced pressure. The resulting oil was chromatographed [SiO2, 0-20% EtOAc:iso-hexane] to give ethyl 3-[4-chloro-1-(2-trimethylsilylethoxymethyl)pyrrolo[2,3-b]pyridin-3-yl]isothiazole-5-carboxylate (P21) (212 mg), LCMS ES+ 438, 440 [M+H]+, Rt=1.80 mins (Generic Basic Method).

Preparation 22 (P22)-2-[(4-chloro-3-pyrimidin-4-yl-pyrrolo[2,3-b]pyridin-1-yl)methoxy]ethyl-trimethyl-silane

Pd(PPh3)4 (1.50 g, 1.20 mmol), CuI (238.00 mg, 1.20 mmol), CsF (3.70 g, 24.40 mmol) and tributyl(pyrimidin-4-yl)stannane reagent (5.40 g, 14.70 mmol) was added to a solution of 2-[(4-chloro-3-iodo-pyrrolo[2,3-b]pyridin-1-yl)methoxy]ethyl-trimethyl-silane (P11) (5.00 g, 12.20 mmol) in DMF (20 ml). The resulting mixture was stirred at 50° C. for 4 hours. After this time, the mixture was poured into ice water and extracted with EtOAc. The combined organics were washed with brine, dried over Na2SO4, filtered and concentrated under reduced pressure. The resulting residue was chromatographed [SiO2, eluting with Pet.Ether:EtOAc=5:1) to afford 2-[(4-chloro-3-pyrimidin-4-yl-pyrrolo[2,3-b]pyridin-1-yl)methoxy]ethyl-trimethyl-silane (P22) (2.10 g, 47.8% yield).
1H NMR (400 MHz, DMSO-d6): δ ppm 9.19 (s, 1H), 8.80 (d, J=7.6 Hz, 1H), 8.36 (m, 2H), 7.81 (d, J=4.2 Hz, 1H), 7.40

(d, J=4.2 Hz, 1H), 5.73 (s, 2H), 3.58 (t, J=8.0 Hz, 2H), 0.84 (t, J=8.0 Hz, 2H), 0.09 (s, 9H)

Preparation 23 (P23)-2-[(4-chloro-3-pyrimidin-5-yl-pyrrolo[2,3-b]pyridin-1-yl)methoxy]ethyl-trimethyl-silane

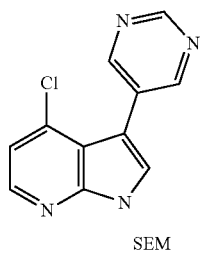 [SMILES: Clc1ccnc2[nH]cc(-c3cncnc3)c12 ; "SEM"]

SEM

2-[(4-chloro-3-iodo-pyrrolo[2,3-b]pyridin-1-yl)methoxy] ethyl-trimethyl-silane (P11) (20.00 g, 41.59 mmol), pyrimidine-5-boronic acid pinacol ester (9.43 g, 45.75 mmol), sodium hydrogen carbonate (10.48 g, 124.77 mmol) and 1,1'-Bis(di-tert-butylphosphino)ferrocene-dichloropalladium (1:1) (1.355 g, 2.08 mmol) were ground together in a round-bottomed flask. The flask was evacuated and flushed with nitrogen (×3). Degassed dioxane:water (3:1-133 ml total) was then added to the flask and the mixture was heated at 150° C. for 1 hour and then 110° C. for a further 18 hours (overnight). The reaction mixture was cooled to room temperature before being concentrated under reduced pressure. The resulting residue was redissolved in EtOAc (200 ml) and washed with water (150 ml). The aqueous layer was further extracted with EtOAc (150 ml). The combined organics were dried over MgSO₄, filtered and concentrated under reduced pressure to give a dark coloured oil. The oil was chromatographed [SiO₂ eluting with 0-60% EtOAc: i-Hexane] to give 2-[(4-chloro-3-pyrimidin-5-yl-pyrrolo[2,3-b]pyridin-1-yl)methoxy]ethyl-trimethyl-silane (P23) (13.154 g, 36.45 mmol, 87.6% yield), as a dark coloured oil, LCMS ES⁺ 361, 363 [M+H]⁺, Rt=1.51 mins (Generic Basic Method).

Preparation 24 (P24)-2-[[4-Chloro-3-(5-methylthiazol-2-yl)pyrrolo[2,3-b]pyridin-1-yl]methoxy]ethyl-trimethyl-silane

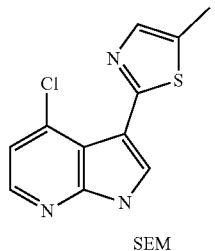 [SMILES: Cc1cnc(-c2c[nH]c3nccc(Cl)c23)s1 ; "SEM"]

SEM

A mixture of 2-[[4-chloro-3-(4,4,5,5-tetramethyl-1,3,2-dioxaborolan-2-yl)pyrrolo[2,3-b]pyridin-1-yl]methoxy] ethyl-trimethyl-silane (P15) (4.00 g, 9.78 mmol), 2-bromo-5-methyl-thiazole (1.15 ml, 11.74 mmol) and tris (dibenzylideneacetone)dipalladium (0) (447.99 mg, 0.49 mmol) was equally separated between 6 flasks. Each flask was purged and evacuated with nitrogen before a degassed solution of 1,4-Dioxane (3 ml) and water (1 ml) was added. The resulting solutions were heated to 80° C. overnight. Further 2-bromo-5-methyl-thiazole (0.479 ml, 4.89 mmol) was added and the reaction mixtures were stirred overnight. The mixtures were allowed to cool to room temperature before being combined and filtered through celite. The liquors were concentrated under reduced pressure and the resulting residue was dissolved in DCM. The organics were washed with water. The aqueous layer was further extracted with DCM (×2). The organics were combined, dried over MgSO₄, filtered and concentrated under reduced pressure. The obtained residue was chromatographed (SiO₂, 0-60% EtOAc:isohexane) to afford 2-[[4-chloro-3-(5-methylthiazol-2-yl)pyrrolo[2,3-b]pyridin-1-yl]methoxy]ethyl-trimethyl-silane (P24) (1.8 g, 4.74 mmol, 48.4% yield) as a yellow oil which solidified upon standing, LCMS ES⁺ 380, 382 [M+H]⁺, Rt=1.70 mins (Generic Basic Method).

The following compounds were prepared in a similar manner to 2-[[4-chloro-3-(5-methylthiazol-2-yl)pyrrolo[2,3-b]pyridin-1-yl]methoxy]ethyl-trimethyl-silane (P24) using 2-[[4-chloro-3-(4,4,5,5-tetramethyl-1,3,2-dioxaborolan-2-yl)pyrrolo[2,3-b]pyridin-1-yl]methoxy]ethyl-trimethyl-silane (P15) and the appropriate halide coupling partner:

| Preparation | Structure | Name | LCMS Data |
| --- | --- | --- | --- |
| P25 | 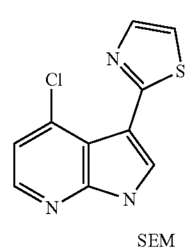 [SMILES: Clc1ccnc2[nH]cc(-c3nccs3)c12 ; "SEM"] | 2-[(4-chloro-3-thiazol-2-yl-pyrrolo[2,3-b]pyridin-1-yl)methoxy]ethyl-trimethyl-silane | ES⁺ 366, 368 M + H]⁺ Rt = 1.63 mins, Generic Basic Method |

Preparation 26 (P26)-2-[[4-chloro-3-(3-pyridyl)pyrrolo[2,3-b]pyridin-1-yl]methoxy]ethyl-trimethyl-silane

2-[(4-chloro-3-iodo-pyrrolo[2,3-b]pyridin-1-yl)methoxy]ethyl-trimethyl-silane (P11) (300 mg, 0.73 mmol) was dissolved in MeCN (3 ml) and THF (3 ml). Sodium carbonate, anhydrous (0.73 mL, 1.47 mmol) was added, followed by bis(triphenylphosphine)palladium(II)chloride (25.76 mg, 0.04 mmol) and 3-pyridylboronic acid pinacol ester (165.56 mg, 0.81 mmol). The reaction mixture was heated to 70° C. for 2 hours. The solvent was removed in vacuo and the residue was partitioned between DCM and water. The organics were concentrated under reduced pressure to give the crude product. The material was chromatographed [SiO$_2$, 0-5% EtOAc in Hexanes] to give 2-[[4-chloro-3-(3-pyridyl)pyrrolo[2,3-b]pyridin-1-yl]methoxy]ethyl-trimethyl-silane (P26) (173 mg), LCMS ES$^+$ 360, 362 [M+H]$^+$, Rt=1.62 mins (Generic Basic Method)

Preparation 27 (P27)-2-[[4-chloro-3-(2-pyridyl)pyrrolo[2,3-b]pyridin-1-yl]methoxy]ethyl-trimethyl-silane

2-[[4-chloro-3-(4,4,5,5-tetramethyl-1,3,2-dioxaborolan-2-yl)pyrrolo[2,3-b]pyridin-1-yl]methoxy]ethyl-trimethyl-silane (P15) (1.00 g, 2.45 mmol), tris(dibenzylideneacetone)dipalladium (0) (112.00 mg, 0.12 mmol), tricyclohexylphosphine (76.75 mg, 0.29 mmol) and potassium phosphate tribasic (1.038 g, 4.89 mmol) were placed in a flask and the flask was evacuated and filled with nitrogen. A solution of 2-bromopyridine (0.7 mL, 7.34 mmol) in 1,4-dioxane (16 ml) and water (8 ml) was degassed and subsequently added to the flask. The resulting mixture was heated to 80° C. under an atmosphere of nitrogen for 20 hours (overnight). After this time, the mixture was allowed to cool to room temperature before being diluted with EtOAc and washed with water (×3). The organics were dried over MgSO4, filtered and concentrated under reduced pressure to give a brown/yellow coloured oil. The oil was chromatographed [SiO$_2$, Hexane:EtOAc 10-80%] to give 2-[[4-chloro-3-(2-pyridyl)pyrrolo[2,3-b]pyridin-1-yl]methoxy]ethyl-trimethyl-silane (P27) as a green coloured oil, LMS ES$^+$ 360, 362 [M+H]$^+$, Rt=1.59 mins (Generic Basic Method).

The following compounds were prepared in a similar manner to 2-[[4-chloro-3-(2-pyridyl)pyrrolo[2,3-b]pyridin-1-yl]methoxy]ethyl-trimethyl-silane (P27) using the appropriate intermediate:

| Preparation | Structure | Name | LCMS Data |
|---|---|---|---|
| P28 | 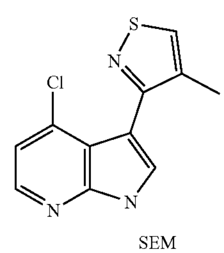 | 2-[[4-chloro-3-(4-methylisothiazol-3-yl)pyrrolo[2,3-b]pyridin-1-yl]methoxy]ethyl-trimethyl-silane | ES$^+$ 380, 382 M + H]$^+$ Rt = 1.66 mins, Generic Basic Method |
| P29 | 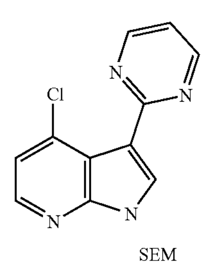 [SMILES: Clc1ccnc2[nH]cc(-c3ncccn3)c12 ; "SEM"] | 2-[(4-chloro-3-pyrimidin-2-yl-pyrrolo[2,3-b]pyridin-1-yl)methoxy]ethyl-trimethyl-silane | ES$^+$ 361, 363 [M + H]$^+$ Rt = 1.51 mins, Generic Basic Method |

| Preparation | Structure | Name | LCMS Data |
|---|---|---|---|
| P30 | 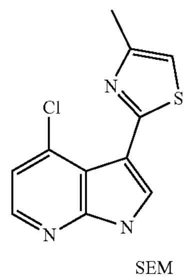 | 2-[[4-chloro-3-(4-methylthiazol-2-yl)pyrrolo[2,3-b]pyridin-1-yl]methoxy]ethyl-trimethyl-silane | ES⁺ 380, 382 M + H]⁺ Rt = 1.71 mins, Generic Basic Method |
| P31 | 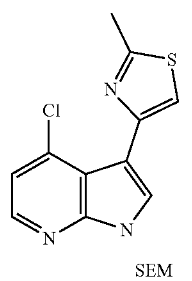 | 2-[[4-chloro-3-(2-methylthiazol-4-yl)pyrrolo[2,3-b]pyridin-1-yl]methoxy]ethyl-trimethyl-silane | ES⁺ 380, 382 [M + H]⁺ Rt = 1.7 mins, Generic Basic Method |
| P32 | 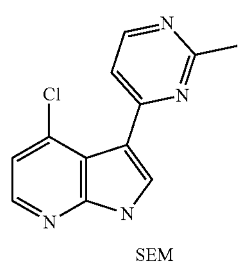 | 2-[[4-chloro-3-(2-methylpyrimidin-4-yl)pyrrolo[2, 3-b]pyridin-1-yl]methoxy]ethyl-trimethyl-silane | ES⁺ 375, 377 [M + H]⁺ Rt = 1.55 mins, Generic Basic Method |
| P33 | 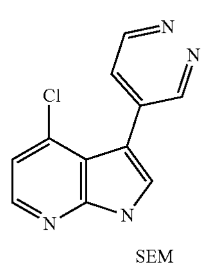 [SMILES: N=C/C=C(\C=N)c1c[nH]c2nccc(Cl)c12 ; "SEM"] | 2-[(4-chloro-3-pyridazin-4-yl-pyrrolo[2,3-b]pyridin-1-yl)methoxy]ethyl-trimethyl-silane | ES⁺ 361, 363 M + H]⁺ Rt = 1.4 mins, Generic Basic Method |
| P34 | 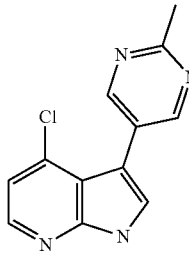 | 2-[[4-chloro-3-(2-methylpyrimidin-5-yl)pyrrolo[2,3-b]pyridin-1-yl]methoxy]ethyl-trimethyl-silane | ES⁺ 375, 377 M + H]⁺ Rt = 0.78 mins, Generic Basic Method |

-continued

| Preparation | Structure | Name | LCMS Data |
|---|---|---|---|
| P35 | 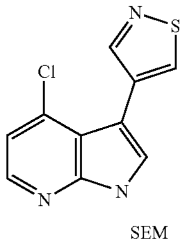 [SMILES: Clc1ccnc2[nH]cc(-c3cnsc3)c12 ; "SEM"] | 2-[(4-chloro-3-isothiazol-4-yl-pyrrolo[2,3-b]pyridin-1-yl)methoxy]ethyl-trimethyl-silane | |
| P36 | 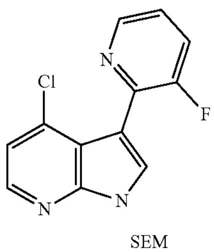 [SMILES: Fc1cccnc1-c1c[nH]c2nccc(Cl)c12 ; "SEM"] | 2-[[4-chloro-3-(3-fluoro-2-pyridyl)pyrrolo[2,3-b]pyridin-1-yl]methoxy]ethyl-trimethyl-silane | ES+ 378, 380 M + H]+ Rt = 1.82 mins, Generic Basic Method |
| P37 | 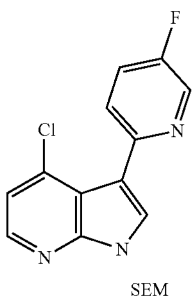 [SMILES: Fc1ccc(-c2c[nH]c3nccc(Cl)c23)nc1 ; "SEM"] | 2-[[4-chloro-3-(5-fluoro-2-pyridyl)pyrrolo[2,3-b]pyridin-1-yl]methoxy]ethyl-trimethyl-silane | ES+ 378, 380 M + H]+ Rt = 1.64 mins, Generic Basic Method |
| P38 | 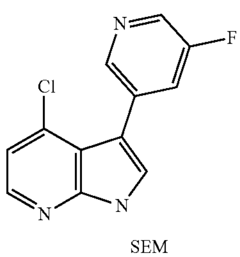 [SMILES: Fc1cncc(-c2c[nH]c3nccc(Cl)c23)c1 ; "SEM"] | 2-[[4-chloro-3-(5-fluoro-3-pyridyl)pyrrolo[2,3-b]pyridin-1-yl]methoxy]ethyl-trimethyl-silane | ES+ 378, 380 M + H]+ Rt = 1.64 mins, Generic Basic Method |
| P39 | 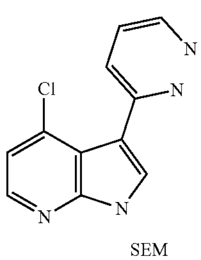 [SMILES: N/C=C\C=C(/N)c1c[nH]c2nccc(Cl)c12 ; "SEM"] | 2-[(4-chloro-3-pyridazin-3-yl-pyrrolo[2,3-b]pyridin-1-yl)methoxy]ethyl-trimethyl-silane | |
| P40 | 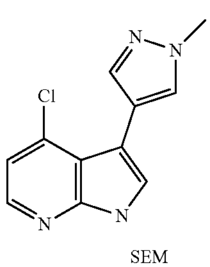 | 2-[[4-chloro-3-(1-methylpyrazol-4-yl)pyrrolo[2,3-b]pyridin-1-yl]methoxy]ethyl-trimethyl-silane | ES+ 363, 365 M + H]+ Rt = 1.51 mins, Generic Basic Method |

-continued

| Preparation | Structure | Name | LCMS Data |
|---|---|---|---|
| P41 | 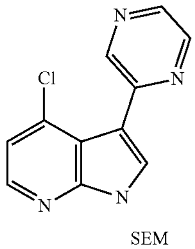 [SMILES: Clc1ccnc2[nH]cc(-c3cnccn3)c12 ; "SEM"] | 2-[(4-chloro-3-pyrazin-2-yl-pyrrolo[2,3-b]pyridin-1-yl)methoxy]ethyl-trimethyl-silane | ES⁺ 361, 363 M + H]⁺ Rt = 1.53 mins, Generic Basic Method |

Preparation 42 (P42)-2-[[4-chloro-3-(3,5-dimethyl-isoxazol-4-yl)pyrrolo[2,3-b]pyridin-1-yl]methoxy]ethyl-trimethyl-silane

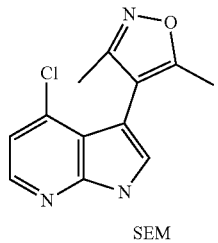 [SMILES: Cc1noc(C)c1-c1c[nH]c2nccc(Cl)c12 ; "SEM"]

3,5-Dimethylisoxazole-4-boronic acid pinacol ester (654.93 mg, 2.94 mmol), 2-[(4-chloro-3-iodo-pyrrolo[2,3-b]pyridin-1-yl)methoxy]ethyl-trimethyl-silane (P11) (1.00 g, 2.45 mmol), palladium (II) acetate (27 mg, 0.123 mmol), 1,1-Bis(di-tert-butylphosphine)ferrocene (1.159 g, 2.45 mmol) and potassium phosphate tribasic (1.558 g, 7.35 mmol) were placed in a reaction vial and the vial was evacuated and purged with nitrogen. THF (1 ml) was added and the resulting mixture was heated to 60° C. overnight. After this time, the reaction mixture was allowed to cool to room temperature before the solvent was removed under reduced pressure. The resulting residue was diluted with DCM (40 ml) and washed with water (20 ml). The aqueous layer was then washed a further time with DCM (40 mL) and the organics combined and washed with brine (40 ml), before concentrating in vacuo. The residue was chromatographed [SiO₂, 0-15% EtOAc:iso-hexane] to give 2-[[4-chloro-3-(3,5-dimethylisoxazol-4-yl)pyrrolo[2,3-b]pyridin-1-yl]methoxy]ethyl-trimethyl-silane (P42) (866 mg, 2.18 mmol, 89% yield) as a pale orange oil, LCMS ES⁺ 378, 380 [M+H]⁺, Rt=1.83 mins (Generic Basic Method).

Preparation 43 (P43)-2-[[4-chloro-3-(1-tetrahydropyran-2-ylpyrazol-4-yl)pyrrolo[2,3-b]pyridin-1-yl]methoxy]ethyl-trimethyl-silane

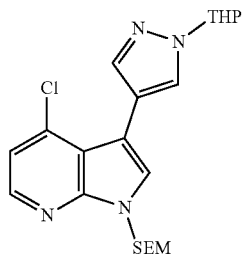

2-[(4-chloro-3-iodo-pyrrolo[2,3-b]pyridin-1-yl)methoxy]ethyl-trimethyl-silane (P11) (300 mg, 0.73 mmol) was dissolved in MeCN (3 ml) and THF (3 ml). Sodium carbonate, anhydrous (0.73 ml, 1.47 mmol) was added, followed by bis(triphenylphosphine)palladium(II)chloride (25.76 mg, 0.04 mmol) and 1-(2-tetrahydropyranyl)-1H-pyrazole-4-boronic acid pinacol ester (224.58 mg, 0.81 mmol). The reaction mixture was heated to 70° C. for 2 hours. The solvent was removed in vacuo and residue partitioned between DCM and water. The organics were concentrated under reduced pressure and the crude material was chromatographed [SiO₂, 0-15% ethyl acetate:hexane] to give 2-[[4-chloro-3-(1-tetrahydropyran-2-ylpyrazol-4-yl)pyrrolo[2,3-b]pyridin-1-yl]methoxy]ethyl-trimethyl-silane (P43) (157 mg) LCMS ES⁺ 434, 436 [M+H]⁺ Rt=1.71 mins (Generic Basic Method).

The following compounds were prepared in a similar manner to 2-[[4-chloro-3-(1-tetrahydropyran-2-ylpyrazol-4-yl)pyrrolo[2,3-b]pyridin-1-yl]methoxy]ethyl-trimethyl-silane (P43) using the appropriate intermediate:

| Preparation | Structure | Name | LCMS Data |
|---|---|---|---|
| P44 | 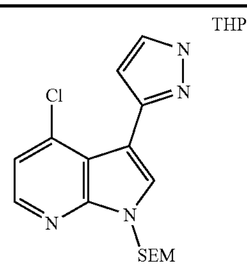 | 2-[[4-chloro-3-(1-tetrahydropyran-2-ylpyrazol-3-yl)pyrrolo[2,3-b]pyridin-1-yl]methoxy]ethyl-trimethyl-silane | ES⁺ 434, 436 M + H]⁺ Rt = 1.69 mins, Generic Basic Method |

Preparation 45 (P45)-2-[[4-chloro-3-[1-(2-trimethyl-silylethoxymethyl)pyrazol-3-yl]pyrrolo[2,3-b]pyridin-1-yl]methoxy]ethyl-trimethyl-silane

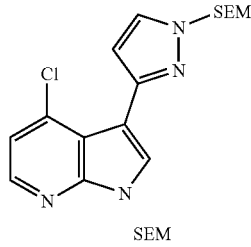 [SMILES: C[Si](C)(C)CCOCn1ccc(-c2c[nH]c3nccc(Cl)c23)n1 ; "SEM"]

To a solution of 2-[(3-bromopyrazol-1-yl)methoxy]ethyl-trimethyl-silane (P16) (700.00 mg, 2.53 mmol), 2-[[4-chloro-3-(4,4,5,5-tetramethyl-1,3,2-dioxaborolan-2-yl)pyrrolo[2,3-b]pyridin-1-yl]methoxy]ethyl-trimethyl-silane (P15) (1.03 g, 2.52 mmol) and NaHCO$_3$ (425 mg, 5.06 mmol) in dioxane (3.0 ml) and water (1.0 ml) was added bis(triphenylphosphine)palladium(II) dichloride (177.00 mg, 0.25 mmol) and the reaction mixture was heated at 100° C. for 18 hours (overnight). After this time, the mixture was concentrated under reduced pressure and the organics were partitioned between EtOAc and water. The combined organics were dried over Na$_2$SO$_4$, concentrated and chromatographed [SiO$_2$] to give 2-[[4-chloro-3-[1-(2-trimethylsilylethoxymethyl)pyrazol-3-yl]pyrrolo[2,3-b]pyridin-1-yl]methoxy]ethyl-trimethyl-silane (P45), (547 mg, 45.2% yield).

Preparation 46 (P46)-2-[[4-chloro-3-(1-tritylpyrazol-4-yl)pyrrolo[2,3-b]pyridin-1-yl]methoxy]ethyl-trimethyl-silane

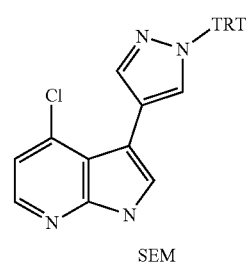

To a solution of 4-(4,4,5,5-tetramethyl-1,3,2-dioxaborolan-2-yl)-1-trityl-pyrazole (P18) (2.45 g, 5.62 mmol), 2-[(4-chloro-3-iodo-pyrrolo[2,3-b]pyridin-1-yl)methoxy]ethyl-trimethyl-silane (P11) (2.29 g, 5.61 mmol) and cesium carbonate (3.66 g, 11.24 mmol) in DMF (10 ml) and water (2 ml) was added tetrakis(triphenylphosphine) palladium (0) (0.65 g, 0.56 mmol) and the reaction mixture was heated at reflux overnight. The mixture was allowed to cool to room temperature before being poured into water. the organics were extracted with DCM and the combined organics were dried over Na$_2$SO$_4$, filtered, concentrated under reduced pressure and subsequently chromatographed [SiO$_2$, 10% EtOAc in Petroleum Ether] to give 2-[[4-chloro-3-(1-tritylpyrazol-4-yl)pyrrolo[2,3-b]pyridin-1-yl]methoxy]ethyl-trimethyl-silane (P46) (1.60 g, 48.2% yield).

Preparation 47 (P47)-4-chloro-1-(p-tolylsulfonyl)-3-(3-pyridyl)pyrrolo[2,3-b]pyridine

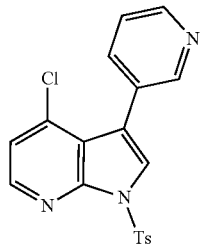 [SMILES: Cc1ccc(S(=O)(=O)n2cc(-c3cccnc3)c3c(Cl)ccnc32)cc1]

To a microwave vial equipped with stirrer bar was added 4-chloro-3-iodo-1-(p-tolylsulfonyl)pyrrolo[2,3-b]pyridine (P12) (192 mg, 0.44 mmol), potassium carbonate anhydrous (128.8 mg, 0.93 mmol), tetrakistriphenylphosphine palladium (25.64 mg, 0.02 mmol) and 3-pyridylboronic acid pinacol ester (100.1 mg, 0.49 mmol). The microwave vial was capped and the vessel flushed and evacuated with nitrogen (×3) before the addition of a degassed solution of dioxane and water (3:1, 1.5 ml). The reaction mixture was heated to 140° C. for 40 minutes. After this time, the reaction was cooled to room temperature, diluted with DCM (20 ml) and washed with water (5 ml). The organics were concentrated under reduced pressure and purified by SCX to give 4-chloro-1-(p-tolylsulfonyl)-3-(3-pyridyl)pyrrolo[2,3-b]pyridine (P47) (152 mg), LCMS ES$^+$ 384 [M+H]$^+$ Rt=1.38 mins (Generic Basic Method).

Preparation 48 (P48)-4-chloro-1-(p-tolylsulfonyl)-3-(1-tetrahydropyran-2-ylpyrazol-4-yl)pyrrolo[2,3-b]pyridine

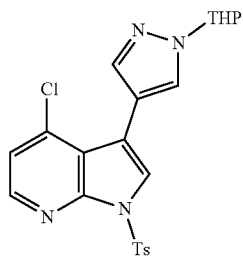

To a microwave vial equipped with stirrer bar was added 4-chloro-3-iodo-1-(p-tolylsulfonyl)pyrrolo[2,3-b]pyridine (P12) (202 mg, 0.47 mmol), anhydrous potassium carbonate (135.51 mg, 0.98 mmol), 1-(2-tetrahydropyranyl)-1H-pyrazole-4-boronic acid pinacol ester (142.85 mg, 0.51 mmol) and tetrakistriphenylphosphine palladium (26.98 mg, 0.02 mmol). The microwave vial was capped and the vessel flushed and evacuated with nitrogen (×3) before the addition of a degassed solution of dioxane and water (3:1, 1 ml). The reaction mixture was heated to 140° C. for 40 minutes. The reaction was cooled to room temperature and the organics removed in vacuo. The aqueous liquor was washed with DCM (2×8 ml). The combined organic portions were washed with brine, dried over magnesium sulfate and concentrated under reduced pressure to give a dark oil. The oil was chromatographed [SiO$_2$, 0-25% (10% MeOH in DCM): DCM] to give 4-chloro-1-(p-tolylsulfonyl)-3-(1-tetrahydropyran-2-ylpyrazol-4-yl)pyrrolo[2,3-b]pyridine (P48) (135 mg) LCMS ES⁺ 457 [M+H]⁺ Rt=1.5 mins (Generic Basic Method).

Preparation 49 (P49)-2-[[5-bromo-4-chloro-3-(1-tetrahydropyran-2-ylpyrazol-3-yl)pyrrolo[2,3-b]pyridin-1-yl]methoxy]ethyl-trimethyl-silane

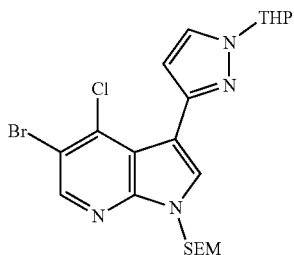

2-[(5-bromo-4-chloro-3-iodo-pyrrolo[2,3-b]pyridin-1-yl)methoxy]ethyl-trimethyl-silane (P14) (2.00 g, 4.10 mmol), potassium carbonate anhydrous (1133.73 mg, 8.20 mmol), dichlorobis(triphenylphosphine)palladium (2.88 mg) and 1-tetrahydropyran-3-yl-4-(4,4,5,5-tetramethyl-1,3,2-dioxaborolan-2-yl)pyrazole (1140.87 mg, 4.10 mmol) were dissolved in THF (2.5 ml) and water (0.50 ml). The reaction mixture was flushed with nitrogen and heated to 120° C. for 1 hour in a microwave vial. The organics were concentrated in vacuo and purified via flash silica chromatography, eluting with EtOAc/Hexane 20:80-100%, to give 2-[[5-bromo-4-chloro-3-(1-tetrahydropyran-2-ylpyrazol-3-yl)pyrrolo[2,3-b]pyridin-1-yl]methoxy]ethyl-trimethyl-silane (P49), LCMS ES⁺ 511/513 [M+H]⁺, Rt=1.3 mins (Generic Basic Method).

Preparation 50 (P50)-4-chloro-3-(2-pyridyl)-1H-pyrrolo[2,3-b]pyridine

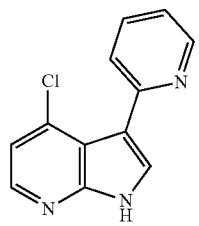 [SMILES: Clc1ccnc2[nH]cc(-c3ccccn3)c12]

2-[[4-chloro-3-(4,4,5,5-tetramethyl-1,3,2-dioxaborolan-2-yl)pyrrolo[2,3-b]pyridin-1-yl]methoxy]ethyl-trimethyl-silane (P15) (73 mg, 0.18 mmol) was dissolved in 1,4-dioxane (1 ml) and water (0.1 ml). Tris(dibenzylideneacetone)dipalladium(0) (6.97 mg, 0.01 mmol), tricyclohexylphosphine (5.16 mg, 0.02 mmol), potassium phosphate tribasic (55.22 mg, 0.26 mmol) and 2-bromopyridine (34.06 ul, 0.3600 mmol) were added and the reaction mixture heated to 150° C. for 10 minutes. The solvent was removed and the residue was partitioned between DCM and water, before filtering through a hydrophobic frit. The solvent was removed in vacuo to give 2-[[4-chloro-3-(2-pyridyl)pyrrolo[2,3-b]pyridin-1-yl]methoxy]ethyl-trimethyl-silane (20 mg). The material was dissolved in 2M hydrogen chloride solution (1.34 ml, 2.68 mmol) and heated to 100° C. for 3 hours. The reaction mixture was diluted with MeOH and purified via SCX. The solvent removed in vacuo to give 4-chloro-3-(2-pyridyl)-1H-pyrrolo[2,3-b]pyridine (P50) (16 mg), LCMS ES⁺ 230, 232 [M+H]⁺ Rt=0.61 mins (Generic Basic Method).

Preparation 51 (P51)-4-chloro-3-(3-pyridyl)-1H-pyrrolo[2,3-b]pyridine

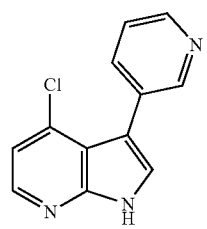 [SMILES: Clc1ccnc2[nH]cc(-c3cccnc3)c12]

2-[[4-chloro-3-(3-pyridyl)pyrrolo[2,3-b]pyridin-1-yl]methoxy]ethyl-trimethyl-silane (P26) (173.00 mg, 0.48 mmol) was suspended in hydrogen chloride solution (3.6 ml, 7.21 mmol, 2N) and heated to 100° C. for 1 hour. The crude reaction mixture was purified via SCX to give 4-chloro-3-(3-pyridyl)-1H-pyrrolo[2,3-b]pyridine (P51) (140 mg), LCMS ES⁺ 230, 232 [M+H]⁺ Rt=0.97 mins (Generic Basic Method).

Preparation 52 (P52)-4-chloro-3-(1H-pyrazol-4-yl)-1H-pyrrolo[2,3-b]pyridine

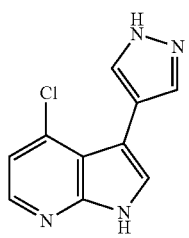 [SMILES: Clc1ccnc2[nH]cc(-c3cn[nH]c3)c12]

2-[[4-chloro-3-(1-tetrahydropyran-2-ylpyrazol-4-yl)pyrrolo[2,3-b]pyridin-1-yl]methoxy]ethyl-trimethyl-silane (P43) (157 mg, 0.36 mmol) was suspended in HCl (2.72 ml, 5.44 mmol) and heated to 100° C. for 1 hour. The crude reaction mixture was purified via SCX to give 4-chloro-3-(1H-pyrazol-4-yl)-1H-pyrrolo[2,3-b]pyridine (P52) (100 mg) LCMS ES⁺ 219, 221 [M+H]⁺ Rt=0.89 mins (Generic Basic Method).

The following compounds were prepared in a similar manner to 4-chloro-3-(1H-pyrazol-4-yl)-1H-pyrrolo[2,3-b]pyridine (P52) using the appropriate intermediate:

| Preparation | Structure | Name | LCMS Data |
|---|---|---|---|
| P53 | 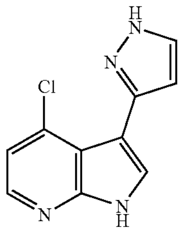 [SMILES: Clc1ccnc2[nH]cc(-c3cc[nH]n3)c12] | 4-chloro-3-(1H-pyrazol-3-yl)-1H-pyrrolo[2,3-b]pyridine | ES⁺ 219, 221 [M + H]⁺ Rt = 0.82 mins, Generic Basic Method |

Preparation 54 (P54)-2-[[5-bromo-3-iodo-4-(1-piperidyl)pyrrolo[2,3-b]pyridin-1-yl]methoxy]ethyl-trimethyl-silane

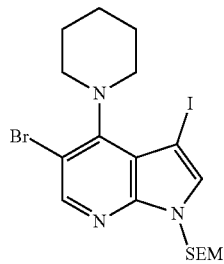 [SMILES: C[Si](C)(C)CCOCn1cc(I)c2c(N3CCCCC3)c(Br)cnc21]

2-[(5-bromo-4-chloro-3-iodo-pyrrolo[2,3-b]pyridin-1-yl)methoxy]ethyl-trimethyl-silane-(P14) (674.00 mg, 1.38 mmol) and piperidine (1.47 ml, 13.82 mmol) in NMP (1.5 ml) were heated at 145° C. in the microwave for 1 hour. The solvent was removed in vacuo and the crude reaction mixture was chromatographed [SiO₂, 0-5% Ethyl Acetate:hexane] to give 2-[[5-bromo-3-iodo-4-(1-piperidyl)pyrrolo[2,3-b]pyridin-1-yl]methoxy]ethyl-trimethyl-silane (P54) (673 mg, 1.13 mmol, 82% yield), LCMS ES⁺ 537[M+H]⁺ Rt=1.4 mins (Very Late Basic Method).

Preparation 55 (P55)-2-[[3-iodo-4-(1-piperidyl)pyrrolo[2,3-b]pyridin-1-yl]methoxy]ethyl-trimethyl-silane

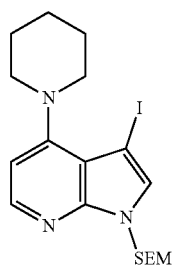 [SMILES: C[Si](C)(C)CCOCn1cc(I)c2c(N3CCCCC3)ccnc21]

2-[(4-chloro-3-iodo-pyrrolo[2,3-b]pyridin-1-yl)methoxy]ethyl-trimethyl-silane (P11) (5.00 g, 12.23 mmol) was solubilised in NMP (20 ml). Piperidine (12.08 ml, 122.3 mmol) was added and the reaction mixture was heated to 145° C. for 4 hours. The reaction mixture was concentrated in vacuo to yield a thick oil which was diluted with methanol (50 ml) resulting in precipitation of a white solid. The solid was collected by filtration to yield 2-[[3-iodo-4-(1-piperidyl)pyrrolo[2,3-b]pyridin-1-yl]methoxy]ethyl-trimethyl-silane (P55) (4.383 g, 9.39 mmol, 76.8% yield) LCMS ES⁺ 458 [M+H]⁺ Rt=1.39 mins (Late Basic Method).

Preparation 56 (P56)-3-iodo-4-(1-piperidyl)-1-(p-tolylsulfonyl)pyrrolo[2,3-b]pyridine

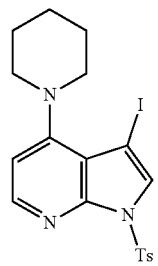 [SMILES: Cc1ccc(S(=O)(=O)n2cc(I)c3c(N4CCCCC4)ccnc32)cc1]

Iodine (1.765 g, 6.96 mmol), KOH solution (aq) (1.95 ml, 34.78 mmol) and 4-(1-piperidyl)-1H-pyrrolo[2,3-b]pyridine (700 mg, 3.48 mmol) were mixed together vigorously with DCM (50 ml) as biphasic mixture for 3 hours. p-Toluenesulfonyl chloride (0.56 ml, 3.83 mmol) was added and the mixture stirred for a further hour. The mixture was concentrated under reduced pressure, redissolved in DCM (20 ml) and washed with NaOH (50 ml, 0.1 mol), before being purified via flash silica chromatography eluting with EtOAc/Hexane to give 3-iodo-4-(1-piperidyl)-1-(p-tolylsulfonyl)pyrrolo[2,3-b]pyridine (P56) (550 mg), LCMS ES⁺ 482.2 [M+H]⁺, Rt=1.78 mins (Generic Basic Method).

Preparation 57 (P57)-Trimethyl-[2-[[4-(1-piperidyl)-3-(4,4,5,5-tetramethyl-1,3,2-dioxaborolan-2-yl)pyrrolo[2,3-b]pyridin-1-yl]methoxy]ethyl]silane

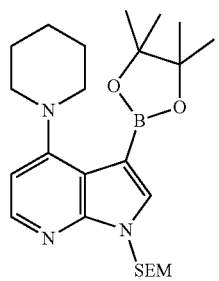 [SMILES: CC1(C)OB(c2cn(COCC[Si](C)(C)C)c3nccc(N4CCCCC4)c23)OC1(C)C]

To a solution of 2-[[3-iodo-4-(1-piperidyl)pyrrolo[2,3-b]pyridin-1-yl]methoxy]ethyl-trimethyl-silane (P55) (4.18 g, 9.13 mmol) stirring in THF (90 ml) under N$_2$ at −78° C. was added butyllithium (12.55 ml, 20.08 mmol) dropwise, with stirring, over the course of 30 minutes. The resulting solution was allowed to stir for 1.5 hours before the dropwise addition of 2-isopropoxy-4,4,5,5-tetramethyl-1,3,2-dioxaborolane (7.45 ml, 36.52 mmol) at −78° C. After two hours the reaction was allowed to warm to room temperature overnight. The reaction mixture was cooled and quenched with NH$_4$Cl (25 ml, sat. aq. soln.) before allowing to warm to room temperature and extracting with EtOAc (1×400 ml, then 2×100 ml). The combined organics were dried over MgSO$_4$ before filtering and concentrating in vacuo to yield a dark purple oil. The oil was chromatographed [SiO$_2$, 0-20% EtOAc:hexanes] to give trimethyl-[2-[[4-(1-piperidyl)-3-(4,4,5,5-tetramethyl-1,3,2-dioxaborolan-2-yl)pyrrolo[2,3-b]pyridin-1-yl]methoxy]ethyl]silane (2.70 g) (P57) LCMS ES$^+$ 457 [M+H]$^+$ Rt=0.78 mins (Generic Basic Method).

Preparation 58 (P58)-tert-butyl N-(2-methyl-3-pyridyl)carbamate

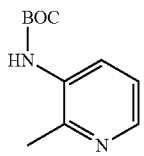

A solution of di-tert-butyl dicarbonate (1.01 g, 4.62 mmol) in dry THF (15 ml) was added to 3-amino-2-methylpyridine (500.00 mg, 4.62 mmol) under an atmosphere of nitrogen. The resulting solution was stirred at room temperature, under an atmosphere of nitrogen overnight. After this time, further di-tert-butyl dicarbonate (500.00 mg) was added and the reaction mixture was stirred for a further 24 hours at room temperature. The solvent was removed under reduced pressure and the resulting residue was chromatographed [SiO$_2$, Hex:EtOAc 1:1] to give tert-butyl N-(2-methyl-3-pyridyl)carbamate (P58) as a pale yellow coloured solid, LCMS ES$^+$ 209 [M+H]$^+$, Rt=1.02 mins (Generic Basic Method).

Preparation 59 (P59)-tert-butyl N-methyl-N-(2-methyl-3-pyridyl)carbamate

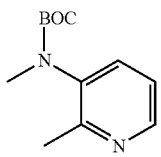 [SMILES: Cc1ncccc1N(C)C(=O)OC(C)(C)C]

A suspension of sodium hydride 60% w/w (115.24 mg, 2.88 mmol) in dry THF (2.6 ml) was stirred at 0° C. under an atmosphere of nitrogen. A solution of tert-butyl N-(2-methyl-3-pyridyl)carbamate (P58) (500.00 mg, 2.4 mmol) in dry THF (1 ml) was added dropwise to the stirred suspension and the resulting suspension was stirred at 0° C. for 30 minutes. After this time, iodomethane (0.18 ml, 2.88 mmol) was added and the suspension was stirred for a further 16 hours warming from 0° C. to room temperature. The reaction was quenched with water and the solvent removed under reduced pressure. The resulting residue was dissolved in DCM. The organics were washed with water, dried over magnesium sulphate and concentrated under reduced pressure to afford crude product. The crude product was chromatographed [SiO$_2$, 50-100% EtOAc in isohexane) to afford tert-butyl N-methyl-N-(2-methyl-3-pyridyl)carbamate (P59) (491 mg), LCMS ES$^+$ 223 [M+H]$^+$, Rt=1.07 mins (Generic Basic Method).

Preparation 60 (P60)-tert-butyl N-methyl-N-[(cis)-2-methyl-3-piperidyl]carbamate

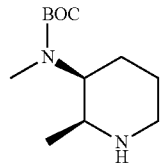 [SMILES: C[C@@H]1NCCC[C@@H]1N(C)C(=O)OC(C)(C)C]

A solution of tert-butyl N-methyl-N-(2-methyl-3-pyridyl)carbamate (P67) (500.00 mg, 2.25 mmol) in EtOH/AcOH was subjected to hydrogenation using the H-cube (5% Rh/C, 60° C., 60 bar, 0.5 ml/min). The solution was cycled through the H-cube for 2 hours. After this time, the solvent was removed under reduced pressure and the resulting residue was dissolved in MeOH and purified by SCX (5 g) to afford tert-butyl N-methyl-N-[(cis)-2-methyl-3-piperidyl]carbamate (P68) (306 mg).

Preparation 61 (P61)-tert-butyl pyrrolo[2,3-c]pyridine-1-carboxylate

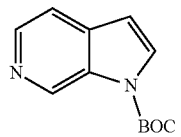 [SMILES: CC(C)(C)OC(=O)n1ccc2ccncc21]

To a solution of triethylamine (0.65 ml, 4.66 mmol) and 6-azaindole (1.00 g, 8.46 mmol) in MeCN (20 ml) stirring at 0° C. was added di-tert-butyl dicarbonate (1.94 ml, 8.46 mmol) dropwise under nitrogen with stirring. The reaction was allowed to warm to room temperature and left to stir over the weekend. Further di-tert-butyl dicarbonate (1.94 ml, 8.46 mmol) was added and stirring continued for 6 hours. The reaction mixture was concentrated under reduced pressure and the oil obtained taken up in DCM and washed with water. The mixture was passed through a hydrophobic frit and the solvent removed under reduced pressure to afford tert-butyl pyrrolo[2,3-c]pyridine-1-carboxylate (P61) (1.90 g). LCMS ES$^+$ 219 [M+H]$^+$, Rt=1.22 mins (Generic Basic Method).

Preparation 62 (P62)-tert-butyl pyrrolo[3,2-c]pyridine-1-carboxylate

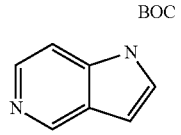

To a solution of triethylamine (0.65 ml, 4.66 mmol) and 5-azaindole (1.00 g, 8.46 mmol) in MeCN (20 ml) stirring at 0° C. was added di-tert-butyl dicarbonate (0.97 ml, 4.23 mmol) dropwise under nitrogen with stirring. The reaction was allowed to warm to room temperature and left to stir over the weekend. Further di-tert-butyl dicarbonate (0.97 ml, 4.23 mmol) was added and stirring continued for 6 hours. The reaction mixture was concentrated under reduced pressure and the oil obtained taken up in DCM and washed with water. The mixture was passed through a hydrophobic frit and solvent removed under reduced pressure to afford tert-butyl pyrrolo[3,2-c]pyridine-1-carboxylate (P62) (1.76 g), LCMS ES$^+$ 219 [M+H]$^+$, Rt=1.19 mins (Generic Basic Method).

Preparation 63 (P63)-tert-butyl (3aR,7aS)-2,3,3a,4,5,6,7,7a-octahydropyrrolo[2,3-c]pyridine-1-carboxylate

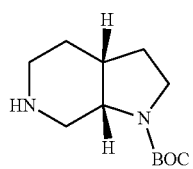

Tert-butyl pyrrolo[2,3-c]pyridine-1-carboxylate (P61) (1.00 g, 4.58 mmol) was dissolved in ethanol (8 ml) and acetic acid (8 ml) and passed through the H-Cube (0.5 ml/min, Controlled H$_2$, Rh/C cartridge, 60° C., 60 Bar), recycling reaction mixture for 3 hours. The solvent was concentrated under reduced pressure and the product purified by SCX to afford tert-butyl (3aR,7aS)-2,3,3a,4,5,6,7,7a-octahydropyrrolo[2,3-c]pyridine-1-carboxylate (P63) (976 mg).

Preparation 64 (P64)-tert-butyl (3aS,7aR)-2,3,3a,4,5,6,7,7a-octahydropyrrolo[3,2-c]pyridine-1-carboxylate

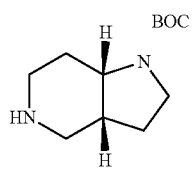

tert-butyl pyrrolo[3,2-c]pyridine-1-carboxylate (P62) (100 mg, 0.46 mmol) was dissolved in ethanol (8 ml) and acetic acid (8 ml) and passed through the H-Cube (0.5 ml/min, controlled H$_2$, Rh/C cartridge, 60° C., 60 Bar), recycling reaction mixture for 3% hours. The solution was concentrated under reduced pressure and the product purified by SCX (500 mg) to afford tert-butyl (3aS,7aR)-2,3,3a,4,5,6,7,7a-octahydropyrrolo[3,2-c]pyridine-1-carboxylate (P64) (50 mg).

Preparation 65 (P65)-6-benzyl-1-tert-butyl (3aR,7aS)-3,3a,4,5,7,7a-hexahydro-2H-pyrrolo[2,3-c]pyridine-1,6-dicarboxylate

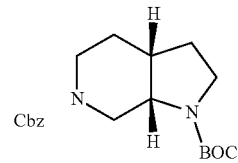

To a solution of tert-butyl (3aR,7aS)-2,3,3a,4,5,6,7,7a-octahydropyrrolo[2,3-c]pyridine-1-carboxylate (P63) (976 mg, 4.31 mmol) and triethylamine (0.72 ml, 5.17 mmol) in THF (15 ml) was added benzyl chloroformate (0.68 ml, 4.74 mmol) dropwise at 0° C. The reaction mixture was warmed to room temperature and stirred overnight. The reaction was quenched with sat. sodium bicarbonate solution, the volatiles removed under reduced pressure and the aqueous layer was washed with DCM. The organics were dried over magnesium sulfate and the solvent was removed under reduced pressure. The residue was chromatographed [SiO$_2$, 0-10% MeOH in DCM], then further chromatographed [SiO$_2$, 40-100% EtOAc in isohexane] to afford 6-benzyl-1-tert-butyl (3aR,7aS)-3,3a,4,5,7,7a-hexahydro-2H-pyrrolo[2,3-c]pyridine-1,6-dicarboxylate (P65) (900 mg), LCMS ES$^+$ 361 [M+H]$^+$, Rt=1.47 mins (Generic Basic Method).

Preparation 66 (P66)-5-benzyl-1-tert-butyl (3aS,7aR)-3,3a,4,6,7,7a-hexahydro-2H-pyrrolo[3,2-c]pyridine-1,5-dicarboxylate

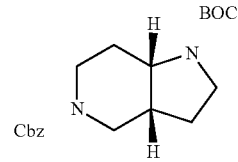

To a solution of tert-butyl (3aS,7aR)-2,3,3a,4,5,6,7,7a-octahydropyrrolo[3,2-c]pyridine-1-carboxylate (P64) (169 mg, 0.75 mmol) and triethylamine (0.12 ml, 0.90 mmol) in THF (4 ml) was added benzyl chloroformate (0.12 ml, 0.82 mmol) dropwise at 0° C. The reaction mixture was warmed to room temperature and stirred overnight. Further benzyl chloroformate (0.12 ml, 0.82 mmol) was added and stirring continued overnight. The reaction was quenched with sat. sodium bicarbonate solution, the volatiles were removed under reduced pressure and the aqueous layer was washed with DCM. The organics were dried over magnesium sulfate and the solvent was removed under reduced pressure. The residue was chromatographed [SiO$_2$, 40-100% EtOAC in isohexane] to afford 5-benzyl-1-tert-butyl (3aS,7aR)-3,3a,4,6,7,7a-hexahydro-2H-pyrrolo[3,2-c]pyridine-1,5-dicarboxylate (P66) (264 mg), LCMS ES$^+$ 305 [M+H-t-Bu]$^+$, Rt=1.44 mins (Generic Basic Method).

Preparation 67 (P67)-Benzyl (3aS,7aS)-1-methyl-3,3a,4,5,7,7a-hexahydro-2H-pyrrolo[2,3-c]pyridine-6-carboxylate

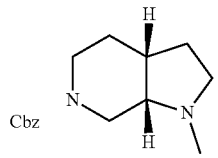

Formaldehyde solution ~37% in water (2.81 ml, 37.45 mmol) and formic acid (1.41 ml, 37.45 mmol) were added to a microwave vial equipped with stirrer bar containing 6-benzyl-1-tert-butyl (3aR,7aS)-3,3a,4,5,7,7a-hexahydro-2H-pyrrolo[2,3-c]pyridine-1,6-dicarboxylate (P65) (900 mg, 2.5 mmol) and heated to 110° C. for 20 minutes in the microwave. The reaction mixture was loaded onto a pre-acidified SCX cartridge, eluting with 2N $NH_3$ in MeOH. The basic liquors were concentrated under reduced pressure to afford benzyl (3aS,7aS)-1-methyl-3,3a,4,5,7,7a-hexahydro-2H-pyrrolo[2,3-c]pyridine-6-carboxylate (P67) (571 mg) as a clear oil, LCMS $ES^+$ 275 $[M+H]^+$, Rt=1.21 mins (Generic Basic Method).

Preparation 68 (P68)-Benzyl (3aS,7aR)-1-methyl-3,3a,4,6,7,7a-hexahydro-2H-pyrrolo[3,2-c]pyridine-5-carboxylate

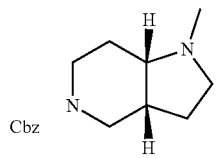

Formaldehyde solution ~37% in water (0.82 ml, 10.99 mmol) and formic acid (0.41 ml, 10.99 mmol) were added to a microwave vial equipped with stirrer bar containing 5-benzyl-1-tert-butyl (3aS,7aR)-3,3a,4,6,7,7a-hexahydro-2H-pyrrolo[3,2-c]pyridine-1,5-dicarboxylate (P66) (264 mg, 0.73 mmol). The reaction mixture was heated to 100° C. for 5 minutes in the microwave. A further 10 equivalents of formaldehyde solution and formic acid were added and the reaction heated for a further 5 minutes at 100° C. The reaction mixture was loaded onto a pre-acidified SCX cartridge, eluting with 2N $NH_3$ in MeOH. The basic liquors were concentrated under reduced pressure to afford benzyl (3aS,7aR)-1-methyl-3,3a,4,6,7,7a-hexahydro-2H-pyrrolo[3,2-c]pyridine-5-carboxylate (P68) (169 mg) as a clear oil, LCMS $ES^+$ 275 $[M+H]^+$, Rt=1.17 mins (Generic Basic Method).

Preparation 69 (P69)-(3aR,7aS)-1-Methyl-2,3,3a,4,5,6,7,7a-octahydropyrrolo[2,3-c]pyridine

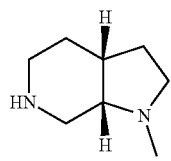

Benzyl (3aR,7aS)-1-methyl-3,3a,4,5,7,7a-hexahydro-2H-pyrrolo[2,3-c]pyridine-6-carboxylate (P67) (571 mg, 2.08 mmol) in ethanol (5 ml) was hydrogenated using H-Cube (10% Pd/C, Full $H_2$, 50° C., 1 ml/min), recycling for 4 hours. Solvent was removed under reduced pressure to afford (3aR,7aS)-1-methyl-2,3,3a,4,5,6,7,7a-octahydropyrrolo[2,3-c]pyridine (P69) (256 mg).

Preparation 70 (P70)-(3aS,7aR)-1-methyl-2,3,3a,4,5,6,7,7a-octahydropyrrolo[3,2-c]pyridine

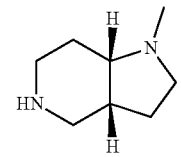

Benzyl (3aS,7aR)-1-methyl-3,3a,4,6,7,7a-hexahydro-2H-pyrrolo[3,2-c]pyridine-5-carboxylate (P68) (169 mg, 0.62 mmol) in ethanol (5 ml) was hydrogenated using H-Cube (10% Pd/C, Full $H_2$, 50° C., 1 ml/min) recycling for 4 hours. Solvent was removed under reduced pressure to afford (3aS,7aR)-1-methyl-2,3,3a,4,5,6,7,7a-octahydropyrrolo[3,2-c]pyridine (P70) (69 mg).

Preparation 71 (P71)-Benzyl N-(3-ethyl-3-piperidyl)carbamate

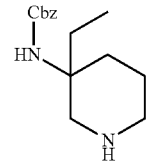

A solution of tert-butyl 3-(benzyloxycarbonylamino)-3-ethyl-piperidine-1-carboxylate (420.00 mg, 1.16 mmol) in DCM (5 ml) was stirred at room temperature. Trifluoroacetic acid (1.77 ml, 23.17 mmol) was added and the resulting solution was stirred at room temperature overnight. After this time, the solvent was removed under reduced pressure and the resulting residue was dissolved in MeOH and purified via SCX (20 g) to afford benzyl N-(3-ethyl-3-piperidyl)carbamate (P71) (314 mg), LCMS $ES^+$ 263 $[M+H]^+$, Rt=1.10 mins (Generic Basic Method).

Preparation 72 (P72)-Benzyl (3S)-3-(4-oxo-1-piperidyl)piperidine-1-carboxylate

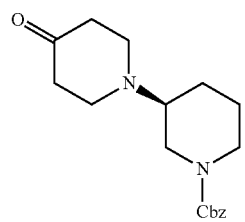

To a round bottomed flask containing stirrer bar was added potassium carbonate anhydrous (1.87 g, 13.53 mmol), benzyl (3S)-3-aminopiperidine-1-carboxylate (2.34 ml, 11.52 mmol), 1,5-dichloropentan-3-one (1.51 ml, 11.52 mmol) and MeCN (50 ml). The reaction stirred at reflux for a total of 24 hours. After this time, the volatiles were removed under reduced pressure and the crude material was re-dissolved in DCM and washed with water. The aqueous layer was washed again with DCM before the organics were combined, dried and concentrated under reduced pressure. The obtained residue was chromatographed [SiO$_2$, (0-10% 2N NH$_3$ in DCM:DCM) to give benzyl (3S)-3-(4-oxo-1-piperidyl)piperidine-1-carboxylate (P72) (1.03 g, 3.25 mmol, 28.2% yield) as a yellow oil, LCMS ES$^+$ 317 [M+H]$^+$, Rt=1.15 mins (Generic Basic Method).

Preparation 73 (P73)-Benzyl (3S)-3-(4-hydroxy-1-piperidyl)piperidine-1-carboxylate

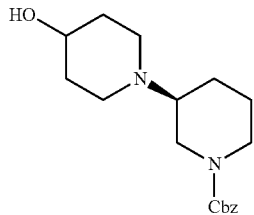 [SMILES: O=C(OCc1ccccc1)N1CCC[C@H](N2CCC(O)CC2)C1]

Sodium borohydride (95.65 mg, 2.53 mmol) was added portion-wise with stirring to benzyl (3S)-3-(4-oxo-1-piperidyl)piperidine-1-carboxylate (P72) (400.00 mg, 1.26 mmol) in methanol (6 ml) at 0° C. The reaction mixture was allowed to warm to room temperature and left to stir for 18 hours. Saturated ammonium chloride solution (5 ml) was added and the volatiles removed under reduced pressure. The aqueous residues were diluted with DCM (50 ml) and further water (10 ml) was added. The organics were combined before drying over magnesium sulfate, filtering and concentrating to give benzyl (3S)-3-(4-hydroxy-1-piperidyl)piperidine-1-carboxylate (P73) (115 mg, 0.88 mmol, 70% yield) as a pale oil, LCMS ES$^+$ 319.3 [M+H]$^+$, Rt=1.02 mins, Generic Basic Method.

Preparation 74 (P74)-Benzyl (3S)-3-(3-hydroxypyrrolidin-1-yl)piperidine-1-carboxylate

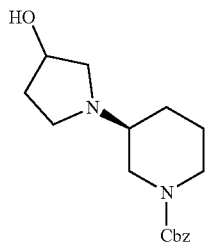

Potassium carbonate anhydrous (745.41 mg, 5.39 mmol), benzyl (3S)-3-aminopiperidine-1-carboxylate (486.00 mg, 2.07 mmol), 1,4-dibromobutan-2-ol (0.29 mL, 2.49 mmol) in MeCN (18 ml) was heated at reflux for 2 days before cooling to room temperature. The volatiles were removed under reduced pressure and the crude material obtained was re-dissolved in DCM (50 ml) and washed with water (40 ml). The organic portions were combined, dried and chromatographed [SiO$_2$, 0-6% 2N NH$_3$ in DCM:MeOH] to give benzyl (3S)-3-(3-hydroxypyrrolidin-1-yl)piperidine-1-carboxylate (P74) (310 mg, 0.97 mmol, 46.6% yield) obtained as a yellow oil, LCMS ES$^+$ 349.4 [M+H]$^+$, Rt=0.97 mins (Generic Basic Method).

Preparation 75 (P75)-Benzyl (3S)-3-(4-fluoro-1-piperidyl)piperidine-1-carboxylate

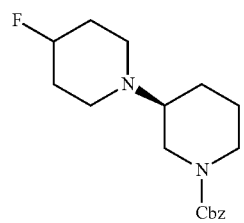 [SMILES: O=C(OCc1ccccc1)N1CCC[C@H](N2CCC(F)CC2)C1]

Benzyl (3S)-3-(4-hydroxy-1-piperidyl)piperidine-1-carboxylate (P73) (150 mg, 0.47 mmol) was dissolved in DCM (7.5 ml) at 0° C. and Deoxo-Fluor solution (0.24 ml, 0.57 mmol) was added dropwise with stirring. The resulting solution was allowed to warm to room temperature and left to stir for 18 hours. The reaction was quenched via the addition of saturated bicarbonate solution (10 ml) with vigorous stirring. The organics were concentrated in vacuo and the crude oil was chromatographed [SiO$_2$ eluting with 0-40%10% 2N NH$_3$ DCM:MeOH] to give benzyl (3S)-3-(4-fluoro-1-piperidyl)piperidine-1-carboxylate (P75) (78 mg, 0.24 mmol, 51.7% yield) as a pale yellow oil, LCMS ES$^+$ 321.3 [M+H]$^+$, Rt=1.33 mins (Generic Basic Method).

Preparation 76 (P76)-Benzyl (3S)-3-(3-fluoropyrrolidin-1-yl)piperidine-1-carboxylate

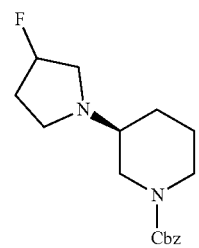 [SMILES: O=C(OCc1ccccc1)N1CCC[C@H](N2CCC(F)C2)C1]

Benzyl (3S)-3-(3-hydroxypyrrolidin-1-yl)piperidine-1-carboxylate (P74) (155.00 mg, 0.51 mmol) was dissolved in DCM (2.5 ml) at 0° C. and Deoxo-Fluor solution (0.26 ml, 0.61 mmol) was added. The resulting solution was allowed to warm to room temperature for 18 hours. The reaction was quenched via the addition of saturated bicarbonate (3 ml) and the organics were concentrated under reduced pressure to afford a brown coloured oil. The oil was chromatographed [SiO$_2$, 0-6% 2N NH$_3$ in MeOH:DCM] to give benzyl (3S)-3-(3-fluoropyrrolidin-1-yl)piperidine-1-carboxylate (P76) (100 mg) a pale brown coloured oil, LCMS ES$^+$ 307.3 [M+H]$^+$, Rt=1.25 mins (Generic Basic Method).

Preparation 77 (P77)-Benzyl (3S)-3-[4-[tert-butyl(diphenyl)silyl]oxy-1-piperidyl]piperidine-1-carboxylate

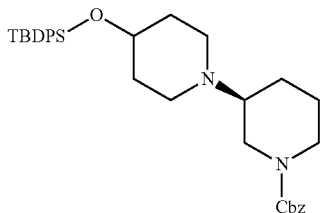

Benzyl (3S)-3-(4-hydroxy-1-piperidyl)piperidine-1-carboxylate (P73) (148.00 mg, 0.46 mmol), triethylamine (0.13 ml, 0.93 mmol) and 4-(dimethylamino)pyridine (5.68 mg, 0.05 mmol) were stirred at 0° C. in DCM (2 ml). Tert-butyl (chloro) diphenylsilane (0.15 mL, 0.56 mmol) was added dropwise with stirring. The solution was warmed to room temperature and stirred for a further 16 hours. The reaction mixture was quenched via the addition of water and the organic layer was concentrated to afford benzyl (3S)-3-[4-[tert-butyl(diphenyl)silyl]oxy-1-piperidyl] piperidine-1-carboxylate (P77) (400 mg, 0.72 mmol) as a pale oil, LCMS ES+ 557.5 [M+H]+, Rt=1.64 mins, Generic Basic Method.

Preparation 78 (P78)-Benzyl (3S)-3-[3-[tert-butyl(diphenyl)silyl]oxypyrrolidin-1-yl]piperidine-1-carboxylate

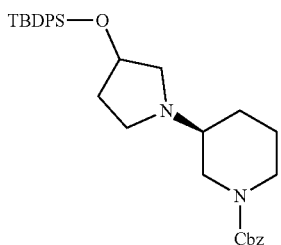

Benzyl (3S)-3-(3-hydroxypyrrolidin-1-yl)piperidine-1-carboxylate (P74) (155.00 mg, 0.51 mmol), triethylamine (0.14 ml, 1.02 mmol) and 4-(dimethylamino)pyridine (6.22 mg, 0.05 mmol) in DCM (2.5 ml) was stirred at 0° C. and tert-butyl(chloro)diphenyl silane (0.16 ml, 0.61 mmol) was added dropwise. The solution was warmed to room temperature and stirred overnight. The reaction mixture was quenched via the addition of water (5 ml), further DCM (20 ml) was added and the organics were concentrated to afford a pale yellow oil which was chromatographed [SiO2, 0-50% EtOAc:iso-hexane] to afford benzyl (3S)-3-[3-[tert-butyl(diphenyl)silyl]oxypyrrolidin-1-yl]piperidine-1-carboxylate (P78) (200 mg, 0.35 mmol, 68.7% yield) as a pale yellow oil, LCMS ES+ 543.6 [M+H]+, Rt=1.54 mins (Generic Basic Method).

Preparation 79 (P79)-tert-butyl (3S)-3-(azetidin-1-yl)piperidine-1-carboxylate

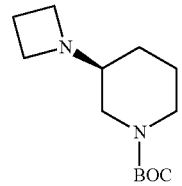 [SMILES: CC(C)(C)OC(=O)N1CCC[C@H](N2CCC2)C1]

(S)-3-Amino-1-N-Boc-piperidine (500.00 mg, 2.50 mmol), 1,3-dibromopropane (0.33 mL, 3.25 mmol), potassium carbonate anhydrous (897.11 mg, 6.49 mmol) were dissolved in MeCN (23 ml) and heated at reflux overnight before cooling to room temperature. The volatiles were removed under reduced pressure, dissolved in EtOAc (50 ml) and washed with saturated sodium bicarbonate solution (40 ml). The organic portion was dried and purified via flash silica chromatography eluting with 0-6% MeOH:DCM to give tert-butyl (3S)-3-(azetidin-1-yl)piperidine-1-carboxylate (P79) (404 mg, 1.68 mmol, 67.3% yield) obtained as a yellow oil, LCMS ES+ 241 [M+H]+, Rt=1.13 mins (Generic Basic Method).

Preparation 80 (P80)-tert-butyl (3S)-3-(1-piperidyl)piperidine-1-carboxylate

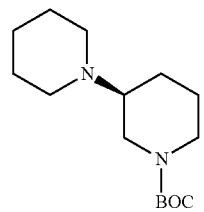 [SMILES: CC(C)(C)OC(=O)N1CCC[C@H](N2CCCCC2)C1]

(S)-3-Amino-1-N-Boc-piperidine (615.00 mg, 3.07 mmol), anhydrous potassium carbonate (1103.44 mg, 7.98 mmol) and 1,5-dibromopentane (0.54 ml, 3.99 mmol) were dissolved in MeCN (25 ml) and heated at reflux overnight before cooling to room temperature. The organics were removed under reduced pressure before being dissolved in EtOAc (50 ml) and washed with 2N NaOH (40 ml). The organics were concentrated under reduced pressure and the residue was purified via flash silica chromatography, eluting with 0-6% MeOH:DCM, to give tert-butyl (3S)-3-(1-piperidyl) piperidine-1-carboxylate (P80) (609 mg, 2.04 mmol, 66.5% yield) obtained as a yellow oil, LCMS ES+ 269 [M+H]+, Rt=1.37 mins (Generic Basic Method).

Preparation 81 (P81)-Benzyl (3R)-3-methylsulfonyloxypiperidine-1-carboxylate

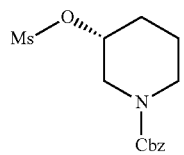 [SMILES: CS(=O)(=O)O[C@@H]1CCCN(C(=O)OCc2ccccc2)C1]

Benzyl (3R)-3-hydroxypiperidine-1-carboxylate (1.44 g, 6.12 mmol) and triethylamine (1.7 mL, 12.23 mmol) were dissolved in DCM (20 mL) and cooled to 0° C. and methanesulfonyl chloride (0.57 mL, 7.34 mmol) was added dropwise with stirring. The reaction mixture was allowed to warm to room temperature overnight. The volatiles were removed under reduced pressure and the resulting residue purified via silica chromatography, eluting with 0-70% EtOAc:iso-hexane, to give benzyl (3R)-3-methylsulfonyloxypiperidine-1-carboxylate (P81) (1.7 g, 5.1537 mmol, 84.263% yield) as a colourless oil, LCMS ES+ 314.2 [M+H]+, Rt=1.17 mins (Generic Basic Method).

Preparation 82 (P82)-Benzyl (3S)-3-pyrrolidin-1-ylpiperidine-1-carboxylate

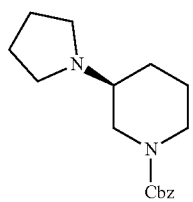 [SMILES: O=C(OCc1ccccc1)N1CCC[C@H](N2CCCC2)C1]

Benzyl (3R)-3-methylsulfonyloxypiperidine-1-carboxylate (P81) (400.00 mg, 1.28 mmol) and pyrrolidine (2.13 ml, 25.53 mmol) were heated to 100° C. for 1½ hours after which time the mixture was cooled, and purified via column chromatography on silica, eluting with 0-6% DCM:MeOH, to give benzyl (3S)-3-pyrrolidin-1-ylpiperidine-1-carboxylate (P82) (120 mg, 0.42 mmol, 32.6% yield) as a yellow oil.

Preparation 83 (P83)-tert-butyl-diphenyl-[[1-[(3S)-3-piperidyl]-4-piperidyl]oxy]silane

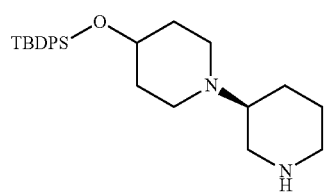

Benzyl (3S)-3-[4-[tert-butyl(diphenyl)silyl]oxy-1-piperidyl]piperidine-1-carboxylate (P77) (400.00 mg, 0.72 mmol) in ethanol (14 ml) was passed through the H-Cube (1 ml/min, Full H₂, 10% Pd/C cartridge at 50° C.) The ethanol eluent was concentrated under reduced pressure to afford tert-butyl-diphenyl-[[1-[(3S)-3-piperidyl]-4-piperidyl]oxy]silane (P83) (280 mg, 0.66 mmol, 92.2% yield) as a colourless oil, LCMS ES+ 423.4 [M+H]+, Rt=1.56 mins (Generic Basic Method).

The following compounds were prepared in a similar manner to tert-butyl-diphenyl-[[1-[(3S)-3-piperidyl]-4-piperidyl]oxy]silane (P83) using the appropriate intermediates:

| Preparation | Structure | Name | LCMS Data |
|---|---|---|---|
| P84 | 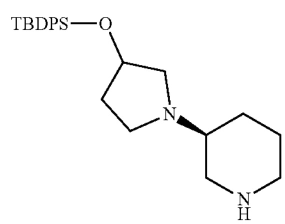 | tert-butyl-diphenyl-[1-[(3S)-3-piperidyl]pyrrolidin-3-yl]oxy-silane | ES+ 409 [M + H]+<br>Rt = 1.45 mins,<br>Generic Basic Method |
| P85 | 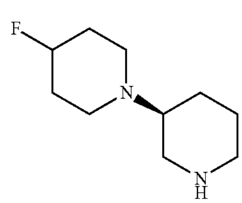 [SMILES: FC1CCN([C@H]2CCCNC2)CC1] | 4-fluoro-1-[(3S)-3-piperidyl]piperidine | ES+ 187 [M + H]+<br>Rt = 0.64 mins,<br>Generic Basic Method |
| P86 | 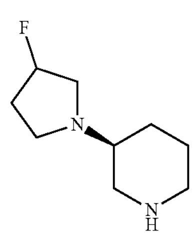 [SMILES: FC1CCN([C@H]2CCCNC2)C1] | (3S)-3-(3-fluoropyrrolidin-1-yl)piperidine | ES+ 172 [M + H]+<br>Rt = 0.71 mins,<br>Generic Basic Method |

Preparation 87 (P87)-tert-butyl-diphenyl-[[(3S)-3-piperidyl]oxy]silane

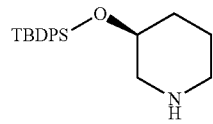

(3S)-piperidin-3-ol hydrochloride (500.00 mg, 3.63 mmol), silver nitrate (1.234 g, 7.27 mmol) and tert-butyl (chloro) diphenylsilane (0.94 ml, 3.63 mmol) was dissolved in pyridine (1.5 ml) and THF (2 ml) and stirred at room temperature overnight (16 h). The precipitate was removed via filtration and the organic liquors were collected and washed with water (30 ml). The solution was concentrated under reduced pressure and purified via flash silica chromatography, eluting with 0-100% 10% MeOH DCM+0.4% 2N NH3:DCM, to give tert-butyl-diphenyl-[[(3S)-3-piperidyl]oxy]silane (P87) (346 mg, 1.02 mmol, 28% yield) as a pale yellow oil, LCMS ES⁺ 340.3 [M+H]⁺, Rt=1.18 mins (Generic Basic Method).

The following compounds were prepared in a similar manner to tert-butyl-diphenyl-[[(3S)-3-piperidyl]oxy]silane (P87) from appropriate intermediates:

| Preparation | Structure | Name | LCMS Data |
|---|---|---|---|
| P88 | TBDPS-O-piperidine structure | tert-butyl-diphenyl-[[(3ft)-3-piperidyl]oxy]silane | ES⁺ 340 [M + H]⁺ Rt = 1.19 mins, Late Basic Method |

Preparation 89 (P89)-4-[(3S)-3-piperidyl]morpholine

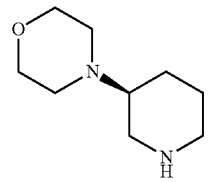 [SMILES: C1CNC[C@@H](N2CCOCC2)C1]

Tert-butyl (3S)-3-morpholinopiperidine-1-carboxylate (40.00 mg, 0.15 mmol) was dissolved in DCM (1 ml) and trifluoroacetic acid (0.23 ml, 2.96 mmol) was added. The volatiles were removed under reduced pressure to afford an orange liquid. The crude product was purified with an SCX cartridge (10 g) and washed with MeOH (5 cv) before eluting with 2N NH₃ in MeOH. The basic liquor was concentrated to afford 4-[(3S)-3-piperidyl] morpholine (P89) (24 mg, 0.14 mmol, 95.3% yield) as a yellow oil.

The following compounds were prepared in a similar manner to 4-[(3S)-3-piperidyl]morpholine (P89) from the appropriate intermediates:

| Preparation | Structure | Name | LCMS Data |
|---|---|---|---|
| P90 | azetidine-piperidine structure | (3S)-3-(azetidin-1-yl)piperidine | |
| P91 | piperidine-piperidine structure | 1-[(3S)-3-piperidyl]piperidine | ES⁺ 349 [M + H]⁺ Rt = 0.49 mins, Late Basic Method |

| Preparation | Structure | Name | LCMS Data |
|---|---|---|---|
| P92 | 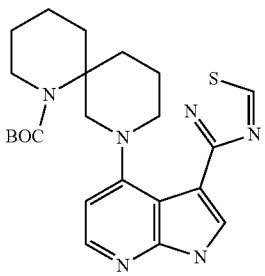 | (3S)-3-pyrrolidin-1-ylpiperidine | |

Preparation 93 (P93)-tert-butyl 8-[3-(1,2,4-thiadiazol-3-yl)-1-(2-trimethylsilylethoxymethyl)pyrrolo[2,3-b]pyridin-4-yl]-1,8-diazaspiro[5.5]undecane-1-carboxylate

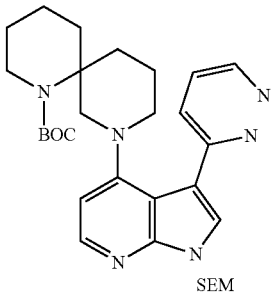

A solution of tert-butyl-1,8-diazaspiro[5.5]undecane-1-carboxylate (790.92 mg, 3.11 mmol), triethylamine (0.43 mL, 3.11 mmol) and ethyl 3-[4-chloro-1-(2-trimethylsilylethoxymethyl)pyrrolo[2,3-b]pyridin-3-yl]-1,2,4-thiadiazole-5-carboxylate (P20) (455.00 mg, 1.04 mmol) in NMP (3 ml) was heated to 160° C. for 3 hours. After this time, the reaction mixture was loaded onto a pre-acidified 10 g SCX cartridge and washed with MeOH (×6 cvs). Product was released following washing with $NH_3$ in MeOH (2N). The basic fractions were concentrated under reduced pressure and purified by silica column chromatography eluting with 0-100% 10% 2N $NH_3$ in MeOH in DCM:DCM to give tert-butyl 8-[3-(1,2,4-thiadiazol-3-yl)-1-(2-trimethylsilylethoxymethyl)pyrrolo[2,3-b]pyridin-4-yl]-1,8-diazaspiro[5.5]undecane-1-carboxylate (P93) (244 mg, 0.42 mmol, 40.3% yield), LCMS ES' 585 [M+H]$^+$, Rt=1.83 mins (Generic Basic Method).

Preparation 94 (P94)-tert-butyl 8-[3-pyridazin-3-yl-1-(2-trimethylsilylethoxymethyl)pyrrolo[2,3-b]pyridin-4-yl]-1,8-diazaspiro[5.5]undecane-1-carboxylate

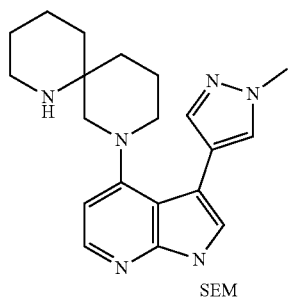

A solution of 2-[(4-chloro-3-pyridazin-3-yl-pyrrolo[2,3-b]pyridin-1-yl)methoxy]ethyl-trimethyl-silane (P39) (500 mg, 1.39 mmol), tert-butyl-1,8-diazaspiro[5.5]undecane-1-carboxylate (704.8 mg, 2.77 mmol) and potassium carbonate (191.47 mg, 1.39 mmol) in anhydrous 1-Butanol (8 ml) was heated to 170° C. for 7 hours. The reaction was repeated and the solutions allowed to cool to room temperature before being combined and concentrated under reduced pressure. The resulting oil was diluted with EtOAc (100 ml) and washed with water (50 ml). The water layer was washed a further time with EtOAc (100 ml). The organics were combined and dried to afford crude product. The residue was chromatographed [$SiO_2$, 50-100% EtOAc in isohexane) to afford tert-butyl 8-[3-pyridazin-3-yl-1-(2-trimethylsilylethoxymethyl)pyrrolo[2,3-b]pyridin-4-yl]-1,8-diazaspiro[5.5]undecane-1-carboxylate (P94) (660 mg, 1.14 mmol), LCMS ES$^+$ 579 [M+H]$^+$, Rt=1.45 mins (Generic Acidic Method).

Preparation 95 (P95)-2-[[4-(1,8-diazaspiro[5.5]undecan-8-yl)-3-(1-methylpyrazol-4-yl)pyrrolo[2,3-b]pyridin-1-yl]methoxy]ethyl-trimethyl-silane A solution of 2-[[4-chloro-3-(1-methylpyrazol-4-yl)pyrrolo[2,3-b]pyridin-1-yl]methoxy]ethyl-trimethyl-silane (P40) (392.00 mg, 1.08 mmol), tert-butyl-1,8-diazaspiro[5.5]undecane-1-carboxylate (412.12 mg, 1.62 mmol) and potassium carbonate, anhydrous (223.92 mg, 1.62 mmol) in 1-Butanol (1 ml) was heated to 170° C. for 6 days. After this time, further tert-butyl-1,8-diazaspiro[5.5]undecane-1-carboxylate (412.12 mg, 1.62 mmol) and 1-Butanol (1 ml) was added and the resulting mixture was then heated at 175° C. for a further 4 days. The reaction was cooled to room temperature and concentrated under reduced pressure to give a dark brown oil. The oil was diluted with EtOAc (100 ml) and washed with water (50 ml). The water layer was extracted with EtOAc (2×50 ml). The combined organics were washed with brine, dried over $MgSO_4$, filtered and concentrated under reduced pressure to give crude product as a dark orange coloured oil. The oil was chromatographed [$SiO_2$, 0-100% (10% 2N $NH_3$/MeOH in DCM):DCM] to give 2-[[4-(1,8-diazaspiro[5.5]undecan-8-yl)-3-(1-methylpyrazol-4-yl)pyrrolo[2,3-b]pyridin-1-yl]methoxy]ethyl-trimethyl-silane (P95) (237 mg, 0.47 mmol), LCMS ES$^+$ 481 [M+H]$^+$, Rt=1.41 mins (Generic Basic Method).

The following compounds were prepared in a similar manner to 2-[[4-(1,8-diazaspiro[5.5]undecan-8-yl)-3-(1-methylpyrazol-4-yl)pyrrolo[2,3-b]pyridin-1-yl]methoxy]ethyl-trimethyl-silane (P95) using the appropriate intermediate:

| Preparation | Structure | Name | LCMS Data |
|---|---|---|---|
| P96 | 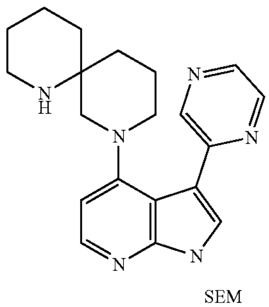 | 2-[[4-(1,8-diazaspiro[5.5]undecan-8-yl)-3-pyrazin-2-yl-pyrrolo[2,3-b]pyridin-1-yl]methoxy]ethyl-trimethyl-silane | ES+ 479 [M + H]+ Rt = 1.42 mins, Generic Basic Method |

Preparation 97 (P97)-2-[[4-(2,6-diazaspiro[4.5]decan-2-yl)-3-(1,2,4-thiadiazol-3-yl)pyrrolo[2,3-b]pyridin-1-yl]methoxy]ethyl-trimethyl-silane

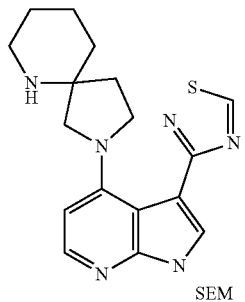

A solution of tert-butyl 2,6-diazaspiro[4.5]decane-6-carboxylate (190.60 mg, 0.79 mmol), triethylamine (0.11 ml, 0.79 mmol), ethyl 3-[4-chloro-1-(2-trimethylsilylethoxymethyl)pyrrolo[2,3-b]pyridin-3-yl]-1,2,4-thiadiazole-5-carboxylate (P20) (116.05 mg, 0.26 mmol) in NMP (1 ml) was heated at 180° C. in the microwave for a total of 6 hours. After this time, the reaction mixture was loaded onto a pre-acidified SCX cartridge (5 g) and washed with MeOH (×6 cvs). The product was released via treatment with NH₃ in MeOH (2N) and dried to give a dark orange coloured oil. The oil was chromatographed [SiO₂ eluting with 0-10% (10% 2N NH₃ in MeOH):DCM] to give 2-[[4-(2,6-diazaspiro[4.5]decan-2-yl)-3-(1,2,4-thiadiazol-3-yl)pyrrolo[2,3-b]pyridin-1-yl]methoxy]ethyl-trimethyl-silane (P97), LCMS ES+ 471 [M+H]+, Rt=1.39 mins (Generic Basic Method).

Preparation 98 (P98)-2-[[4-(1,8-diazaspiro[5.5]undecan-8-yl)-3-pyrimidin-4-yl-pyrrolo[2,3-b]pyridin-1-yl]methoxy]ethyl-trimethyl-silane

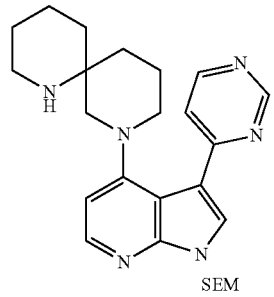

A solution of 2-[(4-chloro-3-pyrimidin-4-yl-pyrrolo[2,3-b]pyridin-1-yl)methoxy]ethyl-trimethyl-silane (P22) (1.00 g, 2.77 mmol), tert-butyl-1,8-diazaspiro[5.5]undecane-1-carboxylate (2.114 g, 8.31 mmol), triethylamine (1.54 ml, 11.08 mmol) and NMP (28 mL) and heated at 130° C. for 3 hours. The reaction was repeated a further 6 times. After this time, the 7 solutions were subsequently heated at 180° C. for a further 6 hours (to remove Boc protecting group). Each of the 7 reaction mixtures were loaded onto a pre-acidified 20 g SCX cartridge. The cartridges were washed with MeOH (5 cv's). Crude product was released following washing with NH₃ in MeOH (2N). The basic fractions were combined and dried to give a dark coloured oil. The oil was chromatographed [SiO₂, eluting with 10-70% (10% 2N NH₃ in MeOH in DCM):DCM]. The residue was further chromatographed [SiO₂, eluting with 10-40% (10% 2N NH₃ in MeOH in DCM):DCM to give 2-[[4-(1,8-diazaspiro[5.5]undecan-8-yl)-3-pyrimidin-4-yl-pyrrolo[2,3-b]pyridin-1-yl]methoxy]ethyl-trimethyl-silane (P98) (3.232 g), as a dark orange coloured oil LCMS ES' 479 [M+H]+, Rt=1.38 mins (Generic Basic Method). 2-[[4-(1,8-diazaspiro[5.5]undecan-8-yl)-3-pyrimidin-4-yl-pyrrolo[2,3-b]pyridin-1-yl]methoxy]ethyl-trimethyl-silane (P98) (3.232 g) was subsequently purified by chiral HPLC (Chiralpak OD, 250×20 mm, 5 um, eluting with MeCN/IPA, with DEA as a modifier) to give; 2-[[4-[(6R)-1,8-diazaspiro[5.5]undecan-8-yl]-3-pyrimidin- 4-yl-pyrrolo[2,3-b]pyridin-1-yl]methoxy]ethyl-trimethyl-silane (P99) and 2-[[4-[(6S)-1,8-diazaspiro[5.5]undecan-8-yl]-3-pyrimidin-4-yl-pyrrolo[2,3-b]pyridin-1-yl]methoxy]ethyl-trimethyl-silane (P100).

Preparation 101 (P101)-2-[[4-(1,8-diazaspiro[5.5]undecan-8-yl)-3-pyrimidin-5-yl-pyrrolo[2,3-b]pyridin-1-yl]methoxy]ethyl-trimethyl-silane

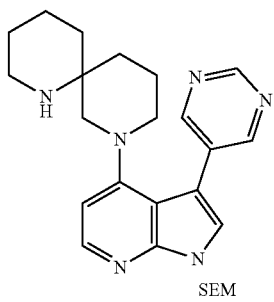

A solution of 2-[(4-chloro-3-pyrimidin-5-yl-pyrrolo[2,3-b]pyridin-1-yl)methoxy]ethyl-trimethyl-silane (P23) (1.00 g, 2.77 mmol), tert-butyl-1,8-diazaspiro[5.5]undecane-1-carboxylate (2.819 g, 11.08 mmol), triethylamine (1.54 mL, 11.08 mmol) in NMP (8 mL) was heated to 180° C. for 24 hours. The reaction was repeated (×5).

Each individual reaction mixture was loaded onto a pre-acidified 20 g SCX cartridge. The cartridge was washed with MeOH and then NH₃ in MeOH (2N soln.). The basic fractions were concentrated under reduced pressure and the residue obtained was chromatographed [SiO₂, 0-80% (10% 2N NH₃ in DCM): DCM] to give 2-[[4-(1,8-diazaspiro[5.5]undecan-8-yl)-3-pyrimidin-5-yl-pyrrolo[2,3-b]pyridin-1-yl]methoxy]ethyl-trimethyl-silane (P101) (5.350 g, 11.18 mmol), as a dark coloured oil, LCMS ES⁺ 479 [M+H]⁺, Rt=1.40 mins (Generic Basic Method) 2-[[4-(1,8-diazaspiro[5.5]undecan-8-yl)-3-pyrimidin-5-yl-pyrrolo[2,3-b]pyridin-1-yl]methoxy]ethyl-trimethyl-silane (P101) (5.350 g, 11.18 mmol) was subsequently purified by HPLC (Lux C1, 250× 20 mm, 5um, eluting with MeCN, with TEA as a modifier) to give; 2-[[4-[(6R)-1,8-diazaspiro[5.5]undecan-8-yl]-3-pyrimidin-5-yl-pyrrolo[2,3-b]pyridin-1-yl]methoxy]ethyl-trimethyl-silane (P102) and 2-[[4-[(6S)-1,8-diazaspiro[5.5]undecan-8-yl]-3-pyrimidin-5-yl-pyrrolo[2,3-b]pyridin-1-yl]methoxy]ethyl-trimethyl-silane (P113).

The following compounds were prepared in a similar manner to above using the appropriate amine and intermediate:

| Preparation | Structure | Name | LCMS Data |
|---|---|---|---|
| P104 | 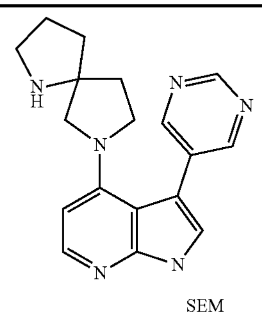 | 2-[[4-(1,7-diazaspiro[4.4]nonan-7-yl)-3-pyrimidin-5-yl-pyrrolo[2,3-b]pyridin-1-yl]methoxy]ethyl-trimethyl-silane | ES⁺ 451 [M + H]⁺ Rt = 1.30 mins, Generic Basic Method |
| P105 | 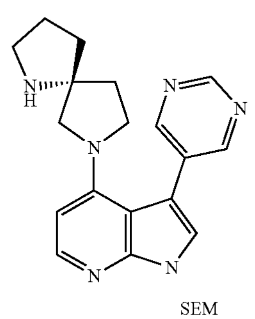 [SMILES: c1ncc(-c2c[nH]c3nccc(N4CC[C@]5(CCCN5)C4)c23)cn1 ; "SEM"] | 2-[[4-[(5R)-1,7-diazaspiro[4.4]nonan-7-yl]-3-pyrimidin-5-yl-pyrrolo[2,3-b]pyridin-1-yl]methoxy]ethyl-trimethyl-silane | |
| P106 | 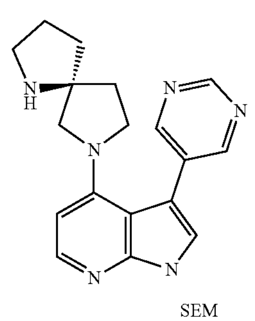 [SMILES: c1ncc(-c2c[nH]c3nccc(N4CC[C@@]5(CCCN5)C4)c23)cn1 ; "SEM"] | 2-[[4-[(5S)-1,7-diazaspiro[4.4]nonan-7-yl]-3-pyrimidin-5-yl-pyrrolo[2,3-b]pyridin-1-yl]methoxy]ethyl-trimethyl-silane | |

-continued

| Preparation | Structure | Name | LCMS Data |
|---|---|---|---|
| P107 | 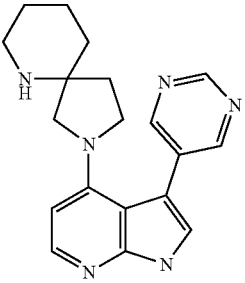 | 2-[[4-(2,6-diazaspiro[4.5]decan-2-yl)-3-pyrimidin-5-yl-pyrrolo[2,3-b]pyridin-1-yl]methoxy]ethyl-trimethyl-silane | ES+ 465 [M + H]+ Rt = 1.34 mins, Generic Basic Method |
| P108 | 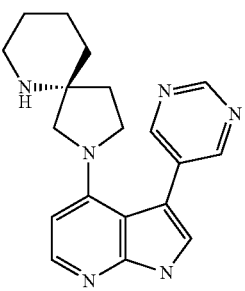 | 2-[[4-[(5R)-2,6-diazaspiro[4.5]decan-2-yl]-3-pyrimidin-5-yl-pyrrolo[2,3-b]pyridin-1-yl]methoxy]ethyl-trimethyl-silane | |
| P109 | 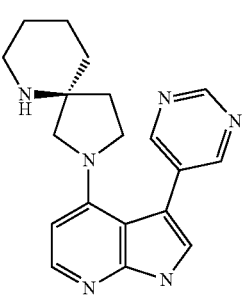 | 2-[[4-[(5S)-2,6-diazaspiro[4.5]decan-2-yl]-3-pyrimidin-5-yl-pyrrolo[2,3-b]pyridin-1-yl]methoxy]ethyl-trimethyl-silane | |
| P110 | 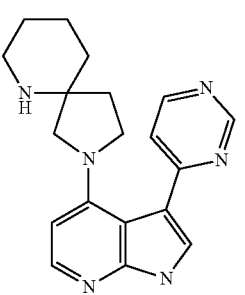 | 2-[[4-(2,6-diazaspiro[4.5]decan-2-yl)-3-pyrimidin-4-yl-pyrrolo[2,3-b]pyridin-1-yl]methoxy]ethyl-trimethyl-silane | ES+ 341 [M + H]+ Rt = 0.83 mins, Generic Basic Method |
| P111 | 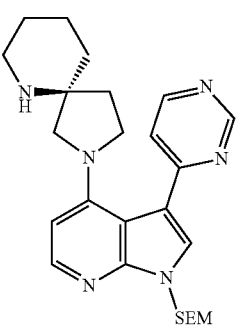 [SMILES: C[Si](C)(C)CCOCn1cc(-c2ccncn2)c2c(N3CC[C@@]4(CCCCN4)C3)ccnc21] | 2-[[4-[(5S)-2,6-diazaspiro[4.5]decan-2-yl]-3-pyrimidin-4-yl-pyrrolo[2,3-b]pyridin-1-yl]methoxy]ethyl-trimethyl-silane | |

-continued

| Preparation | Name | LCMS Data |
|---|---|---|
| P112 | 2-[[4-[(5R)-2,6-diazaspiro[4.5]decan-2-yl]-3-pyrimidin-4-yl-pyrrolo[2,3-b]pyridin-1-yl]methoxy]ethyl-trimethyl-silane | |
| P113 | 4-(2,6-diazaspiro[4.5]decan-2-yl)-1-(2-trimethylsilylethoxymethyl)pyrrolo[2,3-b]pyridine-3-carbonitrile | ES+ 412 [M + H]+<br>Rt = 1.47 mins,<br>Generic Basic Method |
| P114 | 4-(1,7-diazaspiro[4.4]nonan-7-yl)-1-(2-trimethylsilylethoxymethyl)pyrrolo[2,3-b]pyridine-3-carbonitrile | ES+ 398 [M + H]+<br>Rt = 1.40 mins,<br>Generic Basic Method |
| P115 | 2-[[4-(1,8-diazaspiro[5.5]undecan-8-yl)-3-(5-methylthiazol-2-yl)pyrrolo[2,3-b]pyridin-1-yl]methoxy]ethyl-trimethyl-silane | ES+ 498 [M + H]+<br>Rt = 1.33 mins,<br>Generic Basic Method |
| P116 | 2-[[4-[(6R)-1,8-diazaspiro[5.5]undecan-8-yl]-3-(5-methylthiazol-2-yl)pyrrolo[2,3-b]pyridin-1-yl]methoxy]ethyl-trimethyl-silane | |

-continued

| Preparation | Structure | Name | LCMS Data |
|---|---|---|---|
| P117 | 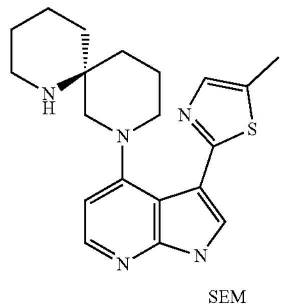 [SMILES: Cc1cnc(-c2c[nH]c3nccc(N4CCC[C@@]5(CCCCN5)C4)c23)s1 ; "SEM"] | 2-[[4-[(6S)-1,8-diazaspiro[5.5]undecan-8-yl]-3-(5-methylthiazol-2-yl)pyrrolo[2,3-b]pyridin-1-yl]methoxy]ethyl-trimethyl-silane | |
| P118 | 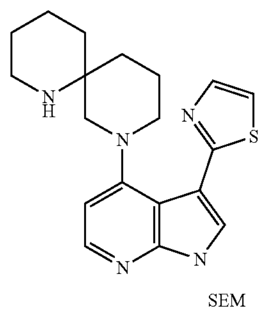 [SMILES: c1csc(-c2c[nH]c3nccc(N4CCCC5(CCCCN5)C4)c23)n1 ; "SEM"] | 2-[[4-(1,8-diazaspiro[5.5]undecan-8-yl)-3-thiazol-2-yl-pyrrolo[2,3-b]pyridin-1-yl]methoxy]ethyl-trimethyl-silane | ES+ 484 [M + H]+<br>Rt = 1.54 mins,<br>Generic Basic Method |
| P119 | 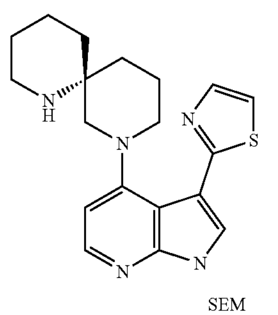 [SMILES: c1csc(-c2c[nH]c3nccc(N4CCC[C@]5(CCCCN5)C4)c23)n1 ; "SEM"] | 2-[[4-[(6R)-1,8-diazaspiro[5.5]undecan-8-yl]-3-thiazol-2-yl-pyrrolo[2,3-b]pyridin-1-yl]methoxy]ethyl-trimethyl-silane | |
| P120 | 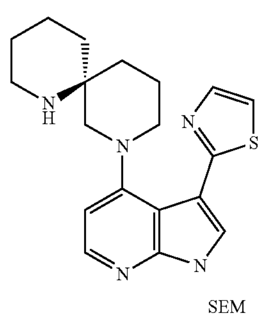 [SMILES: c1csc(-c2c[nH]c3nccc(N4CCC[C@@]5(CCCCN5)C4)c23)n1 ; "SEM"] | 2-[[4-[(6S)-1,8-diazaspiro[5.5]undecan-8-yl]-3-thiazol-2-yl-pyrrolo[2,3-b]pyridin-1-yl]methoxy]ethyl-trimethyl-silane | |
| P121 | 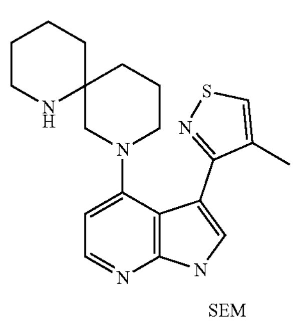 | 2-[[4-(1,8-diazaspiro[5.5]undecan-8-yl)-3-(4-methylisothiazol-3-yl)pyrrolo[2,3-b]pyridin-1-yl]methoxy]ethyl-trimethyl-silane | ES+ 498 [M + H]+<br>Rt = 1.54 mins,<br>Generic Basic Method |

-continued

| Preparation | Structure | Name | LCMS Data |
|---|---|---|---|
| P122 | 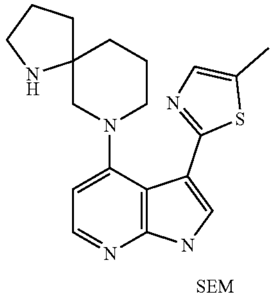 | 2-[[4-(1,9-diazaspiro[4.5]decan-9-yl)-3-(5-methylthiazol-2-yl)pyrrolo[2,3-b]pyridin-1-yl]methoxy]ethyl-trimethyl-silane | ES+ 484 [M + H]+ Rt = 1.50 mins, Generic Basic Method |
| P123 | 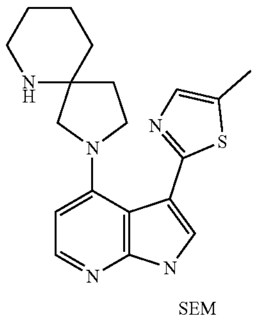 | 2-[[4-(2,6-diazaspiro[4.5]decan-2-yl)-3-(5-methylthiazol-2-yl)pyrrolo[2,3-b]pyridin-1-yl]methoxy]ethyl-trimethyl-silane | ES+ 484 [M + H]+ Rt = 1.52 mins, Generic Basic Method |
| P124 | 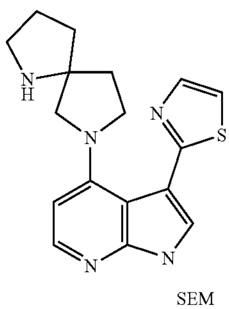 [SMILES: c1csc(-c2c[nH]c3nccc(N4CCC5(CCCN5)C4)c23)n1 ; "SEM"] | 2-[[4-(1,7-diazaspiro[4.4]nonan-7-yl)-3-thiazol-2-yl-pyrrolo[2,3-b]pyridin-1-yl]methoxy]ethyl-trimethyl-silane | ES+ 456 [M + H]+ Rt = 1.35 mins, Generic Basic Method |
| P125 | 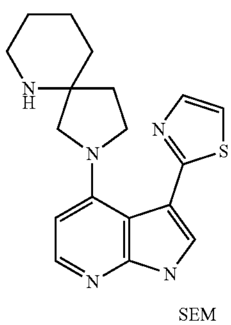 [SMILES: c1csc(-c2c[nH]c3nccc(N4CCC5(CCCCN5)C4)c23)n1 ; "SEM"] | 2-[[4-(2,6-diazaspiro[4.5]decan-2-yl)-3-thiazol-2-yl-pyrrolo[2,3-b]pyridin-1-yl]methoxy]ethyl-trimethyl-silane | ES+ 470 [M + H]+ Rt = 1.44 mins, Generic Basic Method |
| P126 | 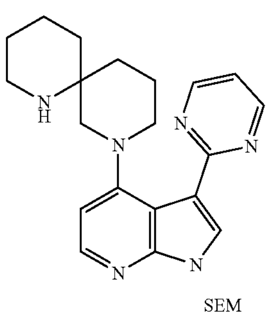 [SMILES: c1cnc(-c2c[nH]c3nccc(N4CCCC5(CCCCN5)C4)c23)nc1 ; "SEM"] | 2-[[4-(1,8-diazaspiro[5.5]undecan-8-yl)-3-pyrimidin-2-yl-pyrrolo[2,3-b]pyridin-1-yl]methoxy]ethyl-trimethyl-silane | ES+ 479 [M + H]+ Rt = 1.43 mins, Generic Basic Method |

-continued

| Preparation | Structure | Name | LCMS Data |
|---|---|---|---|
| P127 | 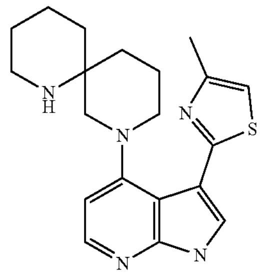 | 2-[[4-(1,8-diazaspiro[5.5]undecan-8-yl)-3-(4-methylthiazol-2-yl)pyrrolo[2,3-b]pyridin-1-yl]methoxy]ethyl-trimethyl-silane | ES⁺ 498 [M + H]⁺ Rt = 1.66 mins, Generic Basic Method |
| P128 | 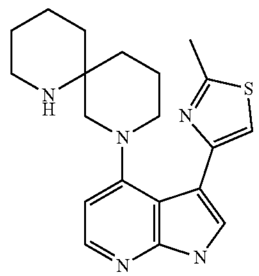 | 2-[[4-(1,8-diazaspiro[5.5]undecan-8-yl)-3-(2-methylthiazol-4-yl)pyrrolo[2,3-b]pyridin-1-yl]methoxy]ethyl-trimethyl-silane | ES⁺ 498 [M + H]⁺ Rt = 1.59 mins, Generic Basic Method |
| P129 | 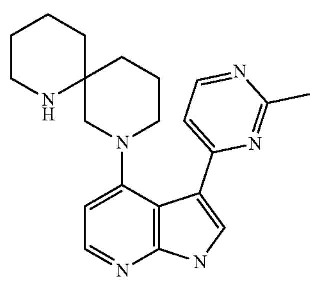 | 2-[[4-(1,8-diazaspiro[5.5]undecan-8-yl)-3-(2-methylpyrimidin-4-yl)pyrrolo[2,3-b]pyridin-1-yl]methoxy]ethyl-trimethyl-silane | LCMS NA |
| P130 | 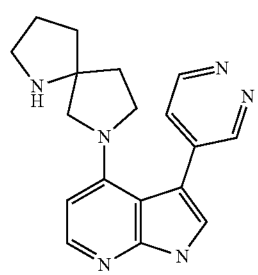 | 2-[[4-(1,7-diazaspiro[4.4]nonan-7-yl)-3-pyridazin-4-yl-pyrrolo[2,3-b]pyridin-1-yl]methoxy]ethyl-trimethyl-silane | ES⁺ 451 [M + H]⁺ Rt = 1.22 mins, Generic Basic Method |
| P131 | 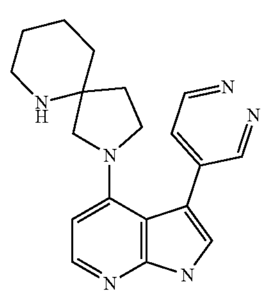 | 2-[[4-(2,6-diazaspiro[4.5]decan-2-yl)-3-pyridazin-4-yl-pyrrolo[2,3-b]pyridin-1-yl]methoxy]ethyl-trimethyl-silane | ES⁺ 465 [M + H]⁺ Rt = 1.26 mins, Generic Basic Method |

| Preparation | Structure | Name | LCMS Data |
|---|---|---|---|
| P132 | 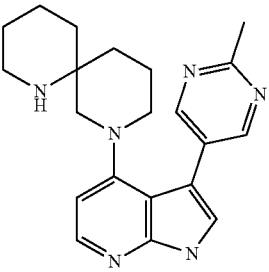 | 2-[[4-(1,8-diazaspiro[5.5]undecan-8-yl)-3-(2-methylpyrimidin-5-yl)pyrrolo[2,3-b]pyridin-1-yl]methoxy]ethyl-trimethyl-silane | ES⁺ 493 [M + H]⁺<br>Rt = 1.44 mins,<br>Generic Basic Method |
| P133 | 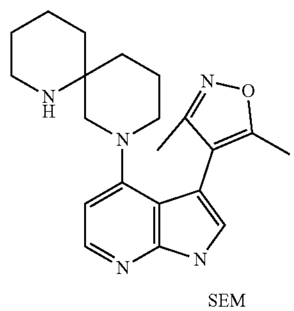 | 2-[[4-(1,8-diazaspiro[5.5]undecan-8-yl)-3-(3,5-dimethylisoxazol-4-yl)pyrrolo[2,3-b]pyridin-1-yl]methoxy]ethyl-trimethyl-silane | ES⁺ 496 [M + H]⁺<br>Rt = 1.57 mins,<br>Generic Basic Method |
| P134 | 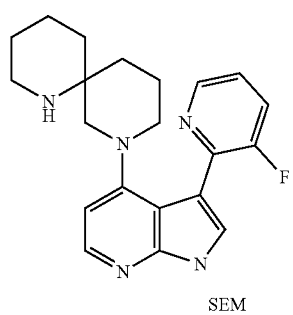 [SMILES: Fc1cccnc1-c1c[nH]c2nccc(N3CCCC4(CCCCN4)C3)c12 ; "SEM"] | 2-[[4-(1,8-diazaspiro[5.5]undecan-8-yl)-3-(3-fluoro-2-pyridyl)pyrrolo[2,3-b]pyridin-1-yl]methoxy]ethyl-trimethyl-silane | ES⁺ 496 [M + H]⁺<br>Rt = 1.51 mins,<br>Generic Basic Method |
| P135 | 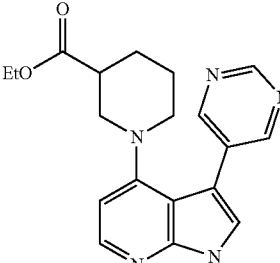 | ethyl 1-[3-pyrimidin-5-yl-1-(2-trimethylsilylethoxymethyl)pyrrolo[2,3-b]pyridin-4-yl]piperidine-3-carboxylate | |

Preparation 136 (P136)-2-[[4-(2,6-diazaspiro[4.5]decan-2-yl)-3-(5-methylthiazol-2-yl)pyrrolo[2,3-b]pyridin-1-yl]methoxy]ethyl-trimethyl-silane

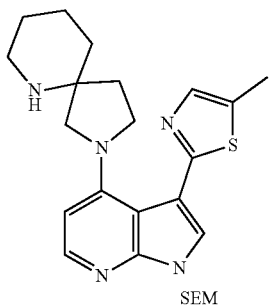

A solution of 2-[[4-chloro-3-(5-methylthiazol-2-yl)pyrrolo[2,3-b]pyridin-1-yl]methoxy]ethyl-trimethyl-silane (P24) (524.00 mg, 1.38 mmol), tert-butyl 2,6-diazaspiro[4.5]decane-6-carboxylate (820.95 mg, 3.42 mmol) and triethylamine (0.48 mL, 3.45 mmol) in NMP (5 ml) was heated in the microwave at 180° C. for a total of 4 hours. The mixture was loaded onto a SCX cartridge (2 g), and the cartridge was washed with initially with MeOH and then $NH_3$ in MeOH (2M). The basic fractions were combined and concentrated under reduced pressure to give a brown coloured oil. The oil was chromatographed [$SiO_2$, 0-10% 2M $NH_3$/MeOH in DCM] to give a yellow coloured oily solid. The residue was further chromatographed (C18) to give 2-[[4-(2,6-diazaspiro[4.5]decan-2-yl)-3-(5-methylthiazol-2-yl)pyrrolo[2,3-b]pyridin-1-yl]methoxy]ethyl-trimethyl-silane (P136) (291 mg) as a dark yellow coloured oily solid, LCMS ES+ 484 [M+H]+, Rt=1.60 mins (Generic Basic Method). 2-[[4-(2,6-diazaspiro[4.5]decan-2-yl)-3-(5-methylthiazol-2-yl)pyrrolo[2,3-b]pyridin-1-yl]methoxy]ethyl-trimethyl-silane (P136) was subsequently purified by chiral HPLC (Lux Cellulose-4, 250×21.2 mm, 5 um, eluting with Heptane:EtOH 70:30, with DEA as a modifier) to give; 2-[[4-[(5R)-2,6-diazaspiro[4.5]decan-2-yl]-3-(5-methylthiazol-2-yl)pyrrolo[2,3-b]pyridin-1-yl]methoxy]ethyl-trimethyl-silane (P137) and 2-[[4-[(5S)-2,6-diazaspiro[4.5]decan-2-yl]-3-(5-methylthiazol-2-yl)pyrrolo[2,3-b]pyridin-1-yl]methoxy]ethyl-trimethyl-silane (P138).

The following compounds were prepared in a similar manner to 2-[[4-(2,6-diazaspiro[4.5]decan-2-yl)-3-(5-methylthiazol-2-yl)pyrrolo[2,3-b]pyridin-1-yl]methoxy]ethyl-trimethyl-silane (P136), using the appropriate amine and chloro-azaindole:

| Preparation | Structure | Name | LCMS Data |
|---|---|---|---|
| P139 | 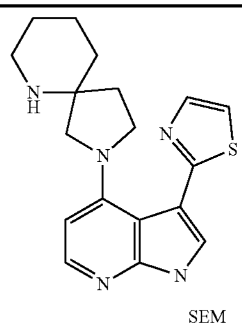 | 2-[[4-(2,6-diazaspiro[4.5]decan-2-yl)-3-thiazol-2-yl-pyrrolo[2,3-b]pyridin-1-yl]methoxy]ethyl-trimethyl-silane | ES+ 470 [M + H]+ Rt = 1.47 mins, Generic Basic Method |
| P140 | 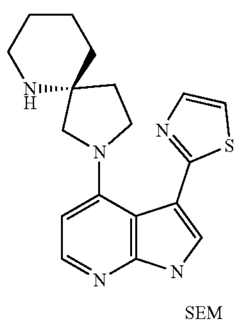 [SMILES: c1csc(-c2c[nH]c3nccc(N4CC[C@]5(CCCCN5)C4)c23)n1 ; "SEM"] | 2-[[4-[(5R)-2,6-diazaspiro[4.5]decan-2-yl]-3-thiazol-2-yl-pyrrolo[2,3-b]pyridin-1-yl]methoxy]ethyl-trimethyl-silane | |
| P141 | 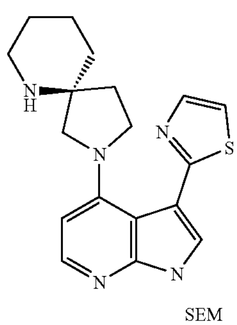 [SMILES: c1csc(-c2c[nH]c3nccc(N4CC[C@@]5(CCCCN5)C4)c23)n1 ; "SEM"] | 2-[[4-[(5S)-2,6-diazaspiro[4.5]decan-2-yl]-3-thiazol-2-yl-pyrrolo[2,3-b]pyridin-1-yl]methoxy]ethyl-trimethyl-silane | |

-continued

| Preparation | Structure | Name | LCMS Data |
|---|---|---|---|
| P142 | 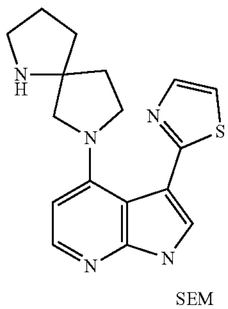 [SMILES: c1csc(-c2c[nH]c3nccc(N4CCC5(CCCN5)C4)c23)n1 ; "SEM"] | 2-[[4-(1,7-diazaspiro[4.4]nonan-7-yl)-3-thiazol-2-yl-pyrrolo[2,3-b]pyridin-1-yl]methoxy]ethyl-trimethyl-silane | ES$^+$ 456 [M + H]$^+$ Rt = 1.42 mins, Generic Basic Method |
| P143 | 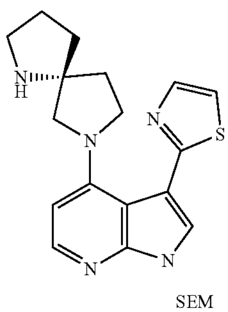 [SMILES: c1csc(-c2c[nH]c3nccc(N4CC[C@]5(CCCN5)C4)c23)n1 ; "SEM"] | 2-[[4-[(5R)-1,7-diazaspiro[4.4]nonan-7-yl]-3-thiazol-2-yl-pyrrolo[2,3-b]pyridin-1-yl]methoxy]ethyl-trimethyl-silane | |
| P144 | 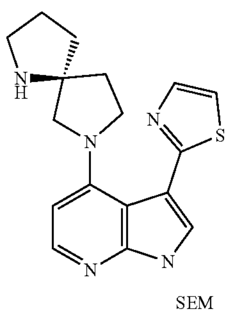 [SMILES: c1csc(-c2c[nH]c3nccc(N4CC[C@@]5(CCCN5)C4)c23)n1 ; "SEM"] | 2-[[4-[(5S)-1,7-diazaspiro[4.4]nonan-7-yl]-3-thiazol-2-yl-pyrrolo[2,3-b]pyridin-1-yl]methoxy]ethyl-trimethyl-silane | |
| P145 | 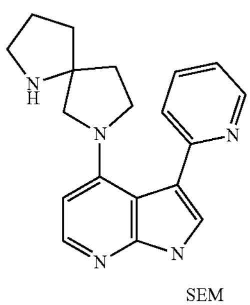 [SMILES: c1ccc(-c2c[nH]c3nccc(N4CCC5(CCCN5)C4)c23)nc1 ; "SEM"] | 2-[[4-(1,7-diazaspiro[4.4]nonan-7-yl)-3-(2-pyridyl)pyrrolo[2,3-b]pyridin-1-yl]methoxy]ethyl-trimethyl-silane | ES$^+$ 450 [M + H]$^+$ Rt = 1.39 mins, Generic Basic Method |
| P146 | 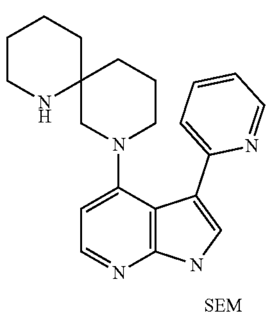 [SMILES: c1ccc(-c2c[nH]c3nccc(N4CCCC5(CCCCN5)C4)c23)nc1 ; "SEM"] | 2-[[4-(1,8-diazaspiro[5.5]undecan-8-yl)-3-(2-pyridyl)pyrrolo[2,3-b]pyridin-1-yl]methoxy]ethyl-trimethyl-silane | ES$^+$ 478 [M + H]$^+$ Rt = 1.51 mins, Generic Basic Method |

| Preparation | Name | LCMS Data |
|---|---|---|
| P147 | 2-[[4-(2,6-diazaspiro[4.5]decan-2-yl)-3-(2-pyridyl)pyrrolo[2,3-b]pyridin-1-yl]methoxy]ethyl-trimethyl-silane | ES⁺ 464 [M + H]⁺ Rt = 1.39 mins, Generic Basic Method |
| P148 | 2-[[4-(1,7-diazaspiro[4.4]nonan-7-yl)-3-(5-methylthiazol-2-yl)pyrrolo[2,3-b]pyridin-1-yl]methoxy]ethyl-trimethyl-silane | ES⁺ 470 [M + H]⁺ Rt = 1.44 mins, Generic Basic Method |
| P149 | 2-[4-(1,7-diazaspiro[4.4]nonan-7-yl)-1H-pyrrolo[2,3-b]pyridin-3-yl]-5-methyl-thiazole | ES⁺ 470 [M + H]⁺ Rt = 0.92 mins, Generic Basic Method |
| P150 | tert-butyl 8-[3-(5-fluoro-2-pyridyl)-1-(2-trimethylsilylethoxymethyl)pyrrolo[2,3-b]pyridin-4-yl]-1,8-diazaspiro[5.5]undecane-1-carboxylate | ES⁺ 470 [M + H]⁺ Rt = 0.92 mins, Generic Basic Method |
| P151 | 2-[[4-(1,8-diazaspiro[5.5]undecan-8-yl)-3-(5-fluoro-3-pyridyl)pyrrolo[2,3-b]pyridin-1-yl]methoxy]ethyl-trimethyl-silane | ES⁺ 496 [M + H]⁺ Rt = 1.58 mins, Generic Basic Method |

-continued

| Preparation | Structure | Name | LCMS Data |
|---|---|---|---|
| P152 | 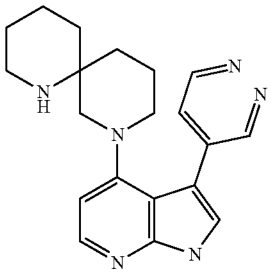 | 2-[[4-(1,8-diazaspiro[5.5]undecan-8-yl)-3-pyridazin-4-yl-pyrrolo[2,3-b]pyridin-1-yl]methoxy]ethyl-trimethyl-silane | ES⁺ 479 [M + H]⁺ Rt = 1.33 mins, Generic Basic Method |
| P153 | 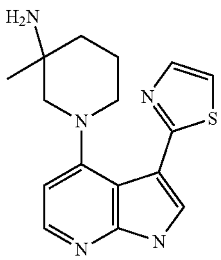 | 3-methyl-1-[3-thiazol-2-yl-1-(2-trimethylsilylethoxymethyl)pyrrolo[2,3-b]pyridin-4-yl]piperidin-3-amine | ES⁺ 444 [M + H]⁺ Rt = 1.37 mins, Generic Basic Method |
| P154 | 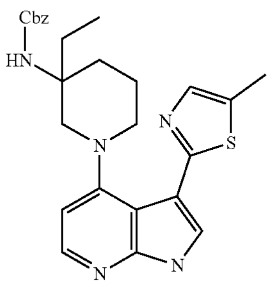 | benzyl N-[3-ethyl-1-[3-(5-methylthiazol-2-yl)-1-(2-trimethylsilylethoxymethyl)pyrrolo[2,3-b]pyridin-4-yl]-3-piperidyl]carbamate | ES⁺ 606 [M + H]⁺ Rt = 1.86 mins, Generic Basic Method |

Preparation 155 (P155)-2-[[4-(1,8-diazaspiro[5.5]undecan-8-yl)-3-isothiazol-3-yl-pyrrolo[2,3-b]pyridin-1-yl]methoxy]ethyl-trimethyl-silane

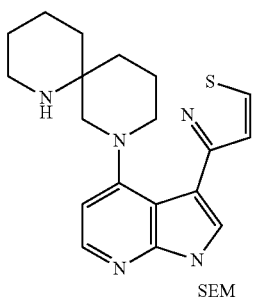

A solution of ethyl 3-[4-chloro-1-(2-trimethylsilylethoxymethyl)pyrrolo[2,3-b]pyridin-3-yl]isothiazole-5-carboxylate (P21) (379.00 mg, 0.87 mmol), tert-butyl-1,8-diazaspiro[5.5]undecane-1-carboxylate (1.10 g, 4.33 mmol), triethylamine (0.6 ml, 4.33 mmol) in NMP (3 ml) was heated to 180° C. for 3 hours. After this time, further tert-butyl-1,8-diazaspiro[5.5]undecane-1-carboxylate (442.00 mg, 1.74 mmol) was added and the reaction mixture heated for a further 4 hours at 180° C. in the microwave. The reaction mixture was loaded onto a pre-acidified SCX cartridge (5 g) and washed with MeOH (×5 cv). Product was released via treatment with NH₃ in MeOH (2N). The basic fractions were concentrated under reduced pressure to give a dark coloured oil. The oil was chromatographed [SiO₂, 0-100% 10% 2N NH₃/MeOH in DCM:DCM] to give 2-[[4-(1,8-diazaspiro[5.5]undecan-8-yl)-3-isothiazol-3-yl-pyrrolo[2,3-b]pyridin-1-yl]methoxy]ethyl-trimethyl-silane (P155) (302 mg, 0.62 mmol, 72.2% yield) as a pale yellow coloured oil. 2-[[4-(1,8-diazaspiro[5.5]undecan-8-yl)-3-isothiazol-3-yl-pyrrolo[2,3-b]pyridin-1-yl]methoxy]ethyl-trimethyl-silane (P155), was subsequently purified by chiral HPLC (Lux Cellulose-4, 250×21.2 mm, 5 um, eluting with 0.1% DEA in MeCN) to give 2-[[4-[(6R)-1,8-diazaspiro[5.5]undecan-8-yl]-3-isothiazol-3-yl-pyrrolo[2,3-b]pyridin-1-yl]methoxy]ethyl-trimethyl-silane (P156) and 2-[[4-[(6S)-1,8-diazaspiro[5.5]undecan-8-yl]-3-isothiazol-3-yl-pyrrolo[2,3-b]pyridin-1-yl]methoxy]ethyl-trimethyl-silane (E237).

The following compounds were prepared in a similar manner to 2-[[4-(1,8-diazaspiro[5.5]undecan-8-yl)-3-isothiazol-3-yl-pyrrolo[2,3-b]pyridin-1-yl]methoxy]ethyl-trimethyl-silane (P155) from the appropriate intermediates. In some cases the title compounds were purified using preparative HPLC.

| Preparation | Structure | Name | LCMS Data |
|---|---|---|---|
| P158 | 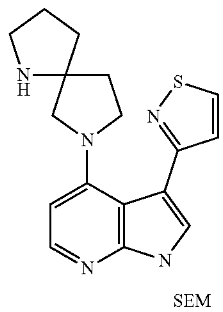 [SMILES: c1cc(N2CCC3(CCCN3)C2)c2c(-c3ccsn3)c[nH]c2n1 ; "SEM"] | 2-[[4-(1,7-diazaspiro[4.4]nonan-7-yl)-3-isothiazol-3-yl-pyrrolo[2,3-b]pyridin-1-yl]methoxy]ethyl-trimethyl-silane | ES+ 456 [M + H]+, Rt = 1.46 mins, Generic Basic Method |

Preparation 159 (P159)-4-(1,8-diazaspiro[5.5]undecan-8-yl)-1-(2-trimethylsilylethoxymethyl)pyrrolo[2,3-b]pyridine-3-carbonitrile

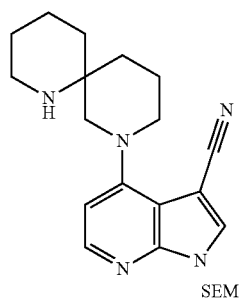

A solution of 4-chloro-1-(2-trimethylsilylethoxymethyl)pyrrolo[2,3-b]pyridine-3-carbonitrile (P13) (800.00 mg, 2.60 mmol), tert-butyl-1,8-diazaspiro[5.5]undecane-1-carboxylate (1.983 g, 7.8 mmol), triethylamine (1.09 ml, 7.8 mmol) in 1,4-dioxane (6 ml) was heated to 180° C. for a total of 12 hours. After this time, the mixture was concentrated under reduced pressure and the resulting residue was dissolved in DCM and washed with water.

The organics were concentrated under reduced pressure. The residue was purified by SCX before being chromatographed [SiO2, 50 g, 0-10% 2M NH3 MeOH:DCM) to afford 4-(1,8-diazaspiro[5.5]undecan-8-yl)-1-(2-trimethylsilylethoxymethyl)pyrrolo[2,3-b]pyridine-3-carbonitrile (P159) (620 mg, 1.38 mmol, 53.3% yield), LCMS ES+ 426 [M+H]+, Rt=1.43 mins (Generic Basic Method). 4-(1,8-diazaspiro[5.5]undecan-8-yl)-1-(2-trimethylsilylethoxymethyl)pyrrolo[2,3-b]pyridine-3-carbonitrile (P159), was subsequently purified by chiral HPLC (Lux Cellulose-4, 250×21.2 mm, 5 um, eluting with 0.2% DEA in MeCN) to give 4-[(6R)-1,8-diazaspiro[5.5]undecan-8-yl]-1-(2-trimethylsilylethoxymethyl)pyrrolo[2,3-b]pyridine-3-carbonitrile (P160) and 4-[(6S)-1,8-diazaspiro[5.5]undecan-8-yl]-1-(2-trimethylsilylethoxymethyl)pyrrolo[2,3-b]pyridine-3-carbonitrile (P161).

Preparation 162 (P162)-tert-butyl N-cyclopropyl-N-[(3S)-1-[3-pyrimidin-4-yl-1-(2-trimethylsilylethoxymethyl)pyrrolo[2,3-b]pyridin-4-yl]-3-piperidyl]carbamate

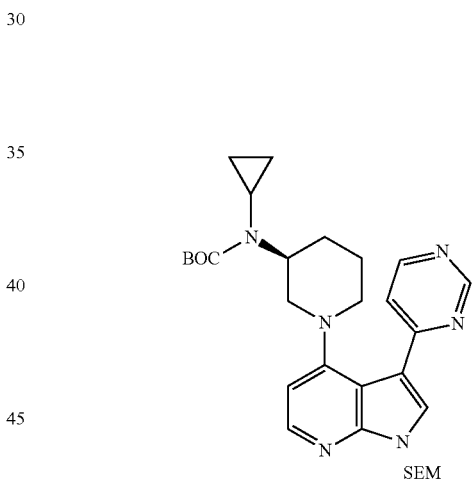

A solution of tert-butyl N-cyclopropyl-N-[(3S)-3-piperidyl]carbamate (133.2 mg, 0.5500 mmol), triethylamine (0.15 ml, 1.11 mmol) and 2-[(4-chloro-3-pyrimidin-4-yl-pyrrolo[2,3-b]pyridin-1-yl)methoxy]ethyl-trimethyl-silane (P22) (100.00 mg, 0.28 mmol), in NMP (1 ml) was heated at 180° C. in the microwave for 2 hours. After this time, the cooled reaction mixture was loaded onto a pre-acidified 5 g SCX cartridge. The cartridge was washed with MeOH (×5 cvs) and the product eluted with NH3 in MeOH (2N). The basic fractions were concentrated under reduced pressure and the residue was purified via preparative HPLC using the generic basic run to give tert-butyl N-cyclopropyl-N-[(3S)-1-[3-pyrimidin-4-yl-1-(2-trimethylsilylethoxymethyl)pyrrolo[2,3-b]pyridin-4-yl]-3-piperidyl]carbamate (P162) (37 mg), LCMS ES+ 565 [M+H]+, Rt=1.73 mins (Generic Basic Method).

The following compounds were prepared in a similar manner to tert-butyl N-cyclopropyl-N-[(3S)-1-[3-pyrimidin-4-yl-1-(2-trimethylsilylethoxymethyl)pyrrolo[2,3-b]pyridin-4-yl]-3-piperidyl]carbamate (P162) from the appropriate intermediates:

| Preparation | Structure | Name | LCMS Data |
| --- | --- | --- | --- |
| P163 | 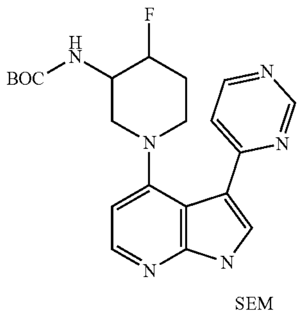 [SMILES: CC(C)(C)OC(=O)NC1CN(c2ccnc3[nH]cc(-c4ccncn4)c23)CCC1F ; "SEM"] | tert-butyl N-[4-fluoro-1-[3-pyrimidin-4-yl-1-(2-trimethylsilylethoxymethyl) pyrrolo[2,3-b]pyridin-4-yl]-3-piperidyl]carbamate | ES+ 543 [M + H]+, Rt = 1.52 mins, Generic Basic Method |
| P164 | 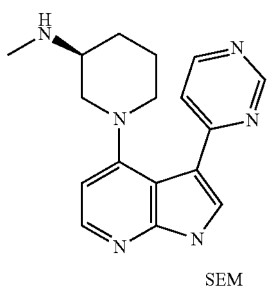 | (3S)-N-methyl-1-[3-pyrimidin-4-yl-1-(2-trimethylsilylethoxymethyl) pyrrolo[2,3-b]pyridin-4-yl]piperidin-3-amine | ES+ 439 [M + H]+, Rt = 1.29 mins, Generic Basic Method |
| P165 | 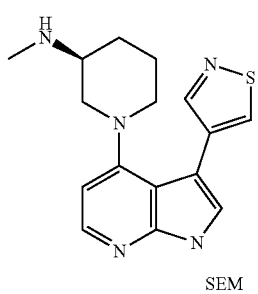 | (3S)-1-[3-isothiazol-4-yl-1-(2-trimethylsilylethoxymethyl) pyrrolo[2,3-b]pyridin-4-yl]-N-methyl-piperidin-3-amine | ES+ 444 [M + H]+, Rt = 1.41 mins, Generic Basic Method |
| P166 | 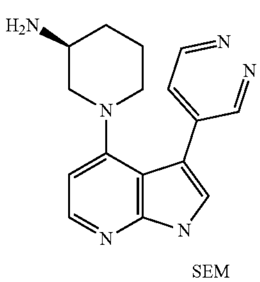 [SMILES: N=C/C=C(\C=N)c1c[nH]c2nccc(N3CCC[C@H](N)C3)c12 ; "SEM"] | (3S)-1-[3-pyridazin-4-yl-1-(2-trimethylsilylethoxymethyl) pyrrolo[2,3-b]pyridin-4-yl]piperidin-3-amine | ES+ 425 [M + H]+, Rt = 1.21 mins, Generic Basic Method |

Preparation 167 (P167)-tert-butyl 7-[3-(5-methylthiazol-2-yl)-1-(2-trimethylsilylethoxymethyl)pyrrolo[2,3-b]pyridin-4-yl]-1,7-diazaspiro[3.4]octane-1-carboxylate

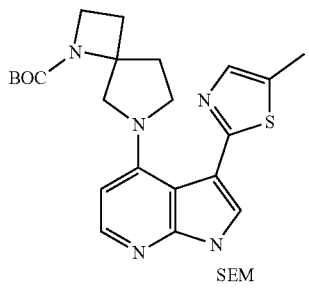

2-[[4-chloro-3-(5-methylthiazol-2-yl)pyrrolo[2,3-b]pyridin-1-yl]methoxy]ethyl-trimethyl-silane (P24) (250.00 mg, 0.66 mmol), tert-butyl 1,7-diazaspiro[3.4]octane-1-carboxylate (167.61 mg, 0.79 mmol) and PEPPSI (44.7 mg, 0.07 mmol) were placed in a microwave vial. The vial was purged and evacuated with nitrogen (×3) before charging with lithium bis(trimethylsilyl)amide solution (1.32 ml, 1.32 mmol) and 1,4-dioxane (0.1 ml). The solution was allowed to stir for 30 minutes at 90° C. before cooling to room temperature. The mixture was passed through celite and the solvent removed under reduced pressure. The residue obtained was diluted with DCM (20 ml) and washed with water (10 ml) and DCM (20 ml), before combining the organics and washing with brine. The liquors were concentrated under reduced pressure to afford a dark oil which chromatographed [SiO$_2$, 0-60% EtOAc:iso-hexane] to give tert-butyl 7-[3-(5-methylthiazol-2-yl)-1-(2-trimethylsilylethoxymethyl)pyrrolo[2,3-b]pyridin-4-yl]-1,7-diazaspiro[3.4]octane-1-carboxylate (P167) (228 mg, 0.369 mmol, 56.1% yield) as a yellow oil, LCMS ES$^+$ 556 [M+H]$^+$, Rt=1.71 mins (Generic Basic Method)

The following compounds were prepared in a similar manner to tert-butyl 7-[3-(5-methylthiazol-2-yl)-1-(2-trimethylsilylethoxymethyl)pyrrolo[2,3-b]pyridin-4-yl]-1,7-diazaspiro[3.4]octane-1-carboxylate (P167) from the appropriate intermediates:

| Preparation | Structure | Name | LCMS Data |
| --- | --- | --- | --- |
| P168 | 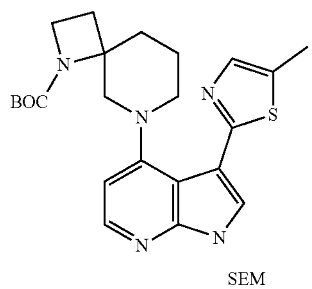 | tert-butyl 8-[3-(5-methylthiazol-2-yl)-1-(2-trimethylsilylethoxymethyl)pyrrolo[2,3-b]pyridin-4-yl]-1,8-diazaspiro[3.5]nonane-1-carboxylate | ES$^+$ 570 [M + H]$^+$, Rt = 1.78 mins, Generic Basic Method |
| P169 | 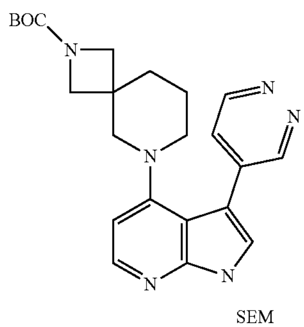 [SMILES: CC(C)(C)OC(=O)N1CC2(CCCN(c3ccnc4[nH]cc(/C(C=N)=C/C=N)c34)C2)C1 ; "SEM"] | tert-butyl 8-[3-pyridazin-4-yl-1-(2-trimethylsilylethoxymethyl)pyrrolo[2,3-b]pyridin-4-yl]-2,8-diazaspiro[3.5]nonane-2-carboxylate | ES$^+$ 551 [M + H]$^+$, Rt = 1.58 mins, Generic Basic Method |
| P170 | 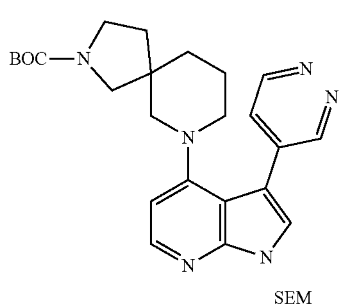 [SMILES: CC(C)(C)OC(=O)N1CCC2(CCCN(c3ccnc4[nH]cc(/C(C=N)=C/C=N)c34)C2)C1 ; "SEM"] | tert-butyl 9-[3-pyridazin-4-yl-1-(2-trimethylsilylethoxymethyl)pyrrolo[2,3-b]pyridin-4-yl]-2,9-diazaspiro[4.5]decane-2-carboxylate | ES$^+$ 551 [M + H]$^+$, Rt = 1.55 mins, Generic Basic Method |

| Preparation | Name | LCMS Data |
|---|---|---|
| P171 | tert-butyl 7-[3-pyridazin-4-yl-1-(2-trimethylsilylethoxymethyl)pyrrolo[2,3-b]pyridin-4-yl]-2,7-diazaspiro[4.4]nonane-2-carboxylate | ES+ 565 [M + H]+, Rt = 1.63 mins, Generic Basic Method |
| P172 | tert-butyl 8-[3-pyrimidin-5-yl-1-(2-trimethylsilylethoxymethyl)pyrrolo[2,3-b]pyridin-4-yl]-2,8-diazaspiro[4.5]decane-2-carboxylate | ES+ 565 [M + H]+, Rt = 1.66 mins, Generic Basic Method |
| P173 | tert-butyl 2-[3-pyrimidin-5-yl-1-(2-trimethylsilylethoxymethyl)pyrrolo[2,3-b]pyridin-4-yl]-2,8-diazaspiro[4.5]decane-8-carboxylate | ES+ 565 [M + H]+, Rt = 1.67 mins, Generic Basic Method |
| P174 | tert-butyl N-methyl-N-[(cis)-2-methyl-1-[3-pyrimidin-5-yl-1-(2-trimethylsilylethoxymethyl)pyrrolo[2,3-b]pyridin-4-yl]-3-piperidyl]carbamate | ES+ 553 [M + H]+, Rt = 1.72 mins, Generic Basic Method |

-continued

| Preparation | Structure | Name | LCMS Data |
|---|---|---|---|
| P175 | 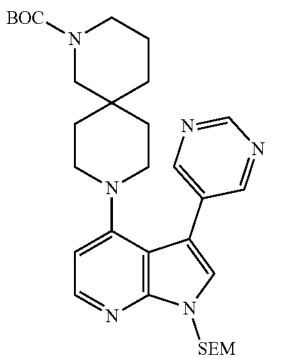 [SMILES: CC(C)(C)OC(=O)N1CCCC2(CCN(c3ccnc4c3c(-c3cncnc3)cn4COCC[Si](C)(C)C)CC2)C1] | tert-butyl 9-[3-pyrimidin-5-yl-1-(2-trimethylsilylethoxymethyl)pyrrolo[2,3-b]pyridin-4-yl]-2,9-diazaspiro[5.5]undecane-2-carboxylate | ES+ 579 [M + H]+, Rt = 1.73 mins, Generic Basic Method |
| P176 | 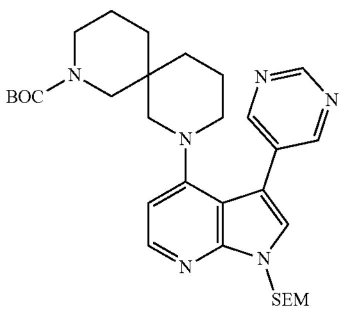 [SMILES: CC(C)(C)OC(=O)N1CCCC2(CCCN(c3ccnc4c3c(-c3cncnc3)cn4COCC[Si](C)(C)C)C2)C1] | tert-butyl 8-[3-pyrimidin-5-yl-1-(2-trimethylsilylethoxymethyl)pyrrolo[2,3-b]pyridin-4-yl]-2,8-diazaspiro[5.5]undecane-2-carboxylate | ES+ 579 [M + H]+, Rt = 1.76 mins, Generic Basic Method |
| P177 | 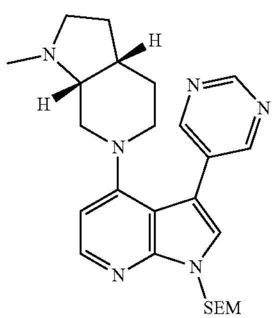 [SMILES: CN1CC[C@@H]2CCN(c3ccnc4c3c(-c3cncnc3)cn4COCC[Si](C)(C)C)C[C@@H]21] | 2-[[4-[(3aR,7aR)-1-methyl-3,3a,4,5,7,7a-hexahydro-2H-pyrrolo[2,3-c]pyridin-6-yl]-3-pyrimidin-5-yl-pyrrolo[2,3-b]pyridin-1-yl]methoxy]ethyl-trimethyl-silane | ES+ 465 [M + H]+, Rt = 1.45 mins, Generic Basic Method |
| P178 | 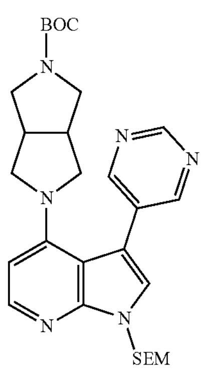 [SMILES: CC(C)(C)OC(=O)N1CC2CN(c3ccnc4c3c(-c3cncnc3)cn4COCC[Si](C)(C)C)CC2C1] | tert-butyl 2-[3-pyrimidin-5-yl-1-(2-trimethylsilylethoxymethyl)pyrrolo[2,3-b]pyridin-4-yl]-1,3,3a,4,6,6a-hexahydropyrrolo[3,4-c]pyrrole-5-carboxylate | ES+ 537 [M + H]+, Rt = 1.60 mins, Generic Basic Method |

| Preparation | Structure | Name | LCMS Data |
|---|---|---|---|
| P179 | 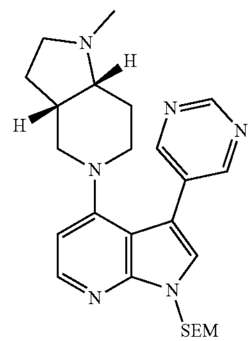 [SMILES: CN1CC[C@H]2CN(c3ccnc4c3c(-c3cncnc3)cn4COCC[Si](C)(C)C)CC[C@H]21] | 2-[[4-[(3aS,7aR)-1-methyl-3,3a,4,6,7,7a-hexahydro-2H-pyrrolo[3,2-c]pyridin-5-yl]-3-pyrimidin-5-yl-pyrrolo[2,3-b]pyridin-1-yl]methoxy]ethyl-trimethyl-silane | ES+ 465 [M + H]+, Rt = 1.43 mins, Generic Basic Method |

Preparation 180 (P180)-tert-butyl 4-[3-pyrimidin-4-yl-1-(2-trimethylsilylethoxymethyl)pyrrolo[2,3-b]pyridin-4-yl]-1,4-diazepane-1-carboxylate

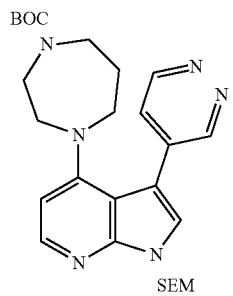

2-[(4-choro-3-pyridazin-4-yl-pyrrolo[2,3-b]pyridin-1-yl)meth oxy]ethyl-trimethyl-silane (P33) (150.00 mg, 0.42 mmol), PEPPSI (28.24 mg, 0.04 mmol) and 1-boc-hexahydro-1,4-diazepine (0.1 ml, 0.50 mmol) were placed in a microwave vial. The vial was purged and evacuated with nitrogen (×3) then charged with degassed 1,4-dioxane (1 ml) and lithium bis(trimethylsilyl)amide solution (1.45 ml, 1.45 mmol). The solution was heated for 2 hours at 90° C. before cooling to room temperature. The mixture was passed through celite and the volatiles removed under reduced pressure. The residue obtained was diluted with DCM (10 ml) and washed with water (10 ml). The aqueous layer was extracted with DCM (10 ml) and the combined organics washed with brine, dried over MgSO₄ and concentrated under reduced pressure to afford an oil which was chromatographed [SiO₂, i-Hexane:EtOAc, 0-100%] to give tert-butyl 4-[3-pyrimidin-4-yl-1-(2-trimethylsilylethoxymethyl)pyrrolo[23-b]pyridin-4-yl]-1,4-diazepane-1-carboxylate (P180) (34 mg), LMS ES+ 525 [M+H]+, Rt=1.51 mins (Generic Basic Method)

The following compounds were prepared in a similar manner to tert-butyl 4-[3-pyrimidin-4-yl-1-(2-trimethylsilylethoxymethyl)pyrrolo[2,3-b]pyridin-4-yl]-1,4-diazepane-1-carboxylate (P180) from the appropriate amine and chloro-azaindole:

| Preparation | Structure | Name | LCMS Data |
|---|---|---|---|
| P181 | 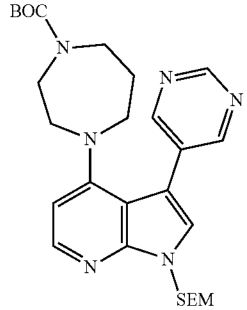 [SMILES: CC(C)(C)OC(=O)N1CCCN(c2ccnc3c2c(-c2cncnc2)cn3COCC[Si](C)(C)C)CC1] | tert-butyl 4-[3-pyrimidin-5-yl-1-(2-trimethylsilylethoxymethyl)pyrrolo[2,3-b]pyridin-4-yl]-1,4-diazepane-1-carboxylate | ES+ 525 [M + H]+, Rt = 1.59 mins, Generic Basic Method |

| Preparation | Structure | Name | LCMS Data |
|---|---|---|---|
| P182 | 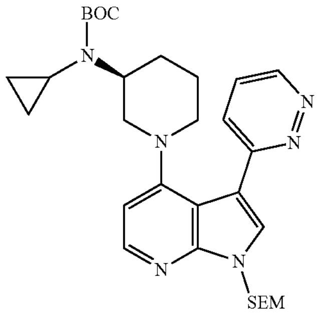 [SMILES: CC(C)(C)OC(=O)N(C1CC1)[C@H]1CCCN(c2ccnc3c2c(-c2cccnn2)cn3COCC[Si](C)(C)C)C1] | tert-butyl N-cyclopropyl-N-[(3S)-1-[3-pyridazin-3-yl-1-(2-trimethylsilylethoxymethyl)pyrrolo[2,3-b]pyridin-4-yl]-3-piperidyl]carbamate | ES$^+$ 566 [M + H]$^+$, Rt = 1.68 mins, Generic Basic Method |
| P183 | 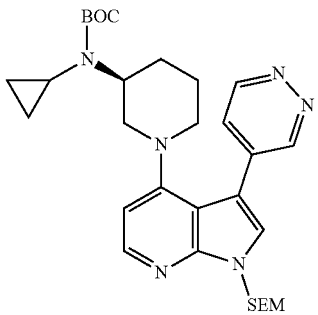 [SMILES: CC(C)(C)OC(=O)N(C1CC1)[C@H]1CCCN(c2ccnc3c2c(-c2ccnnc2)cn3COCC[Si](C)(C)C)C1] | tert-butyl N-cyclopropyl-N-[(3S)-1-[3-pyridazin-4-yl-1-(2-trimethylsilylethoxymethyl)pyrrolo[2,3-b]pyridin-4-yl]-3-piperidyl]carbamate | ES$^+$ 566 [M + H]$^+$, Rt = 1.69 mins, Generic Basic Method |
| P184 | 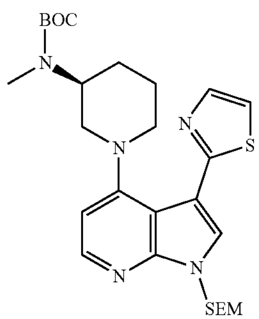 [SMILES: CN(C(=O)OC(C)(C)C)[C@H]1CCCN(c2ccnc3c2c(-c2nccs2)cn3COCC[Si](C)(C)C)C1] | tert-butyl N-methyl-N-[(3S)-1-[3-thiazol-2-yl-1-(2-trimethylsilylethoxymethyl)pyrrolo[2,3-b]pyridin-4-yl]-3-piperidyl]carbamate | ES$^+$ 545 [M + H]$^+$, Rt = 1.04 mins, Late Basic Method |
| P185 | 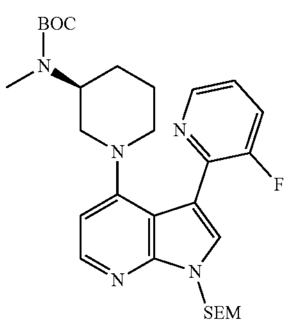 [SMILES: CN(C(=O)OC(C)(C)C)[C@H]1CCCN(c2ccnc3c2c(-c2ncccc2F)cn3COCC[Si](C)(C)C)C1] | tert-butyl N-[(3S)-1-[3-(3-fluoro-2-pyridyl)-1-(2-trimethylsilylethoxymethyl)pyrrolo[2,3-b]pyridin-4-yl]-3-piperidyl]-N-methyl-carbamate | ES$^+$ 556 [M + H]$^+$, Rt = 1.73 mins, Generic Basic Method |
| P186 | 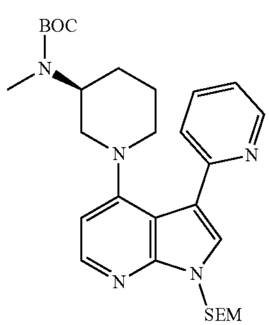 [SMILES: CN(C(=O)OC(C)(C)C)[C@H]1CCCN(c2ccnc3c2c(-c2ccccn2)cn3COCC[Si](C)(C)C)C1] | tert-butyl N-methyl-N-[(3S)-1-[3-(2-pyridyl)-1-(2-trimethylsilylethoxymethyl)pyrrolo[2,3-b]pyridin-4-yl]-3-piperidyl]carbamate | ES$^+$ 538 [M + H]$^+$, Rt = 1.71 mins, Generic Basic Method |

-continued

| Preparation | Structure | Name | LCMS Data |
|---|---|---|---|
| P187 | 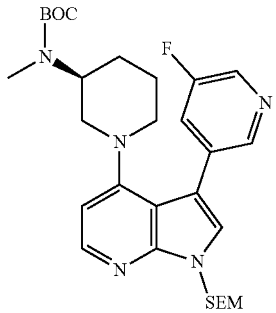 [SMILES: CN(C(=O)OC(C)(C)C)[C@H]1CCCN(c2ccnc3c2c(-c2cncc(F)c2)cn3COCC[Si](C)(C)C)C1] | tert-butyl N-[(3S)-1-[3-(5-fluoro-3-pyridyl)-1-(2-trimethylsilylethoxymethyl)pyrrolo[2,3-b]pyridin-4-yl]-3-piperidyl]-N-methyl-carbamate | ES+ 556 [M + H]+, Rt = 1.71 mins, Generic Basic Method |
| P188 | 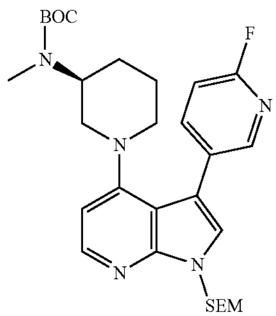 [SMILES: CN(C(=O)OC(C)(C)C)[C@H]1CCCN(c2ccnc3c2c(-c2ccc(F)nc2)cn3COCC[Si](C)(C)C)C1] | tert-butyl N-[(3S)-1-[3-(5-fluoro-2-pyridyl)-1-(2-trimethylsilylethoxymethyl)pyrrolo[2,3-b]pyridin-4-yl]-3-piperidyl]-N-methyl-carbamate | ES+ 556 [M + H]+, Rt = 1.78 mins, Generic Basic Method |
| P189 | 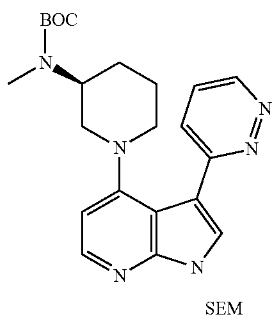 | tert-butyl N-methyl-N-[(3S)-1-[3-pyridazin-3-yl-1-(2-trimethylsilylethoxymethyl)pyrrolo[2,3-b]pyridin-4-yl]-3-piperidyl]carbamate | ES+ 539 [M + H]+, Rt = 1.60 mins, Generic Basic Method |
| P190 | 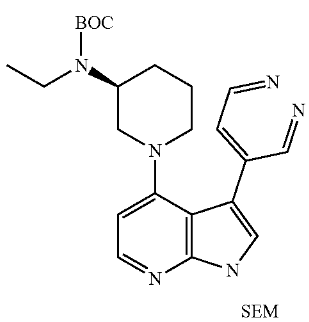 | tert-butyl N-ethyl-N-[(3S)-1-[3-pyridazin-4-yl-1-(2-trimethylsilylethoxymethyl)pyrrolo[2,3-b]pyridin-4-yl]-3-piperidyl]carbamate | ES+ 553 [M + H]+, Rt = 1.65 mins, Generic Basic Method |
| P191 | 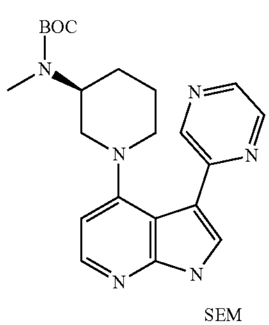 | tert-butyl N-methyl-N-[(3S)-1-[3-pyrazin-2-yl-1-(2-trimethylsilylethoxymethyl)pyrrolo[2,3-b]pyridin-4-yl]-3-piperidyl]carbamate | ES+ 539 [M + H]+, Rt = 1.69 mins, Generic Basic Method |

| Preparation | Structure | Name | LCMS Data |
|---|---|---|---|
| P192 | 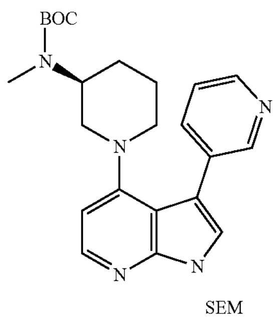 | tert-butyl N-methyl-N-[(3S)-1-[3-(3-pyridyl)-1-(2-trimethylsilylethoxymethyl)pyrrolo[2,3-b]pyridin-4-yl]-3-piperidyl]carbamate | ES+ 539 [M + H]+, Rt = 1.72 mins, Generic Basic Method |
| P193 | 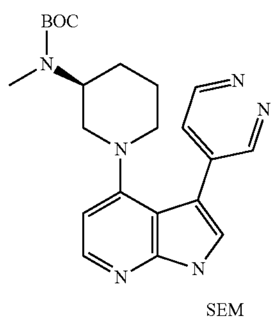 | tert-butyl N-methyl-N-[(3S)-1-[3-pyridazin-4-yl-1-(2-trimethylsilylethoxymethyl)pyrrolo[2,3-b]pyridin-4-yl]-3-piperidyl]carbamate | ES+ 540 [M + H]+, Rt = 1.60 mins, Generic Basic Method |
| P194 | 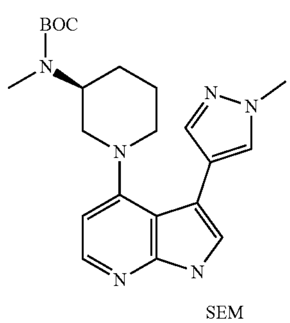 | tert-butyl N-methyl-N-[(3S)-1-[3-(1-methylpyrazol-4-yl)-1-(2-trimethylsilylethoxymethyl)pyrrolo[2,3-b]pyridin-4-yl]-3-piperidyl]carbamate | ES+ 542 [M + H]+, Rt = 1.68 mins, Generic Basic Method |
| P195 | 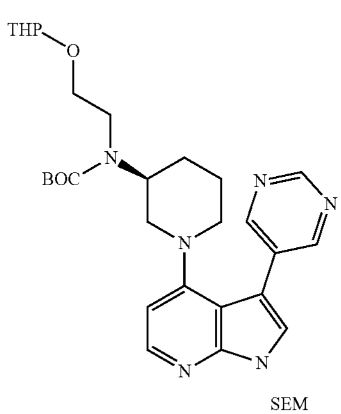 | tert-butyl N-[(3S)-1-[3-pyrimidin-5-yl-1-(2-trimethylsilylethoxymethyl)pyrrolo[2,3-b]pyridin-4-yl]-3-piperidyl]-N-(2-tetrahydropyran-2-yloxyethyl)carbamate | ES+ 654 [M + H]+, Rt = 1.79 mins, Generic Basic Method |

-continued

| Preparation | Structure | Name | LCMS Data |
|---|---|---|---|
| P196 | 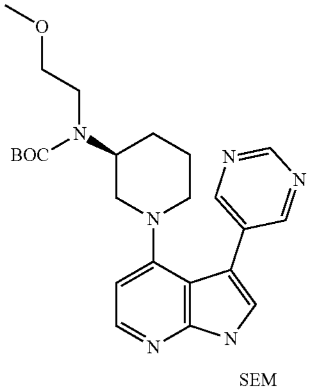 | tert-butyl N-(2-methoxyethyl)-N-[(3S)-1-[3-pyrimidin-5-yl-1-(2-trimethylsilylethoxymethyl)pyrrolo[2,3-b]pyridin-4-yl]-3-piperidyl]carbamate | ES+ 584 [M + H]+, Rt = 1.68 mins, Generic Basic Method |
| P197 | 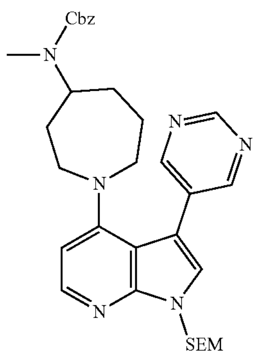 | benzyl N-methyl-N-[1-[3-pyrimidin-5-yl-1-(2-trimethylsilylethoxymethyl)pyrrolo[2,3-b]pyridin-4-yl]azepan-4-yl]carbamate | ES+ 588 [M + H]+, Rt = 1.64 mins, Generic Basic Method |
| P198 | 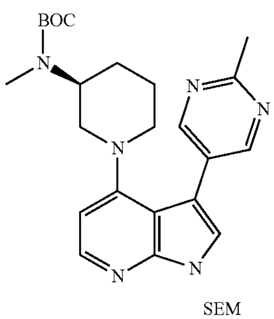 | tert-butyl N-methyl-N-[(3S)-1-[3-(2-methylpyrimidin-5-yl)-1-(2-trimethylsilylethoxymethyl)pyrrolo[2,3-b]pyridin-4-yl]-3-piperidyl]carbamate | ES+ 553 [M + H]+, Rt = 1.64 mins, Late Basic Method |
| P199 | 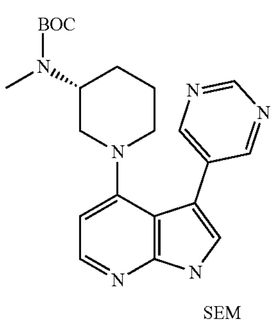 | tert-butyl N-methyl-N-[(3R)-1-[3-pyrimidin-5-yl-1-(2-trimethylsilylethoxymethyl)pyrrolo[2,3-b]pyridin-4-yl]-3-piperidyl]carbamate | ES+ 539 [M + H]+, Rt = 1.69 mins, Late Basic Method |

-continued

| Preparation | Structure | Name | LCMS Data |
|---|---|---|---|
| P200 | 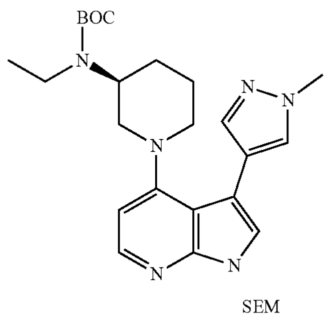 | tert-butyl N-ethyl-N-[(3S)-1-[3-(1-methylpyrazol-4-yl)-1-(2-trimethylsilylethoxymethyl)pyrrolo[2,3-b]pyridin-4-yl]-3-piperidyl]carbamate | ES⁺ 556 [M + H]+, Rt = 1.74 mins, Late Basic Method |
| P201 | 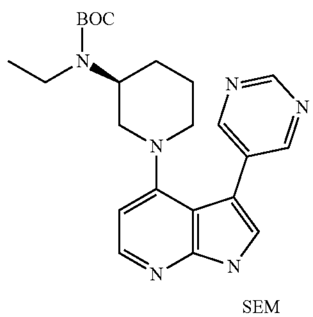 | tert-butyl N-ethyl-N-[(3S)-1-[3-pyrimidin-5-yl-1-(2-trimethylsilylethoxymethyl)pyrrolo[2,3-b]pyridin-4-yl]-3-piperidyl]carbamate | ES⁺ 554 [M + H]+, Rt = 1.75 mins, Late Basic Method |
| P202 | 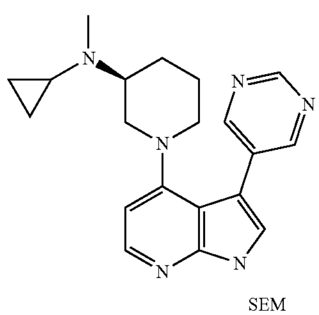 | (3S)-N-cyclopropyl-N-methyl-1-[3-pyrimidin-5-yl-1-(2-trimethylsilylethoxymethyl)pyrrolo[2,3-b]pyridin-4-yl]piperidin-3-amine | ES⁺ 479 [M + H]+, Rt = 1.57 mins, Late Basic Method |
| P203 | 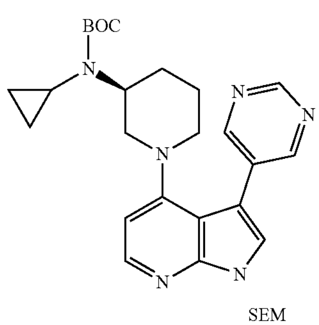 [SMILES: CC(C)(C)OC(=O)N(C1CC1)[C@H]1CCCN(c2ccnc3[nH]cc(-c4cncnc4)c23)C1 ; "SEM"] | tert-butyl N-cyclopropyl-N-[(3S)-1-[3-pyrimidin-5-yl-1-(2-trimethylsilylethoxymethyl)pyrrolo[2,3-b]pyridin-4-yl]-3-piperidyl]carbamate | ES⁺ 565 [M + H]+, Rt = 1.77 mins, Late Basic Method |

Preparation 204 (P204)-tert-butyl 9-[3-pyrimidin-5-yl-1-(2-trimethylsilylethoxymethyl)pyrrolo[2,3-b]pyridin-4-yl]-1,9-diazaspiro[4.5]decane-1-carboxylate

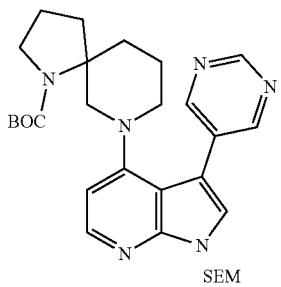

To a microwave vial containing stirrer bar was added 2-[(4-chloro-3-pyrimidin-5-yl-pyrrolo[2,3-b]pyridin-1-yl)methoxy]ethyl-trimethyl-silane (P23) (130.00 mg, 0.36 mmol), potassium tert-butoxide (121.27 mg, 1.08 mmol), PEPPSI (24.47 mg, 0.04 mmol) and tert-butyl-1,7-diazaspiro[4.5]decane-1-carboxylate (103.88 mg, 0.43 mmol). The vial was filled and evacuated with nitrogen (×2) before charging with degassed 1,4-dioxane (1 ml). The reaction mixture was heated to 110° C. overnight before being allowed to cool to room temperature. The crude mixture was quenched via addition of water and the volatiles removed under reduced pressure before washing with DCM (20 ml×2). The organics were concentrated under reduced pressure and the crude oil chromatographed [SiO$_2$, 0-4% MeOH:DCM] to give tert-butyl 9-[3-pyrimidin-5-yl-1-(2-trimethylsilylethoxymethyl)pyrrolo[2,3-b]pyridin-4-yl]-1,9-diazaspiro[4.5]decane-1-carboxylate (P204) (55 mg), LCMS ES$^+$ 565 [M+H]$^+$, Rt=1.73 mins (Generic Basic Method).

The following compounds were prepared in a similar manner to tert-butyl 9-[3-pyrimidin-5-yl-1-(2-trimethylsilylethoxymethyl)pyrrolo[2,3-b]pyridin-4-yl]-1,9-diazaspiro[4.5]decane-1-carboxylate (P204) from the appropriate amine and chloro-azaindole intermediates:

| Preparation | Structure | Name | LCMS Data |
| --- | --- | --- | --- |
| P205 | 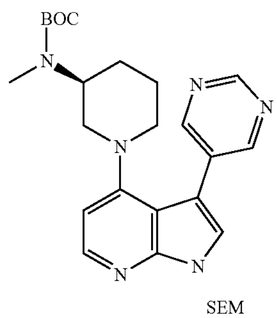 | tert-butyl N-methyl-N-[(3S)-1-[3-pyrimidin-5-yl-1-(2-trimethylsilylethoxymethyl)pyrrolo[2,3-b]pyridin-4-yl]-3-piperidyl]carbamate | ES$^+$ 539 [M + H]$^+$, Rt = 1.66 mins, Generic Basic Method |
| P206 | 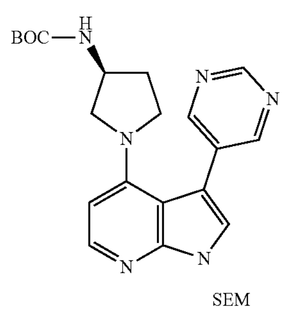 [SMILES: CC(C)(C)OC(=O)N[C@H]1CCN(c2ccnc3[nH]cc(-c4cncnc4)c23)C1 ; "SEM"] | tert-butyl N-[(3S)-1-[3-pyrimidin-5-yl-1-(2-trimethylsilylethoxymethyl)pyrrolo[2,3-b]pyridin-4-yl]pyrrolidin-3-yl]carbamate | ES$^+$ 525 [M + H]$^+$, Rt = 1.59 mins, Generic Basic Method |
| P207 | 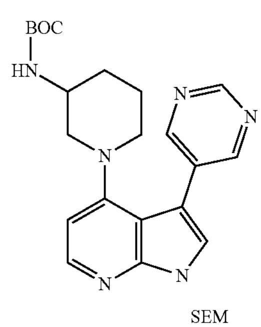 [SMILES: CC(C)(C)OC(=O)NC1CCCN(c2ccnc3[nH]cc(-c4cncnc4)c23)C1 ; "SEM"] | tert-butyl N-[1-[3-pyrimidin-5-yl-1-(2-trimethylsilylethoxymethyl)pyrrolo[2,3-b]pyridin-4-yl]-3-piperidyl]carbamate | ES$^+$ 525 [M + H]$^+$, Rt = 1.59 mins, Generic Basic Method. |

| Preparation | Name | LCMS Data |
|---|---|---|
| P208 | N,N-dimethyl-1-[3-pyrimidin-5-yl-1-(2-trimethylsilylethoxymethyl)pyrrolo[2,3-b]pyridin-4-yl]piperidin-3-amine | ES+ 453 [M + H]+, Rt = 1.41 mins, Generic Basic Method |
| P209 | (3S)-1-[3-(5-methyl-1H-pyrazol-4-yl)-1-(2-trimethylsilylethoxymethyl)pyrrolo[2,3-b]pyridin-4-yl]piperidin-3-amine | ES+ 427 [M + H]+, Rt = 1.24 mins, Generic Basic Method |
| P210 | tert-butyl N-methyl-N-[1-[3-pyrimidin-5-yl-1-(2-trimethylsilylethoxymethyl)pyrrolo[2,3-b]pyridin-4-yl]-3-piperidyl]carbamate | ES+ 539 [M + H]+, Rt = 1.68 mins, Generic Basic Method |
| P211 | tert-butyl N-methyl-N-[1-[3-pyrimidin-5-yl-1-(2-trimethylsilylethoxymethyl)pyrrolo[2,3-b]pyridin-4-yl]-4-piperidyl]carbamate | ES+ 539 [M + H]+, Rt = 1.68 mins, Generic Basic Method |
| P212 | tert-butyl N-[(3R)-1-[3-pyrimidin-5-yl-1-(2-trimethylsilylethoxymethyl)pyrrolo[2,3-b]pyridin-4-yl]-3-piperidyl]carbamate | ES+ 525 [M + H]+, Rt = 1.52 mins, Generic Basic Method |

| Preparation | Structure | Name | LCMS Data |
|---|---|---|---|
| P213 | 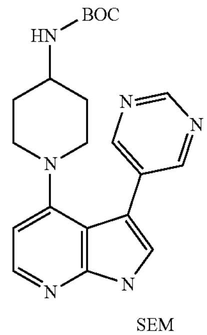 [SMILES: CC(C)(C)OC(=O)NC1CCN(c2ccnc3[nH]cc(-c4cncnc4)c23)CC1 ; "SEM"] | tert-butyl N-[1-[3-pyrimidin-5-yl-1-(2-trimethylsilylethoxymethyl)pyrrolo[2,3-b]pyridin-4-yl]-4-piperidyl]carbamate | ES⁺ 525 [M + H]⁺, Rt = 1.55 mins, Generic Basic Method |
| P214 | 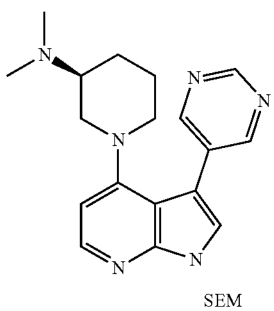 | (3S)-N,N-dimethyl-1-[3-pyrimidin-5-yl-1-(2-trimethylsilylethoxymethyl)pyrrolo[2,3-b]pyridin-4-yl]piperidin-3-amine | ES⁺ 453 [M + H]+, Rt = 1.38 mins, Late Basic Method |

Preparation 215 (P215)-tert-butyl 3-[[3-pyrimidin-5-yl-1-(2-trimethylsilylethoxymethyl)pyrrolo[2,3-b]pyridin-4-yl]amino]azepane-1-carboxylate

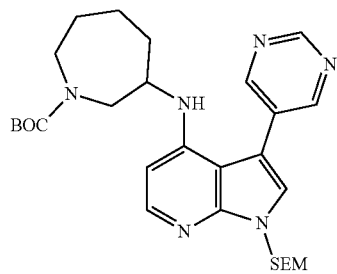 [SMILES: CC(C)(C)OC(=O)N1CCCCC(Nc2ccnc3c2c(-c2cncnc2)cn3COCC[Si](C)(C)C)C1]

2-[(4-chloro-3-pyrimidin-5-yl-pyrrolo[2,3-b]pyridin-1-yl)methoxy]ethyl-trimethyl-silane (P23) (200.00 mg, 0.55 mmol), PEPPSI (37.65 mg, 0.06 mmol) and tert-butyl-3-aminoazepan-1-carboxylate (130.63 mg, 0.61 mmol) was added to a microwave vial equipped with stirrer bar. The vial was purged and evacuated with N₂ (×3) before charging with 1,4-dioxane (0.50 ml) and lithium bis(trimethylsilyl) amide solution (1.11 ml, 1.11 mmol). The resulting solution was stirred at 90° C. for 1 hour. The reaction mixture was cooled to room temperature and concentrated under reduced pressure to afford an oil. The oil was dissolved in DCM (30 ml) and washed with water (10 ml). The aqueous portion was washed further with DCM (30 ml) and the organics combined, washed with brine (40 ml) and concentrated under reduced pressure. The oil was chromatographed [SiO₂ eluting with 0-25% 10% 2N NH₃ in MeOH:DCM] to give tert-butyl 3-[[3-pyrimidin-5-yl-1-(2-trimethylsilylethoxymethyl)pyrrolo[2,3-b]pyridin-4-yl]amino]azepane-1-carboxylate (P215) (86 mg, 0.15 mmol, 27.4% yield) as a pale yellow oil, LCMS ES⁺ 539.45 [M+H]⁺, Rt=1.66 mins, Generic Basic Method.

Preparation 216 (P216)-tert-butyl 4-[1-[3-pyrimidin-5-yl-1-(2-trimethylsilylethoxymethyl)pyrrolo[2,3-b]pyridin-4-yl]-3-piperidyl]piperazine-1-carboxylate

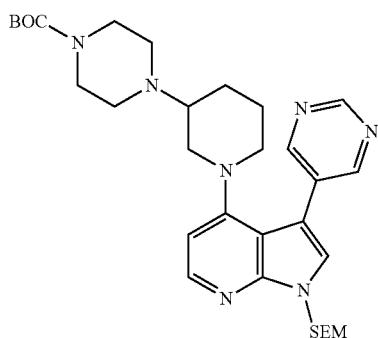

2-[(4-chloro-3-pyrimidin-5-yl-pyrrolo[2,3-b]pyridin-1-yl)methoxy]ethyl-trimethyl-silane (P23) (150.00 mg, 0.42 mmol), PEPPSI (28.24 mg, 0.04 mmol) and tert-butyl 4-(3-piperidyl)piperazine-1-carboxylate (111.95 mg, 0.42 mmol) were added to a microwave vial equipped with stirrer bar. The flask was purged and evacuated with N₂ (×3) before charging with degassed 1,4-dioxane (1 ml). Lithium bis(trimethylsilyl)amide solution (0.83 ml, 0.83 mmol) was added and the solution stirred at 90° C. for 30 minutes. The reaction mixture was cooled to room temperature, concentrated under reduced pressure and diluted with DCM (50 ml) before transferring into a separating funnel and washing with water (20 ml). The aqueous layer was then washed a further time with DCM (50 ml). The organics were combined, dried and the resulting oil was chromatographed [SiO$_2$ eluting with 0-50% (10% 2N NH$_3$) in MeOH:DCM] to give tert-butyl 4-[1-[3-pyrimidin-5-yl-1-(2-trimethylsilylethoxymethyl)pyrrolo[2,3-b]pyridin-4-yl]-3-piperidyl]piperazine-1-carboxylate (P216) (210 mg, 0.35 mmol, 85% yield) as a yellow oil, LCMS ES$^+$ 594.5 [M+H]$^+$, Rt=1.64 mins, Generic Basic Method.

The following compounds were prepared in a similar manner to 2-[(4-chloro-3-pyrimidin-5-yl-pyrrolo[2,3-b]pyridin-1-yl)methoxy]ethyl-trimethyl-silane (P216) from the appropriate amine chloro-azaindole intermediates:

| Preparation | Structure | Name | LCMS Data |
|---|---|---|---|
| P217 | 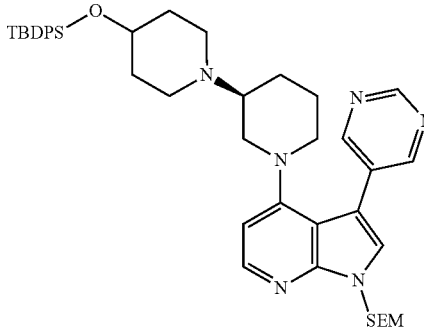 | tert-butyl-diphenyl-[[1-[(3S)-1-[3-pyrimidin-5-yl-1-(2-trimethylsilylethoxymethyl)pyrrolo[2,3-b]pyridin-4-yl]-3-piperidyl]-4-piperidyl]oxy]silane | |
| P218 | 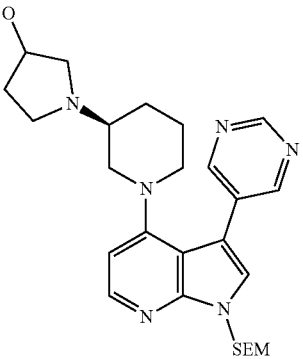 | tert-butyl-diphenyl-[1-[(3S)-1-[3-pyrimidin-5-yl-1-(2-trimethylsilylethoxymethyl)pyrrolo[2,3-b]pyridin-4-yl]-3-piperidyl]pyrrolidin-3-yl]oxy-silane | ES$^+$ 733 [M + H]+, Rt = 1.88 mins, Generic Basic Method |
| P219 | 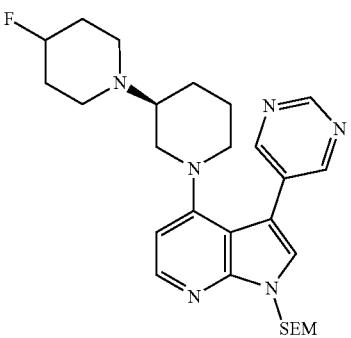 [SMILES: C[Si](C)(C)CCOCn1cc(-c2cncnc2)c2c(N3CCC[C@H](N4CCC(F)CC4)C3)ccnc21] | 2-[[4-[(3S)-3-(4-fluoro-1-piperidyl)-1-piperidyl]-3-pyrimidin-5-yl-pyrrolo[2,3-b]pyridin-1-yl]methoxy]ethyl-trimethyl-silane | ES$^+$ 511 [M + H]+, Rt = 1.56 mins, Generic Basic Method |
| P220 | 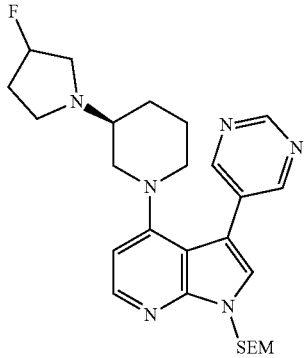 [SMILES: C[Si](C)(C)CCOCn1cc(-c2cncnc2)c2c(N3CCC[C@H](N4CCC(F)C4)C3)ccnc21] | 2-[[4-[(3S)-3-(3-fluoropyrrolidin-1-yl)-1-piperidyl]-3-pyrimidin-5-yl-pyrrolo[2,3-b]pyridin-1-yl]methoxy]ethyl-trimethyl-silane | ES$^+$ 497 [M + H]+, Rt = 1.45 mins, Generic Basic Method |

-continued

| Preparation | Structure | Name | LCMS Data |
|---|---|---|---|
| P221 | 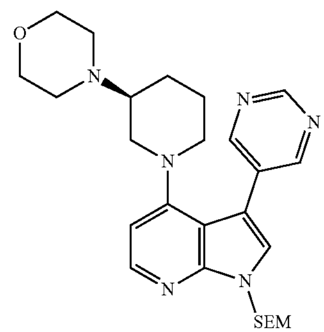 [SMILES: C[Si](C)(C)CCOCn1cc(-c2cncnc2)c2c(N3CCC[C@H](N4CCOCC4)C3)ccnc21] | trimethyl-[2-[[4-[(3S)-3-morpholino-1-piperidyl]-3-pyrimidin-5-yl-pyrrolo[2,3-b]pyridin-1-yl]methoxy]ethyl]silane | ES+ 495 [M + H]+, Rt = 1.38 mins, Generic Basic Method |
| P222 | 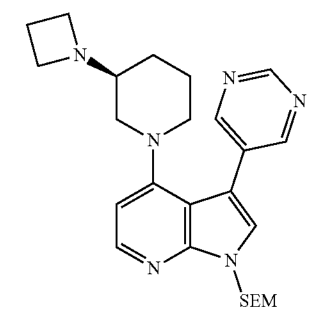 [SMILES: C[Si](C)(C)CCOCn1cc(-c2cncnc2)c2c(N3CCC[C@H](N4CCC4)C3)ccnc21] | 2-[[4-[(3S)-3-(azetidin-1-yl)-1-piperidyl]-3-pyrimidin-5-yl-pyrrolo[2,3-b]pyridin-1-yl]methoxy]ethyl-trimethyl-silane | ES+ 465 [M + H]+, Rt = 1.41 mins, Generic Basic Method |
| P223 | 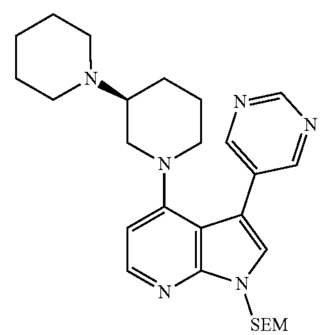 [SMILES: C[Si](C)(C)CCOCn1cc(-c2cncnc2)c2c(N3CCC[C@H](N4CCCCC4)C3)ccnc21] | trimethyl-[2-[[4-[(3S)-3-(1-piperidyl)-1-piperidyl]-3-pyrimidin-5-yl-pyrrolo[2,3-b]pyridin-1-yl]methoxy]ethyl]silane | ES+ 493 [M + H]+, Rt = 1.61 mins, Generic Basic Method |
| P224 | 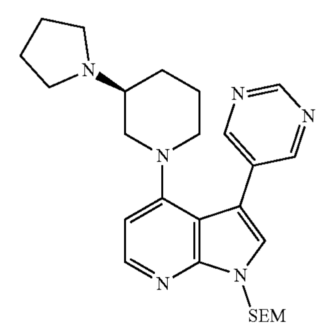 [SMILES: C[Si](C)(C)CCOCn1cc(-c2cncnc2)c2c(N3CCC[C@H](N4CCCC4)C3)ccnc21] | trimethyl-[2-[[3-pyrimidin-5-yl-4-[(3S)-3-pyrrolidin-1-yl-1-piperidyl]pyrrolo[2,3-b]pyridin-1-yl]methoxy]ethyl]silane | ES+ 479 [M + H]+, Rt = 1.46 mins, Generic Basic Method |
| P225 | 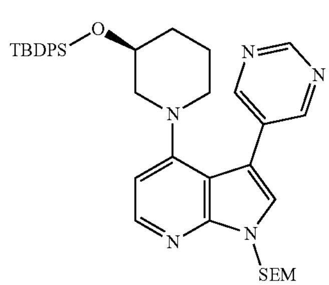 | tert-butyl-diphenyl-[[(3S)-1-[3-pyrimidin-5-yl-1-(2-trimethylsilylethoxymethyl)pyrrolo[2,3-b]pyridin-4-yl]-3-piperidyl]oxy]silane | ES+ 664 [M + H]+, Rt = 1.74 mins, Generic Basic Method |

| Preparation | Structure | Name | LCMS Data |
|---|---|---|---|
| P226 | 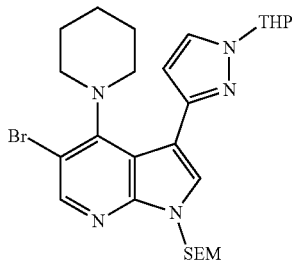 | tert-butyl-diphenyl-[[(3R)-1-[3-pyrimidin-5-yl-1-(2-trimethylsilylethoxymethyl)pyrrolo[2,3-b]pyridin-4-yl]-3-piperidyl]oxy]silane | ES+ 664 [M + H]+, Rt = 1.74 mins, Generic Basic Method |

Preparation 227 (P227)-2-[[5-bromo-4-(1-piperidyl)-3-(1-tetrahydropyran-2-ylpyrazol-3-yl)pyrrolo[2,3-b]pyridin-1-yl]methoxy]ethyl-trimethylsilane

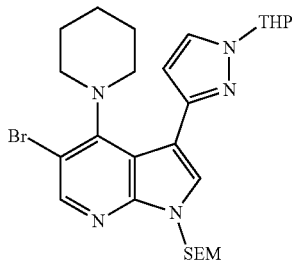

Piperidine (0.42 ml, 3.91 mmol) and 2-[[5-bromo-4-chloro-3-(1-tetrahydropyran-2-ylpyrazol-3-yl)pyrrolo[2,3-b]pyridin-1-yl]methoxy]ethyl-trimethyl-silane (P49) (1.00 g, 1.95 mmol) in MeCN (10 ml) was heated at 180° C. in the microwave for 2 hours. The solution was passed through an SCX and eluted with Methanol/NH₃ to give 2-[[5-bromo-4-(1-piperidyl)-3-(1-tetrahydropyran-2-ylpyrazol-3-yl)pyrrolo[2,3-b]pyridin-1-yl]methoxy]ethyl-trimethyl-silane (P227) (500 mg, 0.62 mmol, 32% yield), LCMS ES+ 562.3/563.3 [M+H]+, Rt=1.63 mins (Late Basic Method).

Preparation 228 (P228)-tert-butyl N-isopropyl-N-[(3S)-1-[3-pyrimidin-5-yl-1-(2-trimethylsilylethoxymethyl)pyrrolo[2,3-b]pyridin-4-yl]-3-piperidyl]carbamate

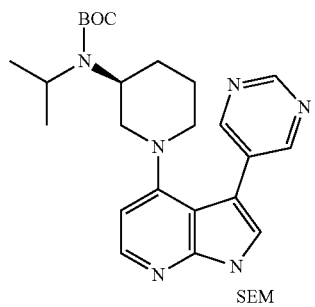

To four separate teflon capped sealed vessels equipped with stirrer bars was added in four equal portions 2-[(4-chloro-3-pyrimidin-5-yl-pyrrolo[2,3-b]pyridin-1-yl)methoxy]ethyl-trimethyl-silane (P23) (600.00 mg, 1.66 mmol), tert-butyl N-isopropyl-N-[(3S)-3-piperidyl]carbamate (0.61 ml, 2.49 mmol), potassium carbonate, anhydrous (459.54 mg, 3.32 mmol) and tert-butanol (1.5 ml). The reaction mixture was heated at 180° C. behind a blast shield for a total of four days. The crude reactions were combined and concentrated under reduced pressure to afford a dark coloured oil. The oil was diluted with EtOAc (50 ml) and washed with water (50 ml). The aqueous layer was extracted with EtOAc (2×50 ml) and the combined organics washed with brine and concentrated in vacuo to give an oil. The oil was loaded onto isolute HM-N resin and chromatographed (SiO₂, EtOAc:i-hexane 0-80%) to give tert-butyl N-isopropyl-N-[(3S)-1-[3-pyrimidin-5-yl-1-(2-trimethylsilylethoxymethyl)pyrrolo[2,3-b]pyridin-4-yl]-3-piperidyl]carbamate (P228) (30 mg), LCMS ES+ 567 [M+H]+, Rt=1.77 mins (Generic Basic Method).

Preparation 229 (P229)-2-[[5-bromo-4-(1-piperidyl)-3-pyrimidin-5-yl-pyrrolo[2,3-b]pyridin-1-yl]methoxy]ethyl-trimethyl-silane

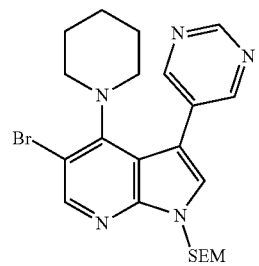 [SMILES: C[Si](C)(C)CCOCn1cc(-c2cncnc2)c2c(N3CCCCC3)c(Br)cnc21]

Tetrakis(triphenylphosphine)palladium (0) (12.6 mg, 0.01 mmol) was dissolved in a mixture of 1,4-dioxane (1 ml) and water (0.3 ml) and degassed for 20 minutes. 2-[[5-bromo-3-iodo-4-(1-piperidyl)pyrrolo[2,3-b]pyridin-1-yl]methoxy]ethyl-trimethyl-silane (P54) (117 mg, 0.22 mmol) was added followed by pyrimidine-5-boronic acid, pinacol ester (44.95 mg, 0.22 mmol) and heated to 80° C. in a microwave vial for 2 hours. The reaction mixture was heated to 90° C. for a further 2 hours. The reaction mixture was partitioned between ethyl acetate and water, and the organics washed with brine. The solvent removed in vacuo and the resulting residue was chromatographed [SiO₂, ethyl acetate:hexane—0-50%] to give 2-[[5-bromo-4-(1-piperidyl)-3-pyrimidin-5- yl-pyrrolo[2,3-b]pyridin-1-yl]methoxy]ethyl-trimethyl-silane (P229) (53 mg), LCMS ES+ 489 [M+H]+ Rt=0.84 mins (Generic Basic Method).

Preparation 230 (P230)-Trimethyl-[2-[[4-(1-piperidyl)-3-(2-tetrahydropyran-2-ylpyrazol-3-yl)pyrrolo[2,3-b]pyridin-1-yl]methoxy]ethyl]silane

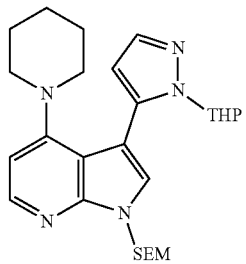

To a microwave vial equipped with stirrer bar was added 2-[[3-iodo-4-(1-piperidyl)pyrrolo[2,3-b]pyridin-1-yl]methoxy]ethyl-trimethyl-silane (P55) (147.00 mg, 0.32 mmol), 1-(2-tetrahydropyranyl)-1H-pyrazole-5-boronic acid pinacol ester (89.39 mg, 0.32 mmol), anhydrous potassium carbonate (93.27 mg, 0.67 mmol) and tetrakistriphenylphosphine palladium (18.57 mg, 0.02 mmol) followed by a mixture of 1,4-dioxane (0.6 ml) and water (0.2 ml). The resulting suspension was degassed for 20 minutes before heating to 140° C. for a further 20 minutes. The reaction mixture was cooled to room temperature and concentrated in vacuo to yield a dark orange oil. The oil was dissolved in DCM (15 ml) and washed with water (10 ml). The organics were concentrated under reduced pressure to afford an orange coloured oil. The oil was chromatographed [SiO2, 0-50% (10% (2N NH3 in MeOH) in DCM:DCM) to give trimethyl-[2-[[4-(1-piperidyl)-3-(2-tetrahydropyran-2-ylpyrazol-3-yl)pyrrolo[2,3-b]pyridin-1-yl]methoxy]ethyl]silane (P230) (55 mg, 0.11 mmol, 36% yield) LCMS ES+ 482[M+H]+ Rt=1.81 mins (Generic Basic Method).

Preparation 231 (P231)-Methyl 4-(tert-butoxycarbonylamino)-1-[3-pyrimidin-5-yl-1-(2-trimethylsilylethoxymethyl)pyrrolo[2,3-b]pyridin-4-yl]piperidine-4-carboxylate

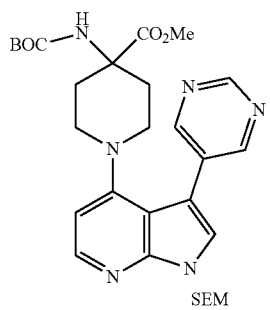

A mixture of 2-[(4-chloro-3-pyrimidin-5-yl-pyrrolo[2,3-b]pyridin-1-yl)methoxy]ethyl-trimethyl-silane (P23) (400 mg, 1.11 mmol), methyl 4-(tert-butoxycarbonylamino)piperidine-4-carboxylate (287.00 mg, 1.11 mmol), palladium (II) acetate (25 mg, 0.11 mmol), BINAP (69 mg, 0.111 mmol) and cesium carbonate (1.08 g, 3.33 mmol) in toluene (4 ml) was stirred at 100° C. overnight under an atmosphere of argon. The mixture was diluted with EtOAc and washed with water and brine, before it was dried over MgSO4, filtered and concentrated under reduced pressure. The residue was purified using preparative-TLC to give methyl 4-(tert-butoxycarbonylamino)-1-[3-pyrimidin-5-yl-1-(2-trimethylsilylethoxymethyl)-pyrrolo[2,3-b]pyridin-4-yl]piperidine-4-carboxylate (P231) (150 mg).

Preparation 232 (P232)-4-(tert-butoxycarbonylamino)-1-[3-pyrimidin-5-yl-1-(2-trimethylsilylethoxymethyl)-pyrrolo[2,3-b]pyridin-4-yl]piperidine-4-carboxylic acid

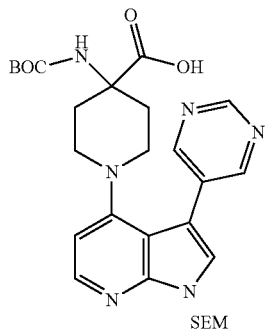

A mixture of methyl 4-(tert-butoxycarbonylamino)-1-[3-pyrimidin-5-yl-1-(2-trimethylsilylethoxymethyl)-pyrrolo[2,3-b]pyridin-4-yl]piperidine-4-carboxylate (P231) (50 mg, 0.086 mmol) and lithium hydroxide monohydrate (18 mg, 0.43 mmol) in H2O (0.5 ml) and THF (0.8 ml) was stirred at room temperature overnight. The reaction mixture was diluted with H2O and washed with EtOAc. The aqueous layer was acidifed to pH=4 with HCl (1N) and extracted with EtOAc. The combined EtOAc layers were dried over Na2SO4 and concentrated under reduced pressure to give 4-(tert-butoxycarbonylamino)-1-[3-pyrimidin-5-yl-1-(2-trimethylsilylethoxymethyl)pyrrolo[2,3-b]pyridin-4-yl]piperidine-4-carboxylic acid (P232) (35 mg)

Preparation 233 (P233)-(2S)-1-(3-cyano-1H-pyrrolo[2,3-b]pyridin-4-yl)pyrrolidine-2-carboxylic acid

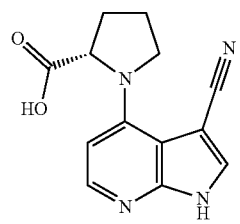 [SMILES: N#Cc1c[nH]c2nccc(N3CCC[C@H]3C(=O)O)c12]

A mixture of 4-chloro-1H-pyrrolo[2,3-b]pyridine-3-carbonitrile (P5) (200.00 mg, 1.13 mmol), (2S)-methyl pyrrolidine-2-carboxylate hydrochloride (186.52 mg, 1.13 mmol) and cesium carbonate (1.834 g, 5.63 mmol) was heated to 130° C. for 10 hours. The product was purified by silica chromatography, eluting with 5% 2N NH3 methanol in DCM, to give (2S)-1-(3-cyano-1H-pyrrolo[2,3-b]pyridin-4- yl)pyrrolidine-2-carboxylic acid (P233) (200 mg, 0.7024 mmol, 62.371% yield), LCMS ES$^+$ 257.2 [M+H]$^+$, Rt=0.58 mins (Late Basic Method).

Preparation 234 (P234)-tert-butyl N-[4-(dimethylcarbamoyl)-1-[3-pyrimidin-5-yl-1-(2-trimethylsilylethoxymethyl)pyrrolo[2,3-b]pyridin-4-yl]-4-piperidyl]carbamate

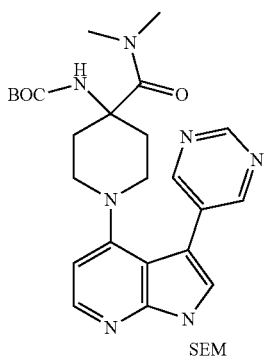

A mixture of 4-(tert-butoxycarbonylamino)-1-[3-pyrimidin-5-yl-1-(2-trimethylsilylethoxymethyl)-pyrrolo[2,3-b]pyridin-4-yl]piperidine-4-carboxylic acid (P232) (35 mg, 0.06 mmol), dimethylamine hydrochloride (9.9 mg, 0.12 mmol), HATU (5 mg, 0.13 mmol) and DIPEA (24 mg, 0.18 mmol) in DMF (1 ml) was stirred at room temperature overnight. After this time, the mixture was poured into water and extracted with EtOAc. The organics were washed with water and brine, dried over Na$_2$SO$_4$, filtered and concentrated under reduced pressure. The residue was purified by preparative-TLC to give tert-butyl N-[4-(dimethylcarbamoyl)-1-[3-pyrimidin-5-yl-1-(2-trimethylsilylethoxymethyl)pyrrolo[2,3-b]pyridin-4-yl]-4-piperidyl]carbamate (P234) (16 mg).

Preparation 235 (P235)-Ethyl 3-methyl-1-[3-pyrimidin-5-yl-1-(2-trimethylsilylethoxymethyl)pyrrolo[2,3-b]pyridin-4-yl]piperidine-3-carboxylate

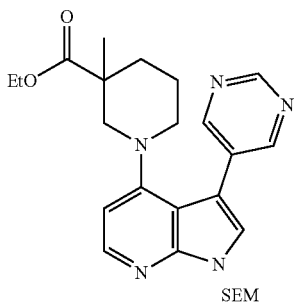 [SMILES: CC1(C(=O)O)CCCN(c2ccnc3[nH]cc(-c4cncnc4)c23)C1]

At −78° C., under an atmosphere of N$_2$, was added lithium bis(trimethylsilyl)amide solution (0.29 ml, 0.29 mmol) to a solution of ethyl 1-[3-pyrimidin-5-yl-1-(2-trimethylsilylethoxymethyl)pyrrolo[2,3-b]pyridin-4-yl]piperidine-3-carboxylate (P135) (137.59 mg, 0.29 mmol) in THF (2 ml). The mixture was stirred at −78° C. for 20 minutes. After this time, iodomethane (0.02 ml, 0.29 mmol) was added and the reaction mixture was allowed to warm to room temperature before stirring for a further 3 hours at room temperature. Additional lithium bis(trimethylsilyl)amide solution (0.29 ml, 0.29 mmol) and iodomethane (0.02 ml, 0.29 mmol) were added at −78° C. and the mixture was allowed to stir for a further 1 hour. The reaction mixture was quenched using ammonium chloride (sat. soln.). The organics were extracted into EtOAc, concentrated under reduced pressure and the resulting residue chromatographed [SiO$_2$, 0-100% EtOAc: Hexane] to give ethyl 3-methyl-1-[3-pyrimidin-5-yl-1-(2-trimethylsilylethoxymethyl)pyrrolo[2,3-b]pyridin-4-yl]piperidine-3-carboxylate (P235) (42 mg), LCMS ES$^+$ 496 [M+H]$^+$, Rt=1.67 mins (Generic Basic Method).

Preparation 236 (P236)-3-Methyl-1-[3-pyrimidin-5-yl-1-(2-trimethylsilylethoxymethyl)pyrrolo[2,3-b]pyridin-4-yl]piperidine-3-carboxylic acid

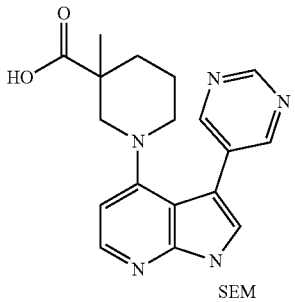

To a solution of ethyl 3-methyl-1-[3-pyrimidin-5-yl-1-(2-trimethylsilylethoxymethyl)pyrrolo[2,3-b]pyridin-4-yl]piperidine-3-carboxylate (P235) (42. mg, 0.08 mmol) in ethanol (1 ml) was added anhydrous lithium hydroxide (2.03 mg, 0.08 mmol). The reaction mixture was stirred at reflux for 3 hours. EtOH removed under reduced pressure and HCl (2N) added dropwise to solution until precipitation of a white solid occurred at pH 4. The organics were extracted with EtOAc, dried over magnesium sulfate and concentrated under reduced pressure to give 3-methyl-1-[3-pyrimidin-5-yl-1-(2-trimethylsilylethoxymethyl)pyrrolo[2,3-b]pyridin-4-yl]piperidine-3-carboxylic acid (P236), LCMS ES$^-$ 466 [M+H]$^+$, Rt=0.99 mins (Generic Basic Method)

Preparation 237 (P237)-3-Methyl-1-[3-pyrimidin-5-yl-1-(2-trimethylsilylethoxymethyl)pyrrolo[2,3-b]pyridin-4-yl]piperidin-3-amine

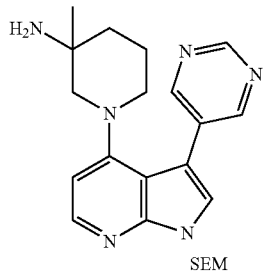 [SMILES: CC1(N)CCCN(c2ccnc3[nH]cc(-c4cncnc4)c23)C1]

To a solution of 3-methyl-1-[3-pyrimidin-5-yl-1-(2-trimethylsilylethoxymethyl)pyrrolo[2,3-b]pyridin-4-yl]piperidine-3-carboxylic acid (P236) (38. mg, 0.08 mmol) in tert-butanol (0.5 ml) was added triethylamine (0.01 ml, 0.10 mmol) and diphenyl phosphoryl azide (0.02 ml, 0.10 mmol). The mixture was heated to 120° C. for 2 hours. After this time, the solution was concentrated under reduced pressure. The resulting residue was dissolved in MeOH and purified via SCX (1 g) before being chromatographed [SiO₂, 0-10% 2N NH₃ in MeOH:DCM) to give 3-methyl-1-[3-pyrimidin-5-yl-1-(2-trimethylsilylethoxymethyl)pyrrolo[2,3-b]pyridin-4-yl]piperidin-3-amine (P237) (14 mg), LCMS ES⁺ 439 [M+H]⁺, Rt=1.29 mins (Generic Basic Method)

Preparation 238 (P238)-3-Ethyl-1-[3-(5-methylthiazol-2-yl)-1-(2-trimethylsilylethoxymethyl)pyrrolo[2,3-b]pyridin-4-yl]piperidin-3-amine

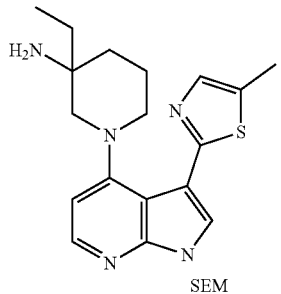 [SMILES: CCC1(N)CCCN(c2ccnc3[nH]cc(-c4ncc(C)s4)c23)C1]

Chlorotrimethylsilane (0.04 ml, 0.34 mmol) was added to a stirred mixture of benzyl N-[3-ethyl-1-[3-(5-methylthiazol-2-yl)-1-(2-trimethylsilylethoxymethyl)-pyrrolo[2,3-b]pyridin-4-yl]-3-piperidyl]carbamate (P154) (69.61 mg, 0.11 mmol) and sodium iodide (51.67 mg, 0.34 mmol) in MeCN (0.50 ml). The reaction was stirred at room temperature over the weekend. Water was added and the solvent removed under reduced pressure. The residue was redissolved in methanol and loaded onto a pre-acidified SCX (1 g) resin. The cartridge was flushed with methanol before eluting the product with ammonia in methanol (2N). The solvent was removed under reduced pressure to afford 3-ethyl-1-[3-(5-methylthiazol-2-yl)-1-(2-trimethylsilylethoxymethyl)-pyrrolo[2,3-b]pyridin-4-yl]piperidin-3-amine (P238) (48.9 mg), LCMS ES⁺ 472 [M+H]⁺, Rt=1.50 mins (Generic Basic Method).

Preparation 239 (P239)-tert-butyl N-[(3S)-1-[3-pyrimidin-5-yl-1-(2-trimethylsilylethoxymethyl)pyrrolo[2,3-b]pyridin-4-yl]-3-piperidyl]carbamate

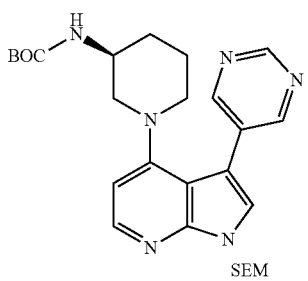 [SMILES: CC(C)(C)OC(=O)N[C@H]1CCCN(c2ccnc3[nH]cc(-c4cncnc4)c23)C1]

To a microwave vial equipped with a stirrer bar was added 2-[(4-chloro-3-pyrimidin-5-yl-pyrrolo[2,3-b]pyridin-1-yl)methoxy]ethyl-trimethyl-silane (P23) (197.00 mg, 0.55 mmol), (S)-3-(boc-amino)piperidine (1.093 g, 5.46 mmol) and DMSO (0.25 ml). The reaction mixture was heated at 145° C. for 4 hours. The cooled reaction mixture was concentrated in vacuo and the residue purified via preparative HPLC using the late basic method to afford tert-butyl N-[(3S)-1-[3-pyrimidin-5-yl-1-(2-trimethylsilylethoxymethyl)pyrrolo[2,3-b]pyridin-4-yl]-3-piperidyl]carbamate (P239), LCMS ES⁺ 525 [M+H]⁺, Rt=1.58 mins (Generic Basic Method).

Preparation 240 (P240)-tert-butyl N-methyl-N-[(3S)-1-[1-(2-trimethylsilylethoxymethyl)-3-[1-(2-trimethylsilylethoxymethyl)pyrazol-3-yl]pyrrolo[2,3-b]pyridin-4-yl]-3-piperidyl]carbamate

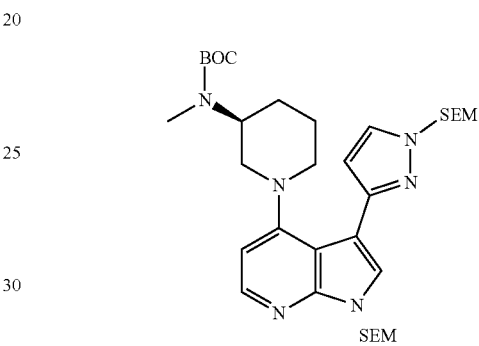

A suspension of 2-[[4-chloro-3-[1-(2-trimethylsilylethoxymethyl)pyrazol-3-yl]pyrrolo[2,3-b]pyridin-1-yl]methoxy]ethyl-trimethyl-silane (P45) (240.00 mg, 0.5 mmol), tert-butyl N-methyl-N-[(3S)-3-piperidyl]carbamate (107.00 mg, 0.50 mmol), BINAP (33 mg, 0.05 mmol), Cs₂CO₃ (326.00 mg, 1.00 mmol) in toluene (3 ml) was heated at 100° C. for 2 days. The mixture was diluted with water and extracted with EtOAc. The combined organics were washed with brine, dried over Na₂SO₄, filtered and concentrated in vacuo. The residue was purified by preparative TLC to afford tert-butyl N-methyl-N-[(3S)-1-[1-(2-trimethylsilylethoxymethyl)-3-[1-(2-trimethylsilylethoxymethyl)pyrazol-3-yl]pyrrolo[2,3-b]pyridin-4-yl]-3-piperidyl]carbamate (P240) (35 mg).

The following compounds were prepared in a similar manner tert-butyl N-methyl-N-[(3S)-1-[1-(2-trimethylsilylethoxymethyl)-3-[1-(2-trimethylsilylethoxymethyl)pyrazol-3-yl]pyrrolo[2,3-b]pyridin-4-yl]-3-piperidyl]carbamate (P240) from the appropriate intermediates:

| Preparation | Structure | Name |
|---|---|---|
| P241 | ![structure] | tert-butyl N-methyl-N-[(3S)-1-[1-(2-trimethylsilylethoxymethyl)-3-(1-tritylpyrazol-4-yl)pyrrolo[2,3-b]pyridin-4-yl]-3-piperidyl]carbamate |

-continued

| Preparation | Structure | Name |
|---|---|---|
| P242 | 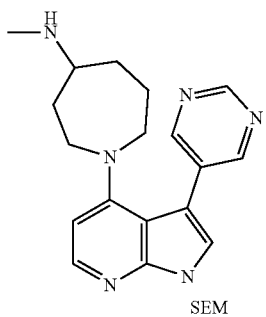 [SMILES: CNC1CCCN(c2ccnc3[nH]cc(-c4cncnc4)c23)CC1] | tert-butyl N-[(3S)-1-[3-cyano-1-(2-trimethylsilylethoxymethyl)pyrrolo[2,3-b]pyridin-4-yl]-3-piperidyl]-N-methyl-carbamate |

Preparation 243 (P243)-N-methyl-1-[3-pyrimidin-5-yl-1-(2-trimethylsilylethoxymethyl)pyrrolo[2,3-b]pyridin-4-yl]azepan-4-amine

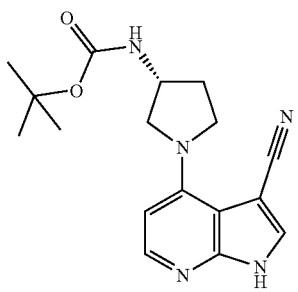 [SMILES: CC(C)(C)OC(=O)N[C@@H]1CCN(c2ccnc3[nH]cc(C#N)c23)C1]

A solution of benzyl N-methyl-N-[1-[3-pyrimidin-5-yl-1-(2-trimethylsilylethoxymethyl)pyrrolo[2,3-b]pyridin-4-yl]azepan-4-yl]carbamate (P197) (100.00 mg, 0.17 mmol) in ethanol (3 ml) was passed through the H-Cube (10% Pd/C, Full $H_2$, 50° C., 1 ml/min) for 80 minutes. After this time, the solvent was removed in vacuo and the residue loaded onto a pre-acidified SCX cartridge. The cartridge was washed with MeOH (×5 cvs) and the product eluted with $NH_3$ in MeOH (2N). The basic fractions were concentrated under reduced pressure and the residue was purified via preparative HPLC using the generic basic run to afford N-methyl-1-[3-pyrimidin-5-yl-1-(2-trimethylsilylethoxymethyl)pyrrolo[2,3-b]pyridin-4-yl]azepan-4-amine (P243) (31.7 mg), LCMS ES+ 453 [M+H]+, Rt=1.14 mins (Generic Basic Method)

Preparation 244 (P244)-tert-butyl N-[(3R)-1-(3-cyano-1H-pyrrolo[2,3-b]pyridin-4-yl)pyrrolidin-3-yl]carbamate (R)-3-(Boc-amino)pyrrolidine (167.80 mg, 0.90 mmol) and 4-chloro-1H-pyrrolo[2,3-b]pyridine-3-carbonitrile (P5) (80 mg, 0.45 mmol) were dissolved in NMP (0.5 ml) and heated at 160° C. for 4 hours. The mixture was passed through an SCX cartridge eluting with MeOH (50 ml). The crude product was eluted with 2N $NH_3$ in MeOH and concentrated under reduced pressure to give tert-butyl N-[(3R)-1-(3-cyano-1H-pyrrolo[2,3-b]pyridin-4-yl)pyrrolidin-3-yl]carbamate (P244) (23 mg, 0.07 mmol, 14.8% yield), LCMS ES+ 353.3 [M+H]+, Rt=0.80 mins (Generic Basic Method).

Preparation 245 (P245)-2-[[4-(1,8-diazaspiro[5.5]undecan-8-yl)-3-(1,2,4-thiadiazol-3-yl)pyrrolo[2,3-b]pyridin-1-yl]methoxy]ethyl-trimethyl-silane

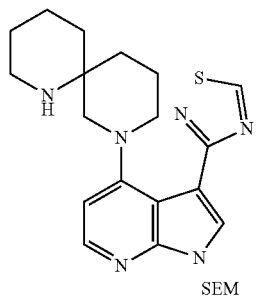 [SMILES: N=C(/N=C\S)c1c[nH]c2nccc(N3CCCC4(CCCCN4)C3)c12]

A solution of tert-butyl 8-[3-(1,2,4-thiadiazol-3-yl)-1-(2-trimethylsilylethoxymethyl)pyrrolo[2,3-b]pyridin-4-yl]-1,8-diazaspiro[5.5]undecane-1-carboxylate (P93) (244.00 mg, 0.42 mmol) in 1,4-dioxane (1 ml) and hydrogen chloride solution (0.08 ml, 0.42 mmol) was stirred at room temperature for 2 hours. After this time, HCl (5N aq. soln.) was added and the reaction mixture was heated to 50° C. for 4 hours. The crude mixture was subsequently loaded onto a pre-acidified 5 g SCX cartridge and washed with MeOH (×4 cvs). Product was isolated following washing with $NH_3$ in MeOH (2N) to give 2-[[4-(1,8-diazaspiro[5.5]undecan-8-yl)-3-(1,2,4-thiadiazol-3-yl)pyrrolo[2,3-b]pyridin-1-yl]methoxy]ethyl-trimethyl-silane (P245) obtained as a pale orange oil, (158 mg, 0.33 mmol, 78.1% yield), LCMS ES+ 484 [M+H]+, Rt=1.53 mins (Generic Basic Method). 2-[[4-(1,8-diazaspiro[5.5]undecan-8-yl)-3-(1,2,4-thiadiazol-3-yl)pyrrolo[2,3-b]pyridin-1-yl]methoxy]ethyl-trimethyl-silane (P245, 347 mg from above and addn. batch), was subsequently purified by chiral HPLC (Lux C1, 250×20 mm, 5 um, eluting with MeOH, with DEA as a modifier) to give 2-[[4-[(6R)-1,8-diazaspiro[5.5]undecan-8-yl]-3-(1,2,4-thiadiazol-3-yl)pyrrolo[2,3-b]pyridin-1-yl]methoxy]ethyl-trimethyl-silane (P246) and 2-[[4-[(6S)-1,8-diazaspiro[5.5]undecan-8-yl]-3-(1,2,4-thiadiazol-3-yl)pyrrolo[2,3-b]pyridin-1-yl]methoxy]ethyl-trimethyl-silane (P247)

Preparation 248 (P248)-tert-butyl-(3R)-3-[3-thiazol-2-yl-1-(2-trimethylsilylethoxymethyl)pyrrolo[2,3-b]pyridin-4-yl]oxypiperidine-1-carboxylate

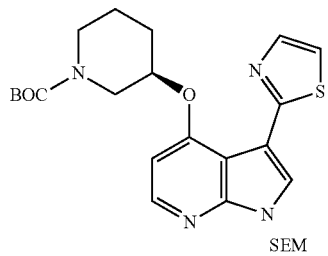 [SMILES: CC(C)(C)OC(=O)N1CCC[C@@H](Oc2ccnc3[nH]cc(-c4nccs4)c23)C1]

To a solution of (R)-1-boc-3-hydroxypiperidine (164.99 mg, 0.82 mmol) in DMF (2 ml), at 0° C., under an atmosphere of nitrogen, was added NaH 60% w/w (32.79 mg, 0.82 mmol). The mixture was stirred at room temperature for 15 minutes. 2-[(4-chloro-3-thiazol-2-yl-pyrrolo[2,3-b]pyridin-1-yl)methoxy]ethyl-trimethyl-silane (P25) (150 mg, 0.41 mmol) was added and the reaction mixture was stirred at room temperature overnight. The mixture was quenched with water and the organics were extracted into ethyl acetate. The combined organics were dried over MgSO$_4$, filtered and concentrated under reduced pressure. The resulting residue was chromatographed [SiO$_2$, 0-100% EtOAc: isohexane) to give tert-butyl (3R)-3-[3-thiazol-2-yl-1-(2-trimethylsilylethoxymethyl)pyrrolo[2,3-b]pyridin-4-yl]oxypiperidine-1-carboxylate (215 mg, 0.41 mmol, 98.8% yield), LCMS ES$^+$ 531 [M+H]$^+$, Rt=1.68 mins (Generic Basic Method).

The following compounds were prepared in a similar manner to tert-butyl-(3R)-3-[3-thiazol-2-yl-1-(2-trimethylsilylethoxymethyl)pyrrolo[2,3-b]pyridin-4-yl]oxypiperidine-1-carboxylate (P248) from the appropriate intermediates:

mg). The residue was dissolved DCM (1.0 ml) and TFA (1.0 ml) was added. The reaction mixture left to stir for 1 hour then purified via SCX. NH$_4$OH (30% aq., 1.0 ml) was added and the solution left to stir for ca 30 minutes. The solution was purified via SCX to give 5-methyl-4-(1-piperidyl)-3-pyrimidin-5-yl-1H-pyrrolo[2,3-b]pyridine (E1) (20 mg, 0.06 mmol, 25% yield), LCMS ES$^+$ 294[M+H]$^+$ Rt=1.08 mins (Generic Basic Method)

The following compounds were prepared in a similar manner to 5-methyl-4-(1-piperidyl)-3-pyrimidin-5-yl-1H-pyrrolo[2,3-b]pyridine (E1) from the appropriate intermediates:

| Example | Structure | Name | LCMS Data |
|---|---|---|---|
| E2 | 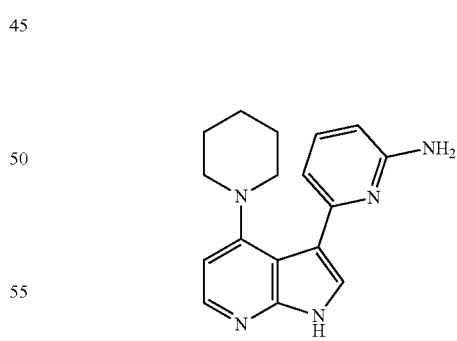 | 5-methyl-4-(1-piperidyl)-3-(1H-pyrazol-4-yl)-1H-pyrrolo[2,3-b]pyridine | ES$^+$ 282 [M + H]$^+$, Rt = 1.07 mins, Generic Basic Method |

| Preparation | Structure | Name | LCMS Data |
|---|---|---|---|
| P249 | 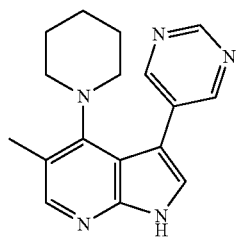 | tert-butyl (3R)-3-[3-pyrimidin-4-yl-1-(2-trimethylsilylethoxymethyl)pyrrolo[2,3-b]pyridin-4-yl]oxypiperidine-1-carboxylate | ES$^+$ 526 [M + H]$^+$, Rt = 1.28 mins, Generic Basic Method |

Example 1 (E1)-5-methyl-4-(1-piperidyl)-3-pyrimidin-5-yl-1H-pyrrolo[2,3-b]pyridine 2-[[5-bromo-4-(1-piperidyl)-3-pyrimidin-5-yl-pyrrolo[2,3-b]pyridin-1-yl]methoxy]ethyl-trimethyl-silane (P229) (120.00 mg, 0.25 mmol) was dissolved in a mixture of 1,4-dioxane (1.6 ml) and water (0.5 ml) and degassed for 20 minutes. Pd$_2$(dba)$_3$ (0.05 mmol), PCy$_3$ (0.12 mmol), K$_3$PO$_4$, (2.00 mmol) was added followed by trimethylboroxine (102.56 ul, 0.74 mmol) and heated to 120° C. for 30 minutes. The reaction mixture was diluted with ethyl acetate and washed with water. The organics were dried over magnesium sulphate and the solvent removed in vacuo. The residue was chromatographed [SiO$_2$, 0-50% ethyl acetate:hexane) to give trimethyl-[2-[[5-methyl-4-(1-piperidyl)-3-pyrimidin-5-yl-pyrrolo[2,3-b]pyridin-1-yl]methoxy]ethyl]silane (35

Example 3 (E3)-6-[4-(1-piperidyl)-1H-pyrrolo[2,3-b]pyridin-3-yl]pyridin-2-amine

To a microwave vial equipped with stirrer bar was added trimethyl-[2-[[4-(1-piperidyl)-3-(4,4,5,5-tetramethyl-1,3,2-dioxaborolan-2-yl)pyrrolo[2,3-b]pyridin-1-yl]methoxy]ethyl]silane (P57) (70 mg, 0.15 mmol), tris(dibenzylideneacetone)dipalladium(0) (6.96 mg, 0.01 mmol), tricyclohexylphosphine (5.16 mg, 0.02 mmol), potassium phosphate tribasic (64.95 mg, 0.31 mmol) and 6-bromopyridin-2-amine (31.76 mg, 0.18 mmol). The vial was purged and evacuated with nitrogen before the addition of a degassed solution of 1,4-dioxane and water (3:1, 0.4 ml). The reaction mixture was subsequently heated to 150° C. for 10 minutes. After cooling to room temperature, DCM (20 ml) and water (10 ml) were added and the organic layer was concentrated in vacuo. The crude oil obtained was chromatographed [SiO₂, 0-100% EtOAc: iso-hexane]. The oil obtained was dissolved in HCl (2N, 3.06 ml, 6.12 mmol) and THF (0.5 ml) and the reaction mixture was heated to 80° C. in the microwave for 40 minutes. The solvent was removed in vacuo and purified via preparative HPLC to afford 6-[4-(1-piperidyl)-1H-pyrrolo[2,3-b]pyridin-3-yl]pyridin-2-amine (E3) (13 mg) LCMS ES⁺ 294[M+H]⁺ Rt=1.19 mins (Generic Basic Method)

The following compounds were prepared in a similar manner to 6-[4-(1-piperidyl)-1H-pyrrolo[2,3-b]pyridin-3-yl]pyridin-2-amine (E3) from the appropriate intermediates:

| Example | Structure | Name | LCMS Data |
| --- | --- | --- | --- |
| E4 | 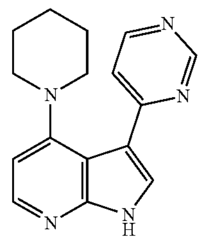 [SMILES: c1cc(-c2c[nH]c3nccc(N4CCCCC4)c23)ncn1] | 4-(1-piperidyl)-3-pyrimidin-4-yl-1H-pyrrolo[2,3-b]pyridine | ES⁺ 280 [M + H]⁺, Rt = 1.08 mins, Generic Basic Method |
| E5 | 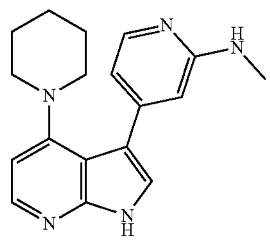 [SMILES: CNc1cc(-c2c[nH]c3nccc(N4CCCCC4)c23)ccn1] | N-methyl-4-[4-(1-piperidyl)-1H-pyrrolo[2,3-b]pyridin-3-yl]pyridin-2-amine | ES⁺ 308 [M + H]⁺, Rt = 1.10 mins, Generic Basic Method |
| E6 | 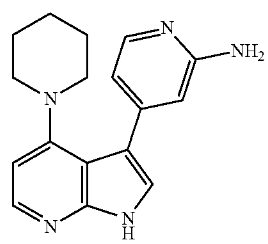 [SMILES: Nc1cc(-c2c[nH]c3nccc(N4CCCCC4)c23)ccn1] | 5-[4-(1-piperidyl)-1H-pyrrolo[2,3-b]pyridin-3-yl]pyridin-3-amine | ES⁺ 294 [M + H]⁺, Rt = 1.00 mins, Generic Basic Method |
| E7 | 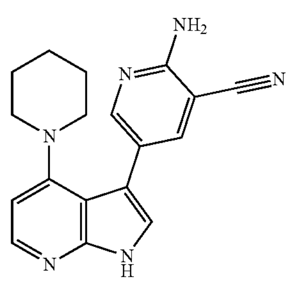 [SMILES: N#Cc1cc(-c2c[nH]c3nccc(N4CCCCC4)c23)cnc1N] | 2-amino-5-[4-(1-piperidyl)-1H-pyrrolo[2,3-b]pyridin-3-yl]pyridine-3-carbonitrile | ES⁺ 319 [M + H]⁺, Rt = 1.14 mins, Generic Basic Method |
| E8 | 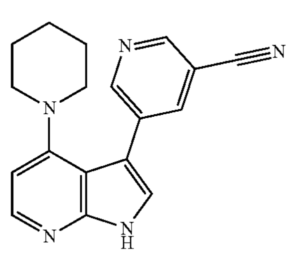 [SMILES: N#Cc1cncc(-c2c[nH]c3nccc(N4CCCCC4)c23)c1] | 5-[4-(1-piperidyl)-1H-pyrrolo[2,3-b]pyridin-3-yl]pyridine-3-carbonitrile | ES⁺ 304 [M + H]⁺, Rt = 1.21 mins, Generic Basic Method |

| Example | Name | LCMS Data |
|---|---|---|
| E9 | 4-[4-(1-piperidyl)-1H-pyrrolo[2,3-b]pyridin-3-yl]pyridin-2-amine | ES+ 294 [M + H]+, Rt = 1.03 mins, Generic Basic Method |
| E10 | 5-[4-(1-piperidyl)-1H-pyrrolo[2,3-b]pyridin-3-yl]pyridin-2-amine | ES+ 294 [M + H]+, Rt = 1.03 mins, Generic Basic Method |
| E11 | 3-(5-fluoro-3-pyridyl)-4-(1-piperidyl)-1H-pyrrolo[2,3-b]pyridine | ES+ 297 [M + H]+, Rt = 1.27 mins, Generic Basic Method |
| E12 | 3-(5-chloro-3-pyridyl)-4-(1-piperidyl)-1H-pyrrolo[2,3-b]pyridine | ES+ 313 [M + H]+, Rt = 1.39 mins, Generic Basic Method |
| E13 | N-methyl-5-[4-(1-piperidyl)-1H-pyrrolo[2,3-b]pyridin-3-yl]pyridine-3-carboxamide | ES+ 336 [M + H]+, Rt = 0.97 mins, Generic Basic Method |
| E14 | 4-(1-piperidyl)-3-pyridazin-4-yl-1H-pyrrolo[2,3-b]pyridine | ES+ 280 [M + H]+, Rt = 0.98 mins, Generic Basic Method |

-continued

| Example | Structure | Name | LCMS Data |
|---|---|---|---|
| E15 | 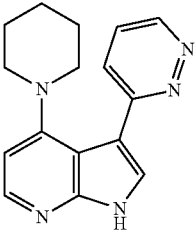 | 4-(1-piperidyl)-3-pyridazin-3-yl-1H-pyrrolo[2,3-b]pyridine | ES⁺ 280 [M + H]⁺, Rt = 1.02 mins, Generic Basic Method |
| E16 | 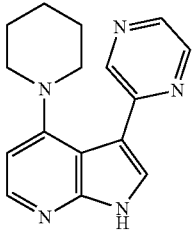 [SMILES: c1cnc(-c2c[nH]c3nccc(N4CCCCC4)c23)cn1] | 4-(1-piperidyl)-3-pyrazin-2-yl-1H-pyrrolo[2,3-b]pyridine | ES⁺ 280 [M + H]⁺, Rt = 1.07 mins, Generic Basic Method |
| E17 | 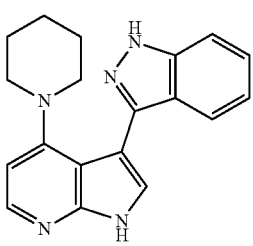 [SMILES: c1ccc2c(-c3c[nH]c4nccc(N5CCCCC5)c34)n[nH]c2c1] | 3-(1H-indazol-3-yl)-4-(1-piperidyl)-1H-pyrrolo[2,3-b]pyridine | ES⁺ 318 [M + H]⁺, Rt = 1.20 mins, Generic Basic Method |
| E18 | 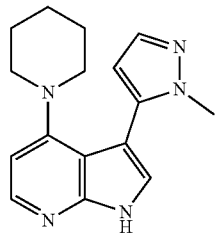 [SMILES: Cn1nccc1-c1c[nH]c2nccc(N3CCCCC3)c12] | 3-(2-methylpyrazol-3-yl)-4-(1-piperidyl)-1H-pyrrolo[2,3-b]pyridine | ES⁺ 282 [M + H]⁺, Rt = 1.12 mins, Generic Basic Method |
| E19 | 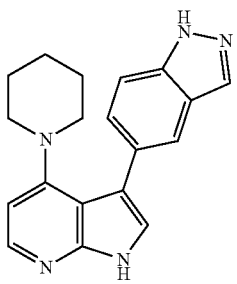 | 3-(1H-indazol-5-yl)-4-(1-piperidyl)-1H-pyrrolo[2,3-b]pyridine | ES⁺ 318 [M + H]⁺, Rt = 1.16 mins, Generic Basic Method |
| E20 | 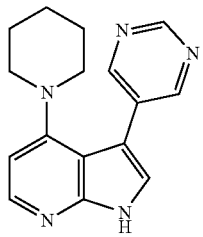 [SMILES: c1ncc(-c2c[nH]c3nccc(N4CCCCC4)c23)cn1] | 4-(1-piperidyl)-3-pyrimidin-5-yl-1H-pyrrolo[2,3-b]pyridine | ES⁺ 280 [M + H]⁺, Rt = 1.04 mins, Generic Basic Method |

-continued

| Example | Structure | Name | LCMS Data |
|---|---|---|---|
| E21 | 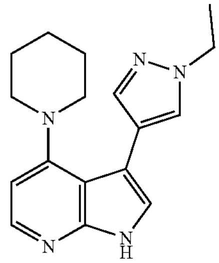 [SMILES: CCn1cc(-c2c[nH]c3nccc(N4CCCCC4)c23)cn1] | 3-(1-ethylpyrazol-4-yl)-4-(1-piperidyl)-1H-pyrrolo[2,3-b]pyridine | ES⁺ 296 [M + H]⁺, Rt = 1.19 mins, Generic Basic Method |
| E22 | 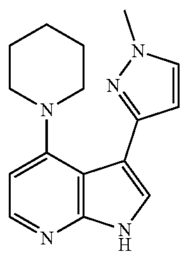 [SMILES: Cn1ccc(-c2c[nH]c3nccc(N4CCCCC4)c23)n1] | 3-(1-methylpyrazol-3-yl)-4-(1-piperidyl)-1H-pyrrolo[2,3-b]pyridine | ES⁺ 282 [M + H]⁺, Rt = 1.14 mins, Generic Basic Method |
| E23 | 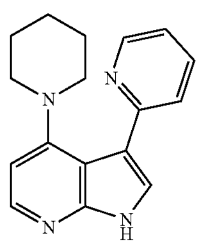 [SMILES: c1ccc(-c2c[nH]c3nccc(N4CCCCC4)c23)nc1] | 4-(1-piperidyl)-3-(2-pyridyl)-1H-pyrrolo[2,3-b]pyridine | ES⁺ 279 [M + H]⁺, Rt = 1.21 mins, Generic Basic Method |
| E24 | 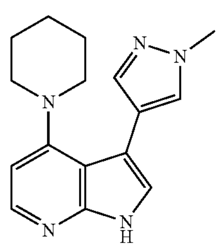 [SMILES: Cn1cc(-c2c[nH]c3nccc(N4CCCCC4)c23)cn1] | 3-(1-methylpyrazol-4-yl)-4-(1-piperidyl)-1H-pyrrolo[2,3-b]pyridine | ES⁺ 282 [M + H]⁺, Rt = 1.10 mins, Generic Basic Method |

Example 25 (E25)-4-(azetidin-1-yl)-3-(2-pyridyl)-1H-pyrrolo[2,3-b]pyridine

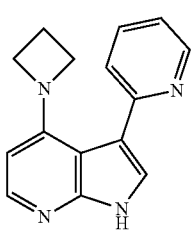 [SMILES: c1ccc(-c2c[nH]c3nccc(N4CCC4)c23)nc1]

4-chloro-3-(2-pyridyl)-1H-pyrrolo[2,3-b]pyridine (P50) (16.81 mg, 0.07 mmol) and dicyclohexyl-[2-(2,6-diisopropoxyphenyl)phenyl]phosphane (0.34 mg) were weighed into a round bottomed flask. Azetidine (5.43 ul, 0.08 mmol), RuPhos Pre catalyst (0.6 mg, 1.28 µmol) and lithium bis(trimethylsilyl)amide solution (0.18 ml, 0.18 mmol) were added and the reaction mixture was heated to 65° C. for 2 hours. The reaction mixture was subsequently heated to 140° C. for 20 minutes in the microwave. The residue was purified via SCX and then preparative HPLC to give 4-(azetidin-1-yl)-3-(2-pyridyl)-1H-pyrrolo[2,3-b]pyridine (E25) (1 mg), LCMS ES⁺ 2511[M+H]⁺ Rt=0.98 mins (Generic Basic Method).

The following compounds were prepared in a similar manner to 4-(azetidin-1-yl)-3-(2-pyridyl)-1H-pyrrolo[2,3-b]pyridine (E25) from the appropriate intermediates:

| Example | Structure | Name | LCMS Data |
|---|---|---|---|
| E26 | 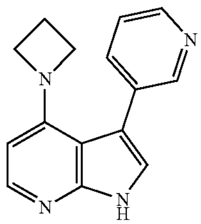 [SMILES: c1cncc(-c2c[nH]c3nccc(N4CCC4)c23)c1] | 4-(azetidin-1-yl)-3-(3-pyridyl)-1H-pyrrolo[2,3-b]pyridine | ES+ 251 [M + H]+, Rt = 0.97 mins, Generic Basic Method |

Example 27 (E27)-4-(azetidin-1-yl)-3-(1H-pyrazol-4-yl)-1H-pyrrolo[2,3-b]pyridine

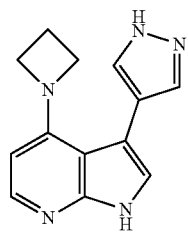

4-chloro-3-(1H-pyrazol-4-yl)-1H-pyrrolo[2,3-b]pyridine (P52) (100.00 mg, 0.46 mmol), Lithium bis(trimethylsilyl) amide solution (1.1 ml, 1.1 mmol), RuPhos Pre catalyst (3.74 mg), dicyclohexyl-[2-(2,6-diisopropoxyphenyl)phenyl]phosphane (2.13 mg) and azetidine (46.24 ul, 0.69 mmol) were added to a microwave vial and the reaction mixture was heated to 140° C. for 20 minutes in the microwave. The crude mixture was purified via SCX followed by preparative HPLC to give 4-(azetidin-1-yl)-3-(1H-pyrazol-4-yl)-1H-pyrrolo[2,3-b]pyridine (E27) (29 mg, 0.12 mmol, 25% yield) LCMS ES+ 240 [M+H]+ Rt=0.87 mins (Generic Basic Method).

The following compounds were prepared in a similar manner to 4-(azetidin-1-yl)-3-(1H-pyrazol-4-yl)-1H-pyrrolo[2,3-b]pyridine (E27) from the appropriate intermediates:

| Example | Structure | Name | LCMS Data |
|---|---|---|---|
| E28 | 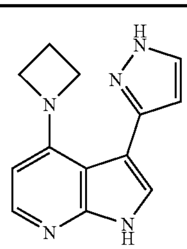 | 4-(azetidin-1-yl)-3-(1H-pyrazol-3-yl)-1H-pyrrolo[2,3-b]pyridine | ES+ 240 [M + H]+, Rt = 0.57 mins, Generic Basic Method |

Example 30 (E30)-4-(4-methyl-1,4-diazepan-1-yl)-1H-pyrrolo[2,3-b]pyridine-3-carbonitrile

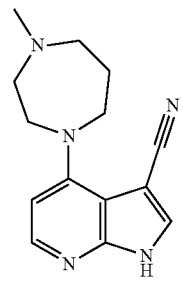

In a microwave vial equipped with stirrer bar containing 4-chloro-1H-pyrrolo[2,3-b]pyridine-3-carbonitrile (P5) (42 mg, 0.24 mmol) was added 1,4-dioxane (0.10 ml) followed by triethylamine (47.86 mg, 0.47 mmol) and 1-methylhomopiperazine (162.04 mg, 1.42 mmol). The resulting suspension was heated to 160° C. for 1 hour. The solvent was removed under reduced pressure to afford oil which was purified via preparative HPLC to give 4-(4-methyl-1,4-diazepan-1-yl)-1H-pyrrolo[2,3-b]pyridine-3-carbonitrile (E30) (7 mg), LCMS ES+ 256 [M+H]+ Rt=0.25 mins (Generic Basic Method).

The following compounds were prepared in a similar manner to 4-(4-methyl-1,4-diazepan-1-yl)-1H-pyrrolo[2,3-b]pyridine-3-carbonitrile (E30) from the appropriate intermediates:

| Example | Structure | Name | LCMS Data |
|---|---|---|---|
| E31 | 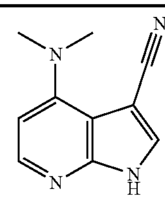 | 4-(dimethylamino)-1H-pyrrolo[2,3-b]pyridine-3-carbonitrile | ES+ 187 [M + H]+, Rt = 0.89 mins, Generic Basic Method |
| E32 | 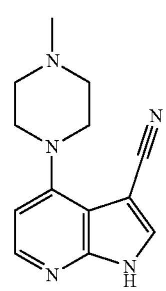 [SMILES: CN1CCN(c2ccnc3[nH]cc(C#N)c23)CC1] | 4-(4-methylpiperazin-1-yl)-1H-pyrrolo[2,3-b]pyridine-3-carbonitrile | ES+ 242 [M + H]+, Rt = 0.81 mins, Generic Basic Method |
| E33 | 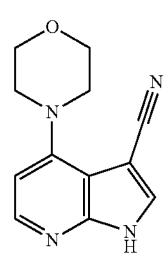 [SMILES: N#Cc1c[nH]c2nccc(N3CCOCC3)c12] | 4-morpholino-1H-pyrrolo[2,3-b]pyridine-3-carbonitrile | ES+ 228 [M + H]+, Rt = 0.83 mins, Generic Basic Method |

Example 34 (E34)-4-piperazin-1-yl-1H-pyrrolo[2,3-b]pyridine-3-carbonitrile

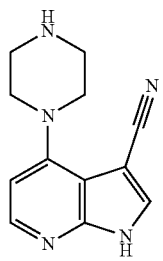 [SMILES: N#Cc1c[nH]c2nccc(N3CCNCC3)c12]

In a microwave vial equipped with stirrer bar containing 4-chloro-1H-pyrrolo[2,3-b]pyridine-3-carbonitrile (P5) (46 mg, 0.26 mmol) was added 1,4-dioxane (0.2 ml) followed by piperazine (89.25 mg, 1.04 mmol). The resulting suspension was heated to 150° C. for 50 minutes. After this time, the reaction mixture was allowed to cool to room temperature before concentrating in vacuo. The oil obtained was diluted with DCM (10 ml) and washed with water (5 ml). The organics were concentrated in vacuo and subsequently purified via preparative HPLC to give 4-piperazin-1-yl-1H-pyrrolo[2,3-b]pyridine-3-carbonitrile (E34) (0.7 mg), LCMS ES+ 228 [M+H]+ Rt=0.70 mins (Generic Basic Method).

The following compounds were prepared in a similar manner to 4-piperazin-1-yl-1H-pyrrolo[2,3-b]pyridine-3-carbonitrile (E34) from the appropriate intermediates:

| Example | Structure | Name | LCMS Data |
|---|---|---|---|
| E35 | 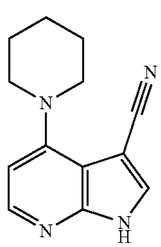 [SMILES: N#Cc1c[nH]c2nccc(N3CCCCC3)c12] | 4-(1-piperidyl)-1H-pyrrolo[2,3-b]pyridine-3-carbonitrile | ES+ 227 [M + H]+, Rt = 0.84 mins, Generic Basic Method |
| E36 | 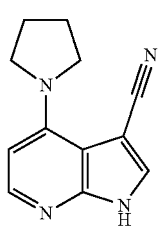 [SMILES: N#Cc1c[nH]c2nccc(N3CCCC3)c12] | 4-pyrrolidin-1-yl-1H-pyrrolo[2,3-b]pyridine-3-carbonitrile | ES+ 213 [M + H]+, Rt = 1.02 mins, Generic Basic Method |

Example 37 (E37)-4-(methylamino)-1H-pyrrolo[2,3-b]pyridine-3-carbonitrile

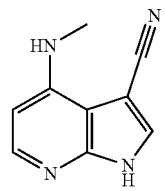

In a microwave vial equipped with stirrer bar containing 4-chloro-1H-pyrrolo[2,3-b]pyridine-3-carbonitrile (P5) (47.4 mg, 0.27 mmol) was added methylamine solution (310.88 mg, 10.00 mmol, 7 ml, 2M). The resulting suspension was heated to 160° C. for a total of 24 hours. The mixture was concentrated in vacuo and purified via preparative HPLC to afford 4-(methylamino)-1H-pyrrolo[2,3-b]pyridine-3-carbonitrile (E37) (3 mg), LCMS ES+ 227 [M+H]+ Rt=0.49 mins (Generic Basic Method).

Example 38 (E38)-4-[(2S)-2-(hydroxymethyl)pyrrolidin-1-yl]-1H-pyrrolo[2,3-b]pyridine-3-carbonitrile

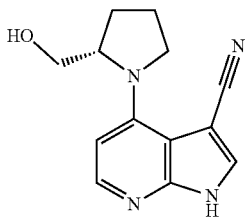 [SMILES: N#Cc1c[nH]c2nccc(N3CCC[C@H]3CO)c12]

To a microwave vial was added (S)-(+)-2-Pyrrolidinemethanol (57 mg, 0.56 mmol) and 4-chloro-1H-pyrrolo[2,3-b]pyridine-3-carbonitrile (P5) (50 mg, 0.24 mmol) in NMP (0.5 ml) and heated at 160° C. for 4 hours. The mixture was purified by silica chromatography, eluting with 0-5% MeOH in DCM, to give 4-[(2S)-2-(hydroxymethyl)pyrrolidin-1-yl]-1H-pyrrolo[2,3-b]pyridine-3-carbonitrile (E38) (23 mg) LCMS ES+ 243.2 [M+H]+, Rt=0.80 mins (Generic Basic Method).

Example 39 (E39)-4-[(2R)-2-(hydroxymethyl)pyrrolidin-1-yl]-1H-pyrrolo[2,3-b]pyridine-3-carbonitrile

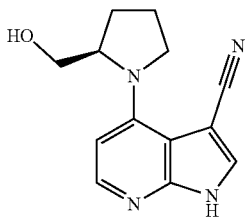 [SMILES: N#Cc1c[nH]c2nccc(N3CCC[C@@H]3CO)c12]

(R)-(−)-2-Pyrrolidinemethanol (56.96 mg, 0.56 mmol) and 4-chloro-1H-pyrrolo[2,3-b]pyridine-3-carbonitrile (P5) (50.0 mg, 0.28 mmol) were dissolved in NMP (0.5 ml) and heated at 160° C. for 4 hours. The mixture was concentrated under reduced pressure and purified by preparative HPLC (middle basic run) to give 4-[(2R)-2-(hydroxymethyl) pyrrolidin-1-yl]-1H-pyrrolo[2,3-b]pyridine-3-carbonitrile (E39), (23 mg) LCMS ES+ 326.2 [M+H]+, Rt=0.79 mins (Generic Basic Method).

Example 40 (E40)-4-[(2S)-2-(phenoxymethyl)pyrrolidin-1-yl]-1H-pyrrolo[2,3-b]pyridine-3-carbonitrile

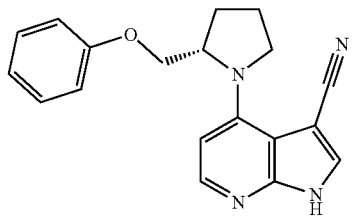 [SMILES: N#Cc1c[nH]c2nccc(N3CCC[C@H]3COc3ccccc3)c12]

4-[(2S)-2-(hydroxymethyl)pyrrolidin-1-yl]-1H-pyrrolo[2,3-b]pyridine-3-carbonitrile (E38) (30 mg, 0.12 mmol), phenol (46.62 mg, 0.50 mmol) and triphenylphosphine (129.92 mg, 0.50 mmol) were dissolved in THF (5 ml). The mixture was cooled to 0° C. and diisopropyl azodicarboxylate (0.1 ml, 0.50 mmol) was added dropwise with vigorous stirring, keeping the temperature below 0° C. After 2 hours, the mixture was warmed to room temperature and stirred for 18 hours. The mixture was purified by preparative HPLC (middle basic method) to give 4-[(2S)-2-(phenoxymethyl)pyrrolidin-1-yl]-1H-pyrrolo[2,3-b]pyridine-3-carbonitrile (E40) (5 mg, 0.01 mmol, 12.1% yield) as a white solid, LCMS ES+ 319.2 [M+H]+, Rt=1.27 mins (Generic Basic Method).

Example 41 (E41)-(3S)—N-cyclopropyl-1-(3-pyrimidin-4-yl-1H-pyrrolo[2,3-b]pyridin-4-yl)piperidin-3-amine

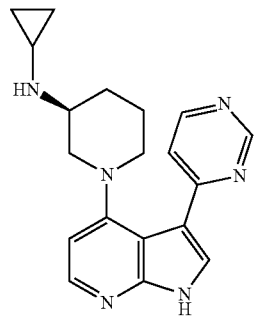 [SMILES: c1cc(-c2c[nH]c3nccc(N4CCC[C@H](NC5CC5)C4)c23)ncn1]

A solution of tert-butyl N-cyclopropyl-N-[(3S)-1-[3-pyrimidin-4-yl-1-(2-trimethylsilylethoxymethyl)pyrrolo[2,3-b]pyridin-4-yl]-3-piperidyl]carbamate (P162) (37 mg, 0.07 mmol) and HCl (aq.) (0.13 ml, 0.66 mmol) in 1,4-dioxane (0.2 ml) was heated at 50° C. for 18 hours. The reaction was allowed to cool to room temperature and loaded onto a pre-acidified SCX cartridge. The cartridge was washed with MeOH (×5 cvs) and the product eluted with NH3 in MeOH (2N). The basic fractions were concentrated under reduced pressure and the residue was purified via preparative HPLC using the generic basic run to give (3S)—N-cyclopropyl-1-(3-pyrimidin-4-yl-1H-pyrrolo[2,3-b]pyridin-4-yl)piperidin-3-amine (E41) (13 mg) (LCMS ES+ 335 [M+H]+, Rt=0.86 mins (Generic Basic Method).

The following compounds were prepared in a similar manner to (3S)—N-cyclopropyl-1-(3-pyrimidin-4-yl-1H-pyrrolo[2,3-b]pyridin-4-yl)piperidin-3-amine (E41) from appropriate intermediates:

| Example | Structure | Name | LCMS Data |
|---|---|---|---|
| E42 | 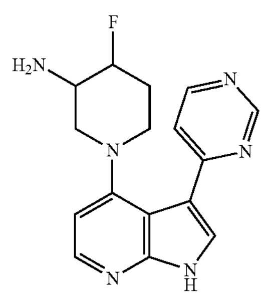 [SMILES: NC1CN(c2ccnc3[nH]cc(-c4ccncn4)c23)CCC1F] | 4-fluoro-1-(3-pyrimidin-4-yl-1H-pyrrolo[2,3-b]pyridin-4-yl)piperidin-3-amine | ES+ 313 [M + H]+, Rt = 0.70 mins, Generic Basic Method |
| E43 | 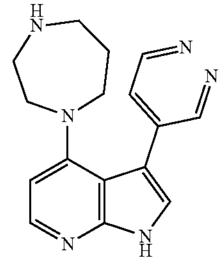 [SMILES: N=C/C=C(\C=N)c1c[nH]c2nccc(N3CCCNCC3)c12] | 4-(1,4-diazepan-1-yl)-3-pyridazin-4-yl-1H-pyrrolo[2,3-b]pyridine | ES+ 295 [M + H]+, Rt = 0.64 mins, Generic Basic Method |

-continued

| Example | Name | LCMS Data |
|---|---|---|
| E44 | 4-(1,4-diazepan-1-yl)-3-pyrimidin-5-yl-1H-pyrrolo[2,3-b]pyridine | ES+ 295 [M + H]+, Rt = 0.66 mins, Generic Basic Method |
| E45 | (3S)-N-cyclopropyl-1-(3-pyridazin-3-yl-1H-pyrrolo[2,3-b]pyridin-4-yl)piperidin-3-amine | ES+ 335 [M + H]+, Rt = 0.86 mins, Generic Basic Method |
| E46 | (3S)-N-cyclopropyl-1-(3-pyridazin-4-yl-1H-pyrrolo[2,3-b]pyridin-4-yl)piperidin-3-amine | ES+ 335 [M + H]+, Rt = 0.83 mins, Generic Basic Method |
| E47 | (3S)-N-methyl-1-(3-thiazol-2-yl-1H-pyrrolo[2,3-b]pyridin-4-yl)piperidin-3-amine | ES+ 314 [M + H]+, Rt = 0.83 mins, Generic CSH Method |
| E48 | (3S)-1-[3-(3-fluoro-2-pyridyl)-1H-pyrrolo[2,3-b]pyridin-4-yl]-N-methyl-piperidin-3-amine | ES+ 326 [M + H]+, Rt = 0.85 mins, Generic Basic Method |
| E49 | (3S)-N-methyl-1-[3-(2-pyridyl)-1H-pyrrolo[2,3-b]pyridin-4-yl]piperidin-3-amine | ES+ 308 [M + H]+, Rt = 0.87 mins, Generic Basic Method |

-continued

| Example | Structure | Name | LCMS Data |
|---|---|---|---|
| E50 | 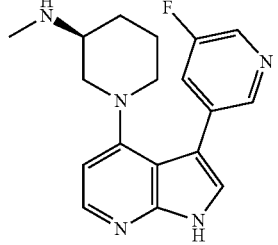 | (3S)-1-[3-(5-fluoro-3-pyridyl)-1H-pyrrolo[2,3-b]pyridin-4-yl]-N-methyl-piperidin-3-amine | ES+ 326 [M + H]+, Rt = 0.90 mins, Generic Basic Method |
| E51 | 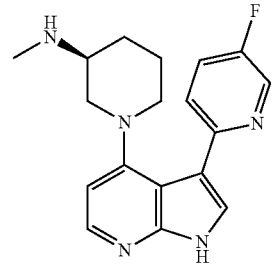 [SMILES: CN[C@H]1CCCN(c2ccnc3[nH]cc(-c4ccc(F)cn4)c23)C1] | (3S)-1-[3-(5-fluoro-2-pyridyl)-1H-pyrrolo[2,3-b]pyridin-4-yl]-N-methyl-piperidin-3-amine | ES+ 326 [M + H]+, Rt = 0.88 mins, Generic Basic Method |
| E52 | 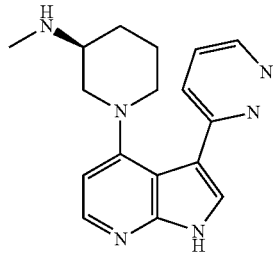 | (3S)-N-methyl-1-(3-pyridazin-3-yl-1H-pyrrolo[2,3-b]pyridin-4-yl)piperidin-3-amine | ES+ 309 [M + H]+, Rt = 0.72 mins, Generic Basic Method |
| E53 | 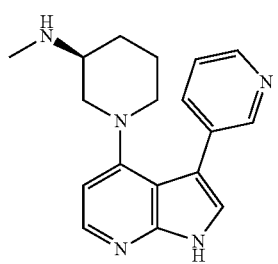 [SMILES: CN[C@H]1CCCN(c2ccnc3[nH]cc(-c4cccnc4)c23)C1] | (3S)-N-methyl-1-[3-(3-pyridyl)-1H-pyrrolo[2,3-b]pyridin-4-yl]piperidin-3-amine | ES+ 308 [M + H]+, Rt = 0.82 mins, Generic Basic Method |
| E54 | 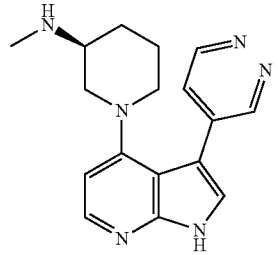 | (3S)-N-methyl-1-(3-pyridazin-4-yl-1H-pyrrolo[2,3-b]pyridin-4-yl)piperidin-3-amine | ES+ 308 [M + H]+, Rt = 0.82 mins, Generic Basic Method |
| E55 | 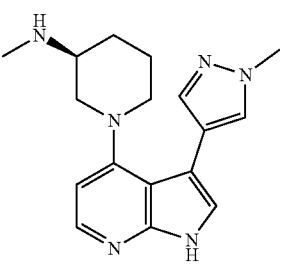 | (3S)-N-methyl-1-[3-(1-methylpyrazol-4-yl)-1H-pyrrolo[2,3-b]pyridin-4-yl]piperidin-3-amine | ES+ 311 [M + H]+, Rt = 0.77 mins, Generic Basic Method |

-continued

| Example | Structure | Name | LCMS Data |
|---|---|---|---|
| E56 | 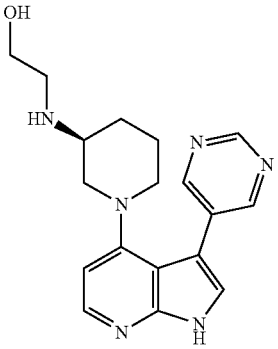 [SMILES: OCCN[C@H]1CCCN(c2ccnc3[nH]cc(-c4cncnc4)c23)C1] | 2-[[(3S)-1-(3-pyrimidin-5-yl-1H-pyrrolo[2,3-b]pyridin-4-yl)-3-piperidyl]amino]ethanol | ES+ 339 [M + H]+, Rt = 0.71 mins, Generic Basic Method |
| E57 | 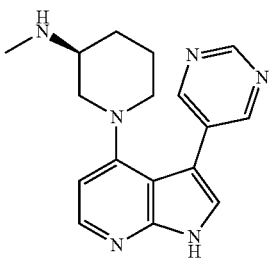 | (3S)-N-methyl-1-(3-pyrimidin-5-yl-1H-pyrrolo[2,3-b]pyridin-4-yl)piperidin-3-amine | ES+ 309 [M + H]+, Rt = 0.78 mins, Generic Basic Method |
| E58 | 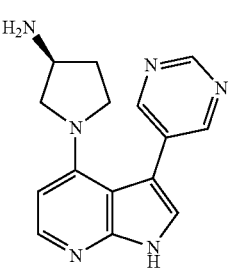 [SMILES: N[C@H]1CCN(c2ccnc3[nH]cc(-c4cncnc4)c23)C1] | (3S)-1-(3-pyrimidin-5-yl-1H-pyrrolo[2,3-b]pyridin-4-yl)pyrrolidin-3-amine | ES+ 281 [M + H]+, Rt = 0.65 mins, Generic Basic Method |
| E59 | 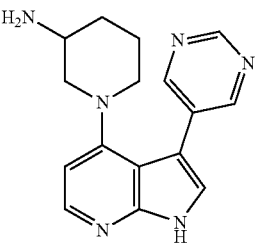 [SMILES: NC1CCCN(c2ccnc3[nH]cc(-c4cncnc4)c23)C1] | 1-(3-pyrimidin-5-yl-1H-pyrrolo[2,3-b]pyridin-4-yl)piperidin-3-amine | ES+ 295 [M + H]+, Rt = 0.71 mins, Generic Basic Method |
| E60 | 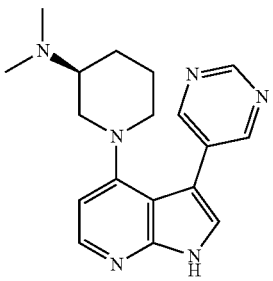 [SMILES: CN(C)[C@H]1CCCN(c2ccnc3[nH]cc(-c4cncnc4)c23)C1] | N,N-dimethyl-1-(3-pyrimidin-5-yl-1H-pyrrolo[2,3-b]pyridin-4-yl)piperidin-3-amine | ES+ 323 [M + H]+, Rt = 0.82 mins, Generic Basic Method |

-continued

| Example | Name | LCMS Data |
|---|---|---|
| E61 | (3S)-1-[3-(5-methyl-1H-pyrazol-4-yl)-1H-pyrrolo[2,3-b]pyridin-4-yl]piperidin-3-amine | ES+ 297 [M + H]+, Rt = 0.72 mins, Generic Basic Method |
| E62 | N-methyl-1-(3-pyrimidin-5-yl-1H-pyrrolo[2,3-b]pyridin-4-yl)piperidin-3-amine | ES+ 309 [M + H]+, Rt = 0.74 mins, Generic Basic Method |
| E63 | N-methyl-1-(3-pyrimidin-5-yl-1H-pyrrolo[2,3-b]pyridin-4-yl)piperidin-4-amine | ES+ 309 [M + H]+, Rt = 0.70 mins, Generic Basic Method |
| E64 | (3R)-1-(3-pyrimidin-5-yl-1H-pyrrolo[2,3-b]pyridin-4-yl)piperidin-3-amine | ES+ 295 [M + H]+, Rt = 0.71 mins, Generic Basic Method |
| E65 | 1-(3-pyrimidin-5-yl-1H-pyrrolo[2,3-b]pyridin-4-yl)piperidin-4-amine | ES+ 295 [M + H]+, Rt = 0.75 mins, Generic Basic Method |

-continued

| Example | Structure | Name | LCMS Data |
|---|---|---|---|
| E66 | 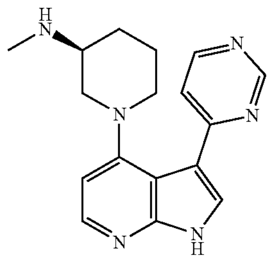 [SMILES: CN[C@H]1CCCN(c2ccnc3[nH]cc(-c4ccncn4)c23)C1] | (3S)-N-methyl-1-(3-pyrimidin-4-yl-1H-pyrrolo[2,3-b]pyridin-4-yl)piperidin-3-amine | ES+ 309 [M + H]+, Rt = 0.76 mins, Generic Basic Method |
| E67 | 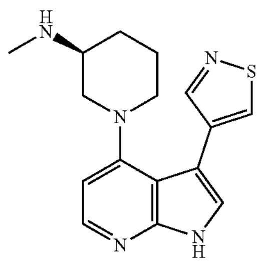 [SMILES: CN[C@H]1CCCN(c2ccnc3[nH]cc(-c4cnsc4)c23)C1] | (3S)-1-(3-isothiazol-4-yl-1H-pyrrolo[2,3-b]pyridin-4-yl)-N-methyl-piperidin-3-amine | ES+ 314 [M + H]+, Rt = 0.89 mins, Generic Basic Method |
| E68 | 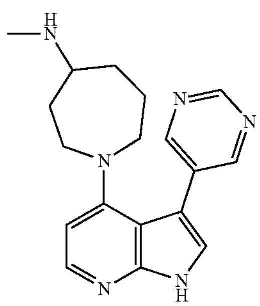 [SMILES: CNC1CCCN(c2ccnc3[nH]cc(-c4cncnc4)c23)CC1] | N-methyl-1-(3-pyrimidin-5-yl-1H-pyrrolo[2,3-b]pyridin-4-yl)azepan-4-amine | ES+ 323 [M + H]+, Rt = 0.68 mins, Generic Basic Method |
| E69 | 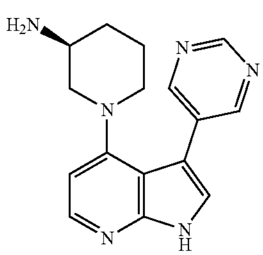 [SMILES: N[C@H]1CCCN(c2ccnc3[nH]cc(-c4cncnc4)c23)C1] | (3S)-1-(3-pyrimidin-5-yl-1H-pyrrolo[2,3-b]pyridin-4-yl)piperidin-3-amine | ES+ 295 [M + H]+, Rt = 0.71 mins, Generic Basic Method |

Example 70 (E70)-5-bromo-4-(1-piperidyl)-3-(1H-pyrazol-3-yl)-1H-pyrrolo[2,3-b]pyridine

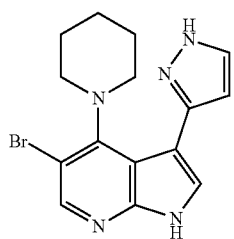 [SMILES: Brc1cnc2[nH]cc(-c3cc[nH]n3)c2c1N1CCCCC1]

2-[[5-bromo-4-(1-piperidyl)-3-(1-tetrahydropyran-2-ylpyrazol-3-yl)pyrrolo[2,3-b]pyridin-1-yl]methoxy]ethyl-trimethyl-silane (P227) (64 mg, 0.13 mmol) was dissolved in THF (0.5 ml) and hydrogen chloride solution (0.67 ml, 1.34 mmol) was added. The mixture was heated at 80° C. for 120 minutes in the microwave. After this time, the mixture was passed through an SCX cartridge, eluting with Methanol/NH₃ and residue obtained was purified by preparative HPLC using the early basic method to give 5-bromo-4-(1-piperidyl)-3-(1H-pyrazol-3-yl)-1H-pyrrolo[2,3-b]pyridine (E70) (5.5 mg) LCMS ES+ 346.2 [M+H]+, Rt=0.73 mins (Generic Basic Method).

Example 71 (E71)-(3S)—N-ethyl-1-(3-pyridazin-4-yl-1H-pyrrolo[2,3-b]pyridin-4-yl)piperidin-3-amine

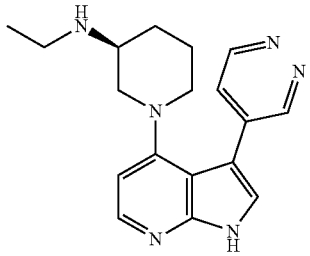 [SMILES: CCN[C@H]1CCCN(c2ccnc3[nH]cc(/C(C=N)=C/C=N)c23)C1]

To a stirred solution of tert-butyl N-ethyl-N-[(3S)-1-[3-pyridazin-4-yl-1-(2-trimethylsilylethoxymethyl)pyrrolo[2,3-b]pyridin-4-yl]-3-piperidyl]carbamate (P190) (71.82 mg, 0.13 mmol) in DCM (1 ml) was added trifluoroacetic acid (0.2 ml, 2.6 mmol) and the resulting mixture stirred at room temperature overnight. The reaction mixture was loaded onto a pre-acidified SCX cartridge. The cartridge was washed with MeOH (×5 cvs) and the product eluted with $NH_3$ in MeOH (2N). The basic fractions were concentrated under reduced pressure and the residue was purified via preparative HPLC using the generic basic run to afford (3S)—N-ethyl-1-(3-pyridazin-4-yl-1H-pyrrolo[2,3-b]pyridin-4-yl)piperidin-3-amine (E71) (14 mg), LCMS $ES^+$ 323 $[M+H]^+$, Rt=0.74 mins (Generic Basic Method).

The following compounds were prepared in a similar manner to (3S)—N-ethyl-1-(3-pyridazin-4-yl-1H-pyrrolo[2,3-b]pyridin-4-yl)piperidin-3-amine (E71) from appropriate intermediates.

| Example | Structure | Name | LCMS Data |
|---|---|---|---|
| E72 | 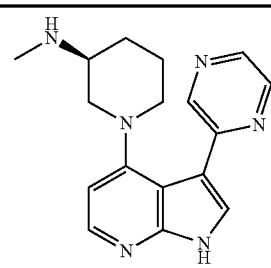 | (3S)-N-methyl-1-(3-pyrazin-2-yl-1H-pyrrolo[2,3-b]pyridin-4-yl)piperidin-3-amine | $ES^+$ 309 $[M + H]^+$, Rt = 0.75 mins, Generic Basic Method |
| E73 | 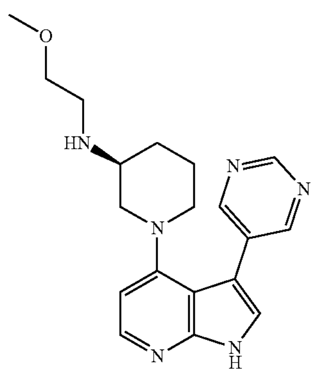 [SMILES: COCCN[C@H]1CCCN(c2ccnc3[nH]cc(-c4cncnc4)c23)C1] | (3S)-N-(2-methoxyethyl)-1-(3-pyrimidin-5-yl-1H-pyrrolo[2,3-b]pyridin-4-yl)piperidin-3-amine | $ES^+$ 353 $[M + H]^+$, Rt = 0.81 mins, Generic Basic Method |
| E74 | 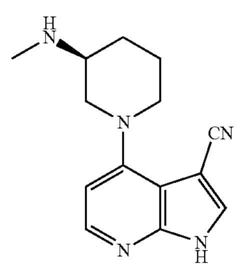 [SMILES: CN[C@H]1CCCN(c2ccnc3[nH]cc(C#N)c23)C1] | 4-[(3S)-3-(methylamino)-1-piperidyl]-1H-pyrrolo[2,3-b]pyridine-3-carbonitrile | $ES^+$ 256 $[M + H]^+$, Rt = 0.31 mins, |
| E75 | 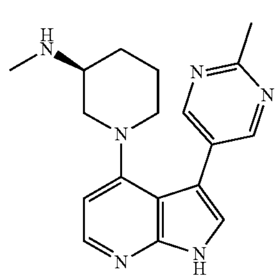 [SMILES: CN[C@H]1CCCN(c2ccnc3[nH]cc(-c4cnc(C)nc4)c23)C1] | (3S)-N-methyl-1-[3-(2-methylpyrimidin-5-yl)-1H-pyrrolo[2,3-b]pyridin-4-yl]piperidin-3-amine | $ES^+$ 323 $[M + H]^+$, Rt = 0.76 mins, Generic Basic Method |

-continued

| Example | Name | LCMS Data |
|---|---|---|
| E76 | (3S)-N-isopropyl-1-(3-pyrimidin-5-yl-1H-pyrrolo[2,3-b]pyridin-4-yl)piperidin-3-amine | ES+ 337 [M + H]+, Rt = 0.84 mins, Generic Basic Method |
| E77 | (3R)-N-methyl-1-(3-pyrimidin-5-yl-1H-pyrrolo[2,3-b]pyridin-4-yl)piperidin-3-amine | ES+ 309 [M + H]+, Rt = 0.74 mins, Generic Basic Method |
| E78 | (3S)-N-ethyl-1-[3-(1-methylpyrazol-4-yl)-1H-pyrrolo[2,3-b]pyridin-4-yl]piperidin-3-amine | ES+ 325 [M + H]+, Rt = 0.81 mins, Generic Basic Method |
| E79 | (3S)-N-ethyl-1-(3-pyrimidin-5-yl-1H-pyrrolo[2,3-b]pyridin-4-yl)piperidin-3-amine | ES+ 323 [M + H]+, Rt = 0.75 mins, Generic Basic Method |
| E80 | ((3S)-N-cyclopropyl-N-methyl-1-(3-pyrimidin-5-yl-1H-pyrrolo[2,3-b]pyridin-4-yl)piperidin-3-amine | ES+ 349 [M + H]+, Rt = 0.98 mins, Generic Basic Method |

-continued

| Example | Structure | Name | LCMS Data |
|---------|-----------|------|-----------|
| E81 | 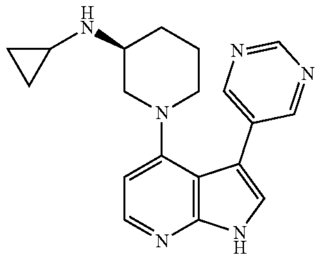 [SMILES: c1ncc(-c2c[nH]c3nccc(N4CCC[C@H](NC5CC5)C4)c23)cn1] | (3S)-N-cyclopropyl-1-(3-pyrimidin-5-yl-1H-pyrrolo[2,3-b]pyridin-4-yl)piperidin-3-amine | ES+ 335 [M + H]+, Rt = 0.80 mins, Generic Basic Method |
| E82 | 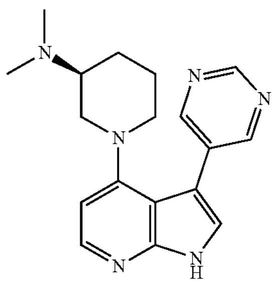 [SMILES: CN(C)[C@H]1CCCN(c2ccnc3[nH]cc(-c4cncnc4)c23)C1] | (3S)-N,N-dimethyl-1-(3-pyrimidin-5-yl-1H-pyrrolo[2,3-b]pyridin-4-yl)piperidin-3-amine | ES+ 323 [M + H]+, Rt = 0.79 mins, Generic Basic Method |
| E83 | 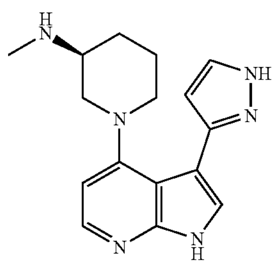 [SMILES: CN[C@H]1CCCN(c2ccnc3[nH]cc(-c4cc[nH]n4)c23)C1] | (3S)-N-methyl-1-[3-(1H-pyrazol-3-yl)-1H-pyrrolo[2,3-b]pyridin-4-yl]piperidin-3-amine | |
| E84 | 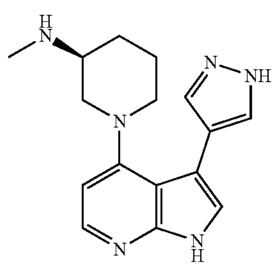 [SMILES: CN[C@H]1CCCN(c2ccnc3[nH]cc(-c4cn[nH]c4)c23)C1] | (3S)-N-methyl-1-[3-(1H-pyrazol-4-yl)-1H-pyrrolo[2,3-b]pyridin-4-yl]piperidin-3-amine | ES+ 297 [M + H]+, Rt = 0.267 mins |
| E85 | 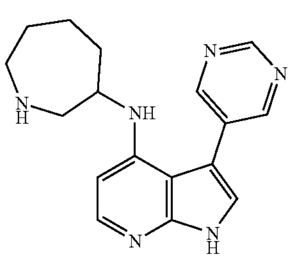 [SMILES: c1ncc(-c2c[nH]c3nccc(NC4CCCCNC4)c23)cn1] | N-(azepan-3-yl)-3-pyrimidin-5-yl-1H-pyrrolo[2,3-b]pyridin-4-amine | ES+ 309 [M + H]+, Rt = 0.60 mins, Generic Basic Method |

209

Example 86 (E86)-[1-(3-pyrimidin-5-yl-1H-pyrrolo[2,3-b]pyridin-4-yl)-3-piperidyl]methanamine

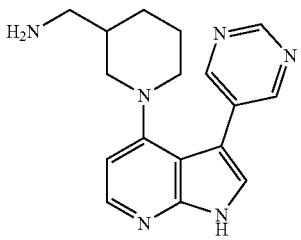 [SMILES: NCC1CCCN(c2ccnc3[nH]cc(-c4cncnc4)c23)C1]

To a microwave vial equipped with stirrer bar was added 2-[(4-chloro-3-pyrimidin-5-yl-pyrrolo[2,3-b]pyridin-1-yl)methoxy]ethyl-trimethyl-silane (P23) (197 mg, 0.55 mmol), tert-butyl N-(3-piperidylmethyl)carbamate (935.72 mg, 4.37 mmol) and DMSO (0.25 ml). The reaction mixture was then heated to 145° C. for 4 hours before allowing to cool to room temperature. The residue was diluted with MeOH and purified via preparative HPLC using the late basic method. The product was dissolved in 2N HCl (1 ml) and THF (0.5 ml) and the mixture heated at 80° C. in the microwave for 45 minutes. The mixture was concentrated under reduced pressure and the resulting residue purified using preparative HPLC (generic basic method) and finally SCX to give [1-(3-pyrimidin-5-yl-1H-pyrrolo[2,3-b]pyridin-4-yl)-3-piperidyl]methanamine (E86) (3 mg), LCMS ES⁺ 309 [M+H]⁺, Rt=0.73 mins (Generic Basic Method).

210

Example 87 (E87)-N-[(3S)-3-piperidyl]-3-pyrimidin-5-yl-1H-pyrrolo[2,3-b]pyridin-4-amine

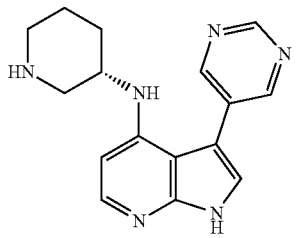 [SMILES: c1ncc(-c2c[nH]c3nccc(N[C@H]4CCCNC4)c23)cn1]

2-[(4-chloro-3-pyrimidin-5-yl-pyrrolo[2,3-b]pyridin-1-yl)methoxy]ethyl-trimethyl-silane (P23) (200 mg, 0.55 mmol), potassium tert-butoxide (186.58 mg, 1.66 mmol), PEPPSI (37.64 mg, 0.06 mmol) and (S)-3-amino-1-N-Boc-piperidine (166.49 mg, 0.83 mmol) were dissolved in 1,4-Dioxane (1 ml), purged with N₂ and the mixture heated to 110° C. overnight before cooling to room temperature. The crude mixture was quenched via the addition of water and the volatiles removed under reduced pressure before washing with water and extracting with DCM (20 ml). 2N HCl was added to the residue and the mixture heated to 80° C. The mixture was purified by preparative HPLC using the early basic run to give N-[(3S)-3-piperidyl]-3-pyrimidin-5-yl-1H-pyrrolo[2,3-b]pyridin-4-amine (E87) (8 mg, 0.03 mmol, 4.6% yield) as a pale yellow solid, LCMS ES⁺ 295.2 [M+H]⁺, Rt=0.7 mins (Generic Basic Method).

The following compounds were prepared in a similar manner to (E87) from appropriate intermediates.

| Example | Structure | Name | LCMS Data |
|---|---|---|---|
| E88 | 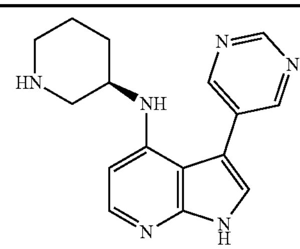 | N-[(3R)-3-piperidyl]-3-pyrimidin-5-yl-1H-pyrrolo[2,3-b]pyridin-4-amine | ES⁺ 295 [M + H]⁺, Rt = 0.70 mins, Generic Basic Method |
| E89 | 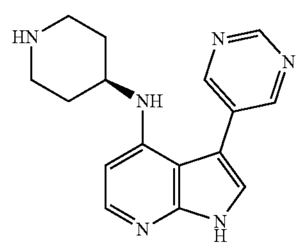 | N-(4-piperidyl)-3-pyrimidin-5-yl-1H-pyrrolo[2,3-b]pyridin-4-amine | ES⁺ 295 [M + H]⁺, Rt = 0.64 mins, Generic Basic Method |
| E90 | 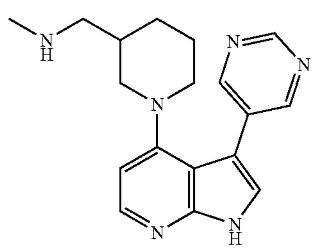 [SMILES: CNCC1CCCN(c2ccnc3[nH]cc(-c4cncnc4)c23)C1] | N-methyl-1-[1-(3-pyrimidin-5-yl-1H-pyrrolo[2,3-b]pyridin-4-yl)-3-piperidyl]methanamine | ES⁺ 323 [M + H]⁺, Rt = 0.44 mins, Generic Basic Method |

Example 91 (E91)-4-(3-piperazin-1-yl-1-piperidyl)-3-pyrimidin-5-yl-1H-pyrrolo[2,3-b]pyridine

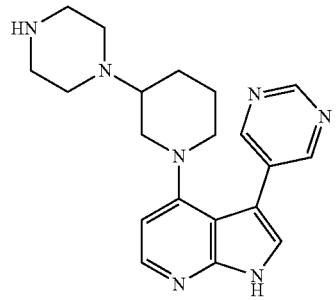 [SMILES: c1ncc(-c2c[nH]c3nccc(N4CCCC(N5CCNCC5)C4)c23)cn1]

tert-butyl 4-[1-[3-pyrimidin-5-yl-1-(2-trimethylsilylethoxymethyl)pyrrolo[2,3-b]pyridin-4-yl]-3-piperidyl]piperazine-1-carboxylate (P216) (210.00 mg, 0.35 mmol) in THF (0.40 ml) with 2N HCl (0.88 ml, 1.77 mmol) was stirred at 60° C. for 4 hours. The resulting solution was placed into a Genevac EZ-2 and the HCl removed. The crude product was purified via preparative HPLC on the generic basic run to give 4-(3-piperazin-1-yl-1-piperidyl)-3-pyrimidin-5-yl-1H-pyrrolo[2,3-b]pyridine (E91) (13 mg) LCMS ES+ 364.3 [M+H]+, Rt=0.48 mins, Generic Basic Method.

Example 92 (E92)-1-[(3S)-1-(3-pyrimidin-5-yl-1H-pyrrolo[2,3-b]pyridin-4-yl)-3-piperidyl]piperidin-4-ol

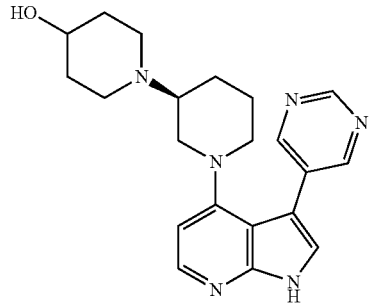 [SMILES: OC1CCN([C@H]2CCCN(c3ccnc4[nH]cc(-c5cncnc5)c34)C2)CC1]

tert-butyl-diphenyl-[[1-[(3S)-1-[3-pyrimidin-5-yl-1-(2-trimethylsilylethoxymethyl) pyrrolo[2,3-b]pyridin-4-yl]-3-piperidyl]-4-piperidyl]oxy]silane (P217) (82 mg, 0.11 mmol) was dissolved in THF (1.0 ml) and 5N HCl (0.22 ml, 1.1 mmol) was added. The resulting solution was heated to 60° C. and allowed to stir for 48 hours. The reaction mixture was cooled to room temperature before being dried in a Genevac EZ-2. The crude product was purified via preparative HPLC on the generic basic run to give 1-[(3S)-1-(3-pyrimidin-5-yl-1H-pyrrolo[2,3-b]pyridin-4-yl)-3-piperidyl]piperidin-4-ol (E92) (15 mg, 0.04 mmol, 34.3% yield) as a pale yellow solid, LCMS ES+ 379.4 [M+H]+, Rt=0.80 mins (Generic Basic Method).

Example 93 (E93)-[(3S)-1-(3-pyrimidin-5-yl-1H-pyrrolo[2,3-b]pyridin-4-yl)-3-piperidyl]pyrrolidin-3-ol

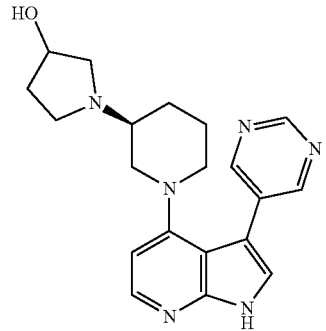 [SMILES: OC1CCN([C@H]2CCCN(c3ccnc4[nH]cc(-c5cncnc5)c34)C2)C1]

Tert-butyl-diphenyl-[1-[(3S)-1-[3-pyrimidin-5-yl-1-(2-trimethylsilylethoxymethyl) pyrrolo[2,3-b]pyridin-4-yl]-3-piperidyl]pyrrolidin-3-yl]oxy-silane (P218) (90.00 mg, 0.12 mmol) was dissolved in DCM (1 ml) and hydrogen chloride solution (0.49 ml, 2.46 mmol) was added and stirred at room temperature overnight. The organics were concentrated in vacuo and the residue was chromatographed [SiO2, 0-6% 2N NH3 in MeOH:DCM] to give [(3S)-1-(3-pyrimidin-5-yl-1H-pyrrolo[2,3-b]pyridin-4-yl)-3-piperidyl]pyrrolidin-3-ol (E93) (30 mg, 0.08 mmol, 63.7% yield) as a beige solid, LCMS ES+ 365.4 [M+H]+, Rt=0.75 mins (Generic Basic Method).

Example 94 (E94)-4-[(3S)-3-(4-fluoro-1-piperidyl)-1-piperidyl]-3-pyrimidin-5-yl-1H-pyrrolo[2,3-b]pyridine

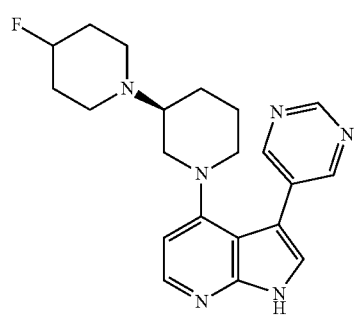 [SMILES: FC1CCN([C@H]2CCCN(c3ccnc4[nH]cc(-c5cncnc5)c34)C2)CC1]

2-[[4-[(3S)-3-(4-fluoro-1-piperidyl)-1-piperidyl]-3-pyrimidin-5-yl-pyrrolo[2,3-b]pyridin-1-yl]methoxy]ethyl-trimethyl-silane (P219) (20.00 mg, 0.04 mmol) was dissolved in DCM (1 ml) and trifluoroacetic acid (0.03 ml, 0.39 mmol) was added and stirred for 18 hours. The reaction mixture was loaded onto a pre-acidified 2 g SCX cartridge and washed with MeOH (×4 cvs). The product was released upon treatment with 7N NH3 in MeOH and dried to give a yellow glass. The glass was lyophilised in MeCN/H2O to give 4-[(3S)-3-(4-fluoro-1-piperidyl)-1-piperidyl]-3-pyrimidin-5-yl-1H-pyrrolo[2,3-b]pyridine (E94) (14.7 mg, 0.04 mmol, 93.7% yield) as a yellow solid, LCMS ES+ 381.4 [M+H]+, Rt=0.99 mins (Generic Basic Method).

The following compounds were prepared in a similar manner to 4-[(3S)-3-(4-fluoro-1-piperidyl)-1-piperidyl]-3-pyrimidin-5-yl-1H-pyrrolo[2,3-b]pyridine (E94) from appropriate intermediates;

| Example | Structure | Name | LCMS Data |
|---|---|---|---|
| E95 | 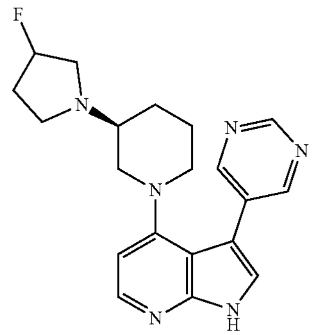 [SMILES: FC1CCN([C@H]2CCCN(c3ccnc4[nH]cc(-c5cncnc5)c34)C2)C1] | 4-[(3S)-3-(3-fluoropyrrolidin-1-yl)-1-piperidyl]-3-pyrimidin-5-yl-1H-pyrrolo[2,3-b]pyridine | ES$^+$ 367 [M + H]$^+$, Rt = 0.88 mins, Generic Basic Method |
| E96 | 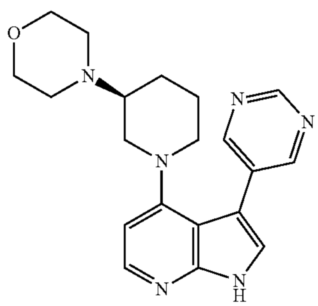 [SMILES: c1ncc(-c2c[nH]c3nccc(N4CCC[C@H](N5CCOCC5)C4)c23)cn1] | 4-[(3S)-1-(3-pyrimidin-5-yl-1H-pyrrolo[2,3-b]pyridin-4-yl)-3-piperidyl]morpholine | ES$^+$ 365 [M + H]$^+$, Rt = 0.88 mins, Generic Basic Method |
| E97 | 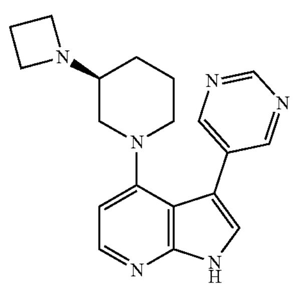 [SMILES: c1ncc(-c2c[nH]c3nccc(N4CCC[C@H](N5CCC5)C4)c23)cn1] | 4-[(3S)-3-(azetidin-1-yl)-1-piperidyl]-3-pyrimidin-5-yl-1H-pyrrolo[2,3-b]pyridine | ES$^+$ 335 [M + H]$^+$, Rt = 0.81 mins, Generic Basic Method |
| E98 | 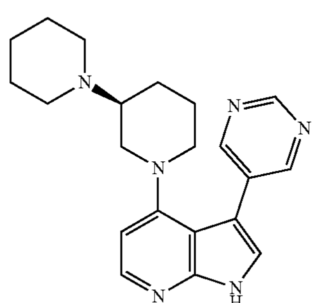 | 4-[(3S)-3-(1-piperidyl)-1-piperidyl]-3-pyrimidin-5-yl-1H-pyrrolo[2,3-b]pyridine | ES$^+$ 363 [M + H]$^+$, Rt = 1.00 mins, Generic Basic Method |
| E99 | 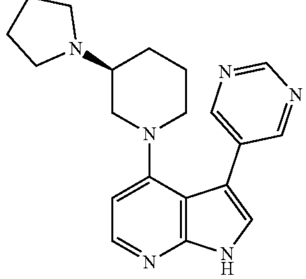 | 3-pyrimidin-5-yl-4-[(3S)-3-pyrrolidin-1-yl-1-piperidyl]-1H-pyrrolo[2,3-b]pyridine | ES$^+$ 349 [M + H]$^+$, Rt = 0.89 mins, Generic Basic Method |

Example 100 (E100)-(3R)-1-(3-pyrimidin-5-yl-1H-pyrrolo[2,3-b]pyridin-4-yl)piperidin-3-ol

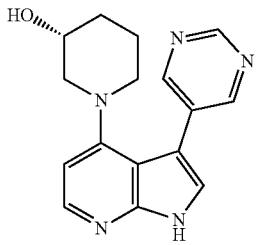 [SMILES: O[C@@H]1CCCN(c2ccnc3[nH]cc(-c4cncnc4)c23)C1]

Tert-butyl-diphenyl-[[(3R)-1-[3-pyrimidin-5-yl-1-(2-trimethylsilylethoxymethyl)pyrrolo[2,3-b]pyridin-4-yl]-3-piperidyl]oxy]silane (P226) (100.00 mg, 0.15 mmol) was dissolved in DCM (0.50 ml) and trifluoroacetic acid (0.12 ml, 1.51 mmol) was added. The resulting solution was allowed to stir at room temperature overnight. The mixture was concentrated in vacuo. The residue dissolved in MeOH (5 ml) and treated with 4N HCl (1.13 mol, 4.52 mmol). The solution was heated to 60° C. The mixture was concentrated under reduced pressure and passed through a SCX cartridge, eluting with 2N $NH_3$ in MeOH. The basic fraction were concentrated under reduced pressure and purified by HPLC using the early basic small fraction method to give (3R)-1-(3-pyrimidin-5-yl-1H-pyrrolo[2,3-b]pyridin-4-yl)piperidin-3-ol (E100) (13 mg, 0.04 mmol, 27.8% yield) as a colourless crystalline solid, LCMS $ES^+$ 296.2 $[M+H]^+$, Rt=0.72 mins (Generic Basic Method).

The following compounds were prepared in a similar manner to (3R)-1-(3-pyrimidin-5-yl-1H-pyrrolo[2,3-b]pyridin-4-yl)piperidin-3-ol (E100) from the appropriate intermediates:

| Example | Structure | Name | LCMS Data |
|---|---|---|---|
| E101 | 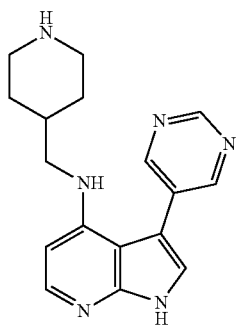 [SMILES: c1ncc(-c2c[nH]c3nccc(NCC4CCNCC4)c23)cn1] | (3S)-1-(3-pyrimidin-5-yl-1H-pyrrolo[2,3-b]pyridin-4-yl)piperidin-3-ol | $ES^+$ 296 $[M + H]^+$, Rt = 0.73 mins, Generic Basic Method |

Example 102 (E102)-N-(4-piperidylmethyl)-3-pyrimidin-5-yl-1H-pyrrolo[2,3-b]pyridin-4-amine 2-[(4-chloro-3-pyrimidin-5-yl-pyrrolo[2,3-b]pyridin-1-yl)methoxy]ethyl-trimethyl-silane (P23) (118.00 mg, 0.33 mmol), potassium tert-butoxide (110.07 mg, 0.98 mmol), PEPPSI (22.22 mg, 0.03 mmol) and 4-(aminomethyl)-1-N-Boc-piperidine (70.07 mg, 0.33 mmol) was dissolved in 1,4-Dioxane (1 ml) and purged with $N_2$. The mixture was heated to 110° C. overnight and quenched with water before diluting with DCM. The organics were concentrated under reduced pressure and purified by preparative HPLC using the generic basic run. The mixture was concentrated in vacuo, dissolved in THF (1 ml) and treated with 2N HCl (2 ml) before being heated in the microwave at 80° C. for 30 minutes to give N-(4-piperidylmethyl)-3-pyrimidin-5-yl-1H-pyrrolo[2,3-b]pyridin-4-amine (E102) (13 mg, 0.04 mmol, 12.2% yield) as a pale yellow solid, LCMS $ES^+$ 309.3 $[M+H]^+$, Rt=0.25 mins (Generic Basic Method).

The following compounds were prepared in a similar manner to N-(4-piperidylmethyl)-3-pyrimidin-5-yl-1H-pyrrolo[2,3-b]pyridin-4-amine (E102) from the appropriate intermediate and amine:

| Example | Structure | Name | LCMS Data |
|---|---|---|---|
| E103 | 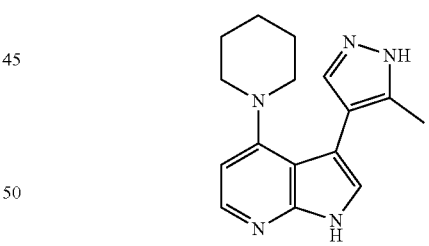 | 4-(4-methyl-1,4-diazepan-1-yl)-3-pyrimidin-5-yl-1H-pyrrolo[2,3-b]pyridine | $ES^+$ 309 $[M + H]^+$, Rt = 0.75 mins, Generic Basic Method |

Example 104 (E104)-3-(5-methyl-1H-pyrazol-4-yl)-4-(1-piperidyl)-1H-pyrrolo[2,3-b]pyridine 3-iodo-4-(1-piperidyl)-1-(p-tolylsulfonyl)pyrrolo[2,3-b]pyridine (P56) (150.00 mg, 0.31 mmol), potassium carbonate anhydrous (86.13 mg, 0.62 mmol), 5-methyl-4-(4,4,5,5-tetramethyl-1,3,2-dioxaborolan-2-yl)-1H-pyrazole (64.83 mg, 0.31 mmol) and dichlorobis(triphenylphosphine)palladium (0.21 mg) was dissolved in ethanol (1.0 ml) and water (0.25 mL). The mixture was degassed and flushed with nitrogen before being heated to 120° C. for 30 minutes. After this time, the mixture was concentrated under reduced pressure and the resulting residue dissolved in methanol (2 ml). KOH (10N, 1 ml) was added and the mixture heated at 80° C. for 30 minutes. The mixture was concentrated under reduced pressure and the residue purified by preparative HPLC (middle basic run) to give 3-(5-methyl-1H-pyrazol- 4-yl)-4-(1-piperidyl)-1H-pyrrolo[2,3-b]pyridine (E104) (1 mg), LCMS ES⁺ 282.3[M+H]⁺, Rt=1.02 mins (Generic Basic Method).

Example 105 (E105)-[1-(3-pyrimidin-5-yl-1H-pyrrolo[2,3-b]pyridin-4-yl)-4-piperidyl]methanamine

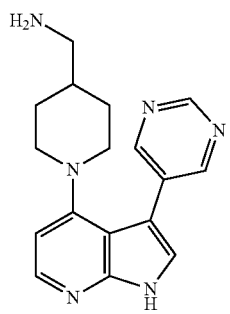 [SMILES: NCC1CCN(c2ccnc3[nH]cc(-c4cncnc4)c23)CC1]

2-[(4-chloro-3-pyrimidin-5-yl-pyrrolo[2,3-b]pyridin-1-yl)methoxy]ethyl-trimethyl-silane (P23) (197.00 mg, 0.55 mmol), tert-butyl N-(4-piperidylmethyl)carbamate (0.94 g, 4.37 mmol) was dissolved in DMSO (0.4 ml). The reaction mixture was heated to 145° C. for 4 hours and concentrated under reduced pressure. The crude product was dissolved in 2N HCl (1 ml) and THF (0.5 ml) and heated at 80° C. in a microwave reactor for 45 minutes. The solution was dried in a Genevac EZ-2 and the resulting yellow glass purified using the generic basic run to give [1-(3-pyrimidin-5-yl-1H-pyrrolo[2,3-b]pyridin-4-yl)-4-piperidyl]methanamine (E105) (1.56 mg, 0.004 mmol, 0.8% yield), LCMS ES⁺ 309.2 [M+H]⁺, Rt=0.22 mins (Generic Basic Method).

Example 106 (E106)-4-(2-benzyl-1-piperidyl)-1H-pyrrolo[2,3-b]pyridine-3-carbonitrile

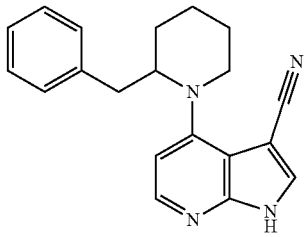 [SMILES: N#Cc1c[nH]c2nccc(N3CCCCC3Cc3ccccc3)c12]

A solution of 2-benzylpiperidine (98.68 mg, 0.56 mmol) and 4-chloro-1H-pyrrolo[2,3-b]pyridine-3-carbonitrile (P5) (50 mg, 0.28 mmol) in NMP (0.5 ml) was heated at 220° C. for 1 hour. The mixture was loaded onto an SCX cartridge and eluted with 2N NH₃ in methanol. The mixture was concentrated under reduced pressure before being purified by preparative HPLC (middle basic run) to give 4-(2-benzyl-1-piperidyl)-1H-pyrrolo[2,3-b]pyridine-3-carbonitrile (E106) (1.5 mg, 0.005 mmol, 1.6% yield), LCMS ES⁺ 317.3 [M+H]⁺, Rt=1.40 mins (Generic Basic Method).

Example 107 (E107)-4-(2-benzylpyrrolidin-1-yl)-1H-pyrrolo[2,3-b]pyridine-3-carbonitrile

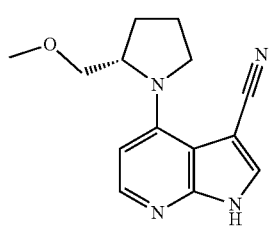

A solution of 2-benzylpyrrolidine (34.96 mg, 0.22 mmol) and 4-chloro-1H-pyrrolo[2,3-b]pyridine-3-carbonitrile (P5) (35 mg, 0.20 mmol) was dissolved in NMP (0.5 ml) and was heated at 160° C. for 4 hours. The mixture was concentrated under reduced pressure and the residue purified by preparative HPLC (middle basic run) to give 4-(2-benzylpyrrolidin-1-yl)-1H-pyrrolo[2,3-b]pyridine-3-carbonitrile (E107) (8 mg, 0.03 mmol, 12.8% yield), LCMS ES⁺ 303.2 [M+H]⁺, Rt=1.31 mins (Generic Basic Method).

The following compounds were prepared in a similar manner to 4-(2-benzylpyrrolidin-1-yl)-1H-pyrrolo[2,3-b]pyridine-3-carbonitrile (E107) using 4-chloro-1H-pyrrolo[2,3-b]pyridine-3-carbonitrile (P5) and the appropriate amine:

| Example | Structure | Name | LCMS Data |
|---|---|---|---|
| E108 | 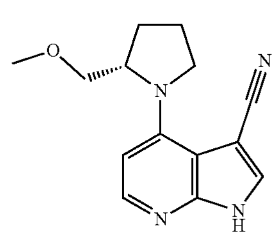 [SMILES: COC[C@@H]1CCCN1c1ccnc2[nH]cc(C#N)c12] | 4-[(2S)-2-(methoxymethyl)pyrrolidin-1-yl]-1H-pyrrolo[2,3-b]pyridine-3-carbonitrile | ES⁺ 257 [M + H]⁺, Rt = 1.00 mins, Generic Basic Method |

-continued

| Example | Structure | Name | LCMS Data |
|---|---|---|---|
| E110 | 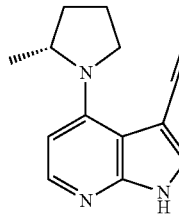 | 4-[(2R)-2-methylpyrrolidin-1-yl]-1H-pyrrolo[2,3-b]pyridine-3-carbonitrile | ES+ 227 [M + H]+, Rt = 1.08 mins, Generic Basic Method |
| E111 | 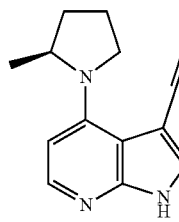 | 4-[(2S)-2-methylpyrrolidin-1-yl]-1H-pyrrolo[2,3-b]pyridine-3-carbonitrile | ES+ 227 [M + H]+, Rt = 1.10 mins, Generic Basic Method |
| E112 | 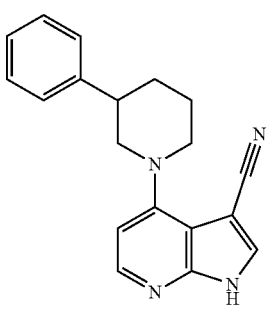 [SMILES: N#Cc1c[nH]c2nccc(N3CCCC(c4ccccc4)C3)c12] | 4-(3-phenyl-1-piperidyl)-1H-pyrrolo[2,3-b]pyridine-3-carbonitrile | ES+ 303 [M + H]+, Rt = 1.35 mins, Generic Basic Method |
| E113 | 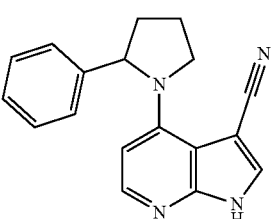 | 4-(2-phenylpyrrolidin-1-yl)-1H-pyrrolo[2,3-b]pyridine-3-carbonitrile | ES+ 289 [M + H]+, Rt = 1.22 mins, Generic Basic Method |

Example 114 (E114)-4-[4-(1,8-diazaspiro[5.5]undecan-8-yl)-1H-pyrrolo[2,3-b]pyridin-3-yl]isothiazole

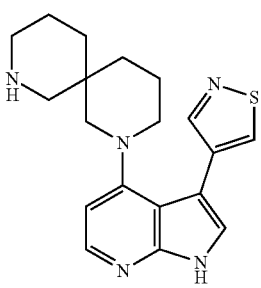

A solution of 2-[(4-chloro-3-isothiazol-4-yl-pyrrolo[2,3-b]pyridin-1-yl)methoxy]ethyl-trimethyl-silane (P35) (200.00 mg, 0.55 mmol) trimethylamine (0.38 ml, 2.73 mmol), tert-butyl 1,8-diazaspiro[5.5]undecane-1-carboxylate (695.09 mg, 2.73 mmol) and NMP (2 ml) was heated to 180° C. for 12 hours in the microwave. Further tert-butyl 1,8-diazaspiro[5.5]undecane-1-carboxylate (695.09 mg, 2.73 mmol) was added and reaction heated in microwave for a further 16 hours at 180° C. After this time, the solution was allowed to cool to room temperature before being purified by SCX (20×10 g) and chromatographed [SiO2, 0-10% NH3 in MeOH/DCM:DCM] and then further purified by preparative HPLC (Basic Method) to give 4-[4-(1,8-diazaspiro[5.5]undecan-8-yl)-1H-pyrrolo[2,3-b]pyridin-3-yl]isothiazole (E114) (54 mg) LCMS ES+ 354 [M+H]+, Rt=0.98 mins (Generic Basic Method)

Example 115 (E115)-3-[4-[(6R)-1,8-diazaspiro[5.5]undecan-8-yl]-1H-pyrrolo[2,3-b]pyridin-3-yl]-1,2,4-thiadiazole

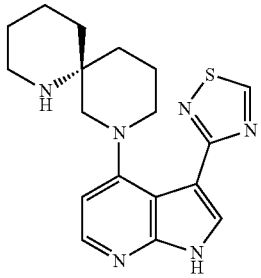 [SMILES: c1cc(N2CCC[C@]3(CCCCN3)C2)c2c(-c3ncsn3)c[nH]c2n1]

A solution of 2-[[4-[(6R)-1,8-diazaspiro[5.5]undecan-8-yl]-3-(1,2,4-thiadiazol-3-yl)pyrrolo[2,3-b]pyridin-1-yl]methoxy]ethyl-trimethyl-silane (P246) (124 mg, 0.26 mmol) and HCl (aq.) soln. (0.51 ml, 2.56 mmol) in 1,4-dioxane (0.1 ml) was heated to 50° C. overnight after which time the temperature was raised to 70° C. for a further 7 hours. The reaction mixture was allowed to cool to room temperature before being loaded onto a pre-acidified 5 g SCX cartridge. The cartridge was washed MeOH (×4 cv's) and the product was released upon treatment with $NH_3$ in MeOH (2N). The basic fractions were concentrated under reduced pressure. The resulting residue was purified via preparative HPLC (generic basic method) to give 3-[4-[(6R)-1,8-diazaspiro[5.5]undecan-8-yl]-1H-pyrrolo[2,3-b]pyridin-3-yl]-1,2,4-thiadiazole (E115) (57 mg), LCMS $ES^+$ 355 $[M+H]^+$, Rt=0.76 mins (Generic Basic Method).

The following compound was prepared in a similar manner to 3-[4-[(6R)-1,8-diazaspiro[5.5]undecan-8-yl]-1H-pyrrolo[2,3-b]pyridin-3-yl]-1,2,4-thiadiazole (E115) from the appropriate intermediate:

Example 117 (E117 or BDP9066)-(6S)-8-(3-pyrimidin-4-yl-1H-pyrrolo[2,3-b]pyridin-4-yl)-1,8-diazaspiro[5.5]undecane

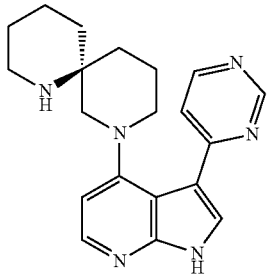

A solution of 2-[[4-[(6S)-1,8-diazaspiro[5.5]undecan-8-yl]-3-pyrimidin-4-yl-pyrrolo[2,3-b]pyridin-1-yl]methoxy]ethyl-trimethyl-silane (P100) (1.00 g, 2.09 mmol) and HCl (aq.) soln. (5M, 4.18 ml 20.89 mmol) in 1,4-dioxane (4 ml) was heated to 75° C. for 72 hours. A second solution of 2-[[4-[(6S)-1,8-diazaspiro[5.5]undecan-8-yl]-3-pyrimidin-4-yl-pyrrolo[2,3-b]pyridin-1-yl]methoxy]ethyl-trimethyl-silane (P100) (500 mg, 1.05 mmol) and HCl (aq.) soln. (5M, 2.09 ml, 10.45 mmol) in 1,4-dioxane (4 mL) was heated to 50° C. for 18 hours, then 75° C. for a further 18 hours. The solutions were combined, concentrated under reduced pressure and loaded onto a pre-acidified SCX cartridge. The cartridge was washed with MeOH (5 cv's), followed by $NH_3$ in MeOH (2N). The basic fractions were concentrated under reduced pressure to give a yellow coloured solid. The solid was triturated with MeCN and MeOH before being dried in vacuo to give (6S)-8-(3-pyrimidin-4-yl-1H-pyrrolo[2,3-b]pyridin-4-yl)-1,8-diazaspiro[5.5]undecane (E117) (849 mg), LCMS $ES^+$ 349 $[M+H]^+$, Rt=0.85 mins (Generic Basic Method).

| Example | Structure | Name | LCMS Data |
|---|---|---|---|
| E116 | 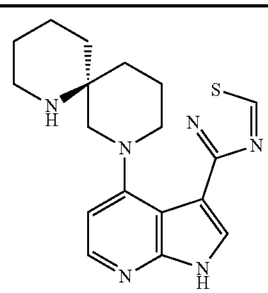 | 3-[4-[(6S)-1,8-diazaspiro[5.5]undecan-8-yl]-1H-pyrrolo[2,3-b]pyridin-3-yl]-1,2,4-thiadiazole | $ES^+$ 355 $[M + H]^+$, Rt = 0.87 mins, Generic Basic Method |
| E237 | 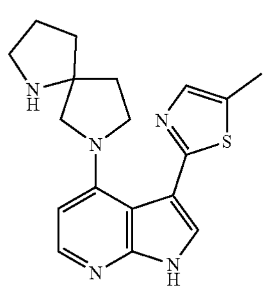 | 2-[4-(1,7-diazaspiro[4.4]nonan-7-yl)-1H-pyrrolo[2,3-b]pyridin-3-yl]-5-methyl-thiazole | $ES^+$ 470 $[M + H]^+$, Rt = 0.92 mins, Generic Basic Method |

Example 118 (E118)-(6R)-8-(3-pyrimidin-4-yl-1H-pyrrolo[2,3-b]pyridin-4-yl)-1,8-diazaspiro[5.5]undecane

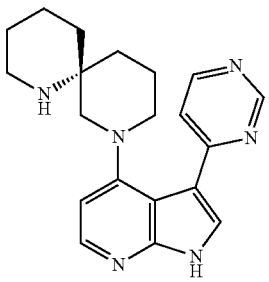

A solution of 2-[[4-[(6R)-1,8-diazaspiro[5.5]undecan-8-yl]-3-pyrimidin-4-yl-pyrrolo[2,3-b]pyridin-1-yl]methoxy]ethyl-trimethyl-silane (P99) and HCl (aq.) soln. (0.78 ml, 3.89 mmol) in 1,4-dioxane (1 ml) was heated to 55° C. for 72 hours. The solution was loaded onto a pre-acidifed SCX cartridge and washed with MeOH (×5 cvs), followed by $NH_3$ in MeOH (2N). The basic fractions were combined and the solution concentrated under reduced pressure. The residue was purified via preparative HPLC using the generic basic run to give (6R)-8-(3-pyrimidin-4-yl-1H-pyrrolo[2,3-b]pyridin-4-yl)-1,8-diazaspiro[5.5]undecane (E118) (65 mg, 0.18 mmol, 47.1% yield) as a pale yellow solid, LCMS $ES^+$ 349 $[M+H]^+$, Rt=0.85 mins (Generic Basic Method)

The following compounds were prepared in a similar manner to (6R)-8-(3-pyrimidin-4-yl-1H-pyrrolo[2,3-b]pyridin-4-yl)-1,8-diazaspiro[5.5]undecane (E118) from appropriate intermediates. In some cases the title compounds was prepared using preparative HPLC.

| Example | Structure | Name | LCMS Data |
|---|---|---|---|
| E119 | 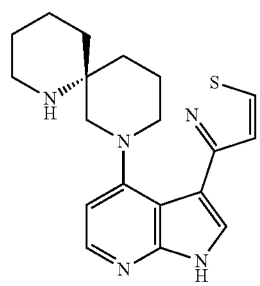 [SMILES: N=C(/C=C\S)c1c[nH]c2nccc(N3CCC[C@]4(CCCCN4)C3)c12] | 3-[4-[(6R)-1,8-diazaspiro[5.5]undecan-8-yl]-1H-pyrrolo[2,3-b]pyridin-3-yl]isothiazole | $ES^+$ 354 $[M + H]^+$, Rt = 0.94 mins, Generic Basic Method |
| E120 | 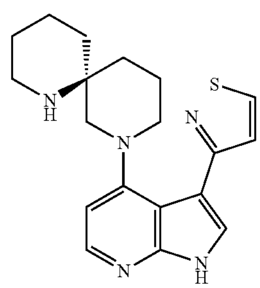 [SMILES: N=C(/C=C\S)c1c[nH]c2nccc(N3CCC[C@@]4(CCCCN4)C3)c12] | 3-[4-[(6S)-1,8-diazaspiro[5.5]undecan-8-yl]-1H-pyrrolo[2,3-b]pyridin-3-yl]isothiazole | $ES^+$ 354 $[M + H]^+$, Rt = 0.94 mins, Generic Basic Method |
| E121 | 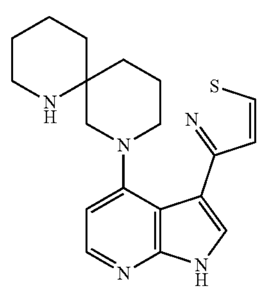 [SMILES: N=C(/C=C\S)c1c[nH]c2nccc(N3CCCC4(CCCCN4)C3)c12] | 3-[4-(1,8-diazaspiro[5.5]undecan-8-yl)-1H-pyrrolo[2,3-b]pyridin-3-yl]isothiazole | $ES^+$ 354 $[M + H]^+$, Rt = 1.00 mins, Generic Basic Method |

Example 122 (E122)-(6S)-8-(3-pyrimidin-5-yl-1H-pyrrolo[2,3-b]pyridin-4-yl)-1,8-diazaspiro[5.5]undecane

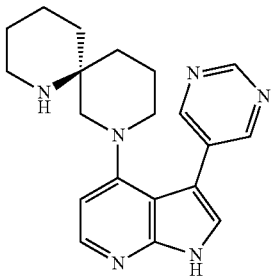 [SMILES: c1ncc(-c2c[nH]c3nccc(N4CCC[C@@]5(CCCCN5)C4)c23)cn1]

A solution of 2-[[4-[(6S)-1,8-diazaspiro[5.5]undecan-8-yl]-3-pyrimidin-5-yl-pyrrolo[2,3-b]pyridin-1-yl]methoxy]ethyl-trimethyl-silane (P103) (1.875 g, 3.92 mmol) and HCl (aq.) (7.83 ml, 39.17 mmol) in 1,4-dioxane (4 ml) was heated at 65° C. for 18 hours. The reaction was repeated a second time, before both batches were allowed to cool to room temperature and combined. The reaction mixtures were concentrated under reduced pressure to give a yellow solid. The residue was chromatographed [C18 eluting with 5-55% Basic Method] and the resulting solid was triturated with MeCN to give (6S)-8-(3-pyrimidin-5-yl-1H-pyrrolo[2,3-b]pyridin-4-yl)-1,8-diazaspiro[5.5]undecane (E122) (770 mg), LCMS ES$^+$ 349 [M+H]$^+$, Rt=0.93 mins (Generic Basic Method).

The following compounds were prepared in a similar manner to (6S)-8-(3-pyrimidin-5-yl-1H-pyrrolo[2,3-b]pyridin-4-yl)-1,8-diazaspiro[5.5]undecane (E122) from appropriate intermediates. In some cases the title compound was purified using preparative HPLC.

| Example | Structure | Name | LCMS Data |
|---|---|---|---|
| E123 | 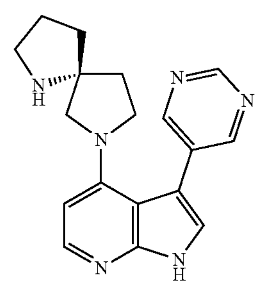 [SMILES: c1ncc(-c2c[nH]c3nccc(N4CC[C@]5(CCCN5)C4)c23)cn1] | 4-[(5R)-1,7-diazaspiro[4.4]nonan-7-yl]-3-pyrimidin-5-yl-1H-pyrrolo[2,3-b]pyridine | ES$^+$ 321 [M + H]$^+$, Rt = 0.76 mins, Generic Basic Method |
| E124 | 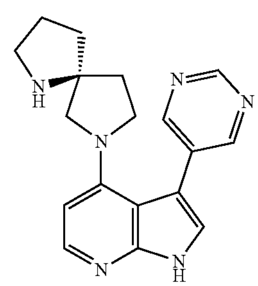 [SMILES: c1ncc(-c2c[nH]c3nccc(N4CC[C@@]5(CCCN5)C4)c23)cn1] | 4-[(5S)-1,7-diazaspiro[4.4]nonan-7-yl]-3-pyrimidin-5-yl-1H-pyrrolo[2,3-b]pyridine | ES$^+$ 321 [M + H]$^+$, Rt = 0.76 mins, Generic Basic Method |
| E125 | 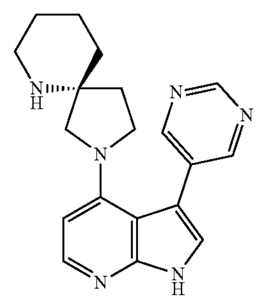 [SMILES: c1ncc(-c2c[nH]c3nccc(N4CC[C@]5(CCCCN5)C4)c23)cn1] | (5R)-2-(3-pyrimidin-5-yl-1H-pyrrolo[2,3-b]pyridin-4-yl)-2,6-diazaspiro[4.5]decane | ES$^+$ 335 [M + H]$^+$, Rt = 0.81 mins, Generic Basic Method |

-continued

| Example | Structure | Name | LCMS Data |
|---|---|---|---|
| E126 | 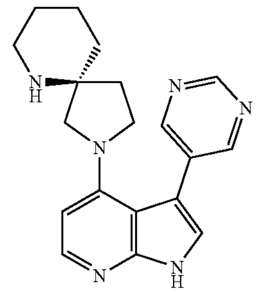 [SMILES: c1ncc(-c2c[nH]c3nccc(N4CC[C@@]5(CCCCN5)C4)c23)cn1] | (5S)-2-(3-pyrimidin-5-yl-1H-pyrrolo[2,3-b]pyridin-4-yl)-2,6-diazaspiro[4.5]decane | ES+ 335 [M + H]+, Rt = 0.81 mins, Generic Basic Method |
| E127 | 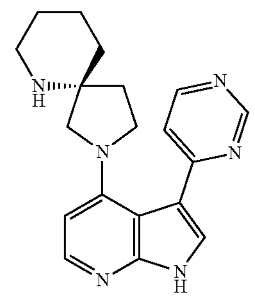 [SMILES: c1cc(-c2c[nH]c3nccc(N4CC[C@]5(CCCCN5)C4)c23)ncn1] | (5R)-2-(3-pyrimidin-4-yl-1H-pyrrolo[2,3-b]pyridin-4-yl)-2,6-diazaspiro[4.5]decane | ES+ 335 [M + H]+, Rt = 0.80 mins, Generic Basic Method |
| E128 | 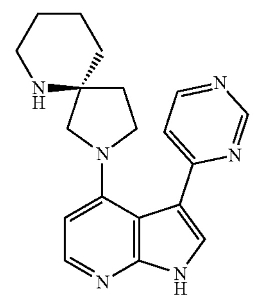 [SMILES: c1cc(-c2c[nH]c3nccc(N4CC[C@@]5(CCCCN5)C4)c23)ncn1] | (5S)-2-(3-pyrimidin-4-yl-1H-pyrrolo[2,3-b]pyridin-4-yl)-2,6-diazaspiro[4.5]decane | ES+ 335 [M + H]+, Rt = 0.79 mins, Generic Basic Method |
| E129 | 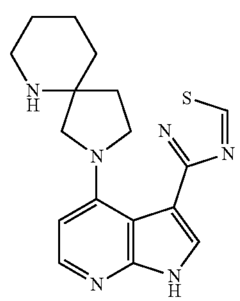 [SMILES: N=C(/N=C\S)c1c[nH]c2nccc(N3CCC4(CCCCN4)C3)c12] | 3-[4-(2,6-diazaspiro[4.5]decan-2-yl)-1H-pyrrolo[2,3-b]pyridin-3-yl]-1,2,4-thiadiazole | ES+ 341 [M + H]+, Rt = 0.83 mins, Generic Basic Method |
| E130 | 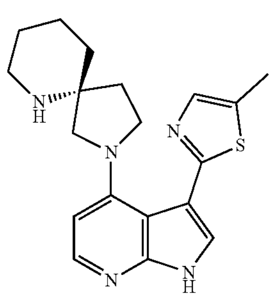 [SMILES: Cc1cnc(-c2c[nH]c3nccc(N4CC[C@]5(CCCCN5)C4)c23)s1] | 2-[4-[(5R)-2,6-diazaspiro[4.5]decan-2-yl]-1H-pyrrolo[2,3-b]pyridin-3-yl]-5-methyl-thiazole | ES+ 354 [M + H]+, Rt = 0.99 mins, Generic Basic Method |

-continued

| Example | Structure | Name | LCMS Data |
|---|---|---|---|
| E131 | 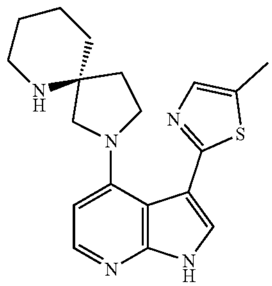 [SMILES: Cc1cnc(-c2c[nH]c3nccc(N4CC[C@@]5(CCCCN5)C4)c23)s1] | 2-[4-[(5S)-2,6-diazaspiro[4.5]decan-2-yl]-1H-pyrrolo[2,3-b]pyridin-3-yl]-5-methylthiazole | ES+ 354 [M + H]+, Rt = 0.99 mins, Generic Basic Method |
| E132 | 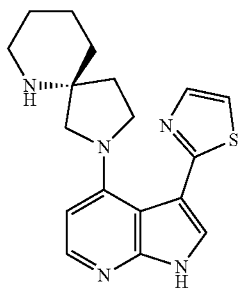 [SMILES: c1csc(-c2c[nH]c3nccc(N4CC[C@]5(CCCCN5)C4)c23)n1] | 2-[4-[(5R)-2,6-diazaspiro[4.5]decan-2-yl]-1H-pyrrolo[2,3-b]pyridin-3-yl]thiazole | ES+ 340 [M + H]+, Rt = 0.91 mins, Generic Basic Method |
| E133 | 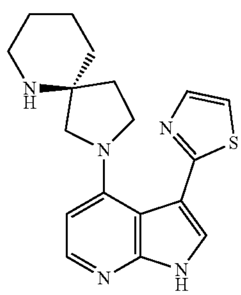 [SMILES: c1csc(-c2c[nH]c3nccc(N4CC[C@@]5(CCCCN5)C4)c23)n1] | 2-[4-[(5S)-2,6-diazaspiro[4.5]decan-2-yl]-1H-pyrrolo[2,3-b]pyridin-3-yl]thiazole | ES+ 340 [M + H]+, Rt = 0.91 mins, Generic Basic Method |
| E134 | 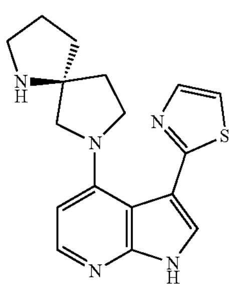 [SMILES: c1csc(-c2c[nH]c3nccc(N4CC[C@@]5(CCCN5)C4)c23)n1] | 2-[4-[(5S)-1,7-diazaspiro[4.4]nonan-7-yl]-1H-pyrrolo[2,3-b]pyridin-3-yl]thiazole | ES+ 326 [M + H]+, Rt = 0.84 mins, Generic Basic Method |
| E135 | 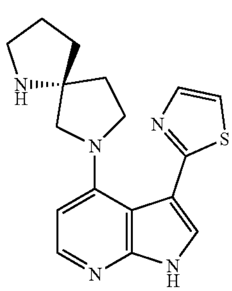 [SMILES: c1csc(-c2c[nH]c3nccc(N4CC[C@]5(CCCN5)C4)c23)n1] | 2-[4-[(5R)-1,7-diazaspiro[4.4]nonan-7-yl]-1H-pyrrolo[2,3-b]pyridin-3-yl]thiazole | ES+ 326 [M + H]+, Rt = 0.84 mins, Generic Basic Method |

-continued

| Example | Structure | Name | LCMS Data |
|---|---|---|---|
| E136 | 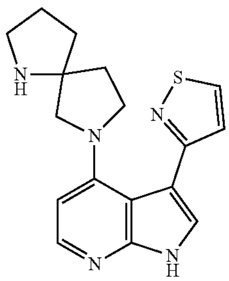 [SMILES: c1cc(N2CCC3(CCCN3)C2)c2c(-c3ccsn3)c[nH]c2n1] | 3-[4-(1,7-diazaspiro[4.4]nonan-7-yl)-1H-pyrrolo[2,3-b]pyridin-3-yl]isothiazole | ES⁺ 326 [M + H]⁺, Rt = 0.86 mins, Generic Basic Method |
| E137 | 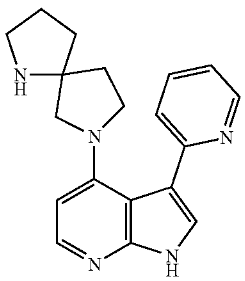 [SMILES: c1ccc(-c2c[nH]c3nccc(N4CCC5(CCCN5)C4)c23)nc1] | 4-(1,7-diazaspiro[4.4]nonan-7-yl)-3-(2-pyridyl)-1H-pyrrolo[2,3-b]pyridine | ES⁺ 320 [M + H]⁺, Rt = 0.88 mins, Generic Basic Method |
| E138 | 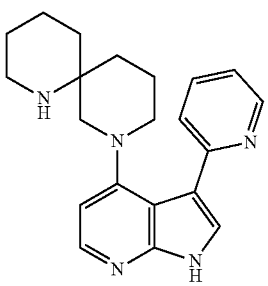 [SMILES: c1ccc(-c2c[nH]c3nccc(N4CCCC5(CCCCN5)C4)c23)nc1] | 8-[3-(2-pyridyl)-1H-pyrrolo[2,3-b]pyridin-4-yl]-1,8-diazaspiro[5.5]undecane | ES⁺ 348 [M + H]⁺, Rt = 0.99 mins, Generic Basic Method |
| E139 | 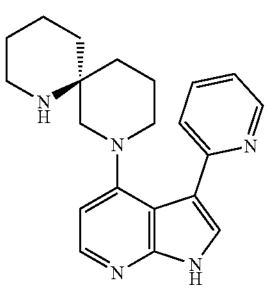 [SMILES: c1ccc(-c2c[nH]c3nccc(N4CCC[C@@]5(CCCCN5)C4)c23)nc1] | (6S)-8-[3-(2-pyridyl)-1H-pyrrolo[2,3-b]pyridin-4-yl]-1,8-diazaspiro[5.5]undecane | ES⁺ 348 [M + H]⁺, Rt = 0.93 mins, Generic Basic Method |
| E140 | 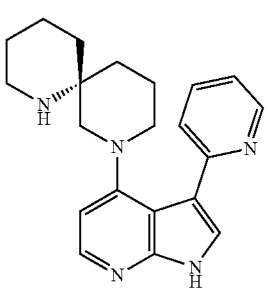 [SMILES: c1ccc(-c2c[nH]c3nccc(N4CCC[C@]5(CCCCN5)C4)c23)nc1] | (6R)-8-[3-(2-pyridyl)-1H-pyrrolo[2,3-b]pyridin-4-yl]-1,8-diazaspiro[5.5]undecane | ES⁺ 348 [M + H]⁺, Rt = 0.92 mins, Generic Basic Method |

-continued

| Example | Structure | Name | LCMS Data |
|---|---|---|---|
| E141 | 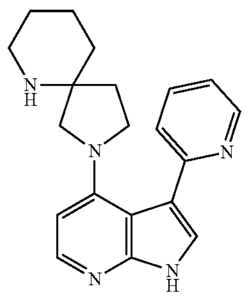 [SMILES: c1ccc(-c2c[nH]c3nccc(N4CCC5(CCCCN5)C4)c23)nc1] | 2-[3-(2-pyridyl)-1H-pyrrolo[2,3-b]pyridin-4-yl]-2,6-diazaspiro[4.5]decane | ES+ 334 [M + H]+, Rt = 0.86 mins, Generic Basic Method |
| E142 | 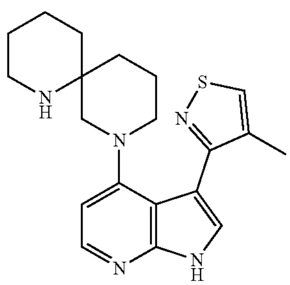 [SMILES: Cc1csnc1-c1c[nH]c2nccc(N3CCCC4(CCCCN4)C3)c12] | 3-[4-(1,8-diazaspiro[5.5]undecan-8-yl)-1H-pyrrolo[2,3-b]pyridin-3-yl]-4-methyl-isothiazole | ES+ 368 [M + H]+, Rt = 0.97 mins, Generic Basic Method |
| E143 | 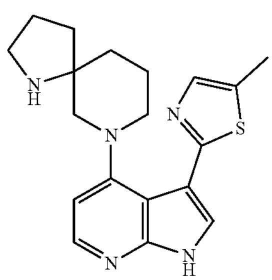 [SMILES: Cc1cnc(-c2c[nH]c3nccc(N4CCCC5(CCCN5)C4)c23)s1] | 2-[4-(1,9-diazaspiro[4.5]decan-9-yl)-1H-pyrrolo[2,3-b]pyridin-3-yl]-5-methyl-thiazole | ES+ 354 [M + H]+, Rt = 0.88 mins, Generic Basic Method |
| E144 | 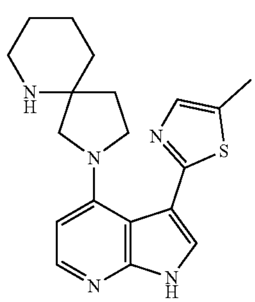 [SMILES: Cc1cnc(-c2c[nH]c3nccc(N4CCC5(CCCCN5)C4)c23)s1] | 2-[4-(2,6-diazaspiro[4.5]decan-2-yl)-1H-pyrrolo[2,3-b]pyridin-3-yl]-5-methyl-thiazole | ES+ 354 [M + H]+, Rt = 0.97 mins, Generic Basic Method |

Example 146 (E146)-2-[4-[(6S)-1,8-diazaspiro[5.5]undecan-8-yl]-1H-pyrrolo[2,3-b]pyridin-3-yl]-5-methyl-thiazole

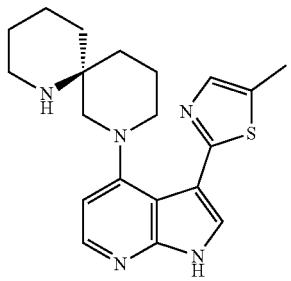 [SMILES: Cc1cnc(-c2c[nH]c3nccc(N4CCC[C@@]5(CCCCN5)C4)c23)s1]

A solution of 2-[[4-[(6S)-1,8-diazaspiro[5.5]undecan-8-yl]-3-(5-methylthiazol-2-yl)pyrrolo[2,3-b]pyridin-1-yl]methoxy]ethyl-trimethyl-silane, (P117) (180.5 mg, 0.36 mmol) and hydrogen chloride solution (1.45 ml, 7.25 mmol) in 1,4-dioxane (3 ml) was heated to 60° C. overnight. The reaction mixture was concentrated under reduced pressure and the sample purified by SCX (2 g) to give 2-[4-[(6S)-1,8-diazaspiro[5.5]undecan-8-yl]-1H-pyrrolo[2,3-b]pyridin-3-yl]-5-methyl-thiazole (E146) (124 mg, 0.32 mmol, 89.3% yield), LCMS ES$^+$ 368 [M+H]$^+$, Rt=0.94 mins (Generic Basic Method).

The following compounds were prepared in a similar manner to 2-[4-[(6S)-1,8-diazaspiro[5.5]undecan-8-yl]-1H-pyrrolo[2,3-b]pyridin-3-yl]-5-methyl-thiazole (E146) from appropriate intermediates.

| Example | Structure | Name | LCMS Data |
|---|---|---|---|
| E147 | 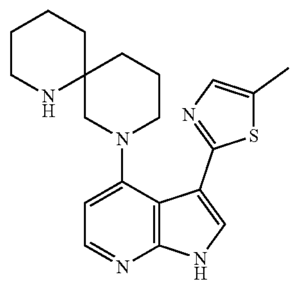 [SMILES: Cc1cnc(-c2c[nH]c3nccc(N4CCCC5(CCCCN5)C4)c23)s1] | 2-[4-(1,8-diazaspiro[5.5]undecan-8-yl)-1H-pyrrolo[2,3-b]pyridin-3-yl]-5-methyl-thiazole | ES$^+$ 368 [M + H]$^+$, Rt = 1.01 mins, Generic Basic Method |
| E148 | 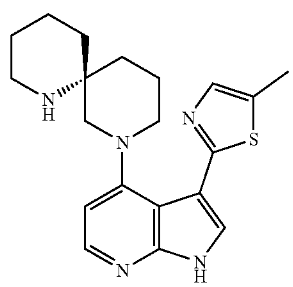 [SMILES: Cc1cnc(-c2c[nH]c3nccc(N4CCC[C@]5(CCCCN5)C4)c23)s1] | 2-[4-[(6R)-1,8-diazaspiro[5.5]undecan-8-yl]-1H-pyrrolo[2,3-b]pyridin-3-yl]-5-methyl-thiazole | ES$^+$ 368 [M + H]$^+$, Rt = 0.95 mins, Generic Basic Method |
| E149 | 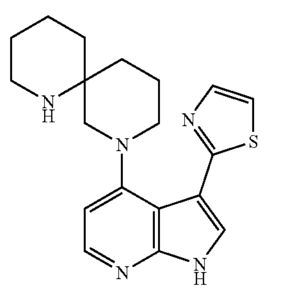 [SMILES: c1csc(-c2c[nH]c3nccc(N4CCCC5(CCCCN5)C4)c23)n1] | 2-[4-(1,8-diazaspiro[5.5]undecan-8-yl)-1H-pyrrolo[2,3-b]pyridin-3-yl]thiazole | ES$^+$ 354 [M + H]$^+$, Rt = 0.93 mins, Generic Basic Method |
| E150 | 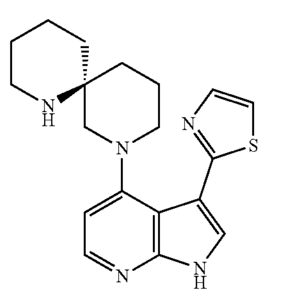 [SMILES: c1csc(-c2c[nH]c3nccc(N4CCC[C@@]5(CCCCN5)C4)c23)n1] | 2-[4-[(6S)-1,8-diazaspiro[5.5]undecan-8-yl]-1H-pyrrolo[2,3-b]pyridin-3-yl]thiazole | ES$^+$ 354 [M + H]$^+$, Rt = 0.92 mins, Generic Basic Method |

-continued

| Example | Structure | Name | LCMS Data |
|---|---|---|---|
| E151 | 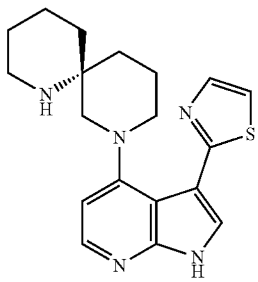 [SMILES: c1csc(-c2c[nH]c3nccc(N4CCC[C@]5(CCCCN5)C4)c23)n1] | 2-[4-[(6R)-1,8-diazaspiro[5.5]undecan-8-yl]-1H-pyrrolo[2,3-b]pyridin-3-yl]thiazole | ES⁺ 354 [M + H]⁺, Rt = 0.90 mins, Generic Basic Method |
| E152 | 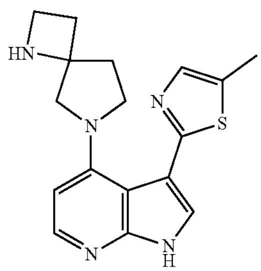 [SMILES: Cc1cnc(-c2c[nH]c3nccc(N4CCC5(CCN5)C4)c23)s1] | 2-[4-(1,7-diazaspiro[3.4]octan-7-yl)-1H-pyrrolo[2,3-b]pyridin-3-yl]-5-methyl-thiazole | ES⁺ 326 [M + H]⁺, Rt = 0.83 mins, Generic Basic Method |
| E153 | 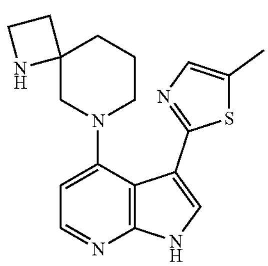 [SMILES: Cc1cnc(-c2c[nH]c3nccc(N4CCCC5(CCN5)C4)c23)s1] | 2-[4-(1,8-diazaspiro[3.5]nonan-8-yl)-1H-pyrrolo[2,3-b]pyridin-3-yl]-5-methyl-thiazole | ES⁺ 340 [M + H]⁺, Rt = 0.89 mins, Generic Basic Method |
| E154 | 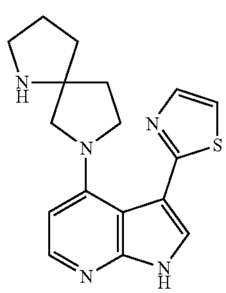 [SMILES: c1csc(-c2c[nH]c3nccc(N4CCC5(CCCN5)C4)c23)n1] | 2-[4-(1,7-diazaspiro[4.4]nonan-7-yl)-1H-pyrrolo[2,3-b]pyridin-3-yl]thiazole | ES⁺ 326 [M + H]⁺, Rt = 0.84 mins, Generic Basic Method |
| E155 | 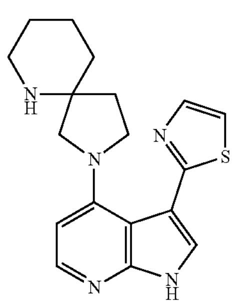 [SMILES: c1csc(-c2c[nH]c3nccc(N4CCC5(CCCCN5)C4)c23)n1] | 2-[4-(2,6-diazaspiro[4.5]decan-2-yl)-1H-pyrrolo[2,3-b]pyridin-3-yl]thiazole | ES⁺ 340 [M + H]⁺, Rt = 0.9 mins, Generic Basic Method |

-continued

| Example | Structure | Name | LCMS Data |
|---|---|---|---|
| E156 | 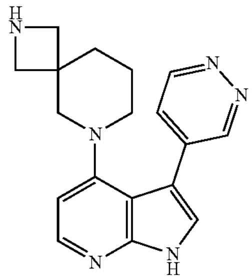 [SMILES: c1cc(-c2c[nH]c3nccc(N4CCCC5(CNC5)C4)c23)cnn1] | 4-(2,6-diazaspiro[3.5]nonan-6-yl)-3-pyridazin-4-yl-1H-pyrrolo[2,3-b]pyridine | ES+ 321 [M + H]+, Rt = 0.66 mins, Generic Basic Method |
| E157 | 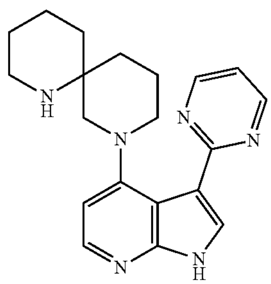 [SMILES: c1cnc(-c2c[nH]c3nccc(N4CCCC5(CCCCN5)C4)c23)nc1] | 8-(3-pyrimidin-2-yl-1H-pyrrolo[2,3-b]pyridin-4-yl)-1,8-diazaspiro[5.5]undecane | ES+ 349 [M + H]+, Rt = 0.83 mins, Generic Basic Method |
| E158 | 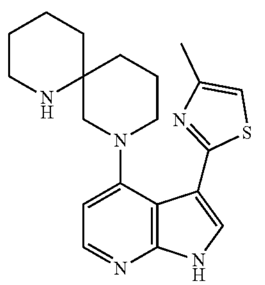 [SMILES: Cc1csc(-c2c[nH]c3nccc(N4CCCC5(CCCCN5)C4)c23)n1] | 2-[4-(1,8-diazaspiro[5.5]undecan-8-yl)-1H-pyrrolo[2,3-b]pyridin-3-yl]-4-methyl-thiazole | ES+ 368 [M + H]+, Rt = 1.04 mins, Generic Basic Method |
| E159 | 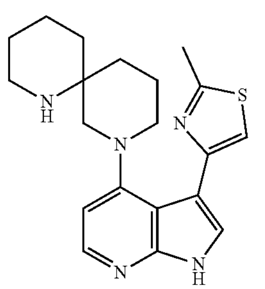 | 4-[4-(1,8-diazaspiro[5.5]undecan-8-yl)-1H-pyrrolo[2,3-b]pyridin-3-yl]-2-methyl-thiazole | ES+ 378 [M + H]+, Rt = 1.64 mins, Generic Basic Method |
| E160 | 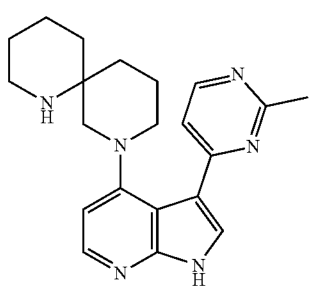 [SMILES: Cc1nccc(-c2c[nH]c3nccc(N4CCCC5(CCCCN5)C4)c23)n1] | 8-[3-(2-methylpyrimidin-4-yl)-1H-pyrrolo[2,3-b]pyridin-4-yl]-1,8-diazaspiro[5.5]undecane | ES+ 363 [M + H]+, Rt = 0.86 mins, Generic Basic Method |

-continued

| Example | Structure | Name | LCMS Data |
|---|---|---|---|
| E161 | 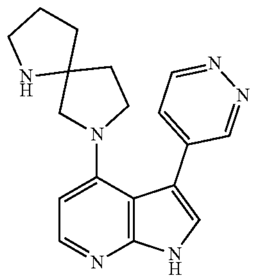 [SMILES: c1cc(-c2c[nH]c3nccc(N4CCC5(CCCN5)C4)c23)cnn1] | 4-(1,7-diazaspiro[4.4]nonan-7-yl)-3-pyridazin-4-yl-1H-pyrrolo[2,3-b]pyridine | ES⁺ 321 [M + H]⁺, Rt = 0.71 mins, Generic Basic Method |
| E162 | 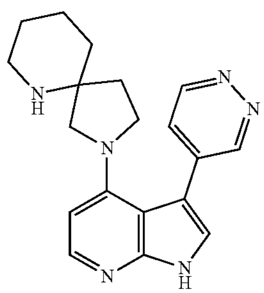 [SMILES: c1cc(-c2c[nH]c3nccc(N4CCC5(CCCCN5)C4)c23)cnn1] | 2-(3-pyridazin-4-yl-1H-pyrrolo[2,3-b]pyridin-4-yl)-2,6-diazaspiro[4.5]decane | ES⁺ 335 [M + H]⁺, Rt = 0.76 mins, Generic Basic Method |
| E163 | 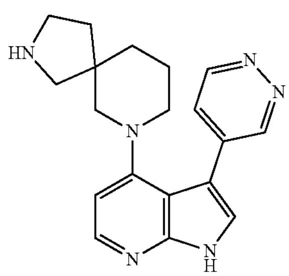 [SMILES: c1cc(-c2c[nH]c3nccc(N4CCCC5(CCNC5)C4)c23)cnn1] | 7-(3-pyridazin-4-yl-1H-pyrrolo[2,3-b]pyridin-4-yl)-2,7-diazaspiro[4.5]decane | ES⁺ 335 [M + H]⁺, Rt = 0.71 mins, Generic Basic Method |
| E164 | 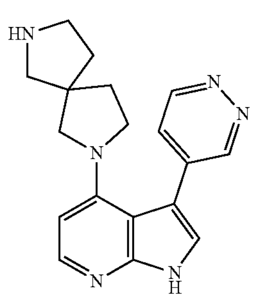 [SMILES: c1cc(-c2c[nH]c3nccc(N4CCC5(CCNC5)C4)c23)cnn1] | 4-(2,7-diazaspiro[4.4]nonan-2-yl)-3-pyridazin-4-yl-1H-pyrrolo[2,3-b]pyridine | ES⁺ 321 [M + H]⁺, Rt = 0.66 mins, Generic Basic Method |
| E165 | 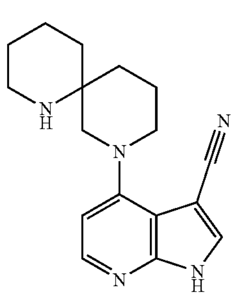 [SMILES: N#Cc1c[nH]c2nccc(N3CCCC4(CCCCN4)C3)c12] | 4-(1,8-diazaspiro[5.5]undecan-8-yl)-1H-pyrrolo[2,3-b]pyridine-3-carbonitrile | ES⁺ 296 [M + H]⁺, Rt = 0.93 mins, Generic Basic Method |

| Example | Structure | Name | LCMS Data |
|---|---|---|---|
| E166 | 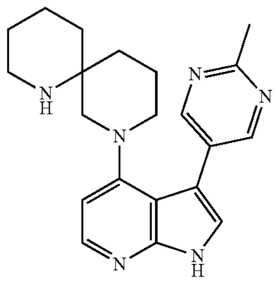 [SMILES: Cc1ncc(-c2c[nH]c3nccc(N4CCCC5(CCCCN5)C4)c23)cn1] | 8-[3-(2-methylpyrimidin-5-yl)-1H-pyrrolo[2,3-b]pyridin-4-yl]-1,8-diazaspiro[5.5]undecane | ES+ 363 [M + H]+, Rt = 0.92 mins, Generic Basic Method |
| E167 | 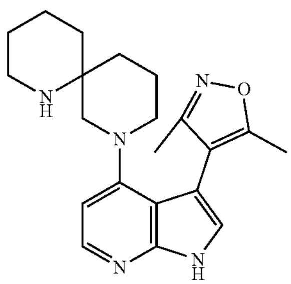 [SMILES: Cc1noc(C)c1-c1c[nH]c2nccc(N3CCCC4(CCCCN4)C3)c12] | 4-[4-(1,8-diazaspiro[5.5]undecan-8-yl)-1H-pyrrolo[2,3-b]pyridin-3-yl]-3,5-dimethyl-isoxazole | ES+ 366 [M + H]+, Rt = 1.05 mins, Generic Basic Method |
| E168 | 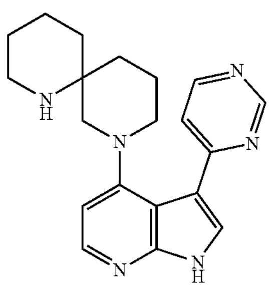 [SMILES: c1cc(-c2c[nH]c3nccc(N4CCCC5(CCCCN5)C4)c23)ncn1] | 8-(3-pyrimidin-4-yl-1H-pyrrolo[2,3-b]pyridin-4-yl)-1,8-diazaspiro[5.5]undecane | ES+ 349 [M + H]+, Rt = 0.44 mins, Generic Acidic Method |
| E169 | 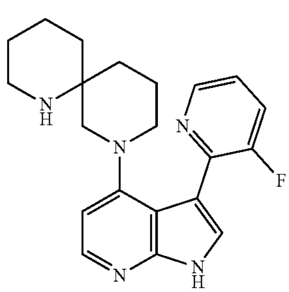 [SMILES: Fc1cccnc1-c1c[nH]c2nccc(N3CCCC4(CCCCN4)C3)c12] | 8-[3-(3-fluoro-2-pyridyl)-1H-pyrrolo[2,3-b]pyridin-4-yl]-1,8-diazaspiro[5.5]undecane | ES+ 366 [M + H]+, Rt = 0.96 mins, Generic Basic Method |
| E170 | 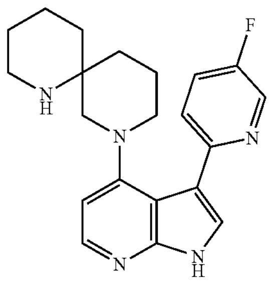 [SMILES: Fc1ccc(-c2c[nH]c3nccc(N4CCCC5(CCCCN5)C4)c23)nc1] | 8-[3-(5-fluoro-2-pyridyl)-1H-pyrrolo[2,3-b]pyridin-4-yl]-1,8-diazaspiro[5.5]undecane | ES+ 366 [M + H]+, Rt = 1.00 mins, Generic Basic Method |

-continued

| Example | Name | LCMS Data |
|---|---|---|
| E171 | 8-[3-(5-fluoro-3-pyridyl)-1H-pyrrolo[2,3-b]pyridin-4-yl]-1,8-diazaspiro[5.5]undecane | ES$^+$ 366 [M + H]$^+$, Rt = 0.98 mins, Generic Basic Method |
| E172 | 8-(3-pyridazin-4-yl-1H-pyrrolo[2,3-b]pyridin-4-yl)-1,8-diazaspiro[5.5]undecane | ES$^+$ 349 [M + H]$^+$, Rt = 0.82 mins, Generic Basic Method |
| E173 | (6R)-8-(3-pyridazin-4-yl-1H-pyrrolo[2,3-b]pyridin-4-yl)-1,8-diazaspiro[5.5]undecane | ES$^+$ 349 [M+H], Rt = 0.85 mins, Generic Basic Method |
| E174 | (6S)-8-(3-pyridazin-4-yl-1H-pyrrolo[2,3-b]pyridin-4-yl)-1,8-diazaspiro[5.5]undecane | ES$^+$ 349 [M + H]$^+$, Rt = 0.83 mins, Generic Basic Method |
| E175 | 8-(3-pyridazin-3-yl-1H-pyrrolo[2,3-b]pyridin-4-yl)-1,8-diazaspiro[5.5]undecane | ES$^+$ 349 [M + H]$^+$, Rt = 0.81 mins, Generic Basic Method |

-continued

| Example | Structure | Name | LCMS Data |
|---|---|---|---|
| E176 | 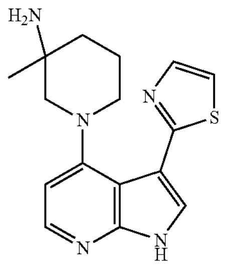 [SMILES: CC1(N)CCCN(c2ccnc3[nH]cc(-c4nccs4)c23)C1] | 3-methyl-1-(3-thiazol-2-yl-1H-pyrrolo[2,3-b]pyridin-4-yl)piperidin-3-amine | ES+ 314 [M + H]+, Rt = 0.8 mins, Generic Basic Method |
| E177 | 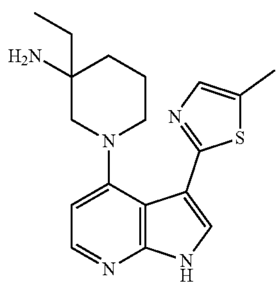 [SMILES: CCC1(N)CCCN(c2ccnc3[nH]cc(-c4ncc(C)s4)c23)C1] | 3-ethyl-1-[3-(5-methylthiazol-2-yl)-1H-pyrrolo[2,3-b]pyridin-4-yl]piperidin-3-amine | ES+ 342 [M + H]+, Rt = 0.94 mins, Generic Basic Method |
| E178 | 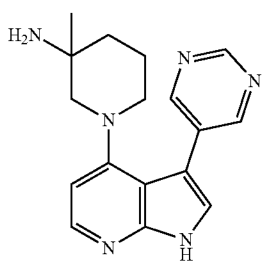 [SMILES: CC1(N)CCCN(c2ccnc3[nH]cc(-c4cncnc4)c23)C1] | 3-methyl-1-(3-pyrimidin-5-yl-1H-pyrrolo[2,3-b]pyridin-4-yl)piperidin-3-amine | ES+ 309 [M + H]+, Rt = 0.75 mins, Generic Basic Method |
| E179 | 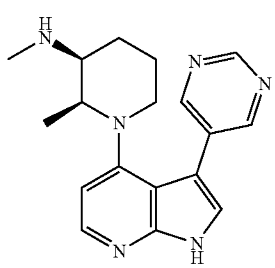 [SMILES: CN[C@H]1CCCN(c2ccnc3[nH]cc(-c4cncnc4)c23)[C@H]1C] | cis-N,2-dimethyl-1-(3-pyrimidin-5-yl-1H-pyrrolo[2,3-b]pyridin-4-yl)piperidin-3-amine | ES+ 323 [M + H]+, Rt = 0.76 mins, Generic Basic Method |

Example 180 (E180)-4-[(3aR,7aR)-1-methyl-3,3a,4,5,7,7a-hexahydro-2H-pyrrolo[2,3-c]pyridin-6-yl]-3-pyrimidin-5-yl-1H-pyrrolo[2,3-b]pyridine

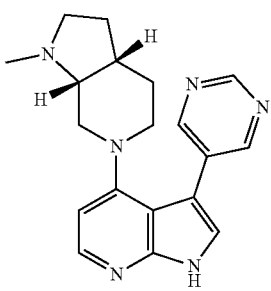 [SMILES: CN1CC[C@@H]2CCN(c3ccnc4[nH]cc(-c5cncnc5)c34)C[C@@H]21]

To a solution of 2-[[4-[(3aR,7aR)-1-methyl-3,3a,4,5,7,7a-hexahydro-2H-pyrrolo[2,3-c]pyridin-6-yl]-3-pyrimidin-5-yl-pyrrolo[2,3-b]pyridin-1-yl]methoxy]ethyl-trimethyl-silane (P177) (81.7 mg, 0.18 mmol) in 1,4-dioxane (1 ml) was added aqueous hydrogen chloride solution (5 N, 0.7 ml, 3.52 mmol) and reaction mixture stirred at 60° C. for 2 hours, then at overnight at room temperature. Further aqueous hydrogen chloride solution (5 N, 0.7 ml, 3.52 mmol) was added and stirring continued at 60° C. for 6 hours. The reaction mixture was purified by SCX (1 g), eluting with 2N NH3 in MeOH, to afford 4-[(3aR,7aR)-1-methyl-3,3a,4,5,7,7a-hexahydro-2H-pyrrolo[2,3-c]pyridin-6-yl]-3-pyrimidin-5-yl-1H-pyrrolo[2,3-b]pyridine (E180) (51 mg), LCMS ES+ 335 [M+H]+, Rt=0.85 mins (Generic Basic Method).

249

Example 181 (E181)-4-(1-piperidyl)-3-(1H-pyrazol-5-yl)-1H-pyrrolo[2,3-b]pyridine

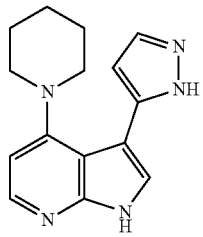 [SMILES: c1cc(-c2c[nH]c3nccc(N4CCCCC4)c23)[nH]n1]

To a solution of trimethyl-[2-[[4-(1-piperidyl)-3-(2-tetrahydropyran-2-ylpyrazol-3-yl)pyrrolo[2,3-b]pyridin-1-yl]methoxy]ethyl]silane (P230) (55 mg, 0.11 mmol) in ethanol (1 ml) was added 2M HCl (1.03 ml, 2.06 mmol) before heating to 80° C. for 18 hours. After this time, the reaction mixture was concentrated in vacuo to yield a yellow oil. The oil was purified via preparative HPLC to afford 4-(1-piperidyl)-3-(1H-pyrazol-5-yl)-1H-pyrrolo[2,3-b]pyridine (E181)(15.2 mg) as a white solid, LCMS ES$^+$ 268[M+H]$^+$ Rt=1.06 mins (Generic Basic Method)

Example 182 (E182)-4-(1-piperidyl)-3-(3-pyridyl)-1H-pyrrolo[2,3-b]pyridine

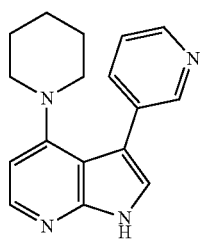 [SMILES: c1cncc(-c2c[nH]c3nccc(N4CCCCC4)c23)c1]

In a microwave vial equipped with stirrer bar was added a solution of 4-chloro-1-(p-tolylsulfonyl)-3-(3-pyridyl)pyrrolo[2,3-b]pyridine (P47) (152 mg, 0.40 mmol) in 1,4-dioxane (0.2 ml) followed by piperidine (0.59 ml, 5.94 mmol). The resulting suspension was heated to 140° C. for 8 hours. The reaction mixture was cooled to room temperature. The reaction mixture was concentrated in vacuo to yield a yellow solid. The solid was dissolved in MeOH (4 ml) and treated with 4N KOH (2 ml) before heating to 60° C. for 1 hour. The solvent removed in vacuo and the resulting solid was dissolved in MeOH. 5N HCl was added until the solution was pH 5. The solvent was removed in vacuo and the residue was purified by SCX followed by preparative HPLC to yield 4-(1-piperidyl)-3-(3-pyridyl)-1H-pyrrolo[2,3-b]pyridine (E182) (10.5 mg) as a white solid, LCMS ES$^+$ 279[M+H]$^+$ Rt=1.13 mins (Generic Basic Method).

250

Example 183 (E183)-4-(1-piperidyl)-3-(1H-pyrazol-4-yl)-1H-pyrrolo[2,3-b]pyridine In a microwave vial equipped with stirrer bar was added a solution of 4-chloro-1-(p-tolylsulfonyl)-3-(1-tetrahydropyran-2-ylpyrazol-4-yl)pyrrolo[2,3-b]pyridine (P48) (135 mg, 0.30 mmol) in 1,4-dioxane (0.2 ml) followed by piperidine (0.15 ml, 1.48 mmol). The resulting suspension was heated to 140° C. for 4 hours. The solution was heated for a further four times at 140° C. for 4 hours, adding further piperidine (5 equivs.) each time. The reaction mixture was allowed to cool to room temperature before concentrating in vacuo to yield a brown oil. The oil was dissolved in DCM (10 ml) and washed with water (5 ml). The organics were concentrated under reduced pressure. The crude product was dissolved in MeOH and treated with 2M HCl (0.8 ml) and the resulting solution was stirred for 18 hours (overnight) at room temperature. The reaction mixture was concentrated under reduced pressure. The residue was dissolved in MeOH. 4N KOH (1 ml) was added and the solution was heated for 1 hour at 50° C. The volatiles were removed under reduced pressure to yield crude product as an oily solid. The solid was purified via preparative HPLC to give 4-(1-piperidyl)-3-(1H-pyrazol-4-yl)-1H-pyrrolo[2,3-b]pyridine (E183) (1.8 mg) LCMS ES$^+$ 268 [M+H]$^+$ Rt=0.97 mins (Generic Basic Method).

Example 184 (E184)-4-(2,6-diazaspiro[4.5]decan-2-yl)-1H-pyrrolo[2,3-b]pyridine-3-carbonitrile

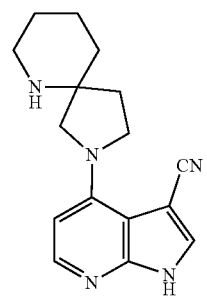

A solution of 4-(2,6-diazaspiro[4.5]decan-2-yl)-1-(2-trimethylsilylethoxymethyl)pyrrolo[2,3-b]pyridine-3-carbonitrile (P113) (200 mg, 0.49 mmol) in dry 1,4-dioxane (2.43 ml) was stirred at room temperature under an atmosphere of nitrogen. Trifluoroacetic acid (2 ml, 26.12 mmol) was added and the reaction mixture was heated to 75° C. for 48 hours.

The reaction mixture was cooled to room temperature before the solvent was removed under reduced pressure to give a brown coloured oil. The oil was purified using SCX (5 g cartridge), washing initially with MeOH and then with NH₃/MeOH (2M). The basic fractions were combined and concentrated under reduced pressure to give a yellow coloured oil, which solidified upon standing. The solid was triturated using DMS0, washed with MOH and dried to give 4-(2,6-diazaspiro[4.5]decan-2-yl)-1H-pyrrolo[2,3-b]pyridine-3-carbonitrile (E184) (13 mg, 0.04 mmol, 9% yield), LCMS ES$^+$ 282 [M+H]$^+$, Rt=0.89 mins (Generic Basic Method)

The following compounds were prepared in a similar manner to 4-(2,6-diazaspiro[4.5]decan-2-yl)-1H-pyrrolo[2,3-b]pyridine-3-carbonitrile (E184) from the appropriate intermediates:

| Example | Structure | Name | LCMS Data |
|---|---|---|---|
| E185 | 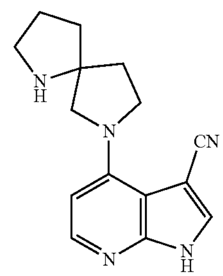 [SMILES: N#Cc1c[nH]c2nccc(N3CCC4(CCCN4)C3)c12] | 4-(1,7-diazaspiro[4.4]nonan-7-yl)-1H-pyrrolo[2,3-b]pyridine-3-carbonitrile | ES$^+$ 268 [M + H]$^+$, Rt = 0.82 mins, Generic Basic Method |
| E186 | 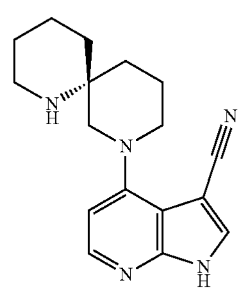 [SMILES: N#Cc1c[nH]c2nccc(N3CCC[C@]4(CCCCN4)C3)c12] | 4-[(6R)-1,8-diazaspiro[5.5]undecan-8-yl]-1H-pyrrolo[2,3-b]pyridine-3-carbonitrile | ES$^+$ 296 [M + H]$^+$, Rt = 0.86 mins, Generic Basic Method |
| E187 | 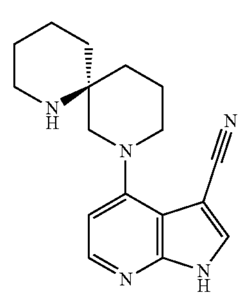 [SMILES: N#Cc1c[nH]c2nccc(N3CCC[C@@]4(CCCCN4)C3)c12] | 4-[(6S)-1,8-diazaspiro[5.5]undecan-8-yl]-1H-pyrrolo[2,3-b]pyridine-3-carbonitrile | ES$^+$ 296 [M + H]$^+$, Rt = 0.87 mins, Generic Basic Method |

Example 188 (E188)-8-[3-(1-methylpyrazol-4-yl)-1H-pyrrolo[2,3-b]pyridin-4-yl]-1,8-diazaspiro[5.5]undecane

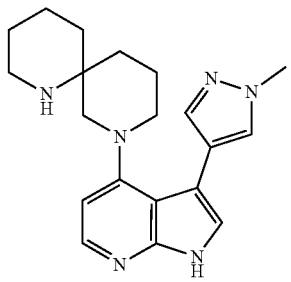 [SMILES: Cn1cc(-c2c[nH]c3nccc(N4CCCC5(CCCCN5)C4)c23)cn1]

A solution of 2-[[4-(1,8-diazaspiro[5.5]undecan-8-yl)-3-(1-methylpyrazol-4-yl)pyrrolo[2,3-b]pyridin-1-yl]methoxy]ethyl-trimethyl-silane (P95) (237 mg, 0.49 mmol) in DCM (2 ml) and trifluoroacetic acid (0.57 ml, 7.4 mmol) was stirred at room temperature overnight. The reaction mixture was loaded onto a pre-acidified SCX cartridge (20 g) before washing with MeOH (240 ml). The crude product was released via treatment with 2N NH$_3$ in MeOH. Fractions containing desired product were concentrated under reduced pressure to give a yellow glass. The residue was chromatographed [C18, 0-100% (0.1% NH$_4$OH in MeCN):MeCN] and the resulting residue further chromatographed [SiO$_2$, 0-100% (10% 2N NH$_3$/MeOH in DCM):DCM) to give 8-[3-(1-methylpyrazol-4-yl)-1H-pyrrolo[2,3-b]pyridin-4-yl]-1,8-diazaspiro[5.5]undecane (E188) (54 mg), LCMS ES$^+$ 351 [M+H]$^+$, Rt=0.9 mins (Generic Basic Method).

The following compounds were prepared in a similar manner to 8-[3-(1-methylpyrazol-4-yl)-1H-pyrrolo[2,3-b]pyridin-4-yl]-1,8-diazaspiro[5.5]undecane (E188) from the appropriate intermediates:

| Example | Structure | Name | LCMS Data |
|---|---|---|---|
| E189 | 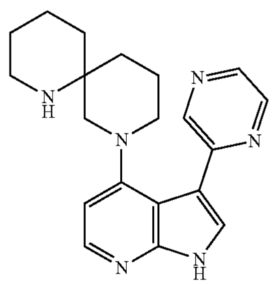 [SMILES: c1cnc(-c2c[nH]c3nccc(N4CCCC5(CCCCN5)C4)c23)cn1] | 8-(3-pyrazin-2-yl-1H-pyrrolo[2,3-b]pyridin-4-yl)-1,8-diazaspiro[5.5]undecane | ES$^+$ 349 [M + H]$^+$, Rt = 1.01 mins, Generic Basic Method |
| E190 | 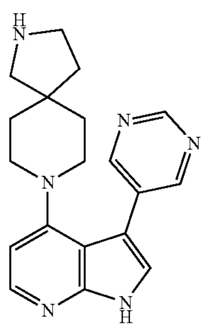 [SMILES: c1ncc(-c2c[nH]c3nccc(N4CCC5(CCNC5)CC4)c23)cn1] | 8-(3-pyrimidin-5-yl-1H-pyrrolo[2,3-b]pyridin-4-yl)-2,8-diazaspiro[4.5]decane | ES$^+$ 335 [M + H]$^+$, Rt = 0.68 mins, Generic Basic Method |
| E191 | 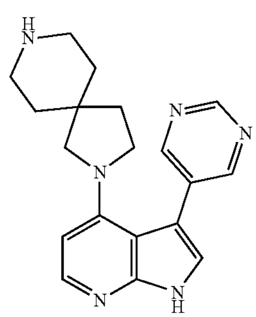 [SMILES: c1ncc(-c2c[nH]c3nccc(N4CCC5(CCNCC5)C4)c23)cn1] | 2-(3-pyrimidin-5-yl-1H-pyrrolo[2,3-b]pyridin-4-yl)-2,8-diazaspiro[4.5]decane | ES$^+$ 335 [M + H]$^+$, Rt = 0.69 mins, Generic Basic Method |

-continued

| Example | Structure | Name | LCMS Data |
|---|---|---|---|
| E192 | 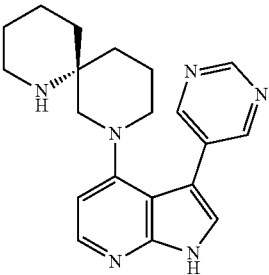 [SMILES: c1ncc(-c2c[nH]c3nccc(N4CCC[C@]5(CCCCN5)C4)c23)cn1] | (6R)-8-(3-pyrimidin-5-yl-1H-pyrrolo[2,3-b]pyridin-4-yl)-1,8-diazaspiro[5.5]undecane | ES+ 349 [M + H]+, Rt = 0.87 mins, Generic Basic Method |
| E193 | 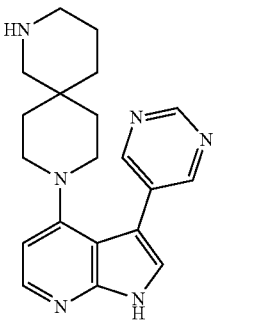 [SMILES: c1ncc(-c2c[nH]c3nccc(N4CCC5(CCCNC5)CC4)c23)cn1] | 9-(3-pyrimidin-5-yl-1H-pyrrolo[2,3-b]pyridin-4-yl)-2,9-diazaspiro[5.5]undecane | ES+ 349 [M + H]+, Rt = 0.77 mins, Generic Basic Method |
| E194 | 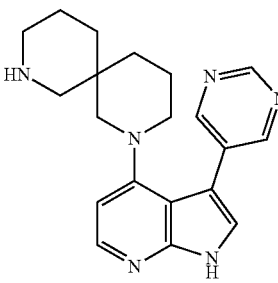 | 2-(3-pyrimidin-5-yl-1H-pyrrolo[2,3-b]pyridin-4-yl)-2,8-diazaspiro[5.5]undecane | ES+ 349 [M + H]+, Rt = 0.79 mins, Generic Basic Method |
| E195 | 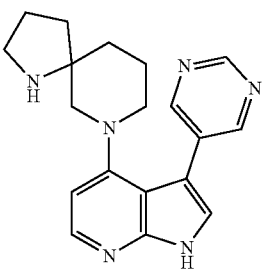 [SMILES: c1ncc(-c2c[nH]c3nccc(N4CCCC5(CCCN5)C4)c23)cn1] | 9-(3-pyrimidin-5-yl-1H-pyrrolo[2,3-b]pyridin-4-yl)-1,9-diazaspiro[4.5]decane | ES+ 335 [M + H]+, Rt = 0.8 mins, Generic Basic Method |
| E196 | 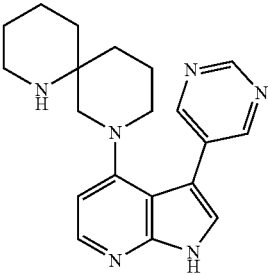 [SMILES: c1ncc(-c2c[nH]c3nccc(N4CCCC5(CCCCN5)C4)c23)cn1] | 8-(3-pyrimidin-5-yl-1H-pyrrolo[2,3-b]pyridin-4-yl)-1,8-diazaspiro[5.5]undecane | ES+ 349 [M + H]+, Rt = 0.89 mins, Generic Basic Method |

Example 197 (E197)-4-[(3R)-3-aminopyrrolidin-1-yl]-1H-pyrrolo[2,3-b]pyridine-3-carbonitrile

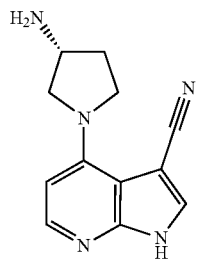 [SMILES: N#Cc1c[nH]c2nccc(N3CC[C@@H](N)C3)c12]

Tert-butyl N-[(3R)-1-(3-cyano-1H-pyrrolo[2,3-b]pyridin-4-yl)pyrrolidin-3-yl]carbamate (P244) (140 mg, 0.43 mmol) was dissolved in DCM (1.5 ml) and trifluoroacetic acid (0.65 ml, 8.55 mmol) was added. The solution was stirred at room temperature for 5 hours. After this time, the mixture was concentrated in vacuo and the residue was purified via preparative HPLC (early basic method) to give 4-[(3R)-3-aminopyrrolidin-1-yl]-1H-pyrrolo[2,3-b]pyridine-3-carbonitrile (E197) (0.65 mg, 0.003 mmol, 0.7% yield) as a white solid, LCMS ES$^+$ 228.2 [M+H]$^+$, Rt=0.69 mins (Generic Basic Method).

Example 198 (E198)-4-amino-N,N-dimethyl-1-(3-pyrimidin-5-yl-1H-pyrrolo[2,3-b]pyridin-4-yl)piperidine-4-carboxamide

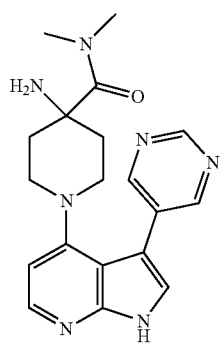 [SMILES: CN(C)C(=O)C1(N)CCN(c2ccnc3[nH]cc(-c4cncnc4)c23)CC1]

A mixture of tert-butyl N-[4-(dimethylcarbamoyl)-1-[3-pyrimidin-5-yl-1-(2-trimethylsilylethoxymethyl)pyrrolo[2,3-b]pyridin-4-yl]-4-piperidyl]carbamate (16 mg, 0.023 mmol) (P234) and TFA (1 ml) in DCM (0.5 ml) was stirred at room temperature overnight. The mixture was concentrated under reduced pressure and the resulting residue dissolved in ammonium hydroxide (1 ml) and MeOH (1 ml). The solution was heated at reflux for 2 hours. After this time, the solution was concentrated under reduced pressure and the residue was diluted with water. A precipitate formed which was collected by filtration and dried to give 4-amino-N,N-dimethyl-1-(3-pyrimidin-5-yl-1H-pyrrolo[2,3-b]pyridin-4-yl)piperidine-4-carboxamide (E198) (7.3 mg).

Example 199 (E199)-4-(2,3,3a,4,6,6a-hexahydro-1H-pyrrolo[3,4-c]pyrrol-5-yl)-3-pyrimidin-5-yl-1H-pyrrolo[2,3-b]pyridine

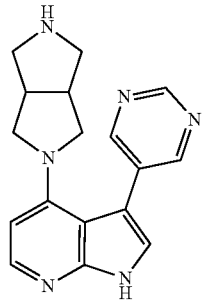 [SMILES: c1ncc(-c2c[nH]c3nccc(N4CC5CNCC5C4)c23)cn1]

To a solution of tert-butyl 2-[3-pyrimidin-5-yl-1-(2-trimethylsilylethoxymethyl)pyrrolo[2,3-b]pyridin-4-yl]-1,3,3a,4,6,6a-hexahydropyrrolo[3,4-c]pyrrole-5-carboxylate (P178) (38 mg, 0.07 mmol) in 1,4-dioxane was added aqueous hydrogen chloride solution (5 N, 0.14 ml, 0.71 mmol) and the reaction mixture stirred at 60° C. for 2 hours, then a further 48 hours at room temperature. The solvent was removed in genevac, the residue dissolved in MeOH and purified by SCX (1 g), eluting with 7N NH$_3$ in MeOH. Trace hemi-aminal product was deprotected by dissolving in MeOH/NH$_4$OH and stirring overnight at room temperature. The solvent was removed under reduced to afford 4-(2,3,3a,4,6,6a-hexahydro-1H-pyrrolo[3,4-c]pyrrol-5-yl)-3-pyrimidin-5-yl-1H-pyrrolo[2,3-b]pyridine (E199) (6.6 mg), LCMS ES$^+$ 307 [M+H]$^+$, Rt=0.63 mins (Generic Basic Method).

Example 200 (E200)-4-[(3aS,7aR)-1-methyl-3,3a,4,6,7,7a-hexahydro-2H-pyrrolo[3,2-c]pyridin-5-yl]-3-pyrimidin-5-yl-1H-pyrrolo[2,3-b]pyridine

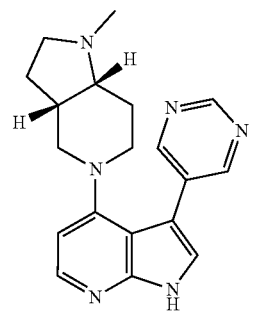 [SMILES: CN1CC[C@H]2CN(c3ccnc4[nH]cc(-c5cncnc5)c34)CC[C@H]21]

To a solution of 2-[[4-[(3aS,7aR)-1-methyl-3,3a,4,6,7,7a-hexahydro-2H-pyrrolo[3,2-c]pyridin-5-yl]-3-pyrimidin-5-yl-pyrrolo[2,3-b]pyridin-1-yl]methoxy]ethyl-trimethyl-silane (P179) (11.8 mg, 0.03 mmol) in 1,4-dioxane was added aqueous hydrogen chloride solution (5 N, 0.1 ml, 0.51 mmol) and reaction mixture stirred at 60° C. for 2 hours, then overnight at room temperature. Further aqueous hydrogen chloride solution (5 N, 0.1 ml, 0.51 mmol) was added and stirring continued at 60° C. 6 hours. The reaction mixture was purified by SCX (1 g), eluting with 7N NH$_3$ in MeOH). Approximately 10% impurity remained so residue was again dissolved in 1,4-dioxane (0.2 ml), aqueous hydrogen chloride solution (5 N, 0.1 ml, 0.51 mmol) added and reaction stirred at 65° C. for 2 hours. The solvent was removed in genevac, the residue dissolved in MeOH and purified by SCX (1 g, eluting with 7N $NH_3$ in MeOH) to afford 4-[(3aS,7aR)-1-methyl-3,3a,4,6,7,7a-hexahydro-2H-pyrrolo[3,2-c]pyridin-5-yl]-3-pyrimidin-5-yl-1H-pyrrolo[2,3-b]pyridine (E200) (6.1 mg), LCMS $ES^+$ 335 $[M+H]^+$, Rt=0.86 mins (Generic Basic Method).

Example 201 (E201)-4-[(2S)-2-(4-methyl-1,4-diazepane-1-carbonyl)pyrrolidin-1-yl]-1H-pyrrolo[2,3-b]pyridine-3-carbonitrile

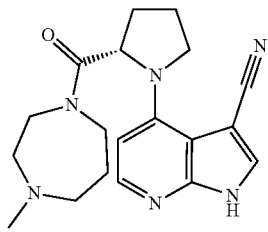 [SMILES: CN1CCCN(C(=O)[C@@H]2CCCN2c2ccnc3[nH]cc(C#N)c23)CC1]

(2S)-1-(3-cyano-1H-pyrrolo[2,3-b]pyridin-4-yl)pyrrolidine-2-carboxylic acid (P233) (50 mg, 0.20 mmol), 1-hydroxybenzotriazole hydrate (41.83 mg, 0.27 mmol), 1-methylhomopiperazine (22.28 mg, 0.20 mmol) were dissolved in DMF (5 ml) flushed with nitrogen and stirred for 20 minutes. 1-(3-Dimethylaminopropyl)-3-ethylcarbodiimide hydrochloride (52.37 mg, 0.27 mmol) was added and the mixture left to stir overnight at room temperature. The mixture was concentrated under reduced pressure and purified by HPLC using the early basic method to give 4-[(2S)-2-(4-methyl-1,4-diazepane-1-carbonyl)pyrrolidin-1-yl]-1H-pyrrolo[2,3-b]pyridine-3-carbonitrile (E201) (7.8 mg, 0.02 mmol, 10.8% yield), LCMS $ES^+$ 353.3 $[M+H]^+$, Rt=0.80 mins (Late Basic Method).

The following compounds were prepared in a similar manner to 4-[(2S)-2-(4-methyl-1,4-diazepane-1-carbonyl)pyrrolidin-1-yl]-1H-pyrrolo[2,3-b]pyridine-3-carbonitrile (E201) from (2S)-1-(3-cyano-1H-pyrrolo[2,3-b]pyridin-4-yl)pyrrolidine-2-carboxylic acid (P233) and the appropriate amine:

| Example | Structure | Name | LCMS Data |
|---|---|---|---|
| E202 | 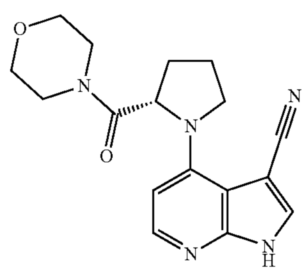 [SMILES: N#Cc1c[nH]c2nccc(N3CCC[C@H]3C(=O)N3CCOCC3)c12] | 4-[(2S)-2-(morpholine-4-carbonyl)pyrrolidin-1-yl]-1H-pyrrolo[2,3-b]pyridine-3-carbonitrile | $ES^+$ 326 [M+ H]$^+$, Rt = 0.79 mins, Generic Basic Method |
| E203 | 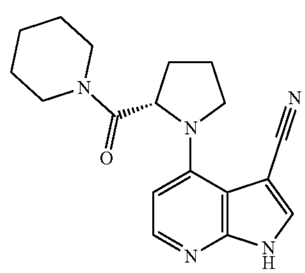 [SMILES: N#Cc1c[nH]c2nccc(N3CCC[C@H]3C(=O)N3CCCCC3)c12] | 4-[(2S)-2-(piperidine-1-carbonyl)pyrrolidin-1-yl]-1H-pyrrolo[2,3-b]pyridine-3-carbonitrile | $ES^+$ 324 [M+ H]$^+$, Rt = 0.97 mins, Generic Basic Method |
| E204 | 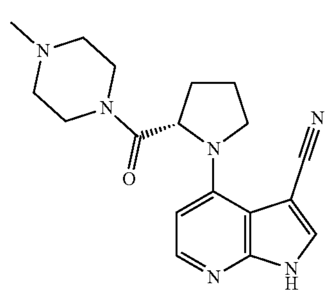 [SMILES: CN1CCN(C(=O)[C@@H]2CCCN2c2ccnc3[nH]cc(C#N)c23)CC1] | 4-[(2S)-2-(4-methylpiperazine-1-carbonyl)pyrrolidin-1-yl]-1H-pyrrolo[2,3-b]pyridine-3-carbonitrile | $ES^+$ 339 [M+ H]$^+$, Rt = 0.78 mins, Generic Basic Method |

Example 205 (E205)-N-[(3S)-1-(3-pyridazin-4-yl-1H-pyrrolo[2,3-b]pyridin-4-yl)-3-piperidyl]acetamide

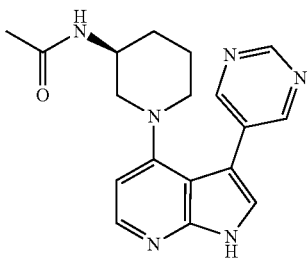 [SMILES: CC(=O)N[C@H]1CCCN(c2ccnc3[nH]cc(-c4cncnc4)c23)C1]

To a solution of (3S)-1-[3-pyridazin-4-yl-1-(2-trimethylsilylethoxymethyl)pyrrolo[2,3-b]pyridin-4-yl]piperidin-3-amine (P166) (14. mg, 0.03 mmol) and triethylamine (0.01 ml, 0.07 mmol) in DCM (0.1 ml) cooled to 0° C. was added acetic anhydride (4 µL, 0.04 mmol). The reaction mixture was allowed to warm to room temperature and stirred for 30 minutes. The solution was concentrated under reduced pressure then 1,4-dioxane (0.1 ml) and hydrogen chloride solution (0.13 ml, 0.66 mmol) were added. The reaction mixture was stirred at 40° C. over the weekend. The cooled reaction mixture was loaded onto a pre-acidified SCX cartridge. The cartridge was washed with MeOH (×5 cvs) and the product eluted with NH₃ in MeOH (2N). The basic fractions were concentrated under reduced pressure and the residue was purified via preparative HPLC using the generic basic run to afford N-[(3S)-1-(3-pyridazin-4-yl-1H-pyrrolo[2,3-b]pyridin-4-yl)-3-piperidyl]acetamide (E205) (5.5 mg, 0.02 mmol, 49.5% yield) LCMS ES+ 337 [M+H]+, Rt=0.73 mins (Generic Basic Method).

Example 206 (E206)-(6S)-1-methyl-8-(3-pyrimidin-4-yl-1H-pyrrolo[2,3-b]pyridin-4-yl)-1,8-diazaspiro[5.5]undecane

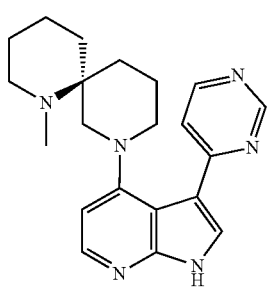 [SMILES: CN1CCCC[C@@]12CCCN(c1ccnc3[nH]cc(-c4ccncn4)c13)C2]

Formaldehyde solution (37% in water, 0.01 ml, 0.54 mmol) and one drop of acetic acid were added to a stirred solution of (6S)-8-(3-pyrimidin-4-yl-1H-pyrrolo[2,3-b]pyridin-4-yl)-1,8-diazaspiro[5.5]undecane (E117) (25 mg, 0.07 mmol) in methanol (0.3 ml). The mixture was stirred at room temperature for 10 minutes before sodium triacetoxyborohydride (30.27 mg, 0.14 mmol) was added. The resulting mixture was stirred at room temperature overnight. The solution was purified by SCX (2 g) to give crude product. Trituration from a solution MeOH and DMSO gave (6S)-1-methyl-8-(3-pyrimidin-4-yl-1H-pyrrolo[2,3-b]pyridin-4-yl)-1,8-diazaspiro[5.5]undecane (E206) (8 mg, 0.02 mmol, 29.2% yield), LCMS ES+ 363 [M+H]+, Rt=0.9 mins (Generic Basic Method).

Example 207 (E207)-(6S)-1-ethyl-8-(3-pyrimidin-4-yl-1H-pyrrolo[2,3-b]pyridin-4-yl)-1,8-diazaspiro[5.5]undecane

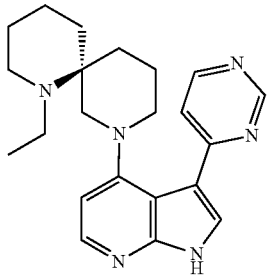 [SMILES: CCN1CCCC[C@@]12CCCN(c1ccnc3[nH]cc(-c4ccncn4)c13)C2]

Acetaldehyde (0.03 ml, 0.49 mmol) and one drop of acetic acid were added to a stirred solution of (6S)-8-(3-pyrimidin-4-yl-1H-pyrrolo[2,3-b]pyridin-4-yl)-1,8-diazaspiro[5.5]undecane (E117) (20 mg, 0.06 mmol) in methanol (0.3 ml). The mixture was stirred at room temperature for 10 minutes before the addition of sodium triacetoxyborohydride (24.21 mg, 0.11 mmol). The reaction mixture was subsequently stirred at room temperature overnight. After this time, further acetaldehyde and sodium triacetoxyborohydride were added portionwise until reaction was complete. The mixture was purified by SCX (2 g) to give crude product which was purified further via preparative HPLC (generic basic method) to give (6S)-1-ethyl-8-(3-pyrimidin-4-yl-1H-pyrrolo[2,3-b]pyridin-4-yl)-1,8-diazaspiro[5.5]undecane (E207) (8 mg, 0.02 mmol, 35.2% yield), LCMS ES+ 377 [M+H]+, Rt=0.98 mins (Generic Basic Method).

The following examples were prepared in similar manner to (6S)-1-ethyl-8-(3-pyrimidin-4-yl-1H-pyrrolo[2,3-b]pyridin-4-yl)-1,8-diazaspiro[5.5]undecane (E207) from the appropriate intermediates:

| Example | Structure | Name | LCMS Data |
|---|---|---|---|
| E208 | 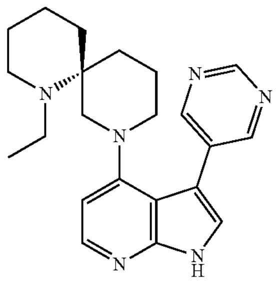 [SMILES: CCN1CCCC[C@]12CCCN(c1ccnc3[nH]cc(-c4cncnc4)c13)C2] | (6R)-1-ethyl-8-(3-pyrimidin-5-yl-1H-pyrrolo[2,3-b]pyridin-4-yl)-1,8-diazaspiro[5.5]undecane | ES$^+$ 377 [M + H]$^+$, Rt = 0.91 mins, Generic Basic Method |

Example 209 (E209)-2-[4-(1-ethyl-1,8-diazaspiro[5.5]undecan-8-yl)-1H-pyrrolo[2,3-b]pyridin-3-yl]thiazole

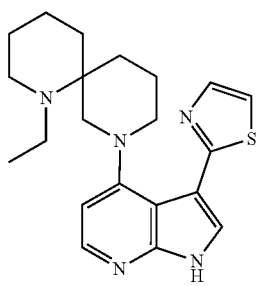 [SMILES: CCN1CCCCC12CCCN(c1ccnc3[nH]cc(-c4nccs4)c13)C2]

Acetaldehyde (0.03 ml, 0.49 mmol) was added to a stirred solution of 2-[4-(1,8-diazaspiro[5.5]undecan-8-yl)-1H-pyrrolo[2,3-b]pyridin-3-yl]thiazole (E149) (23 mg, 0.07 mmol) and one drop of acetic acid in methanol (0.3 ml). The mixture was stirred at room temperature, under nitrogen for 10 minutes. After this time, sodium triacetoxyborohydride (27.45 mg, 0.13 mmol) was added. The reaction was stirred at room temperature for 1 hour. The sample was purified by SCX (1 g) before being further purified using preparative HPLC (Basic Method) to give 2-[4-(1-ethyl-1,8-diazaspiro[5.5]undecan-8-yl)-1H-pyrrolo[2,3-b]pyridin-3-yl]thiazole (E209) (7 mg, 0.02 mmol, 26.8% yield), LCMS ES$^+$ 382 [M+H]$^+$, Rt=1.24 mins (Generic Basic Method).

The following compounds were prepared in a similar manner to 2-[4-(1-ethyl-1,8-diazaspiro[5.5]undecan-8-yl)-1H-pyrrolo[2,3-b]pyridin-3-yl]thiazole (E209) using the appropriate amine and aldehyde:

| Example | Structure | Name | LCMS Data |
|---|---|---|---|
| E210 | 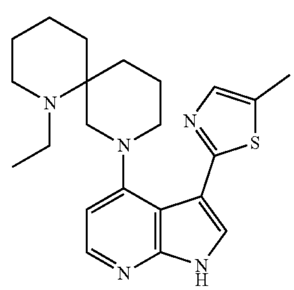 [SMILES: CCN1CCCCC12CCCN(c1ccnc3[nH]cc(-c4ncc(C)s4)c13)C2] | 2-[4-(1-ethyl-1,8-diazaspiro[5.5]undecan-8-yl)-1H-pyrrolo[2,3-b]pyridin-3-yl]-5-methyl-thiazole | ES$^+$ 396 [M + H]$^+$, Rt = 1.31 mins, Generic Basic Method |
| E211 | 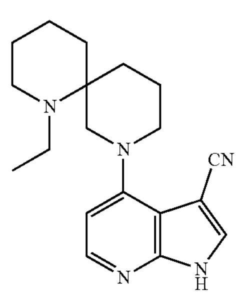 [SMILES: CCN1CCCCC12CCCN(c1ccnc3[nH]cc(C#N)c13)C2] | 4-(1-ethyl-1,8-diazaspiro[5.5]undecan-8-yl)-1H-pyrrolo[2,3-b]pyridine-3-carbonitrile | ES$^+$ 324 [M + H]$^+$, Rt = 1.18 mins, Generic Basic Method |

Example 212 (E212)-2-[4-[[(3R)-3-piperidyl]oxy]-1H-pyrrolo[2,3-b]pyridin-3-yl]thiazole

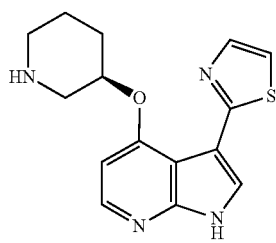 [SMILES: c1csc(-c2c[nH]c3nccc(O[C@@H]4CCCNC4)c23)n1]

To a solution of tert-butyl (3R)-3-[3-thiazol-2-yl-1-(2-trimethylsilylethoxymethyl)pyrrolo[2,3-b]pyridin-4-yl]oxypiperidine-1-carboxylate (P248) (251.00 mg, 0.47 mmol) in 1,4-dioxane (2.0 ml) was added hydrogen chloride solution (1.67 ml, 8.34 mmol). The mixture was heated to 60° C. overnight. The solvent was removed under reduced pressure and the sample was purified by SCX (2 g) and further purified by preparative HPLC to afford 2-[4-[[(3R)-3-piperidyl]oxy]-1H-pyrrolo[2,3-b]pyridin-3-yl]thiazole (E212) (133.00 mg, 0.42 mmol, 88.9% yield), LCMS ES$^+$ 301 [M+H]$^+$, Rt=0.83 mins (Generic Basic Method).

The following compounds were prepared in a similar manner to 2-[4-[[(3R)-3-piperidyl]oxy]-1H-pyrrolo[2,3-b]pyridin-3-yl]thiazole (E212) from the appropriate intermediates:

| Example | Structure | Name | LCMS Data |
|---|---|---|---|
| E213 | 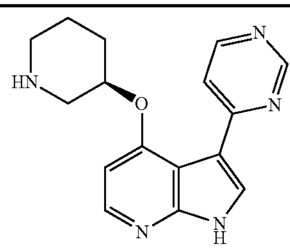 | 3-pyrimidin-4-yl-4-[[(3R)-3-piperidyl[oxy]-1H-pyrrolo[2,3-b]pyridine | ES$^+$ 296 [M + H]$^+$ Rt = 0.72 mins, Generic Basic Method |

Example 214 (E214)-4-[[(3R)-3-piperidyl]methoxy]-3-pyrimidin-5-yl-1H-pyrrolo[2,3-b]pyridine

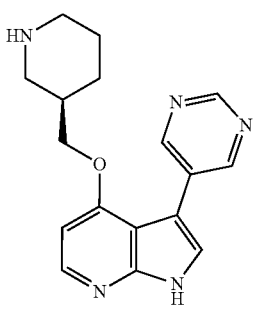 [SMILES: c1ncc(-c2c[nH]c3nccc(OC[C@@H]4CCCNC4)c23)cn1]

To a round bottomed flask containing a stirrer bar was added NaH 60% w/w (88.66 mg, 2.22 mmol) and (R)-1-BOC-3-(hydroxymethyl)piperidine (477.21 mg, 2.22 mmol) in DMF (1.5 ml). The mixture was stirred at room temperature for 15 minutes, before 2-[(4-chloro-3-pyrimidin-5-yl-pyrrolo[2,3-b]pyridin-1-yl)methoxy]ethyl-trimethyl-silane (P23) (400.00 mg, 1.11 mmol) was added. The mixture was stirred at room temperature overnight. The reaction was quenched with water and the product was extracted with ethyl acetate (×3). The organics were washed with water, combined, dried over MgSO$_4$ and concentrated under reduced pressure. The crude product was dissolved in THF and transferred to a microwave vial. 2N HCl (2.0 ml) was added and the solution was heated in the microwave at 80° C. for 4 hours. The volatiles were removed and the crude product was purified using preparative HPLC to give 4-[[(3R)-3-piperidyl]methoxy]-3-pyrimidin-5-yl-1H-pyrrolo[2,3-b]pyridine (E214) (29.7 mg, 0.09 mmol, 8.2% yield) as a white solid, LCMS ES$^+$ 310 [M+H]$^+$, Rt=0.63 mins (Generic Basic Method), The following compounds were prepared in a similar manner to 4-[[(3R)-3-piperidyl]methoxy]-3-pyrimidin-5-yl-1H-pyrrolo[2,3-b]pyridine (E214) from the appropriate intermediates;

| Example | Structure | Name | LCMS Data |
|---|---|---|---|
| E215 | 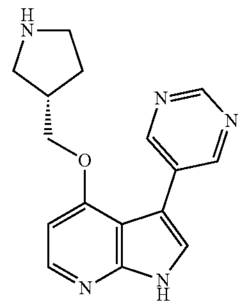 | 3-pyrimidin-5-yl-4-[[(3S)-pyrrolidin-3-yl]methoxy]-1H-pyrrolo[2,3-b]pyridine | ES⁺ 296 [M + H]⁺ Rt = 0.58 mins, Generic Basic Method |
| E216 | 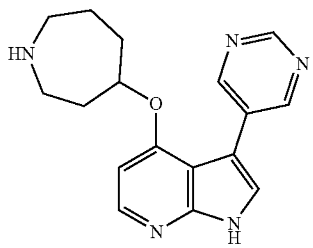 [SMILES: c1ncc(-c2c[nH]c3nccc(OC4CCCNCC4)c23)cn1] | 4-(azepan-4-yloxy)-3-pyrimidin-5-yl-1H-pyrrolo[2,3-b]pyridine | ES⁺ 310 [M + H]⁺ Rt = 0.76 mins, Generic Basic Method |
| E217 | 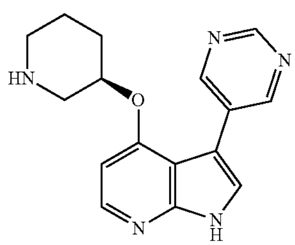 [SMILES: c1ncc(-c2c[nH]c3nccc(O[C@@H]4CCCNC4)c23)cn1] | 4-[[(3R)-3-piperidyl]oxy]-3-pyrimidin-5-yl-1H-pyrrolo[2,3-b]pyridine | ES⁺ 296 [M + H]⁺ Rt = 0.70 mins, Generic Basic Method |

Example 218 (E218)-4-[[(3S)-3-piperidyl]methoxy]-3-pyrimidin-5-yl-1H-pyrrolo[2,3-b]pyridine

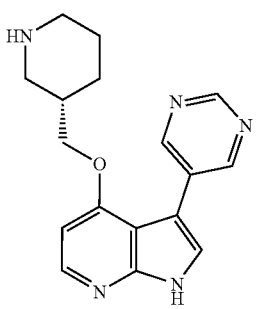 [SMILES: c1ncc(-c2c[nH]c3nccc(OC[C@H]4CCCNC4)c23)cn1]

To a round bottomed flask containing stirrer bar was added NaH 60% w/w (132.98 mg, 3.32 mmol) and N—BOC-(3S)-3-(hydroxymethyl)piperidine (715.82 mg, 3.32 mmol) in DMF (0.8 ml). The mixture was stirred at room temperature for 15 minutes. 2-[(4-chloro-3-pyrimidin-5-yl-pyrrolo[2,3-b]pyridin-1-yl)methoxy]ethyl-trimethyl-silane (P23) (400. mg, 1.11 mmol) was added and the mixture was stirred at room temperature overnight. The reaction was quenched with water and the product subsequently extracted into ethyl acetate (×3). The organics were washed with water, dried over MgSO₄, filtered and concentrated under reduced pressure. The crude product was dissolved in THF and 2N HCl (2 ml) was added. The solution was heated in the microwave at 80° C. for 4 hours. After this time, the volatiles were removed, and the product was purified by preparative HPLC, and further purified using SCX, washing initially with MeOH and then 60% 2N NH₃ in MeOH to give 4-[[(3S)-3-piperidyl]methoxy]-3-pyrimidin-5-yl-1H-pyrrolo[2,3-b]pyridine (E218) (46 mg) as a white solid, LCMS ES⁺ 310 [M+H], Rt=0.77 mins (Generic Basic Method).

The following compounds were prepared in a similar manner to 4-[[(3S)-3-piperidyl]methoxy]-3-pyrimidin-5-yl-1H-pyrrolo[2,3-b]pyridine (E218) from the appropriate intermediates:

| Example | Structure | Name | LCMS Data |
|---|---|---|---|
| E219 | 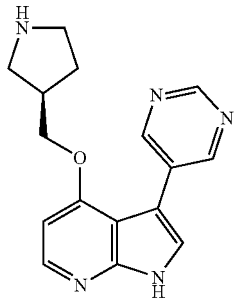 | 3-pyrimidin-5-yl-4-[[(3R)-pyrrolidin-3-yl]methoxy]-1H-pyrrolo[2,3-b]pyridine | ES+ 296 [M + H]+ Rt = 0.69 mins, Generic Basic Method |
| E220 | 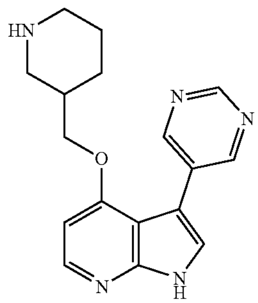 [SMILES: c1ncc(-c2c[nH]c3nccc(OCC4CCCNC4)c23)cn1] | 4-(3-piperidylmethoxy)-3-pyrimidin-5-yl-1H-pyrrolo[2,3-b]pyridine | ES+ 310 [M + H]+ Rt = 0.68 mins, Generic Basic Method |
| E221 | 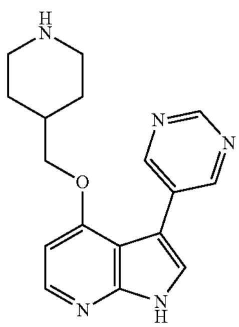 [SMILES: c1ncc(-c2c[nH]c3nccc(OCC4CCNCC4)c23)cn1] | 4-(4-piperidylmethoxy)-3-pyrimidin-5-yl-1H-pyrrolo[2,3-b]pyridine | ES+ 310 [M + H]+ Rt = 0.66 mins, Generic Basic Method |
| E222 | 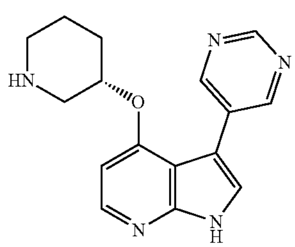 [SMILES: c1ncc(-c2c[nH]c3nccc(O[C@H]4CCCNC4)c23)cn1] | 4-[[(3S)-3-piperidyl]oxy]-3-pyrimidin-5-yl-1H-pyrrolo[2,3-b]pyridine | ES+ 296 [M + H]+ Rt = 0.71 mins, Generic Basic Method |
| E223 | 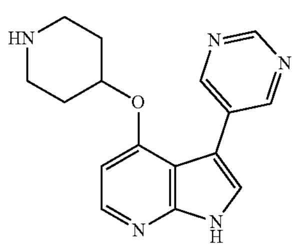 [SMILES: c1ncc(-c2c[nH]c3nccc(OC4CCNCC4)c23)cn1] | 4-(4-piperidyloxy)-3-pyrimidin-5-yl-1H-pyrrolo[2,3-b]pyridine | ES+ 296 [M + H]+ Rt = 0.66 mins, Generic Basic Method |

Example 224 (E224)-4-[[(3R)-1-methyl-3-piperidyl]methoxy]-3-pyrimidin-5-yl-1H-pyrrolo[2,3-b]pyridine

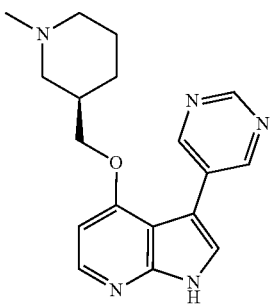 [SMILES: CN1CCC[C@@H](COc2ccnc3[nH]cc(-c4cncnc4)c23)C1]

Formaldehyde solution (37% in water, 0.14 ml, 1.82 mmol) was added to a stirred solution of 4-[[(3R)-3-piperidyl]methoxy]-3-pyrimidin-5-yl-1H-pyrrolo[2,3-b]pyridine (E214) (75 mg, 0.24 mmol) in a mixture of methanol (1.5 ml) and DCM (1.5 ml). The mixture was stirred at room temperature, under nitrogen for 10 minutes then sodium triacetoxyborohydride (102.27 mg, 0.48 mmol) was added. The reaction was stirred at room temperature for 4 hours, then quenched by addition of water. The mixture was concentrated in vacuo and the resulting residue was dissolved in a mixture of DCM and methanol and loaded onto a pre-acidified 2 g SCX cartridge. The cartridge was flushed with methanol (15 ml), before the product was eluted with 2 N ammonia in methanol (15 ml). The solvent was removed in vacuo to afford a white solid which was further purified by preparative HPLC (early basic method) to afford 4-[[(3R)-1-methyl-3-piperidyl]methoxy]-3-pyrimidin-5-yl-1H-pyrrolo[2,3-b]pyridine (E224) (13.7 mg, 0.04 mmol, 16.6% yield) as a white solid, LCMS ES+ 324 [M+H]+, Rt=0.7 mins (Generic Basic Method).

The following compounds were prepared in a similar manner to 4-[[(3R)-1-methyl-3-piperidyl]methoxy]-3-pyrimidin-5-yl-1H-pyrrolo[2,3-b]pyridine (E224) from the appropriate intermediates:

| Example | Structure | Name | LCMS Data |
|---|---|---|---|
| E225 | 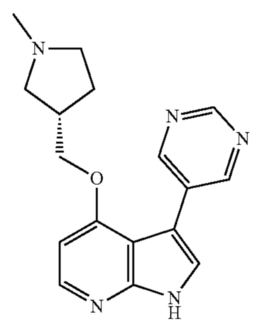 [SMILES: CN1CC[C@H](COc2ccnc3[nH]cc(-c4cncnc4)c23)C1] | 4-[[(3S)-1-methylpyrrolidin-3-yl]methoxy]-3-pyrimidin-5-yl-1H-pyrrolo[2,3-b]pyridine | ES+ 310 [M + H]+ Rt = 0.65 mins, Generic Basic Method |
| E226 | 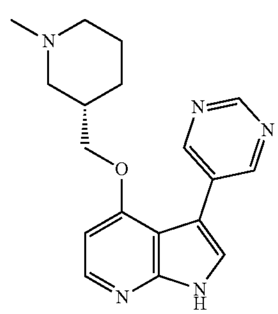 [SMILES: CN1CCC[C@H](COc2ccnc3[nH]cc(-c4cncnc4)c23)C1] | 3-pyrimidin-5-yl-4-[[(3S)-1-methyl-3-piperidyl]methoxy]-1H-pyrrolo[2,3-b]pyridine | ES+ 324 [M + H]+ Rt = 0.64 mins, Generic Basic Method |

Biology (Example 236)

MRCKα, MRCKβ, ROCK1 and ROCK2 Kinase Assays

MRCKα, MRCKβ, ROCK1 and ROCK2 assays were performed using an IMAP fluorescence polarization assay format (Molecular Devices Inc.). 8-12 nM of each kinase (Life Technologies) was incubated for 60 min at room temperature with 100 nM FAM-S6-ribosomal protein derived peptide (synthesized by Alta Biosciences, University of Birmingham UK) in the presence of 1 μM ATP and 0.5 mM MgCl$_2$ in 20 mM Tris buffer (pH 7.4) containing 0.01% Tween-20 and 1 mM DTT (MRCKα and β); or 1 μM ATP, 10 mM MgCl$_2$ in 20 mM Tris buffer (pH 7.5) containing 0.25 mM EGTA 0.01% Triton X-100 and 1 mM DTT (ROCK1 and ROCK2). Typically, dose response analyses were performed over concentration ranges from 0.005-100 μM. Reactions were stopped by adding 2 assay volumes of 0.25% (v/v) IMAP binding reagent in 1×IMAP binding buffer A (Molecular Devices). After 30 min incubation to allow binding reagent to bind phosphorylated peptide, fluorescence polarization was measured on a Tecan Saphire$^2$ plate reader at excitation (470 nm) and emission (530 nm) wavelengths. Inhibition was calculated using no inhibitor and no enzyme controls as 0 and 100% inhibition, respectively.

Table 1 provides results of the MRCKα, MRCKβ, ROCK1 and ROCK2 kinase assays described above for examples of the present invention.

TABLE 1

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E116 | 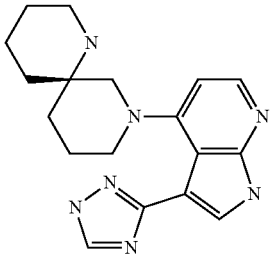 [SMILES: c1cc(N2CCC[C@@]3(CCCCN3)C2)c2c(-c3nc[nH]n3)c[nH]c2n1] | 0.0122 | 0.0124 | 85.09 | 39.41 |
| E120 | 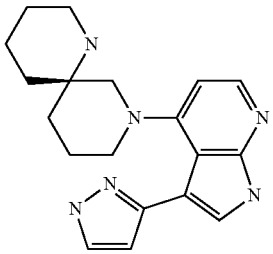 [SMILES: c1cc(N2CCC[C@@]3(CCCCN3)C2)c2c(-c3cc[nH]n3)c[nH]c2n1] | 0.0049 | 0.0147 | 23.78 | 4.732 |
| E117 | 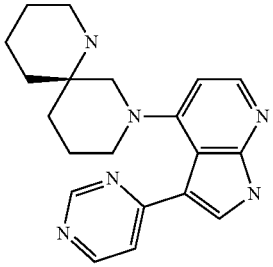 [SMILES: c1cc(-c2c[nH]c3nccc(N4CCC[C@@]5(CCCCN5)C4)c23)ncn1] | 0.0136 | 0.0233 | 18.39 | 5.385 |
| E150 | 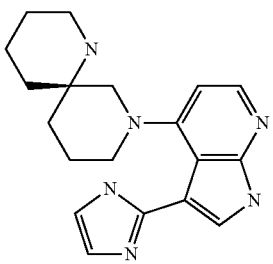 [SMILES: c1c[nH]c(-c2c[nH]c3nccc(N4CCC[C@@]5(CCCCN5)C4)c23)n1] | 0.0332 | 0.0246 | 56.87 | 21.74 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E174 | 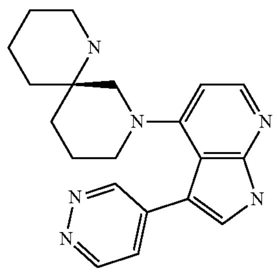 [SMILES: c1cc(-c2c[nH]c3nccc(N4CCC[C@@]5(CCCCN5)C4)c23)cnn1] | | 0.0256 | 404.8 | |
| E206 | 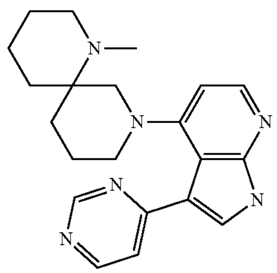 | 0.0189 | 0.0277 | 20.59 | 4.186 |
| E133 | 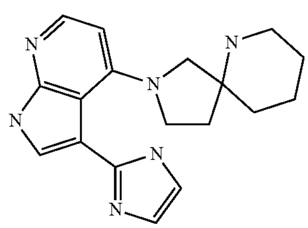 [SMILES: c1c[nH]c(-c2c[nH]c3nccc(N4CCC5(CCCCN5)C4)c23)n1] | 0.0149 | 0.03 | 25.88 | 6.414 |
| E209 | 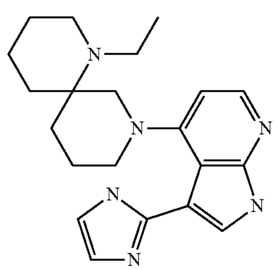 [SMILES: CCN1CCCCC12CCCN(c1ccnc3[nH]cc(-c4ncc[nH]4)c13)C2] | 0.1011 | 0.0389 | 126.9 | 29.89 |
| E139 | 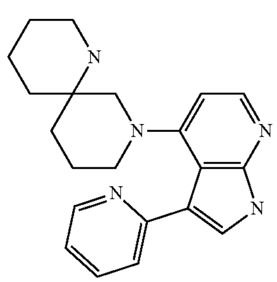 | 0.0435 | 0.0391 | 99.11 | 40.95 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E207 | 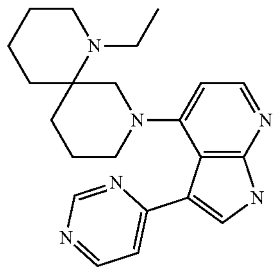 [SMILES: CCN1CCCCC12CCCN(c1ccnc3[nH]cc(-c4ccncn4)c13)C2] | 0.0275 | 0.0395 | 20.03 | 8.343 |
| E121 | 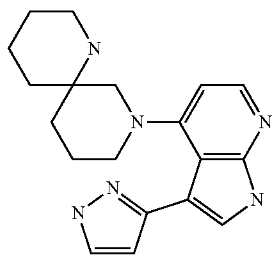 [SMILES: c1cc(N2CCCC3(CCCCN3)C2)c2c(-c3cc[nH]n3)c[nH]c2n1] | | 0.0488 | 385.5 | |
| E146 | 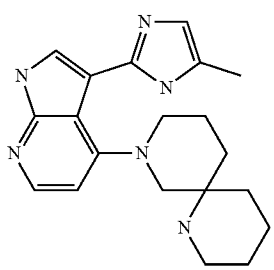 [SMILES: Cc1cnc(-c2c[nH]c3nccc(N4CCCC5(CCCCN5)C4)c23)[nH]1] | 0.0493 | 0.0539 | 203.3 | 100.4 |
| E126 | 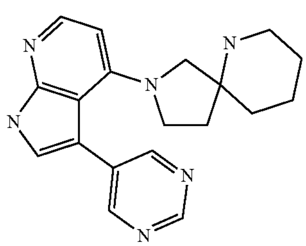 [SMILES: c1ncc(-c2c[nH]c3nccc(N4CCC5(CCCCN5)C4)c23)cn1] | 0.0413 | 0.057 | 68.27 | 23.14 |
| E131 | 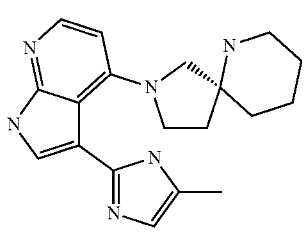 [SMILES: Cc1cnc(-c2c[nH]c3nccc(N4CC[C@@]5(CCCCN5)C4)c23)[nH]1] | 0.021 | 0.0601 | 107.2 | 24.84 |
| E149 | 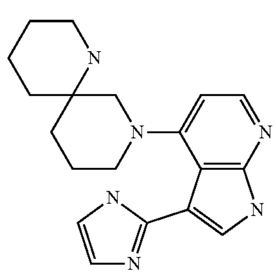 | | 0.0633 | 304.5 | |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E210 | 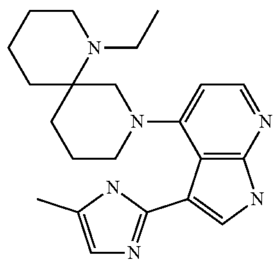 [SMILES: CCN1CCCCC12CCCN(c1ccnc3[nH]cc(-c4ncc(C)[nH]4)c13)C2] | 0.1271 | 0.0634 | 50250 | 151.6 |
| E171 | | | 0.0639 | 0.0648 | 206.75 | 85.155 |
| E168 | 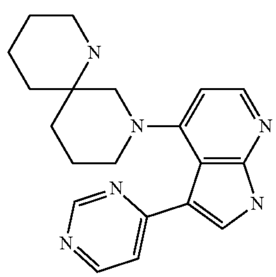 | | 0.065 | 88.95 | 30.91 |
| E128 | 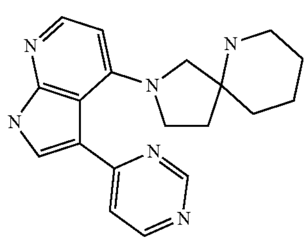 [SMILES: c1cc(-c2c[nH]c3nccc(N4CCC5(CCCCN5)C4)c23)ncn1] | 0.0317 | 0.0652 | 10.61 | 4.412 |
| E138 | 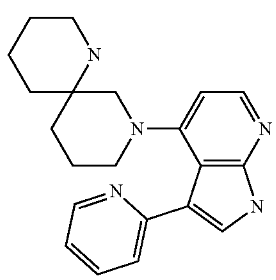 | | 0.0726 | 318.7 | |

TABLE 1-continued
| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E114 | 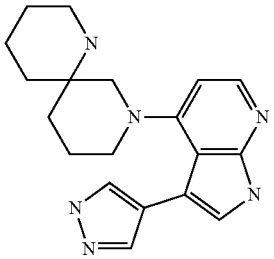 [SMILES: c1cc(N2CCCC3(CCCCN3)C2)c2c(-c3cn[nH]c3)c[nH]c2n1] | 0.0683 | 0.0813 | 18.26 | 6.415 |
| E155 | 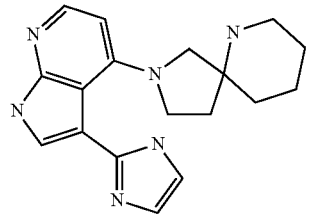 |  | 0.0822 | 79.5 |  |
| E177 | 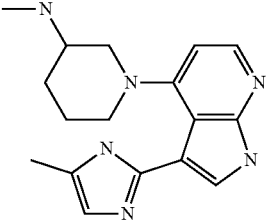 [SMILES: CNC1CCCN(c2ccnc3[nH]cc(-c4ncc(C)[nH]4)c23)C1] | 0.0822 | 0.0888 | 33.68 | 96.24 |
| E236 | 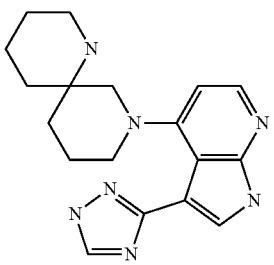 [SMILES: c1cc(N2CCCC3(CCCCN3)C2)c2c(-c3nc[nH]n3)c[nH]c2n1] | 0.0945 | 0.0898 | 389.9 | 104.6 |
| E176 | 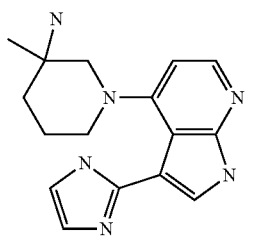 [SMILES: CC1(N)CCCN(c2ccnc3[nH]cc(-c4ncc[nH]4)c23)C1] | 0.0934 | 0.0923 | 67.06 | 42 |
| E147 | 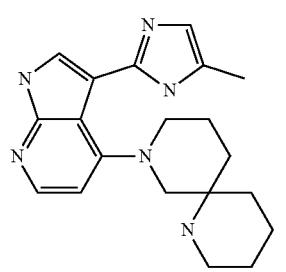 [SMILES: Cc1cnc(-c2c[nH]c3nccc(N4CCCC5(CCCCN5)C4)c23)[nH]1] |  | 0.0924 | 100000 |  |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E170 | 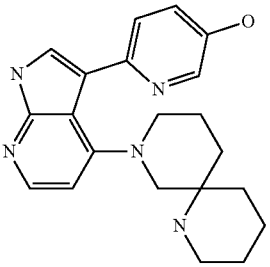 [SMILES: Oc1ccc(-c2c[nH]c3nccc(N4CCCC5(CCCCN5)C4)c23)nc1] | 0.1696 | 0.1001 | 563.7 | 164.75 |
| E169 | 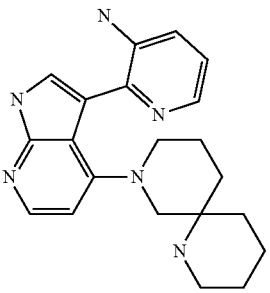 [SMILES: Nc1cccnc1-c1c[nH]c2nccc(N3CCCC4(CCCCN4)C3)c12] | 0.1893 | 0.1064 | 860.8 | 261.5 |
| E136 | 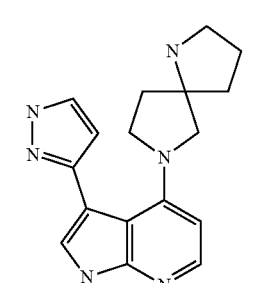 | 0.2069 | 0.1202 | 70.73 | 14.2 |
| E213 | 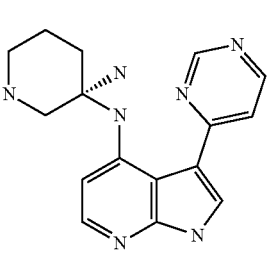 [SMILES: N[C@@]1(Nc2ccnc3[nH]cc(-c4ccncn4)c23)CCCNC1] | | 0.1437 | 3.839 | |
| E144 | 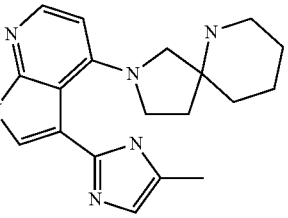 | | 0.1537 | 385.6 | |
| E66 | 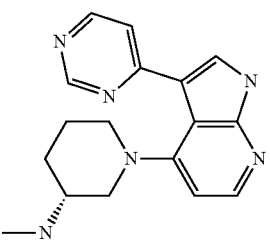 | 0.2377 | 0.1704 | 240.9 | 99.19 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E187 | 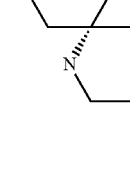 | 0.2493 | 0.1791 | 152.1 | 44.24 |
| E178 | 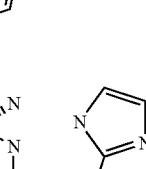 | 0.5173 | 0.1812 | 423.1 | 118.6 |
| E212 | 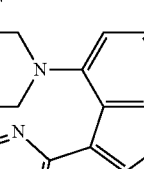 | 0.1848 | 0.1844 | 29.89 | 7.569 |
| E41 | 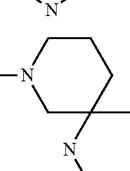 | | 0.2024 | 34.41 | |
| E142 | 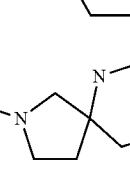 | 0.2162 | 0.2033 | 103.6 | 33640 |
| E129 | 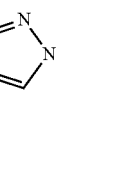 | 0.0518 | 0.2064 | 108.2 | 23.57 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E162 | 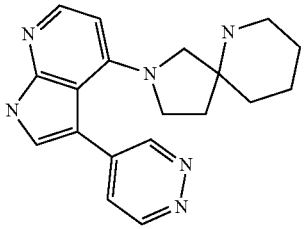 | | 0.2186 | 16.85 | |
| E46 | 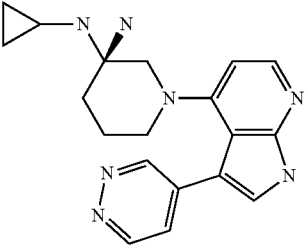 | 0.322 | 0.2383 | 11.91 | 232.7 |
| E165 | 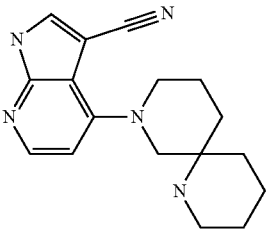 [SMILES: N#Cc1c[nH]c2nccc(N3CCC[C@@]4(CCCCN4)C3)c12] | | 0.2492 | 174.2 | |
| E67 | 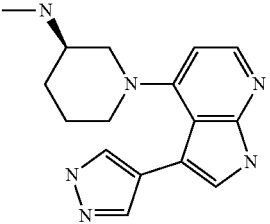 [SMILES: CN[C@@H]1CCCN(c2ccnc3[nH]cc(-c4cn[nH]c4)c23)C1] | | 0.273 | 108.9 | 36.38 |
| E134 | 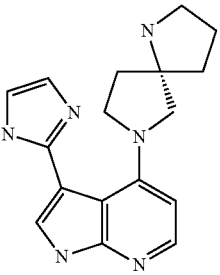 | 0.1904 | 0.3027 | 111.4 | 30.04 |
| E47 | 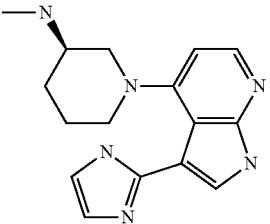 [SMILES: CN[C@@H]1CCCN(c2ccnc3[nH]cc(-c4ncc[nH]4)c23)C1] | 0.1579 | 0.3037 | 595.1 | 102.6 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E42 | 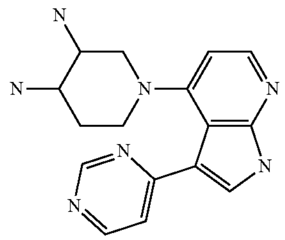 [SMILES: NC1CCN(c2ccnc3[nH]cc(-c4ccncn4)c23)CC1N] | | 0.3227 | 79.58 | |
| E211 | 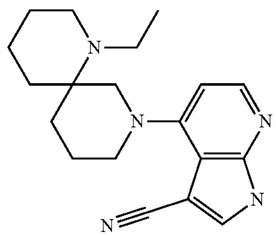 [SMILES: CCN1CCCCC12CCCN(c1ccnc3[nH]cc(C#N)c13)C2] | 0.6313 | 0.3514 | 244.8 | 34.27 |
| E158 | 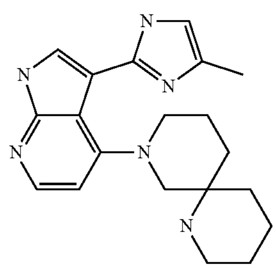 [SMILES: Cc1c[nH]c(-c2c[nH]c3nccc(N4CCCC5(CCCCN5)C4)c23)n1] | | 0.3605 | 100000 | |
| E154 | 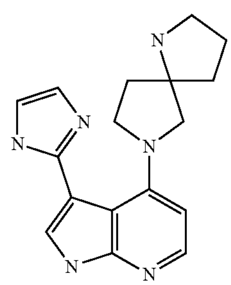 | | 0.3701 | 239.3 | |
| E184 | 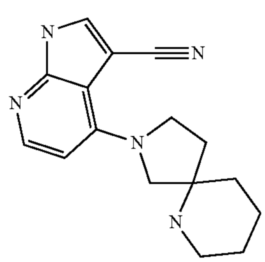 [SMILES: N#Cc1c[nH]c2nccc(N3CCC4(CCCCN4)C3)c12] | 0.4813 | 21.85 | | |
| E49 | 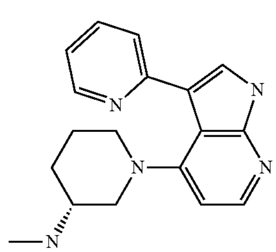 [SMILES: CN[C@@H]1CCCN(c2ccnc3[nH]cc(-c4ccccn4)c23)C1] | | 0.5056 | 50753 | 271.9 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E141 | 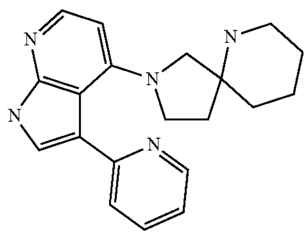 [SMILES: c1ccc(-c2c[nH]c3nccc(N4CCC5(CCCCN5)C4)c23)nc1] | | 0.5494 | 109.2 | |
| E122 | 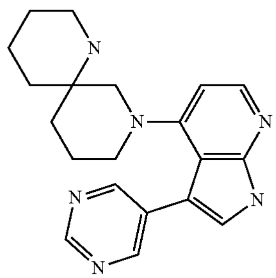 [SMILES: c1ncc(-c2c[nH]c3nccc(N4CCCC5(CCCCN5)C4)c23)cn1] | 0.0284 | 0.58515 | 195.75 | 77.695 |
| E172 | 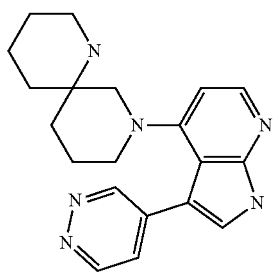 [SMILES: c1cc(-c2c[nH]c3nccc(N4CCCC5(CCCCN5)C4)c23)cnn1] | | 0.72285 | 33.65 | 14.55 |
| E50 | 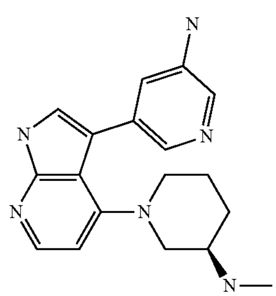 [SMILES: CN[C@@H]1CCCN(c2ccnc3[nH]cc(-c4cncc(N)c4)c23)C1] | | 0.7292 | 2053 | 577.8 |
| E54 | 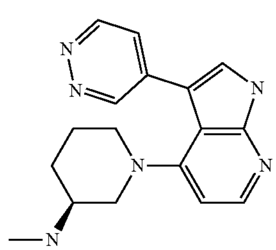 [SMILES: CN[C@H]1CCCN(c2ccnc3[nH]cc(-c4ccnnc4)c23)C1] | 0.2744 | 0.78625 | 132.795 | 44.53 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E166 | 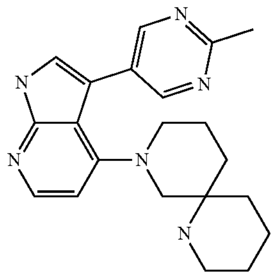 [SMILES: Cc1ncc(-c2c[nH]c3nccc(N4CCCC5(CCCCN5)C4)c23)cn1] | | 0.7863 | 100000 | |
| E71 | 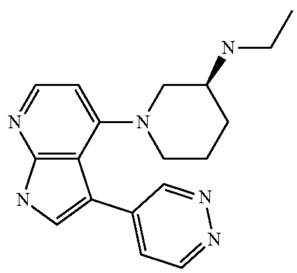 [SMILES: CCN[C@H]1CCCN(c2ccnc3[nH]cc(-c4ccnnc4)c23)C1] | | 0.80165 | 152.355 | 73.885 |
| E143 | 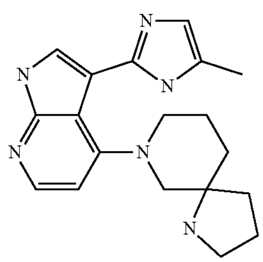 [SMILES: Cc1cnc(-c2c[nH]c3nccc(N4CCCC5(CCCN5)C4)c23)[nH]1] | | 0.8821 | 100000 | |
| E9 | 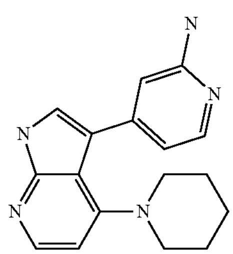 [SMILES: Nc1cc(-c2c[nH]c3nccc(N4CCCCC4)c23)ccn1] | | 0.8865 | 1.5 | 1.25 |
| E119 | 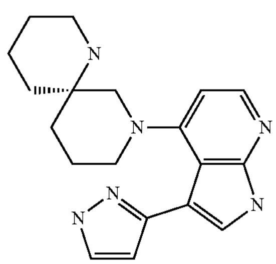 [SMILES: c1cc(N2CCC[C@]3(CCCCN3)C2)c2c(-c3cc[nH]n3)c[nH]c2n1] | | 0.907 | 100000 | |
| E237 | 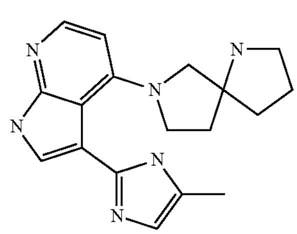 [SMILES: Cc1cnc(-c2c[nH]c3nccc(N4CCC5(CCCN5)C4)c23)[nH]1] | | 0.9304 | 100000 | |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E161 | 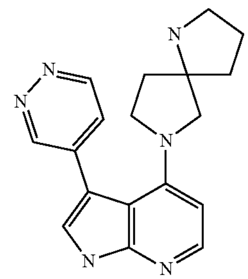 [SMILES: c1cc(-c2c[nH]c3nccc(N4CCC5(CCCN5)C4)c23)cnn1] | | 0.9328 | 34.12 | |
| E124 | 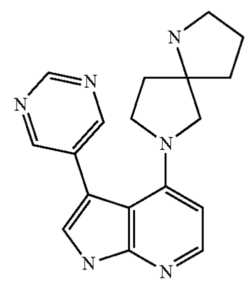 [SMILES: c1ncc(-c2c[nH]c3nccc(N4CCC5(CCCN5)C4)c23)cn1] | | 0.9466 | 76.91 | |
| E193 | 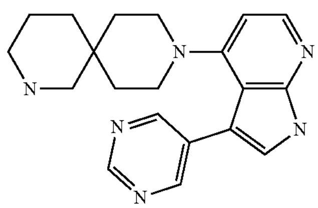 [SMILES: c1ncc(-c2c[nH]c3nccc(N4CCC5(CCCNC5)CC4)c23)cn1] | 0.2175 | 0.96905 | 22.27 | 15.18 |
| E190 | 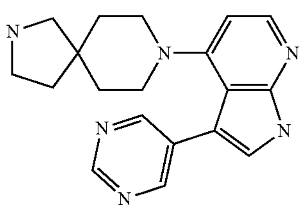 [SMILES: c1ncc(-c2c[nH]c3nccc(N4CCC5(CCNC5)CC4)c23)cn1] | | 0.973 | 9.3 | 8.7 |
| E159 | 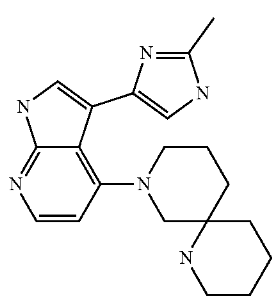 [SMILES: Cc1nc(-c2c[nH]c3nccc(N4CCCC5(CCCCN5)C4)c23)c[nH]1] | | 1.002 | 100000 | |
| E105 | 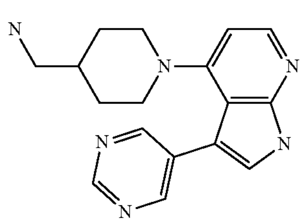 [SMILES: NCC1CCN(c2ccnc3[nH]cc(-c4cncnc4)c23)CC1] | | 1.0036 | 10.1 | 9.5 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E238 | 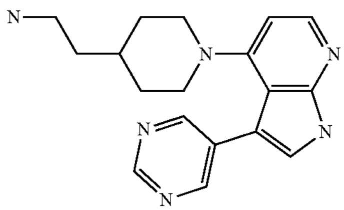 [SMILES: NCCC1CCN(c2ccnc3[nH]cc(-c4cncnc4)c23)CC1] | | 1.02415 | 14.25 | 18.35 |
| E157 | 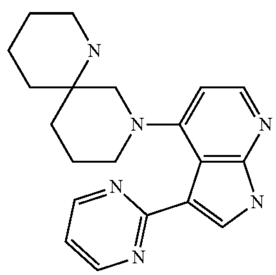 [SMILES: c1cnc(-c2c[nH]c3nccc(N4CCCC5(CCCCN5)C4)c23)nc1] | 1.336 | 1.044 | 100000 | 100000 |
| E214 | 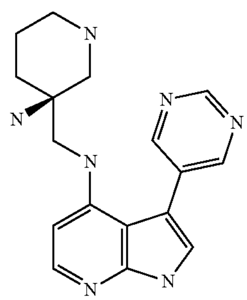 [SMILES: N[C@@]1(CNc2ccnc3[nH]cc(-c4cncnc4)c23)CCCNC1] | | 1.075 | 41.965 | 32.1 |
| E220 | 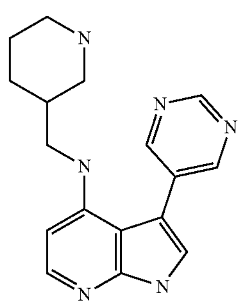 [SMILES: c1ncc(-c2c[nH]c3nccc(NCC4CCCNC4)c23)cn1] | | 1.075 | 34 | 40.7 |
| E68 | 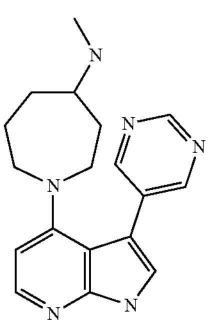 [SMILES: CNC1CCCN(c2ccnc3[nH]cc(-c4cncnc4)c23)CC1] | 0.3824 | 1.0867 | 55.875 | 36.925 |

TABLE 1-continued
| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E6 | 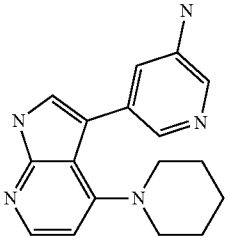 | 1.11325 | 3.5 | 1.9 | |
| E164 | 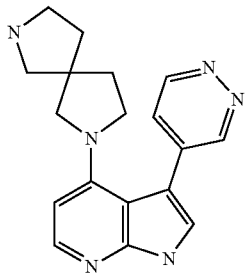 [SMILES: c1cc(-c2c[nH]c3nccc(N4CCC5(CCNC5)C4)c23)cnn1] | | 1.121 | 0.4475 | |
| E218 | 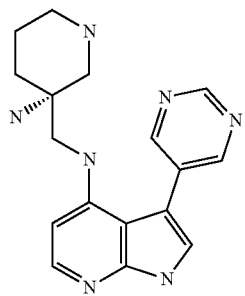 [SMILES: N[C@]1(CNc2ccnc3[nH]cc(-c4cncnc4)c23)CCCNC1] | 0.1891 | 1.15 | 18.625 | 17.64 |
| E173 | 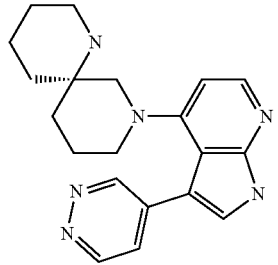 [SMILES: c1cc(-c2c[nH]c3nccc(N4CCC[C@]5(CCCCN5)C4)c23)cnn1] | | 1.178 | 294.1 | |
| E53 | 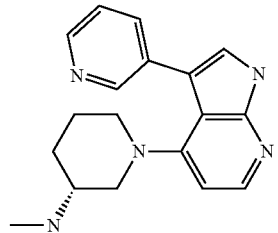 | | 1.2697 | 50527 | 334.7 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E189 | 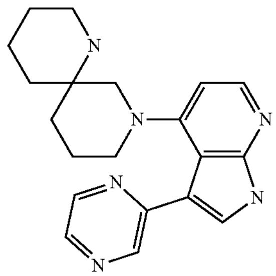 [SMILES: c1cnc(-c2c[nH]c3nccc(N4CCCC5(CCCCN5)C4)c23)cn1] | 0.1314 | 1.3083 | 642.7 | 167 |
| E196 | 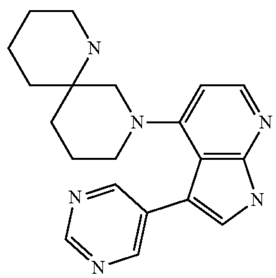 [SMILES: c1ncc(-c2c[nH]c3nccc(N4CCCC5(CCCCN5)C4)c23)cn1] | 5.1 | 133535 | 212.7 | 176.8 |
| E110 | 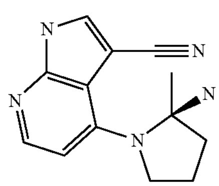 [SMILES: C[C@]1(N)CCCN1c1ccnc2[nH]cc(C#N)c12] | 4.6 | 1.438 | 2.775 | 2.438 |
| E118 | 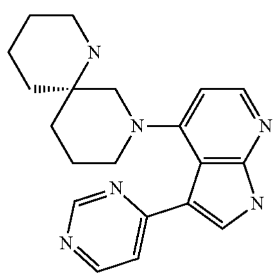 [SMILES: c1cc(-c2c[nH]c3nccc(N4CCC[C@]5(CCCCN5)C4)c23)ncn1] | 2.887 | 1.4725 | 50278.8 | 299.3 |
| E175 | 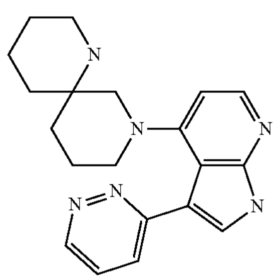 [SMILES: c1cnnc(-c2c[nH]c3nccc(N4CCCC5(CCCCN5)C4)c23)c1] | 0.2565 | 1.50275 | 1861 | 546.55 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E188 | 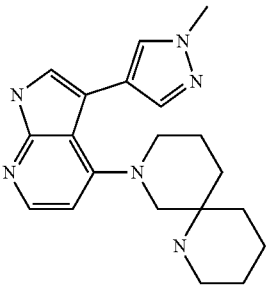 [SMILES: Cn1cc(-c2c[nH]c3nccc(N4CCCC5(CCCCN5)C4)c23)cn1] | 0.5983 | 1.5192 | 93.6 | 28.805 |
| E65 | 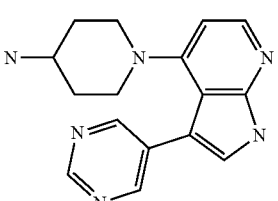 |  | 1.6498 | 127.5 | 138.2 |
| E156 | 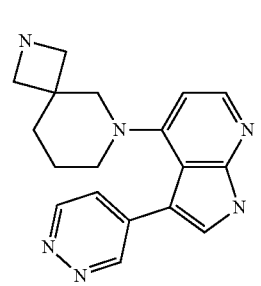 [SMILES: c1cc(-c2c[nH]c3nccc(N4CCCC5(CNC5)C4)c23)cnn1] |  | 1.686 | 57.44 |  |
| E48 | 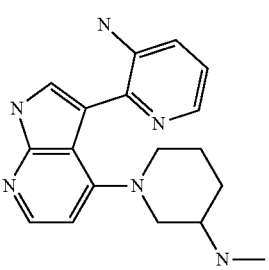 [SMILES: CNC1CCCN(c2ccnc3[nH]cc(-c4ncccc4N)c23)C1] |  | 1.734 | 3529 | 756.2 |
| E216 | 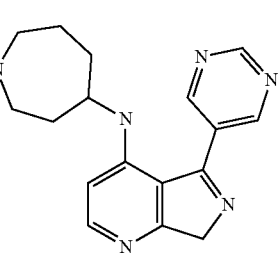 | 1.131 | 1.7785 | 66.825 | 55.775 |
| E186 | 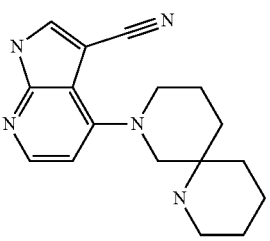 | 1.834 | 346.6 |  |  |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E86 | 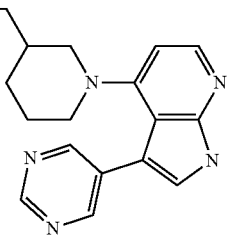 | 4.6 | 1.847 | 8.2 | 10.5 |
| E83 | 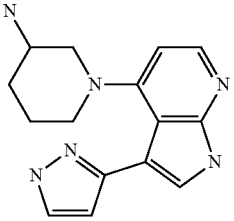 | 0.4807 | 1.852651111 | 196 | |
| E52 | 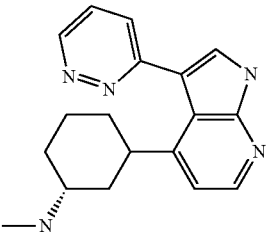 | 0.566 | 1.8585 | 2207 | 510.05 |
| E185 | 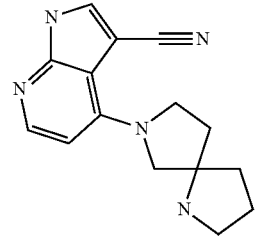 [SMILES: N#Cc1c[nH]c2nccc(N3CCC4(CCCN4)C3)c12] | | 1.924 | 13.63 | |
| E63 | 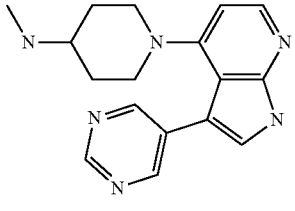 [SMILES: CNC1CCN(c2ccnc3[nH]cc(-c4cncnc4)c23)CC1] | | 1.9825 | 137.8 | 91.2 |
| E191 | 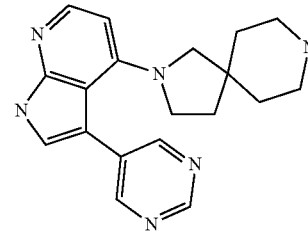 | | 2.0515 | 9.2845 | 7.6995 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E56 | 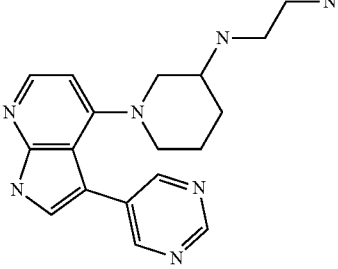 | | 2.2315 | 1386 | 573.1 |
| E79 | 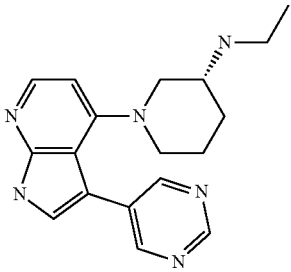 [SMILES: CCN[C@@H]1CCCN(c2ccnc3[nH]cc(-c4cncnc4)c23)C1] | 1.226 | 2.2725 | 50675 | 447.65 |
| E57 | 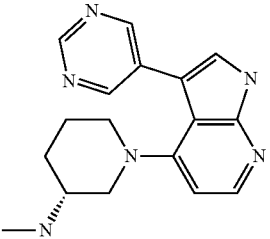 [SMILES: CN[C@@H]1CCCN(c2ccnc3[nH]cc(-c4cncnc4)c23)C1] | 2.93035 | 2.343 | 50704 | 545.45 |
| E163 | 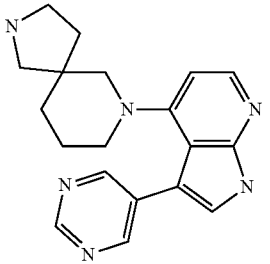 [SMILES: c1ncc(-c2c[nH]c3nccc(N4CCCC5(CCNC5)C4)c23)cn1] | | 2.401 | 16.68 | |
| E115 | 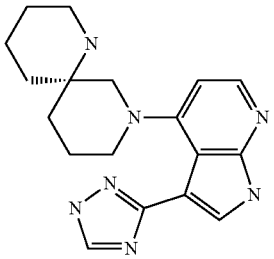 | | 2.479 | 100000 | |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E43 | 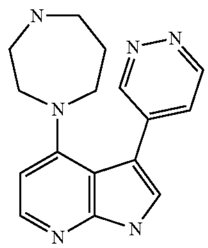 [SMILES: c1cc(-c2c[nH]c3nccc(N4CCCNCC4)c23)cnn1] | | 2.613 | 59.45 | |
| E69 | 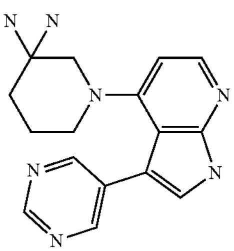 | 4.5 | 2.7215 | 460.5 | 274.1 |
| E194 | 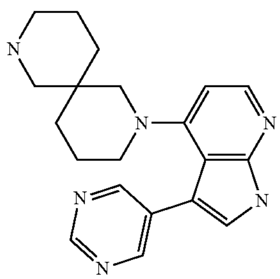 [SMILES: c1ncc(-c2c[nH]c3nccc(N4CCCC5(CCCNC5)C4)c23)cn1] | 0.6525 | 2.72955 | 83.64 | 53.98 |
| E160 | 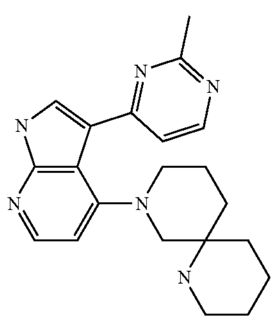 [SMILES: Cc1nccc(-c2c[nH]c3nccc(N4CCCC5(CCCCN5)C4)c23)n1] | | 2.758 | 100000 | |
| E45 | 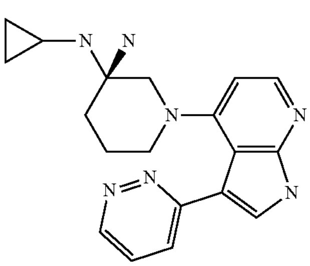 [SMILES: N[C@]1(NC2CC2)CCCN(c2ccnc3[nH]cc(-c4cccnn4)c23)C1] | | 2.775 | 100000 | |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E137 | 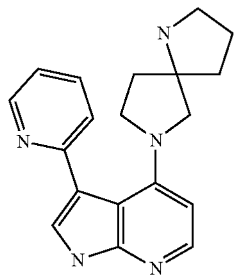 [SMILES: c1ccc(-c2c[nH]c3nccc(N4CCC5(CCCN5)C4)c23)nc1] | | 2.835 | 100000 | |
| E72 | 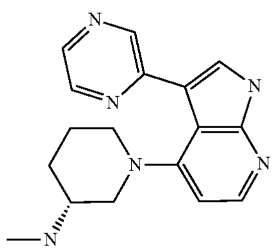 [SMILES: CN[C@@H]1CCCN(c2ccnc3[nH]cc(-c4cnccn4)c23)C1] | 0.6295 | 2.984 | 51065.5 | 267.6 |
| E5 | 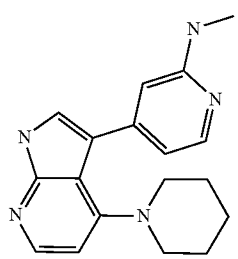 [SMILES: CNc1cc(-c2c[nH]c3nccc(N4CCCCC4)c23)ccn1] | | 3.018 | 40.8 | 22.5 |
| E200 | 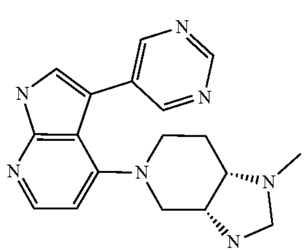 [SMILES: CN1CN[C@@H]2CN(c3ccnc4[nH]cc(-c5cncnc5)c34)CC[C@@H]21] | | 3.125 | 195.6 | 145.2 |
| E151 | 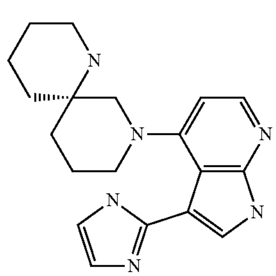 [SMILES: c1c[nH]c(-c2c[nH]c3nccc(N4CCC[C@]5(CCCCN5)C4)c23)n1] | | 3.206 | 114.5 | |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E195 | 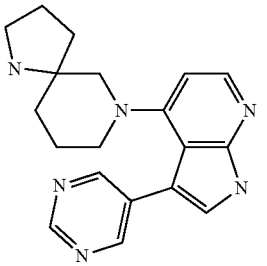 [SMILES: c1ncc(-c2c[nH]c3nccc(N4CCCC5(CCCN5)C4)c23)cn1] | 4.6895 | 3.274 | 332.3 | 174.35 |
| E224 | 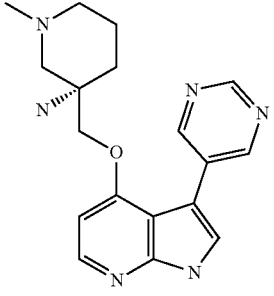 [SMILES: CN1CCC[C@@](N)(COc2ccnc3[nH]cc(-c4cncnc4)c23)C1] | 1.91 | 3.291 | 151.8 | 101.56 |
| E81 | 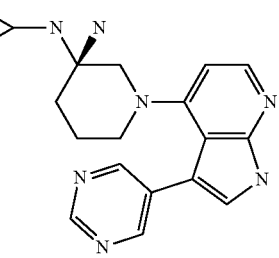 | 0.9349 | 3.3605 | 357.45 | 184.05 |
| E84 | 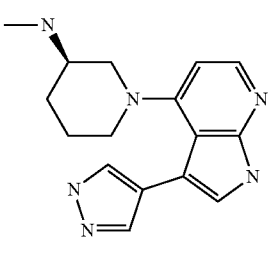 [SMILES: CN[C@@H]1CCCN(c2ccnc3[nH]cc(-c4cn[nH]c4)c23)C1] | 0.522 | 3.42415 | 167 | 37.24 |
| E58 | 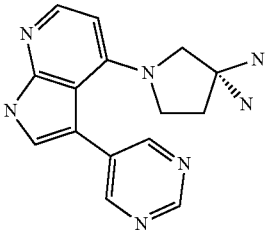 |  | 3.478 | 157.5 | 85.8 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E219 | 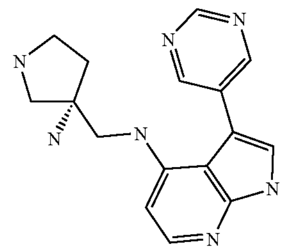 [SMILES: N[C@@]1(CNc2ccnc3[nH]cc(-c4cncnc4)c23)CCNC1] | 2.517 | 3.7125 | 57.62 | 52.57 |
| E99 | 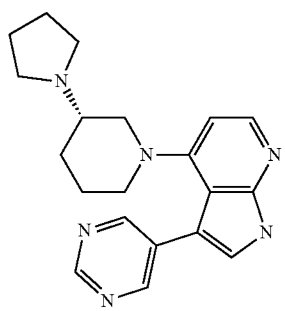 [SMILES: c1ncc(-c2c[nH]c3nccc(N4CCC[C@H](N5CCCC5)C4)c23)cn1] | 5.8 | 3.812 | 1675 | 603.2 |
| E215 | 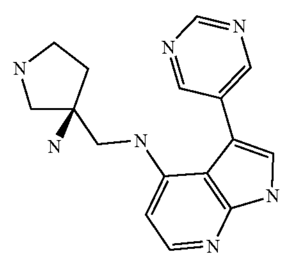 [SMILES: N[C@]1(CNc2ccnc3[nH]cc(-c4cncnc4)c23)CCNC1] | | 3.858 | 47.755 | 34.7 |
| E108 | 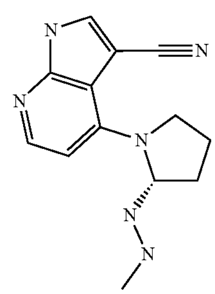 [SMILES: CNN[C@H]1CCCN1c1ccnc2[nH]cc(C#N)c12] | | 3.89 | 21.75 | 18.79 |
| E97 | 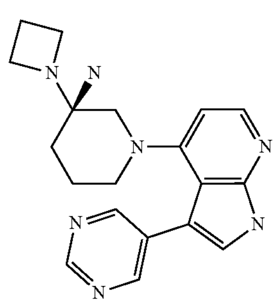 [SMILES: N[C@]1(N2CCC2)CCCN(c2ccnc3[nH]cc(-c4cncnc4)c23)C1] | 5.2 | 3.9325 | 686.2 | 365.8 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E217 | 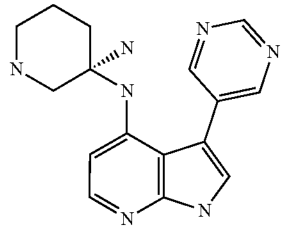 [SMILES: N[C@@]1(Nc2ccnc3[nH]cc(-c4cncnc4)c23)CCCNC1] | | 4.0075 | 113.85 | 77.45 |
| E148 | 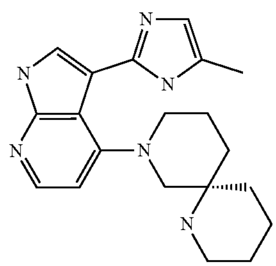 [SMILES: Cc1cnc(-c2c[nH]c3nccc(N4CCC[C@]5(CCCCN5)C4)c23)[nH]1] | | 4.022 | 100000 | |
| E62 | 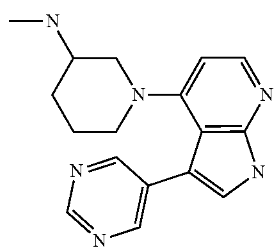 [SMILES: CNC1CCCN(c2ccnc3[nH]cc(-c4cncnc4)c23)C1] | | 4.1 | 359.6 | 314.3 |
| E132 | 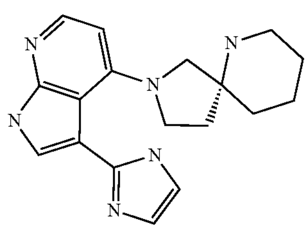 [SMILES: c1c[nH]c(-c2c[nH]c3nccc(N4CC[C@]5(CCCCN5)C4)c23)n1] | | 4.113 | 100000 | |
| E98 | 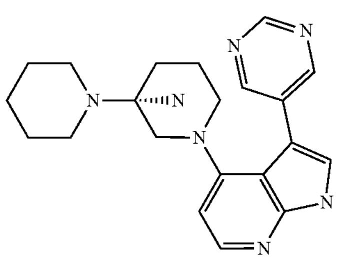 | 7.9 | 4.236 | 2531 | 979.3 |
| E205 | 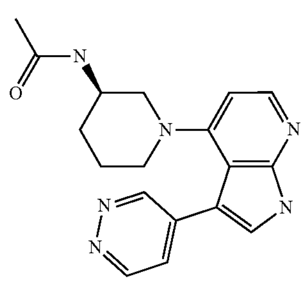 [SMILES: CC(=O)N[C@@H]1CCCN(c2ccnc3[nH]cc(-c4ccnnc4)c23)C1] | | 4.431 | 113.4 | |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E44 | 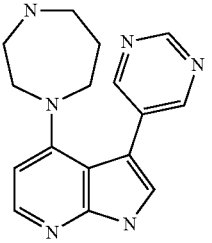 [SMILES: c1ncc(-c2c[nH]c3nccc(N4CCCNCC4)c23)cn1] | | 4.501 | 461.3 | |
| E152 | 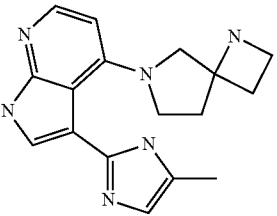 [SMILES: Cc1cnc(-c2c[nH]c3nccc(N4CCC5(CCN5)C4)c23)[nH]1] | | 4.648 | 100000 | |
| E93 | 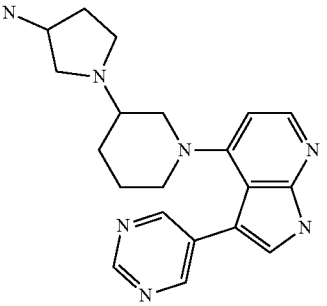 [SMILES: NC1CCN(C2CCCN(c3ccnc4[nH]cc(-c5cncnc5)c34)C2)C1] | 11.6 | 4.779 | 2375 | 830 |
| E92 | 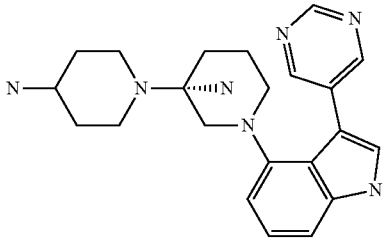 | | 4.966 | 4999 | 1514 |
| E226 | 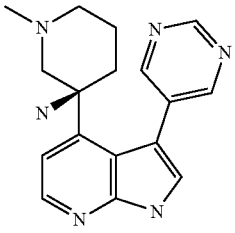 [SMILES: CN1CCC[C@](N)(c2ccnc3[nH]cc(-c4cncnc4)c23)C1] | | 4.996 | 149.7 | 111.4 |
| E38 | 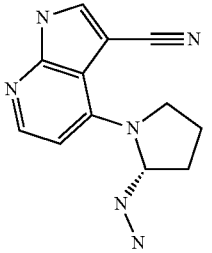 | | 5.081 | 16.65 | 12.68 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E73 | 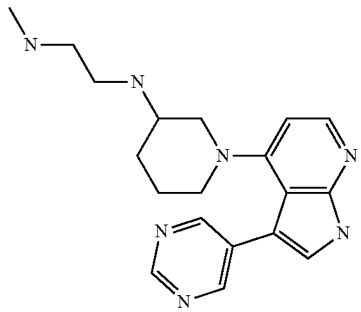 [SMILES: CNCCNC1CCCN(c2ccnc3[nH]cc(-c4cncnc4)c23)C1] | | 5.7075 | 2060 | 963.6 |
| E30 | 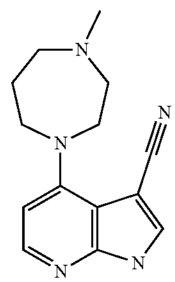 [SMILES: CN1CCCN(c2ccnc3[nH]cc(C#N)c23)CC1] | 12.84 | 5.73 | 24.3 | 20.25 |
| E223 | 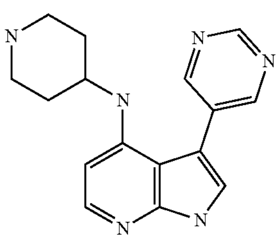 [SMILES: c1ncc(-c2c[nH]c3nccc(NC4CCNCC4)c23)cn1] | | 5.8365 | 153.35 | 107.5 |
| E90 | 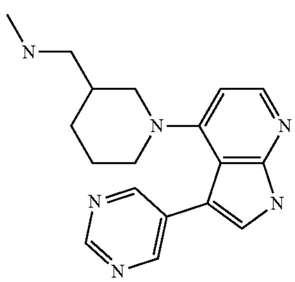 [SMILES: CNCC1CCCN(c2ccnc3[nH]cc(-c4cncnc4)c23)C1] | | 6.008 | 147.8 | 216.9 |
| E183 | 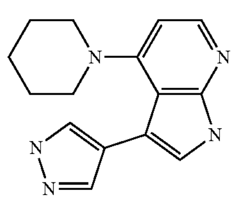 [SMILES: c1cc(N2CCCCC2)c2c(-c3cn[nH]c3)c[nH]c2n1] | 12.55 | 6.0295 | 31.04 | 12.26 |
| E74 | 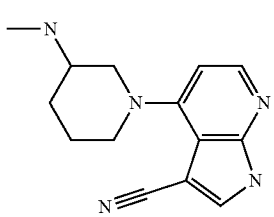 [SMILES: CNC1CCCN(c2ccnc3[nH]cc(C#N)c23)C1] | | 6.157 | 636.8 | 221.9 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E199 | 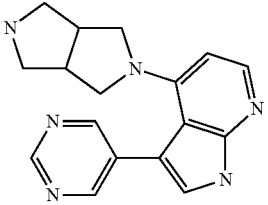 [SMILES: c1ncc(-c2c[nH]c3nccc(N4CC5CNCC5C4)c23)cn1] | | 6.322 | 222.5 | 198.9 |
| E59 | 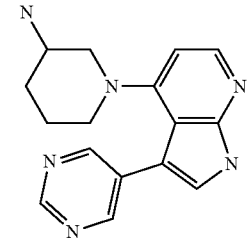 [SMILES: NC1CCCN(c2ccnc3[nH]cc(-c4cncnc4)c23)C1] | | 6.9 | 317.5 | 154.4 |
| E95 | 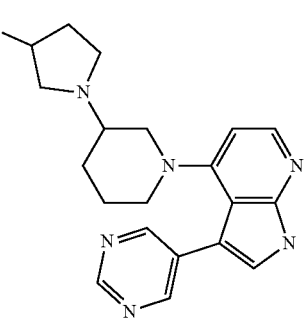 | 19.4 | 6.984 | 689.2 | 395.4 |
| E88 | 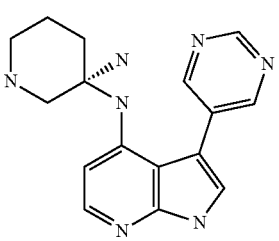 [SMILES: N[C@@]1(Nc2ccnc3[nH]cc(-c4cncnc4)c23)CCCNC1] | | 7.2105 | 85.185 | 70.4 |
| E130 | 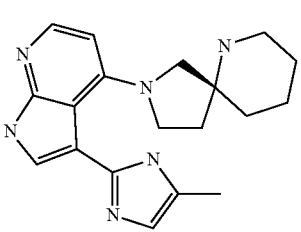 [SMILES: Cc1cnc(-c2c[nH]c3nccc(N4CC[C@]5(CCCCN5)C4)c23)[nH]1] | | 7.229 | 100000 | |
| E55 | 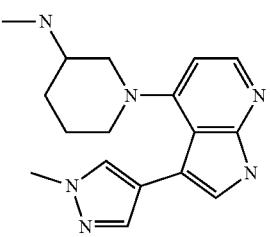 [SMILES: CNC1CCCN(c2ccnc3[nH]cc(-c4cnn(C)c4)c23)C1] | 18.85 | 7.307 | 301.3 | 128.95 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E140 | 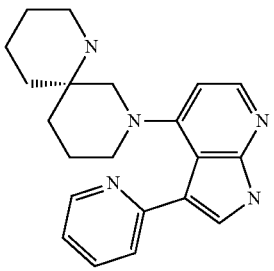 [SMILES: c1ccc(-c2c[nH]c3nccc(N4CCC[C@]5(CCCCN5)C4)c23)nc1] | | 7.333 | 97.71 | |
| E51 | 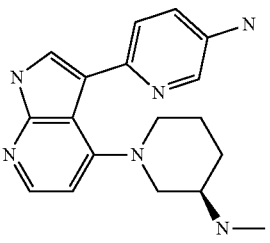 [SMILES: CN[C@@H]1CCCN(c2ccnc3[nH]cc(-c4ccc(N)cn4)c23)C1] | | 7.4055 | 8929 | 2192 |
| E239 | 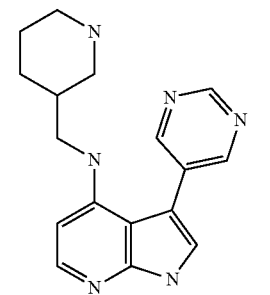 [SMILES: c1ncc(-c2c[nH]c3nccc(NCC4CCCNC4)c23)cn1] | | 7.847 | 103.15 | 93.3 |
| E80 | 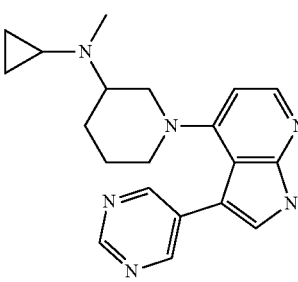 | | 8.3 | 498.7 | 227.6 |
| E240 | 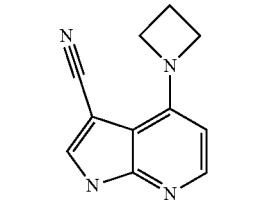 [SMILES: N#Cc1c[nH]c2nccc(N3CCC3)c12] | | 8.309 | 38.74 | 21.56 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E192 | 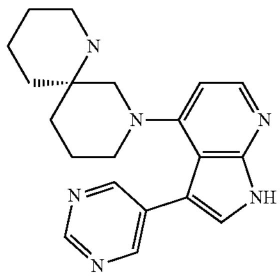 [SMILES: c1ncc(-c2c[nH]c3nccc(N4CCC[C@]5(CCCCN5)C4)c23)cn1] | | 8.3285 | 50453.75 | 427.5 |
| E78 | 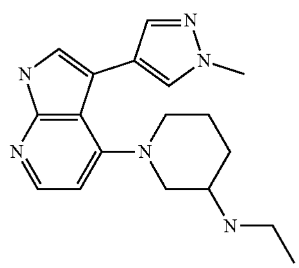 [SMILES: CCNC1CCCN(c2ccnc3[nH]cc(-c4cnn(C)c4)c23)C1] | 3.482 | 8.508 | 105.335 | 61.475 |
| E197 | 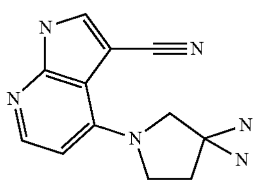 [SMILES: N#Cc1c[nH]c2nccc(N3CCC(N)(N)C3)c12] | | 8.82 | 19.8 | 7 |
| E35 | 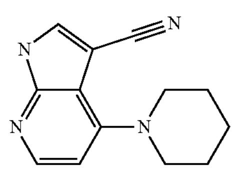 [SMILES: N#Cc1c[nH]c2nccc(N3CCCCC3)c12] | 14.26 | 9.014 | 57.94 | 15.99 |
| E94 | 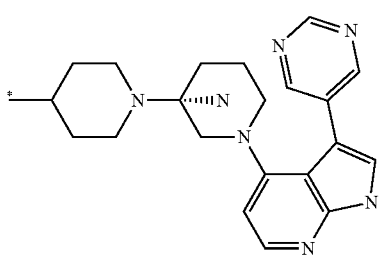 | | 9.329 | 913.3 | 495.2 |
| E153 | 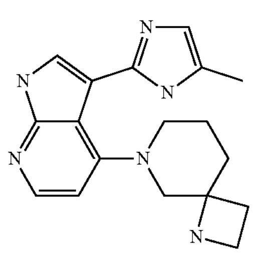 [SMILES: Cc1cnc(-c2c[nH]c3nccc(N4CCCC5(CCN5)C4)c23)[nH]1] | | 9.364 | 100000 | |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E14 | 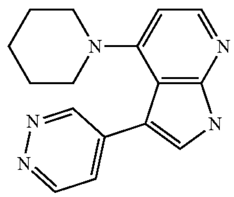 [SMILES: c1cc(-c2c[nH]c3nccc(N4CCCCC4)c23)cnn1] | | 9.405 | 9 | 6.5 |
| E181 | 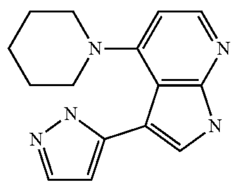 [SMILES: c1cc(-c2c[nH]c3nccc(N4CCCCC4)c23)[nH]n1] | 9.1 | 9.4505 | 25.01 | 15.45 |
| E208 | 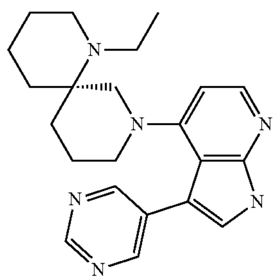 [SMILES: CCN1CCCC[C@]12CCCN(c1ccnc3[nH]cc(-c4cncnc4)c13)C2] | | 9.727 | 1214 | 395.6 |
| E123 | 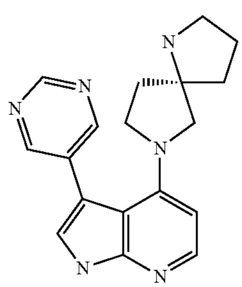 [SMILES: c1ncc(-c2c[nH]c3nccc(N4CC[C@]5(CCCN5)C4)c23)cn1] | | 9.884 | 100000 | |
| E135 | 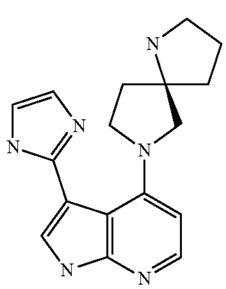 [SMILES: c1c[nH]c(-c2c[nH]c3nccc(N4CC[C@]5(CCCN5)C4)c23)n1] | | 10.32 | 100000 | |
| E77 | 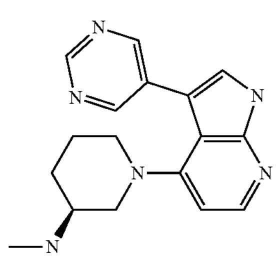 [SMILES: CN[C@H]1CCCN(c2ccnc3[nH]cc(-c4cncnc4)c23)C1] | | 10.5 | 378.8 | 248.5 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E225 | 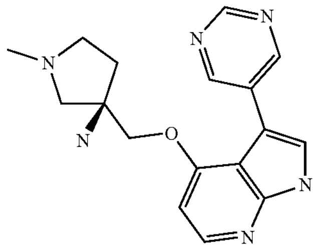 [SMILES: CN1CC[C@](N)(COc2ccnc3[nH]cc(-c4cncnc4)c23)C1] | | 11.45 | 189.8 | 139.7 |
| E61 | 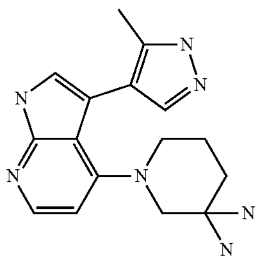 [SMILES: Cc1[nH]ncc1-c1c[nH]c2nccc(N3CCCC(N)(N)C3)c12] | | 11.5 | 93.2 | 68.3 |
| E127 | | | 11.58 | 174.7 | | |
| E241 | 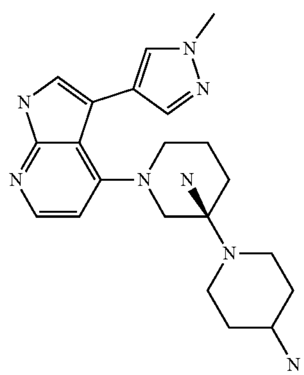 | | 11.9 | 542.6 | 224.1 |
| E82 | 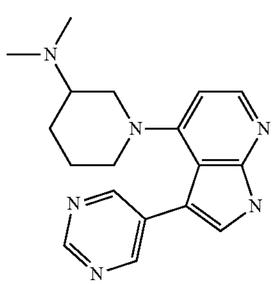 [SMILES: CN(C)C1CCCN(c2ccnc3[nH]cc(-c4cncnc4)c23)C1] | 17.2 | 13.125 | 647.5 | 361.7 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E60 | 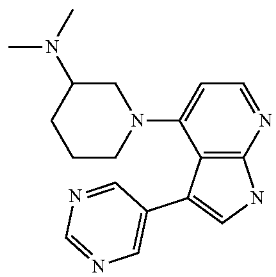 [SMILES: CN(C)C1CCCN(c2ccnc3[nH]cc(-c4cncnc4)c23)C1] | | 13.65 | 403.6 | 201.1 |
| E102 | 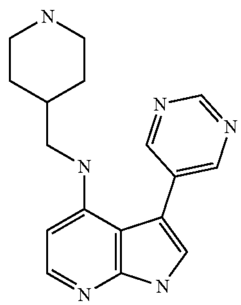 [SMILES: c1ncc(-c2c[nH]c3nccc(NCC4CCNCC4)c23)cn1] | | 13.95 | 38.18 | 51.2 |
| E85 | 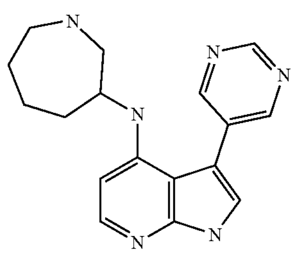 [SMILES: c1ncc(-c2c[nH]c3nccc(NC4CCCCNC4)c23)cn1] | | 14.104 | 421.3 | 459.5 |
| E64 | 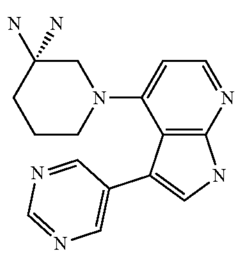 | | 14.8 | 166.4 | 390.1 |
| E4 | 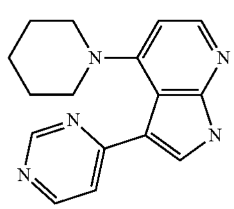 | | 15.47 | 28.3 | 19.7 |
| E31 | 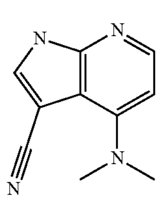 | 47.89 | 16.68 | 43.59 | 24.08 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E103 | 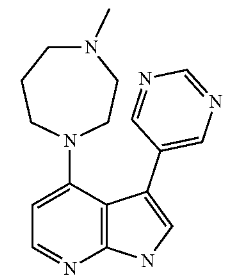 [SMILES: CN1CCCN(c2ccnc3[nH]cc(-c4cncnc4)c23)CC1] | | 18.7 | 252.1 | 160.8 |
| E182 | 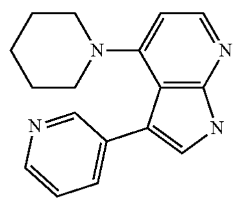 [SMILES: c1cncc(-c2c[nH]c3nccc(N4CCCCC4)c23)c1] | 9 | 18.821 | 132.3 | 90.04 |
| E242 | 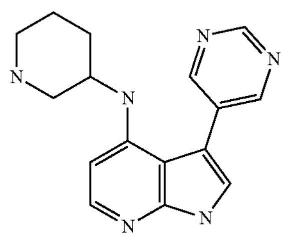 [SMILES: c1ncc(-c2c[nH]c3nccc(NC4CCCNC4)c23)cn1] | | 19.3 | 217.3 | 164.6 |
| E89 | 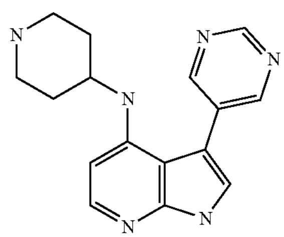 [SMILES: c1ncc(-c2c[nH]c3nccc(NC4CCNCC4)c23)cn1] | | 20.54 | 108.8 | 92.7 |
| E243 | 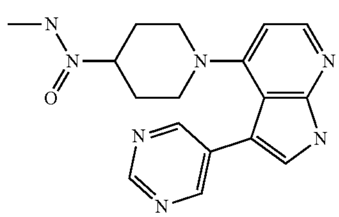 | | 20.95 | | |
| E101 | 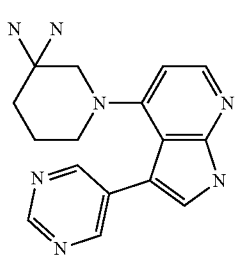 [SMILES: NC1(N)CCCN(c2ccnc3[nH]cc(-c4cncnc4)c23)C1] | | 22.5 | 567.1 | 362.6 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E75 | 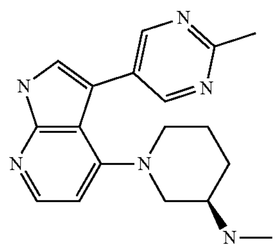 [SMILES: CN[C@@H]1CCCN(c2ccnc3[nH]cc(-c4cnc(C)nc4)c23)C1] | | 25.37 | 21690 | 6415 |
| E96 | 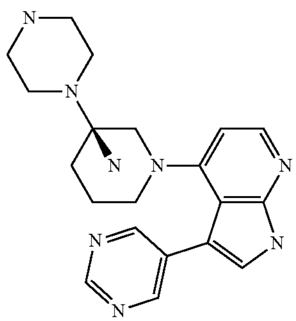 | | 28.8 | 1299 | 876.4 |
| E28 | 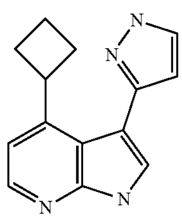 [SMILES: c1cc(C2CCC2)c2c(-c3cc[nH]n3)c[nH]c2n1] | | 29.4 | 14.4 | 9.8 |
| E39 | 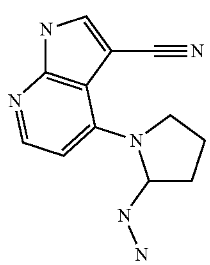 [SMILES: N#Cc1c[nH]c2nccc(N3CCCC3NN)c12] | | 29.7 | 102.8 | 86.8 |
| E125 | 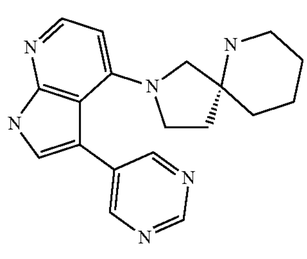 [SMILES: c1ncc(-c2c[nH]c3nccc(N4CC[C@]5(CCCCN5)C4)c23)cn1] | | 31.27 | 424.4 | |
| E2 | 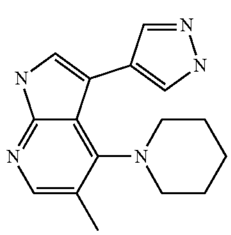 [SMILES: Cc1cnc2[nH]cc(-c3cn[nH]c3)c2c1N1CCCCC1] | 19.7 | 36.36 | 207.1 | 102.4 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E24 | 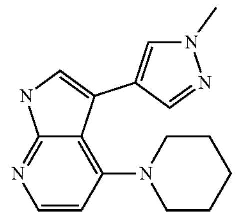 [SMILES: Cn1cc(-c2c[nH]c3nccc(N4CCCCC4)c23)cn1] | | 37.62 | 43.5 | 20.81 |
| E111 | 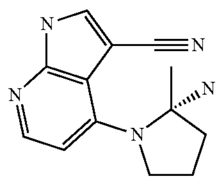 [SMILES: C[C@@]1(N)CCCN1c1ccnc2[nH]cc(C#N)c12] | 123.4 | 39.67 | 85.24 | 25.5 |
| E3 | 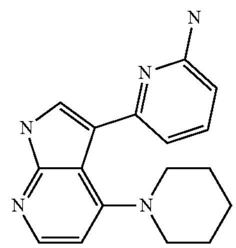 [SMILES: Nc1cccc(-c2c[nH]c3nccc(N4CCCCC4)c23)n1] | | 39.9 | 28.6 | 13.8 |
| E37 | 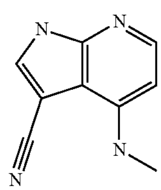 | 125.4 | 39.93 | 43.78 | 30.28 |
| E20 | 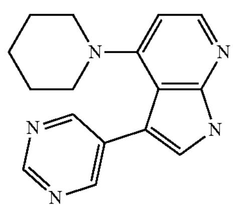 [SMILES: c1ncc(-c2c[nH]c3nccc(N4CCCCC4)c23)cn1] | 14.2 | 40.695 | 471.9 | 515.7 |
| E11 | 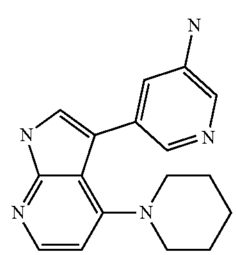 [SMILES: Nc1cncc(-c2c[nH]c3nccc(N4CCCCC4)c23)c1] | | 42.3 | 755.4 | 373.9 |
| E198 | 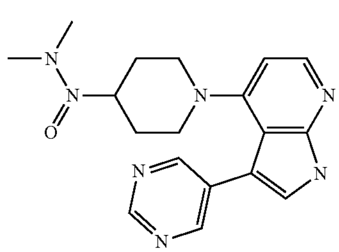 | | 42.91 | | |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E91 | 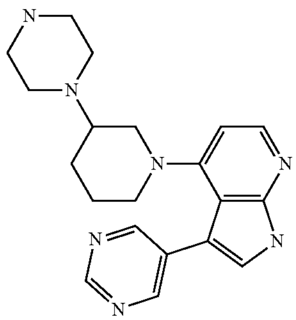 [SMILES: c1ncc(-c2c[nH]c3nccc(N4CCCC(N5CCNCC5)C4)c23)cn1] | | 49.5 | 230.7 | 162.7 |
| E222 | 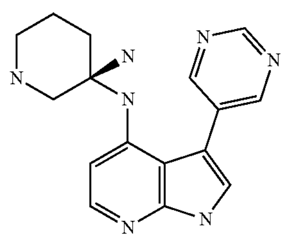 [SMILES: N[C@]1(Nc2ccnc3[nH]cc(-c4cncnc4)c23)CCCNC1] | 28.38 | 50.645 | 50879 | 50671.5 |
| E10 | 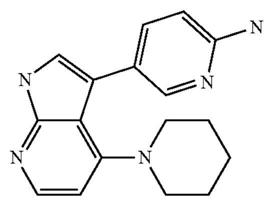 [SMILES: Nc1ccc(-c2c[nH]c3nccc(N4CCCCC4)c23)cn1] | | 51.8 | 74.9 | 45.7 |
| E34 | 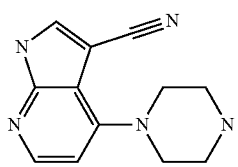 [SMILES: N#Cc1c[nH]c2nccc(N3CCNCC3)c12] | | 52.81 | 43.59 | 23.76 |
| E87 | 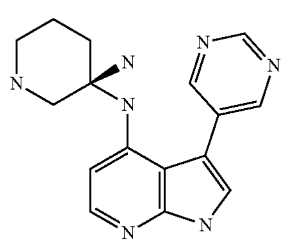 [SMILES: N[C@]1(Nc2ccnc3[nH]cc(-c4cncnc4)c23)CCCNC1] | 33.58 | 54.255 | 50269 | 325.5 |
| E15 | 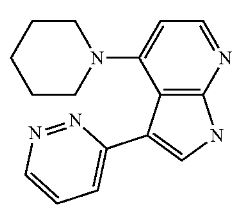 [SMILES: c1cnnc(-c2c[nH]c3nccc(N4CCCCC4)c23)c1] | | 56.52 | 482.5 | 362.2 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E26 | 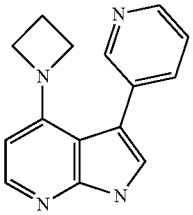 | | 57.6 | 545.1 | 262.8 |
| E16 | 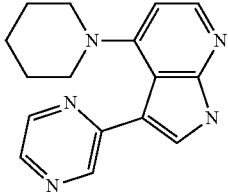 [SMILES: c1cnc(-c2c[nH]c3nccc(N4CCCCC4)c23)cn1] | | 61.8 | 504.1 | 158.6 |
| E1 | 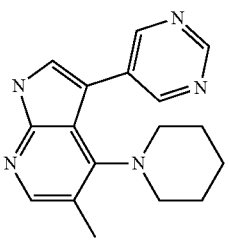 [SMILES: Cc1cnc2[nH]cc(-c3cncnc3)c2c1N1CCCCC1] | | 64.6 | 14950 | 6503 |
| E100 | 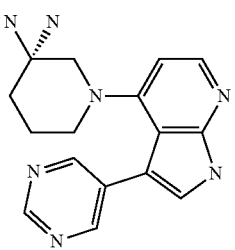 | | 71.3 | 504.7 | 277.2 |
| E36 | 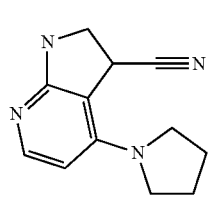 [SMILES: N#CC1CNc2nccc(N3CCCC3)c21] | 82.14 | 78.94 | 90.56 | 65.85 |
| E33 | 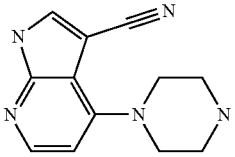 [SMILES: N#Cc1c[nH]c2nccc(N3CCNCC3)c12] | | 87.14 | 195.5 | 126.8 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E107 | 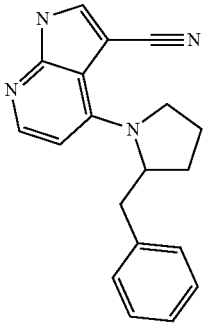 [SMILES: N#Cc1c[nH]c2nccc(N3CCCC3Cc3ccccc3)c12] | | 90.35 | 1883 | 2822 |
| E167 | 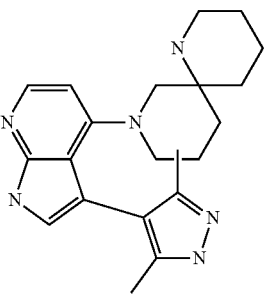 | | 108.1 | 100000 | |
| E113 | 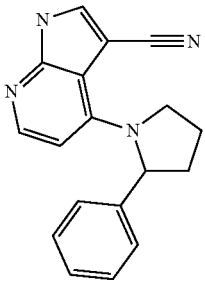 [SMILES: N#Cc1c[nH]c2nccc(N3CCCC3c3ccccc3)c12] | | 111.4 | 388 | 143.7 |
| E204 | 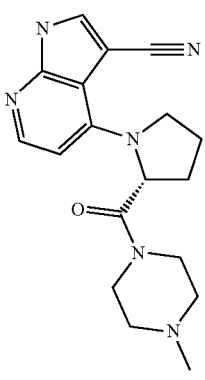 [SMILES: CN1CCN(C(=O)[C@H]2CCCN2c2ccnc3[nH]cc(C#N)c23)CC1] | | 118.9 | 557.6 | 762 |
| E180 | 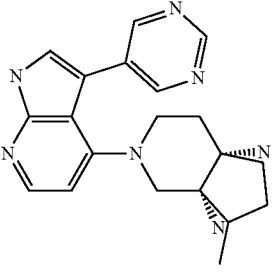 [SMILES: CC1CC[C@]2(N)CCN(c3ccnc4[nH]cc(-c5cncnc5)c34)C[C@]12N] | | 124.3 | 3420 | 1582 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E179 | 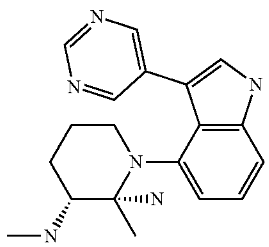 [SMILES: CN[C@@H]1CCCN(c2cccc3[nH]cc(-c4cncnc4)c23)[C@]1(C)N] | | 127.6 | 1289 | 1090 |
| E27 | 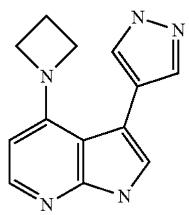 [SMILES: c1cc(N2CCC2)c2c(-c3cn[nH]c3)c[nH]c2n1] | | 129.5 | 712.6 | 381.1 |
| E23 | 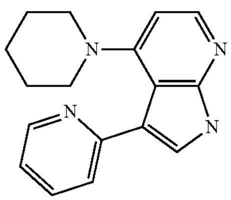 [SMILES: c1ccc(-c2c[nH]c3nccc(N4CCCCC4)c23)nc1] | | 134.4 | 1686 | 699.1 |
| E32 | 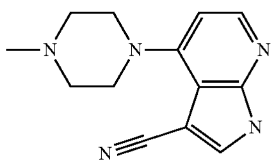 [SMILES: CN1CCN(c2ccnc3[nH]cc(C#N)c23)CC1] | | 146.6 | 237 | 164 |
| E201 | 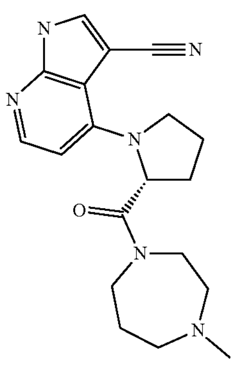 [SMILES: CN1CCCN(C(=O)[C@H]2CCCN2c2ccnc3[nH]cc(C#N)c23)CC1] | | 147.1 | 1045 | 702.6 |
| E25 | 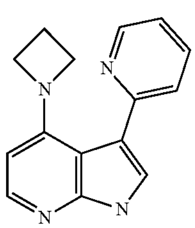 [SMILES: c1ccc(-c2c[nH]c3nccc(N4CCC4)c23)nc1] | | 178 | 10000 | 1502 |

TABLE 1-continued

| Example No. | Structure | MRCK-a Average Ki (nM) | MRCK-B Average Ki (nM) | ROCK1 Average Ki (nM) | ROCK2 Average Ki (nM) |
| --- | --- | --- | --- | --- | --- |
| E21 | 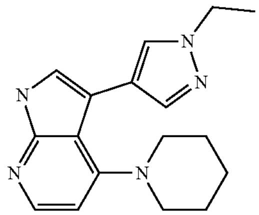 [SMILES: CCn1cc(-c2c[nH]c3nccc(N4CCCCC4)c23)cn1] | | 188.4 | 74.93 | 67.88 |
| E19 | 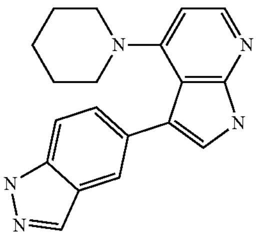 [SMILES: c1cc(N2CCCCC2)c2c(-c3ccc4[nH]ncc4c3)c[nH]c2n1] | | 213.3 | 143.8 | 114.6 |
| E104 | 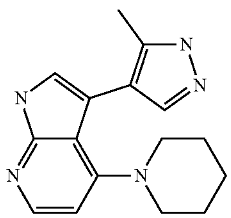 [SMILES: Cc1[nH]ncc1-c1c[nH]c2nccc(N3CCCCC3)c12] | | 222.1 | 302.9 | 197.6 |
| E40 | 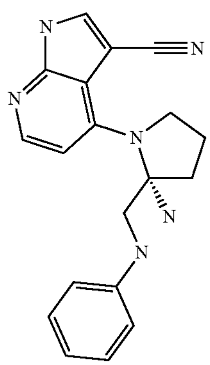 [SMILES: N#Cc1c[nH]c2nccc(N3CCC[C@@]3(N)CNc3ccccc3)c12] | | 247.4 | 2150 | 1073 |
| E70 | 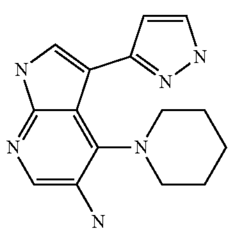 [SMILES: Nc1cnc2[nH]cc(-c3cc[nH]n3)c2c1N1CCCCC1] | | 345.8 | 1297 | 276.1 |
| E7 | 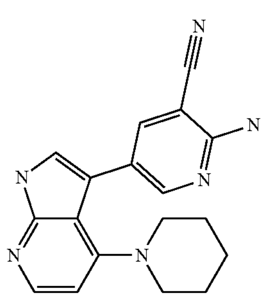 [SMILES: N#Cc1cc(-c2c[nH]c3nccc(N4CCCCC4)c23)cnc1N] | | 357.1 | 501 | 245 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E12 | 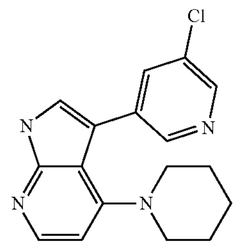 | | 366.2 | 2146 | 574.5 |
| E13 | 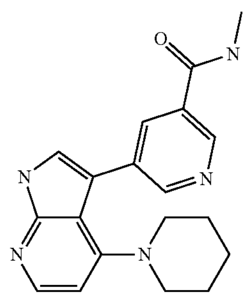 [SMILES: CNC(=O)c1cncc(-c2c[nH]c3nccc(N4CCCCC4)c23)c1] | | 378.3 | 10000 | 1745 |
| E8 | 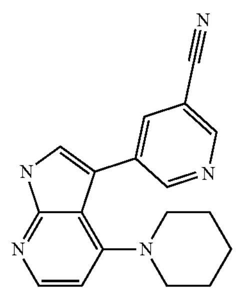 [SMILES: N#Cc1cncc(-c2c[nH]c3nccc(N4CCCCC4)c23)c1] | | 540.7 | 10000 | 3271 |
| E112 | 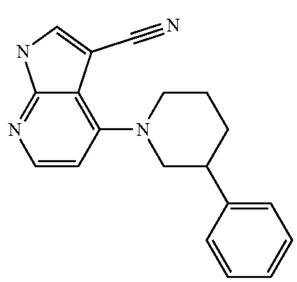 [SMILES: N#Cc1c[nH]c2nccc(N3CCCC(c4ccccc4)C3)c12] | | 558.5 | 681.5 | 727.5 |
| E22 | 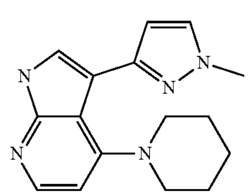 [SMILES: Cn1ccc(-c2c[nH]c3nccc(N4CCCCC4)c23)n1] | | 656 | 10000 | 3219 |

TABLE 1-continued
| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E17 | 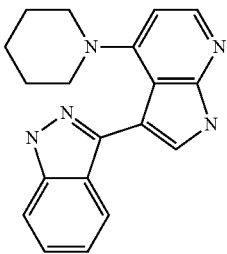 [SMILES: c1ccc2c(-c3c[nH]c4nccc(N5CCCCC5)c34)n[nH]c2c1] | | 696 | 10000 | 10000 |
| E203 | 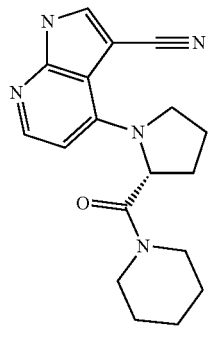 [SMILES: N#Cc1c[nH]c2nccc(N3CCC[C@@H]3C(=O)N3CCCCC3)c12] | | 804.1 | | |
| E106 | 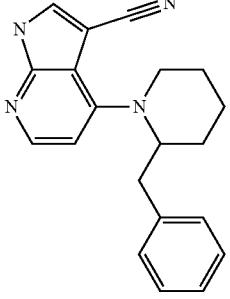 | | 805.4 | 10000 | 10000 |
| E18 | 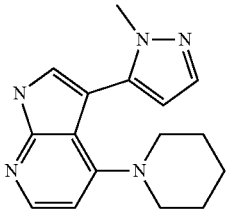 [SMILES: Cn1nccc1-c1c[nH]c2nccc(N3CCCCC3)c12] | | 817.6 | 10000 | 2480 |
| E76 | 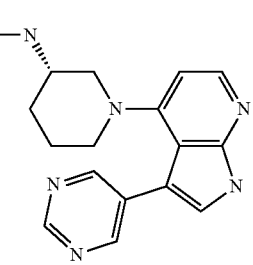 | | 870.8 | 32350 | 16760 |

TABLE 1-continued

| Example No. | Structure | MRCK-a Average Ki (nM) | MRCK-B Average Ki (nM) | ROCK1 Average Ki (nM) | ROCK2 Average Ki (nM) |
|---|---|---|---|---|---|
| E202 | 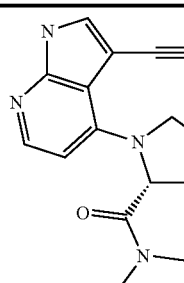 | | 991.8 | 10000 | 10000 |

MRCKβ, ROCK1 and ROCK2 Cellular Assays

MDA-MB-231 cells expressing doxycycline inducible ROCK1, ROCK2 or MRCKβ kinase domains were plated at $1.1 \times 10^5$ cells per well of a 12 well plate. After 24 hours, cells were treated with 1 μg/ml doxycycline for 18 hours to induce kinase domain expression and then tested over a suitable concentration range with compounds of the invention for 60 minutes. Cells were then washed with PBS and lysed with Tris-SDS lysis Buffer (50 mM Tris-HCl pH7.4, 0.5% (v/v) SDS, 1×PhosStop Inhibitors (04 906 837 001; Roche) and 1×Complete Protease Inhibitors (04 693 124 001; Roche)). Whole cell lysates were clarified by passing through QIAshredder spin columns, separated by SDS-PAGE, and quantitative immunoblotting performed using a LI-COR Odyssey IR scanner to determine pMLC (T18/S19) and α-Tubulin levels.

Table 2 provides the results of testing examples of the present invention in the cellular assays described above.

TABLE 2

| Example No. | Structure | Cellular assay - MRCK-b inhibition MEAN (μM) | Cellular assay - ROCK1 inhibition MEAN (μM) |
|---|---|---|---|
| E116 | 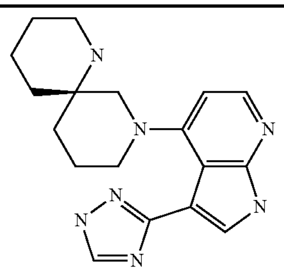 | 0.1424 | >30 |
| E120 | 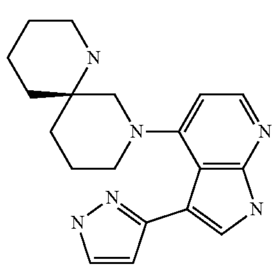 [SMILES: c1cc(N2CCC[C@@]3(CCCCN3)C2)c2c(-c3cc[nH]n3)c[nH]c2n1] | 0.0133 | 15.42 |

TABLE 2-continued

| Example No. | Structure | Cellular assay - MRCK-b inhibition MEAN (μM) | Cellular assay - ROCK1 inhibition MEAN (μM) |
|---|---|---|---|
| E117 | 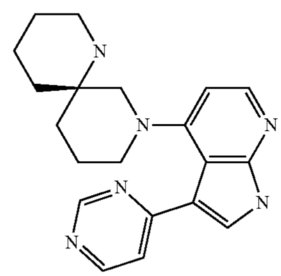 [SMILES: c1cc(-c2c[nH]c3nccc(N4CCC[C@@]5(CCCCN5)C4)c23)ncn1] | 0.0283 | 10.6 |
| E150 | 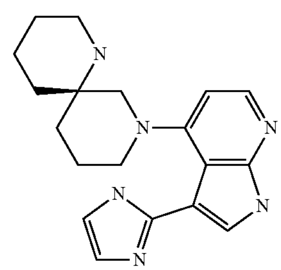 [SMILES: c1c[nH]c(-c2c[nH]c3nccc(N4CCC[C@@]5(CCCCN5)C4)c23)n1] | 0.0422 | >30 |
| E174 | 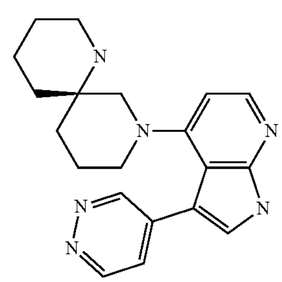 [SMILES: c1cc(-c2c[nH]c3nccc(N4CCC[C@@]5(CCCCN5)C4)c23)cnn1] | 0.0509 | 2.253 |

TABLE 2-continued

| Example No. | Structure | Cellular assay - MRCK-b inhibition MEAN (μM) | Cellular assay - ROCK1 inhibition MEAN (μM) |
| --- | --- | --- | --- |
| E206 | 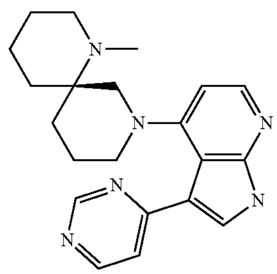 [SMILES: CN1CCCC[C@@]12CCCN(c1ccnc3[nH]cc(-c4ccncn4)c13)C2] | 0.138 | >30 |
| E133 | 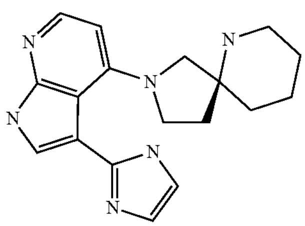 [SMILES: c1c[nH]c(-c2c[nH]c3nccc(N4CC[C@@]5(CCCCN5)C4)c23)n1] | 0.1075 | |
| E209 | 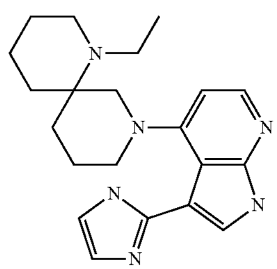 [SMILES: CCN1CCCCC12CCCN(c1ccnc3[nH]cc(-c4ncc[nH]4)c13)C2] | 0.1088 | >30 |
| E139 | 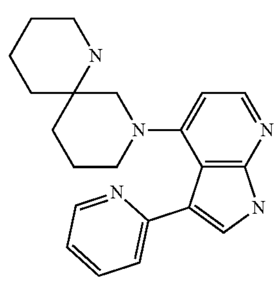 | 0.1071 | >30 |
| E207 | 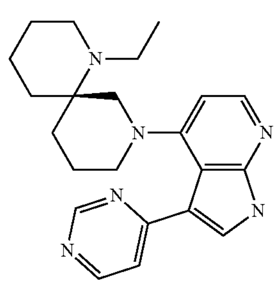 [SMILES: CCN1CCCC[C@@]12CCCN(c1ccnc3[nH]cc(-c4ccncn4)c13)C2] | 0.1704 | >30 |

TABLE 2-continued

| Example No. | Structure | Cellular assay - MRCK-b inhibition MEAN (μM) | Cellular assay - ROCK1 inhibition MEAN (μM) |
| --- | --- | --- | --- |
| E146 | 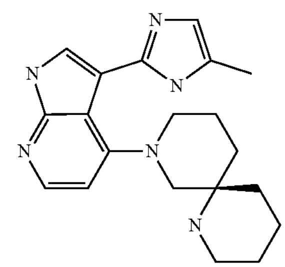 [SMILES: Cc1cnc(-c2c[nH]c3nccc(N4CCC[C@@]5(CCCCN5)C4)c23)[nH]1] | 0.1499 | >30 |
| E126 | 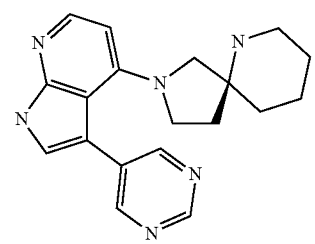 [SMILES: c1ncc(-c2c[nH]c3nccc(N4CC[C@@]5(CCCCN5)C4)c23)cn1] | 1.268 | >30 |
| E131 | 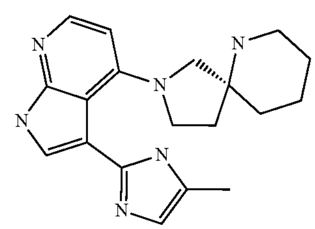 [SMILES: Cc1cnc(-c2c[nH]c3nccc(N4CC[C@@]5(CCCCN5)C4)c23)[nH]1] | 0.3185 | >30 |
| E210 | 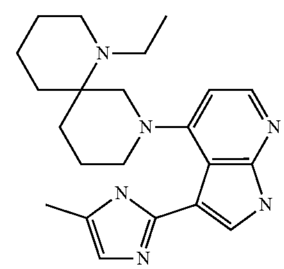 [SMILES: CCN1CCCCC12CCCN(c1ccnc3[nH]cc(-c4ncc(C)[nH]4)c13)C2] | 0.7012 | >30 |
| E171 | 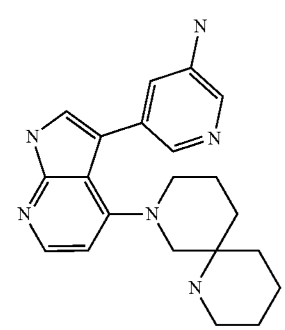 [SMILES: Nc1cncc(-c2c[nH]c3nccc(N4CCCC5(CCCCN5)C4)c23)c1] | 0.233 | |

TABLE 2-continued
| Example No. | Structure | Cellular assay - MRCK-b inhibition MEAN (μM) | Cellular assay - ROCK1 inhibition MEAN (μM) |
|---|---|---|---|
| E168 | 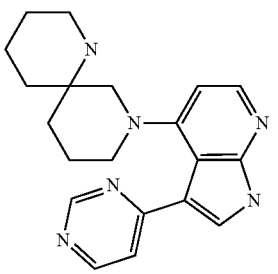 | <0.03 | |
| E128 | 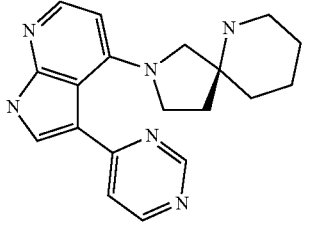 | 0.4204 | |
| E114 | 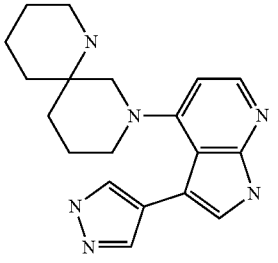 [SMILES: c1cc(N2CCCC3(CCCCN3)C2)c2c(-c3cn[nH]c3)c[nH]c2n1] | 0.0405 | |
| E155 | 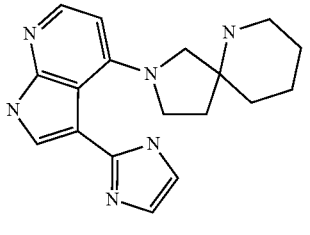 [SMILES: c1c[nH]c(-c2c[nH]c3nccc(N4CCC5(CCCCN5)C4)c23)n1] | 0.2185 | |
| E177 | 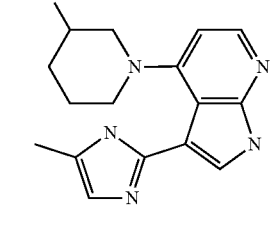 | 0.2735 | >30 |
| E236 | 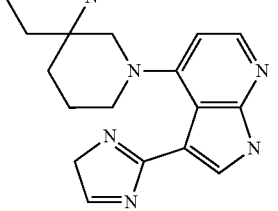 | 0.1451 | >30 |
| E176 | 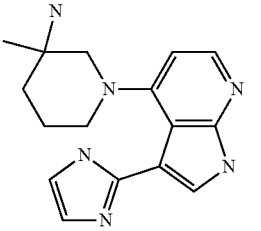 [SMILES: CC1(N)CCCN(c2ccnc3[nH]cc(-c4ncc[nH]4)c23)C1] | 0.2548 | |
| E170 | 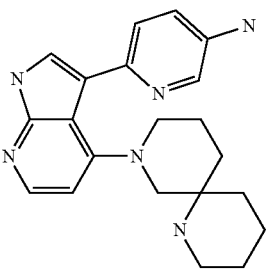 | 0.6116 | |
| E169 | 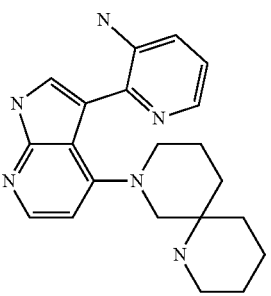 [SMILES: Nc1cccnc1-c1c[nH]c2nccc(N3CCCC4(CCCCN4)C3)c12] | 0.7324 | |
| E136 | 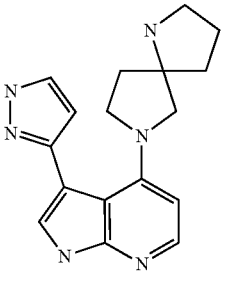 [SMILES: c1cc(N2CCC3(CCCN3)C2)c2c(-c3cc[nH]n3)c[nH]c2n1] | 0.4566 | >30 |
| E66 | 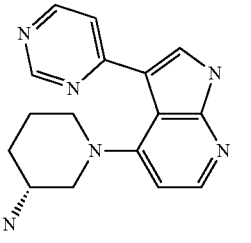 | 1.777 | |

TABLE 2-continued

| Example No. | Structure | Cellular assay - MRCK-b inhibition MEAN (μM) | Cellular assay - ROCK1 inhibition MEAN (μM) |
|---|---|---|---|
| E187 | 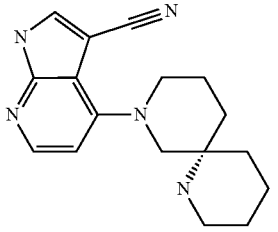 [SMILES: N#Cc1c[nH]c2nccc(N3CCC[C@@]4(CCCCN4)C3)c12] | 0.782 | >30 |
| E178 | 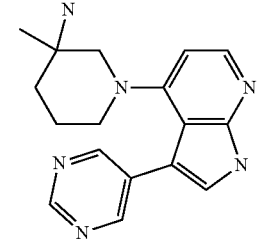 [SMILES: CC1(N)CCCN(c2ccnc3[nH]cc(-c4cncnc4)c23)C1] | 0.6222 | |
| E212 | 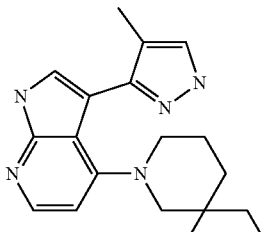 | 0.426 | 14.35 |
| E142 | 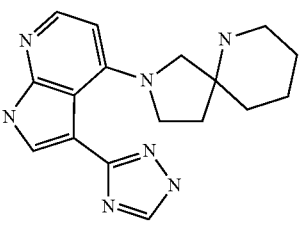 [SMILES: c1cc(N2CCC3(CCCCN3)C2)c2c(-c3nc[nH]n3)c[nH]c2n1] | 1.215 | >30 |
| E129 | 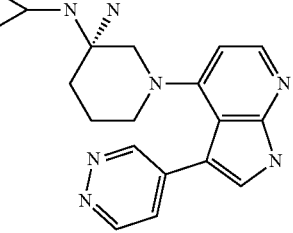 | 0.7286 | |
| E46 | 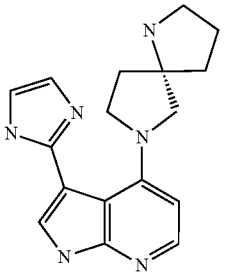 | 1.54 | |
| E134 | 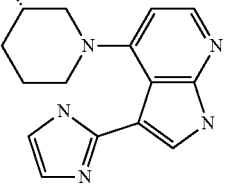 | 0.7871 | >30 |
| E47 | 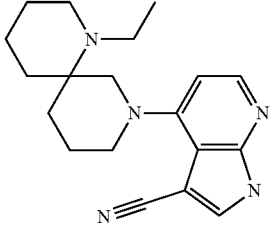 [SMILES: CCN1CCCCC12CCCN(c1ccnc3[nH]cc(C#N)c13)C2] | 1.531 | |
| E211 | 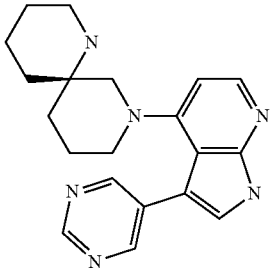 [SMILES: c1ncc(-c2c[nH]c3nccc(N4CCC[C@@]5(CCCCN5)C4)c23)cn1] | 0.9525 | >30 |
| E122 | | 0.1014 | >30 |

In Vitro Selectivity Profiles

Ten point dose response curves (starting from a specific concentration 1/3 dilution) were used to generate $IC_{50}$ values for the E150 and E117 compounds against the kinase targets listed in tables 3 and 4 below.

Commercially available assays were used for CDK1/cyclin B, CDK2/cyclin A, PKCα, PKCγ (Z'-LYTE® assay;

Life Technologies) and CDK9/cyclin T1 (ADAPTA® assay; Life Technologies) dose response curves.

Table 3 shows the results of testing example E150 of the present and Table 4 shows the results of testing E117 (BDP9066).

TABLE 3

Example compound E150 selectivity in vitro.
(ND = not determined)

| Kinase | $IC_{50}$ | $K_m$ ATP (µM) | $K_i$ (nM) | Fold selectivity |
|---|---|---|---|---|
| MRCKβ | 6.9 | 1 | 1.15 | 1 |
| CDK1/cyclin B | >5000 | 34 | ND | ND |
| CDK2/cyclin A | >5000 | 31 | ND | ND |
| CDK9/cyclin T1 | 532 | 32 | 299 | 260 |
| PKCα | 125 | 37 | 50 | 43.5 |
| PKCγ | 197 | 25 | 98.5 | 85.7 |
| ROCK1 | 406 | 3.1 | 251 | 218 |
| STK22D | 4360 | 9.0 | 2065 | 1796 |

TABLE 4

Example compund E117 (BDP9066) selectivity in vitro.

| Kinase | $IC_{50}$ (nM) | $K_m$ ATP (µM) | $K_i$ (nM) | Fold selectivity |
|---|---|---|---|---|
| MRCKβ | 8.3 | 1 | 1.38 | 1 |
| CDK1/cyclin B | 845 | 34 | 487 | 353 |
| CDK2/cyclin A | 299 | 31 | 166 | 120 |
| CDK9/cyclin T1 | 67 | 32 | 38.1 | 27.6 |
| PKCα | 299 | 37 | 178 | 129 |
| PKCγ | 998 | 25 | 499 | 362 |
| ROCK1 | 141 | 3.1 | 54.0 | 39 |
| STK22D | 287 | 9.0 | 136 | 99 |

In Viva Action of Example Compound E117 (Also Referred to as BDP9066) on Mouse Skin Cancer
Mouse Models Parental MDA MB 231 D3H$_2$LN Luc cells or MRCKαβ KO cells (3.5×106) were subcutaneously injected in the right flank of CD-1 immunocompromised nude mice. Mice were culled and sampled 2 weeks post-injection before tumors reached 12 mm diameters.

Mouse genetic skin cancer models expressing activated Hras alone, or with c-Fos plus conditional deletion of Pten, in epidermal keratinocytes form papillomas that convert to carcinoma as described [Greenhalgh et al., Mol Carcinog 1993; 7:99-110; Yao et al., J Cell Sci 2008; 121:1758-69; Macdonald et al., Oncogene 2014; 33:4132-43].

To study the effect of E117/BDP9066 on MRCKα pS1003 staining in mouse skin, 5 FVB mice were treated topically with 50 µL of 80% (v/v) DMSO (vehicle) and 5 FVB mice were treated topically with of 25 µg of E117/BDP9066 in 50 µL 80% (v/v) DMSO. Treatments were applied 4 times per mouse over 2 days. Mice were culled 2 hours after final treatment. Skin and blood E117/BDP9066 concentrations were measured by Pharmidex. To study E117/BDP9066 pharmacokinetics on mouse skin and blood, FVB mice were treated topically once with 10 µg or 25 µg E117/BDP9066 in 80% (v/v) DMSO, 4 times daily with 25 µg E117/BDP9066 in 80% (v/v) DMSO, or 8 times daily (4 successive days on, 2 days off, then 4 days on) with 80% (v/v) DMSO or 25 µg E117/BDP9066 in 80% (v/v) DMSO. Mice were culled 2 hours, 4 hours, 8 hours or 24 hours after final treatment. Skin and blood E117/BDP9066 concentrations were measured by Pharmidex.

For DMBA/TPA experiments, 40 FVB mice were treated topically with 25 µg DMBA in acetone on day 1. From day 5, 4.7 µg TPA in acetone was applied 3 times weekly. From day 5, 20 mice were treated with 25 µg E117/BDP9066 in 50 µL 80% (v/v) DMSO and 20 mice were treated with 50 µL 80% (v/v) DMSO 5 times per week. Experimenters were fully blinded to the identity of treatment groups. Mice weights and general conditions were monitored at least 2 times per week, tumor sizes and numbers were recorded weekly. Mice were culled when papillomas reached 12 mm in diameter. Analysis of tumor volume and papilloma numbers were performed blinded to the identity of treatment groups. Skin and blood E117/BDP9066 concentrations were measured by Pharmidex.

Statistics

Data analysis was performed using GraphPad Prism. Statistical tests used for each data set are indicated in respective figure legends.

Results

The results are shown in FIGS. 1A to 1K, which show the results obtained following the in vivo application of Example compound E117 (referred to as BDP9066 in the Figures) in the DMBA/TPA mouse model of squamous cell carcinoma.

FIG. 1: (A) Topical application of 4×25 µg E117/BDP9066 over 2 days to dorsal skin led to measurable drug levels in the skin that were significantly higher than in blood. Results shown are means±SD from 5 independent mice, each indicated by a data point. Two-tailed Mann-Whitney test of significance (**=p<0.01). (B) Representative MRCKα pS1003 immunohistochemical staining of mouse skin sections (left) topically treated with DMSO or 4×25 µg E117/BDP9066 over 2 days. Scale bars represent 100 µm. Topical administration of E117/BDP9066 (square dots) led to significant reduction in positive epidermal staining for MRCKα pS1003. Results shown are means±SD from 5 independent mice per condition, each indicated by a data point. Two-tailed Mann-Whitney test of significance (*=p<0.05). (C). Skin (left) or blood (right) E117/BDP9066 concentrations following topical administration of a single 10 µg dose or 4×25 µg doses of E117/BDP9066 over 2 days. Results shown are means±SD from 3 independent mice per condition, each indicated by a data point. (D) Skin (left) or blood (right) E117/BDP9066 concentrations following topical administration of a single 25 µg dose (pink/light dots) or 8×25 µg doses of E117/BDP9066 (red/dark dots; 4 days on, 2 days off, 4 days on) at indicated times after final administration. Results shown are means±SD from 3 independent mice per condition, each indicated by a data point. (E) Timeline of DMBA (green arrow), TPA (purple arrow), DMSO (black arrow) or E117/BDP9066 (red arrow) administration, with each day represented by a rectangle. (F) Representative images of cagemate DMBA/TPA treated mice with topical application of DMSO or E117/BDP9066 as indicated. (G) Total endpoint papilloma numbers per mouse. Results shown are means±SD from 20 independent mice per condition, each indicated by a data point. (H) Total tumor volume (left) and average papilloma volume (right) per mouse. Results shown are means±SD from 20 independent mice per condition, each indicated by a data point. Two tailed unpaired t-tests were used to determine significance (*=p<0.05). (I) Blood and skin E117/BDP9066 concentrations at endpoint. Results shown are means±SD from 3 independent mice for blood and 10 mice for skin, each indicated by a data point. Two-tailed Mann-Whitney test of significance (**=p<0.001). (J) Representative MRCKα pS1003 staining of DMBA/TPA skin sections treated topically with DMSO or E117/BDP9066. Scale bars represent 100 μm. (K). Cytoplasmic histoscores of MRCKα pS1003 staining of DMBA/TPA treated skin (left) or papilloma (right) sections that had been administered DMSO (black dots) or E117/BDP9066 (red dots). Results shown are means±SD from 19 independent mice per condition, each indicated by a data point. Two tailed unpaired t-tests were used to determine significance (*=p<0.05).

Discussion

E117/BDP9066 was evaluated for in vivo pharmacological proof-of-concept as an SCC chemotherapeutic agent. Topical application of 25 μg E117/BDP9066 on FVB mouse skin twice per day for 2 days led to 26 μM mean E117/BDP9066 concentration in skin, but only 0.04 μM in blood (FIG. 1A). E117/BDP9066 application led to significantly reduced epidermal MRCKα pS1003 positive staining (FIG. 1B). To determine how repeated dosing would affect E117/BDP9066 accumulation and distribution, skin and blood concentrations were determined after 10 μg was administered once, or 25 μg was repeated over 4 days (FIG. 1C). Although relative to the single 10 μg dose, repeated 25 μg doses did result in 2.8 fold higher concentrations in skin (FIG. 1C, left panel), and 4 fold higher concentrations in blood (FIG. 1C, right panel), these differences were less than the 10 fold difference in total E117/BDP9066 administered, indicating that compound accumulation was less than additive. To characterize clearance, E117/BDP9066 was either given once at a 25 μg dose, or 8 times on a 4 days on, 2 days off, 4 days on schedule, and then compound concentrations were determined in skin and blood at 2, 4, 8 and 24 hours following the final dose. In either dosing regimen, over 16 μM E117/BDP9066 was detected in skin 24 hours after final dosing (FIG. 1D, left panel), while the low levels detected in blood were undetectable after 24 hours (FIG. 1D, right panel). These results indicated that it was possible to achieve sustainable E117/BDP9066 levels in mouse skin by repeated topical application, which were sufficient to induce phenotypic responses in squamous cell carcinoma cells in vitro, without significant compound accumulation following sequential administration.

FVB mice were then topically treated with 25 μg DMBA (FIG. 1E, green arrow), then with 4.7 μg TPA 3 times per week (FIG. 1E, purple arrow). In addition, mice were topically treated with 25 μg E117/BDP9066, or an equal volume of DMSO vehicle control (FIG. 1E, red arrow), 5 times per week (5 days on, 2 days off) for 14 weeks. At study end, skin papillomas in the E117/BDP9066 treated group appeared visually smaller than in the DMSO treated group (FIG. 1F). Although total papilloma numbers per mouse were not different between the DMSO and E117/BDP9066 treatment groups (FIG. 1G), both the total tumor volume (FIG. 1H, left panel) and average papilloma volume (FIG. 1H, right panel) per mouse were significantly reduced in the E117/BDP9066 treatment group. Topical E117/BDP9066 application resulted in undetectable compound in blood, and >1 μM mean E117/BDP9066 concentration in skin at experimental endpoint (FIG. 1I), which was associated with significant decreases in MRCKα pS1003 immunohistochemistry staining (FIG. 1J) and reduced histoscores both in the treated skin area (FIG. 1K, left panel) and in papillomas (FIG. 1K, right panel). These results provide pharmacological proof-of-concept evidence indicating in vivo therapeutic actions of E117/BDP9066.

Inhibition of Radiation Driven, MRCK Dependent GBM Cell Invasion by Treatment with Example Compound E117 (BDP9066) In Vitro and In Vivo In Vitro Models Cells were irradiated using an Xstrahl RX225 radiation cabinet (195 kV X-rays, dose rate 1.39 Gy/minute). For sub confluent migration assays, 2×105 cells per well were plated at in 6 well dishes and migration imaged by timelapse microscopy capturing images every 15 mins. Migration velocity was calculated using single cell tracking via ImageJ analysis. For ex vivo migration assays, cell were seeded onto fresh 1 mm coronal brain slices obtained from 6-8 week old C57BL/6 mice in culture medium (described above) and allowed to establish overnight with incubation at 37° C., 5% $CO_2$. Brain slices were then inverted onto Lumox 35 mm dishes (8 μm, Sarstedt) and secured with Nucleport Track-Etch membrane (Whatman) sealed with Matrigel. Migration was captured via confocal timelapse microscopy with images taken every 15 mins. Migration velocity was calculated using single cell tracking via ImageJ analysis.

Mouse Models

Female CD1 nude mice were orthotopically injected with 1×105 G7 or U87MG cells into the subventricular zone as previously described (16, 17). Tumours were allowed to establish for before magnetic resonance imaging (MRI) to confirm presence of tumour. Radiation treatments were conducted using an XSrtahl Small Animal Radiation Research Platform (SARRP). 5 mg/kg BDP-9066 or vehicle (20% propylene glycol/80% PBS) was given subcutaneously twice daily or at stated time before cull for PK analysis. Tumours were sub-dissected and fresh frozen specimens sent for PK analysis (Vertex, UK). Formalin fixed, paraffin embedded sections were stained for Ki67, HLA or phosphoMYPT1 then scanned using a Hamamatsu Nanozoomer Slide scanning machine with Leica SlidePath Slide imaging software. Algorithms were optimised for each stain individually and automated, quantitative analysis undertaken. The defining of contralateral regions was performed blinded.

Statistics

Data analysis was performed using GraphPad Prism. Statistical tests used for each data set are indicated in respective figure legends.

Results

The results are shown in FIGS. 2 to 6, which show the activation of MRCK driven motility by radiotherapy (RT) and its inhibition by treatment with Example compound E117 in vitro and in vivo.

FIG. 2. The downstream targets of MRCK, MYPT1 and MLC2, are phosphorylated in response to radiation and is concomitant with an increase in GBM cell motility in vitro and in vivo. (A) Two primary cell lines, E2 and G7, were treated with 0, 2 or 5 Gy and protein lysates extracted after 24 hours. Western blot analysis was undertaken to assay levels of pMYPT1. Actin and tubulin were used as loading controls and $\gamma$-$H_2AX$ as a marker of radiation induced DNA damage. (B) (i) E2 cells were treated with 0 or 2 Gy and stained by immunofluorescence for pMLC2. Cells were imaged using an Operetta high-throughput imaging platform. Green: pMLC2; yellow: actin; red: whole cell dye; blue: DAPI; Scale bar: 100 μm. (ii) Automated image analysis was undertaken to compare pMLC2 levels in control and irradiated cells. Data are derived from two biological repeats, each analysing >400 cells per condition. Statistical analysis: two tailed, unpaired t test. ****p<0.0001 (C) Cohorts of mice bearing G7 intracranial tumours were subjected to 3×2 Gy fractions of whole brain irradiation or left untreated. Brain sections were stained by IHC for pMYPT1 levels (i). Levels of nuclear and cytoplasmic pMYPT1 were quantified by automated analysis using SlidePath; n=5 (no RT) and 6 (3×2 Gy). Scale bar: 100 μm.

Statistical analysis: two tailed, unpaired t test. N.S.=not significant, *p<0.05. (D) E2 and G7 were treated with 0 or 2 Gy and their motility analysed in a sub-confluent migration assay using time-lapse microscopy and single cell tracking. (i) Example track plots of individual control and irradiated cells. (ii) Comparison of control and irradiated cell speed. (E) Fluorescently labelled E2 or G7 cells were irradiated with 2 Gy or left untreated and seeded onto fresh murine brain slices. Cell motility was analysed using confocal time-lapse microscopy (i). (ii) Cell speed was measured using single cell tracking. Data from 3 biological replicates. Scale bar: 50 µm Statistical analysis: Mann-Whitney test, p<0.005, p<0.0001. (F) (i) Brain sections from control and irradiated mice bearing G7 intracranial tumours were stained via IHC for Ki67 to indicate presence of cycling GBM tumour cells. (ii) % Ki67 positive cells in the tumour bulk were quantified using automated analysis in specimens from mice culled 10 days after initiation of treatment; n=6 in both cohorts. (ii) The percentage of Ki67 positive cells in the contralateral hemisphere of mice culled 17 days after initiation of treatment was quantified using automated image analysis. Scale bar: 1 mm. Statistical analysis: two tailed, unpaired t test. N.S.=not significant, p<0.005.

FIG. 3. Inhibition of MRCK activity opposes radiation driven motility. (A) G7 cells were transfected with siRNAs targeting MRCKα and MRCKβ, alone or in combination. (i) Cell lysates were analysed by Western blotting for MRCKα, MRCKβ and pMYPT1 levels. (B) Treated cells were exposed to 0 Gy or 2 Gy and imaged in a sub-confluent migration assay. Cell speed was measured by single cell tracking. Statistical analysis: Mann-Whitney test, N.S.=not significant, *<p 0.05, p<0.005, *p<0.001 (C) E2 and G7 cells were exposed to 0 Gy or 2 Gy radiation in the presence of DMSO or BDP-9066 and cell speed measured in a subconfluent migration assay using timelapse microscopy and single cell tracking. Data from 3 biological replicates. (D) Fluorescently labelled E2 cells were exposed to 0 Gy or 2 Gy radiation and seeded onto fresh murine brain slices. Cell motility was assayed in the presence of DMSO or BDP-9066 by confocal timelapse microscopy and single cell tracking using ImageJ. Data from 3 biological replicates. For all in vitro and ex vivo motility assays statistical analysis was performed using Mann-Whitney test: N.S.=not significant, *<p 0.05, p<0.005, *p<0.001, ****p<0.0001. (E) E2 and G7 cells were exposed to 2 Gy in the presence of increasing amounts of BDP-9066 followed by time-lapse microscopy and single cell tracking. Baseline value of 34% was calculated from the average of 10 non-motile, non-irradiated cells. Data from 3 biological replicates.

FIG. 4. BDP-9066 does not affect cell survival at anti-invasive concentrations but induces a robust dose dependent response in biomarker and morphological assays in cells treated with irradiation. (A) Cell viability assays performed on G7 cells treated with increasing concentrations of BDP-9066; data plotted relative to vehicle control. (B) Clonogenic survival assays performed on G7 and E2 cells irradiated in the presence of vehicle or 0.1 µM BDP-9066. N.S.=not significant. (C) E2 cells treated with 2 Gy radiation (i) or 0 Gy (ii) in the presence of increasing amounts of BDP-9066, and stained by immunofluorescence for pMLC2. Cells were imaged using an Operetta high-throughput imaging platform. Automated image analysis was used to compare pMLC2 levels. Data from two biological repeats with >400 cells per condition per biological replicate. Data plotted as a percentage of vehicle. (D) E2 cells were exposed to 0 or 2 Gy radiation in the presence of DMSO or BDP-9066. Cells were imaged using an Operetta high-throughput imaging platform. Red: actin, blue: DAPI, Scale bar: 100 µm. Automated image analysis was undertaken to quantify changes in neurite morphology. Data from >1000 cells.

FIG. 5. BDP-9066 penetrates intracranial GBM xenografts and inhibits radiation induced infiltration of GBM cells in vivo and activation of MRCK biomarker. (A) Mice bearing U87MG (i) or G7 (ii) intracranial tumours were injected subcutaneously with 5 mg/Kg BDP-9066 30 mins prior to cull. Tumours were sub-dissected from normal brain tissue and analysed by mass spectrometry to determine total compound levels ('Total'). These levels were adjusted using a determined PPB free value of 72.7% to estimate available BDP-9066 levels in the tumours ('Free'); n=4 (U87MG) and 10 (G7); CL=contralateral. (B) Outline of experiment to measure in vivo GBM cell response to BDP-9066. G7 intracranial tumours were allowed to establish for 12 weeks before initiation of treatment. The study was randomised and blinded. (C) Cohorts of mice from (B) were culled and excised brains subjected to IHC for Ki67 followed by automated analysis to determine extent of contralateral hemisphere invasion by GBM cells. Scale bar: 1 mm. Statistical analysis: two tailed, unpaired t test. *p<0.05. (D) Brain sections were stained by IHC for pMYPT1 levels (i). Levels of nuclear and cytoplasmic pMYPT1 were quantified by automated analysis using SlidePath. Statistical analysis: two tailed, unpaired t test. *p<0.05.

Figure 6A:
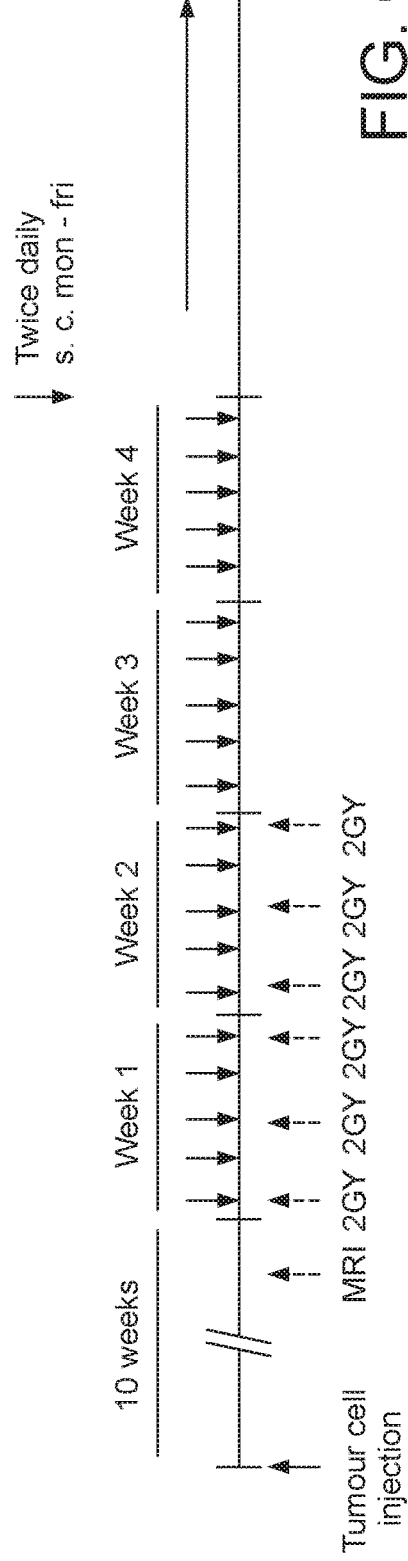
Figure 6B:
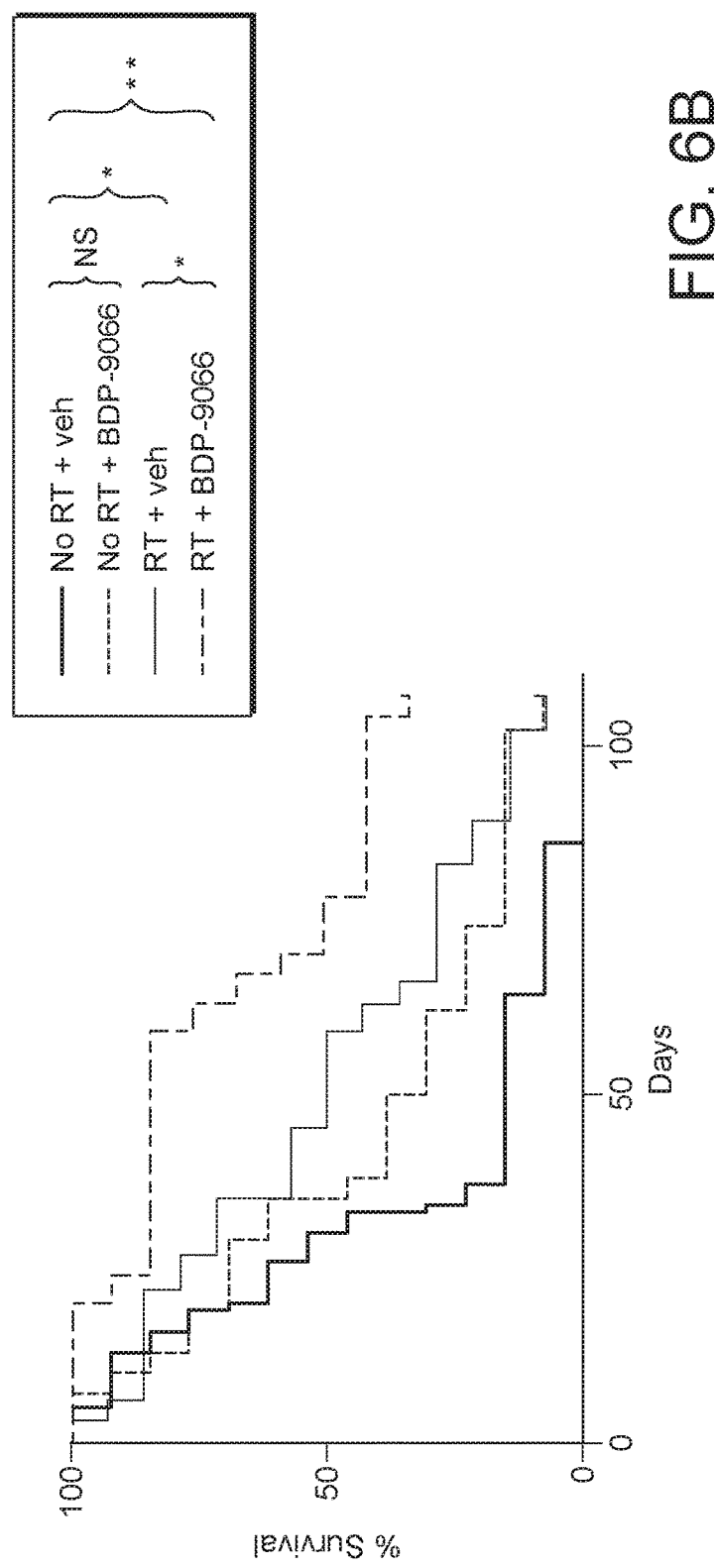

FIG. 6. Combining BDP-9066 with RT confers a significant survival advantage on mice bearing intracranial GBM tumours. (A) Outline of experiment to measure in vivo survival to BDP-9066 treatment. G7 intracranial tumours were allowed to establish for 10 weeks before initiation of treatment. Mice in the RT cohorts received 6×2 Gy whole brain RT over the course of two weeks. Only mice that were culled after the first 3 fractions of RT were included in the analysis to allow for any treatment benefit to take effect. The study was randomised, blinded and the mice stratified across the cohorts based on starting tumour size as assessed by T2 MRI. (B) Kaplan-Meier plot showing survival data. N.S.=not significant, *<p 0.05, **p<0.005. Statistical analysis: Log-rank (Mantel-Cox) test.

Discussion

Figure 2A:
Figure 2B:
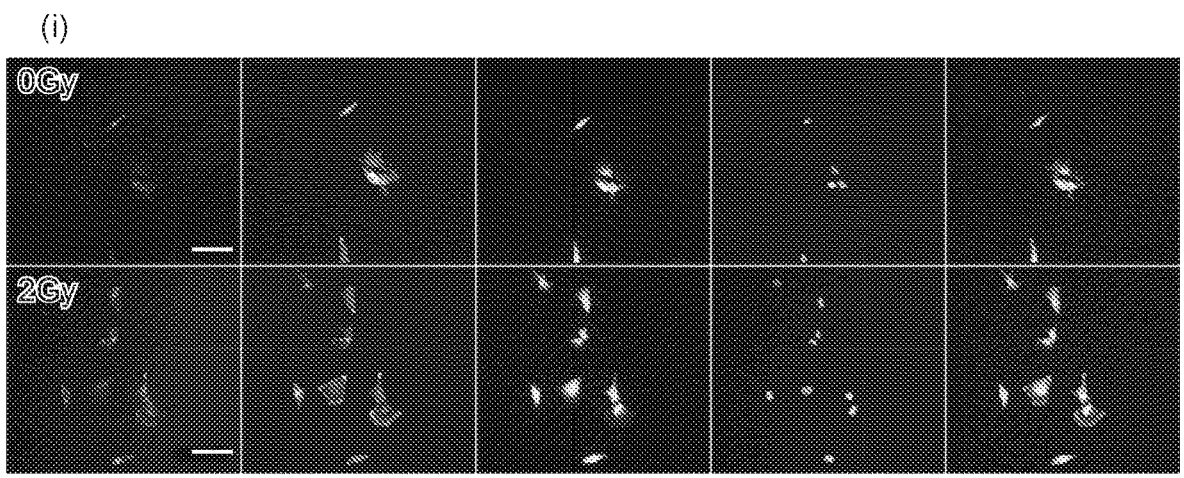
Figure 2B:
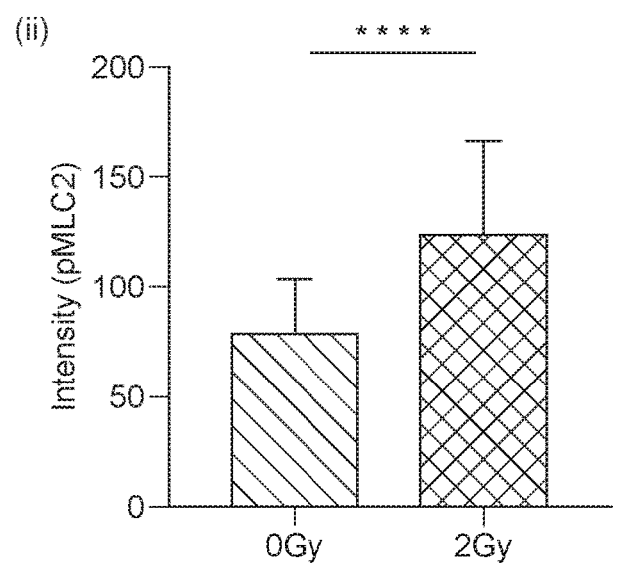
Figure 2E:
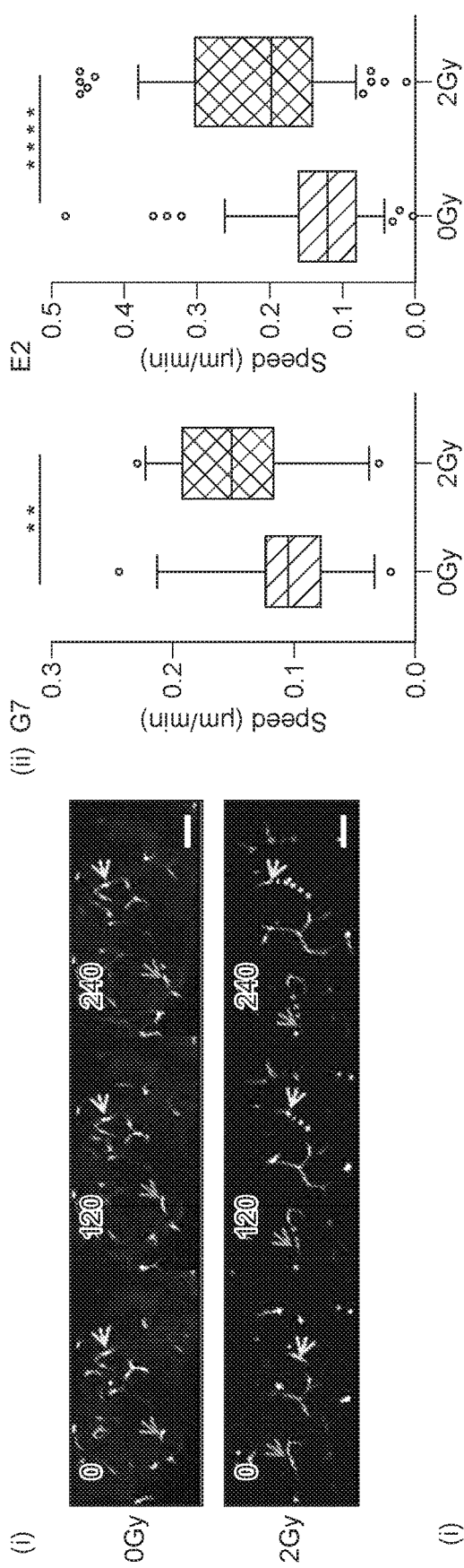
Figure 2F:
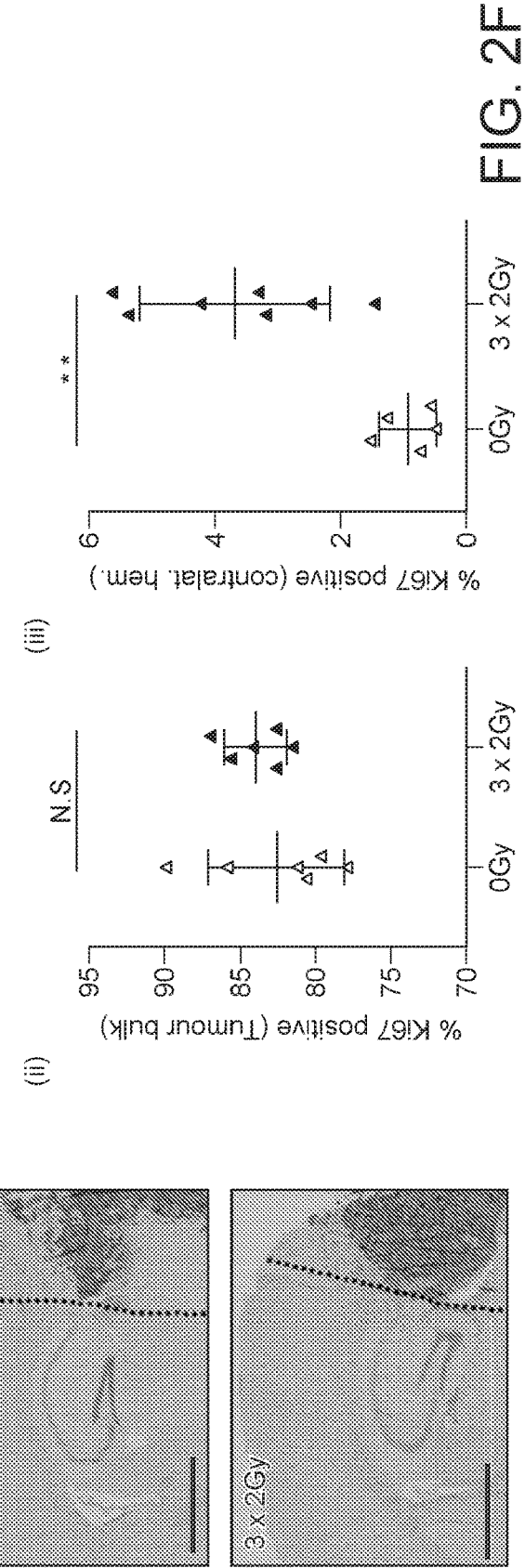

The downstream targets of MRCK are upregulated by radiation in vitro and in vivo and this is associated with an increase in GBM invasion. Since the majority of GBM patients receive radiotherapy we explored whether MRCK activity was affected by radiation. As shown in FIG. 2A, Western blot analysis of two different primary human GBM cell lines, G7 and E2, showed that radiation induced an increase in phosphorylation levels of the MRCK biomarker, MYPT1. To confirm this observation, immunofluorescence analysis of pMLC2, another downstream biomarker of MRCK, was undertaken using a high throughput imaging platform and automated analysis (FIG. 2B). This unbiased technique clearly indicated a significant increase in pMLC2 levels upon irradiation of GBM cells in vitro.

To confirm that this phenomenon also occurs in vivo, histological staining and automated analysis of pMYPT1 levels was performed in samples from whole-brain irradiated (3×2 Gy fractions) and non-irradiated cohorts of mice bearing intracranial G7 xenograft tumours sacrificed 5 days after the last radiation dose. Although no change in nuclear pMYPT1 was detected, we observed significant upregulation of cytoplasmic pMYPT1 at the invasive tumour edge (FIG. 2C). This suggests that MRCK activity is not only upregulated acutely by irradiation, but may also be maintained by a longer term 'switch' in intracellular signalling.

The results shown in FIG. 2 D-E show that the activation of MRCK targets is concomitant with an increase in GBM cell motility both in vitro (D), ex vivo (E) and in vivo (F) indicating the potential use of MRCK inhibition to oppose GBM invasion during radiotherapy (RT).

Figure 3A:
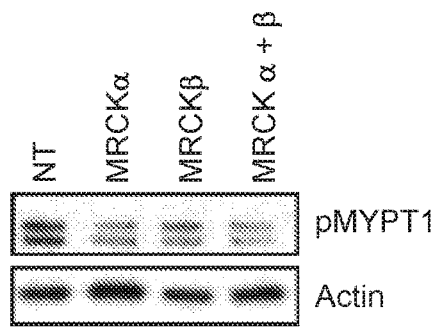
Figure 3B:
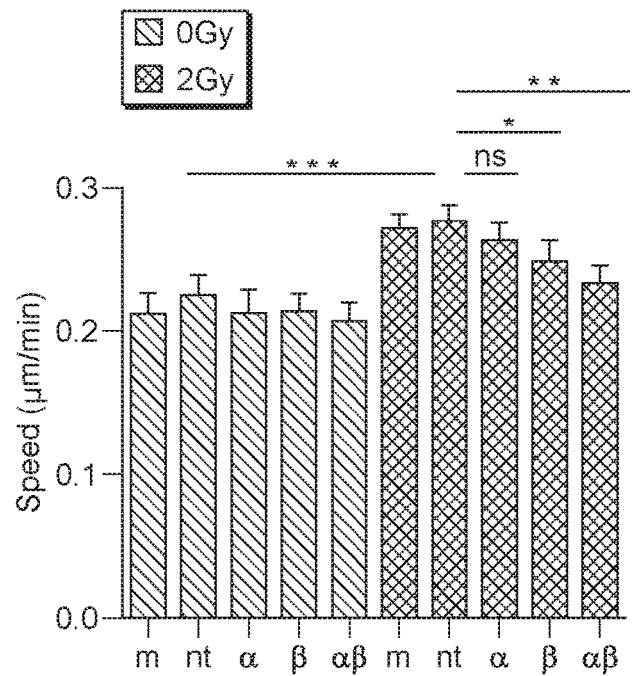
Figure 3C:
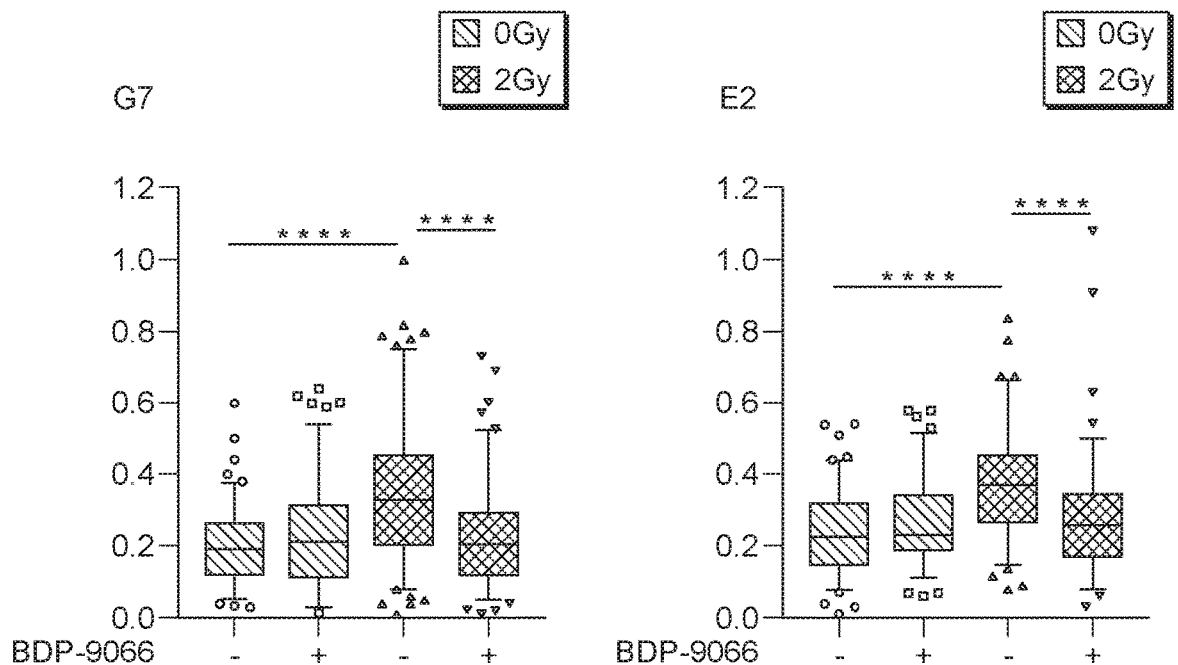
Figure 3D:
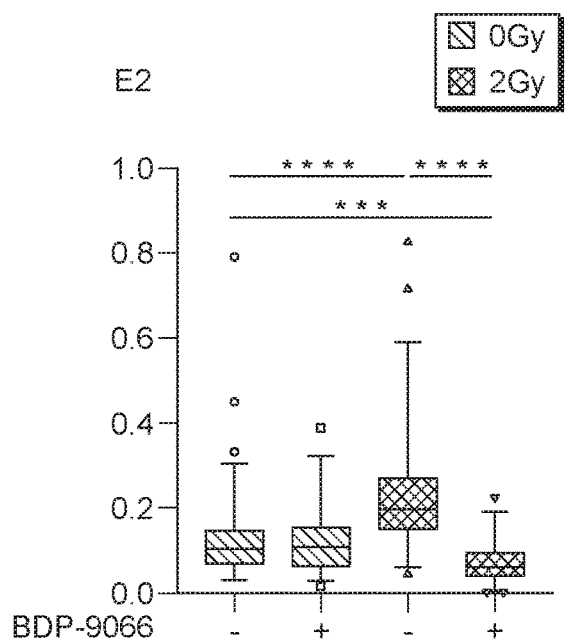

MRCK plays an essential role in driving radiation induced migration. To probe whether increased cell migration requires enhanced MRCK activity, and to assess its relative contribution, we performed subconfluent migration assays in G7 cells in which MRCKα and β had been downregulated by siRNA targeting (FIGS. 3A and B). Ablation of both MRCK isoforms concomitantly was found to inhibit pMYPT1 expression and to reduce migration speed to the levels observed in non-irradiated control cells. These findings strongly indicate that MRCK, and not ROCK, is primarily responsible for the downstream signalling to MYPT1 and MLC2 that drives radiation induced migration in GBM cells.

Figure 3E:
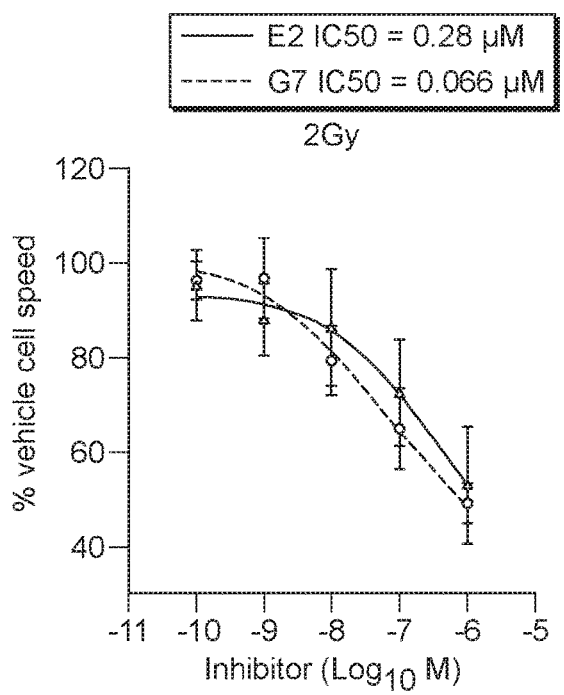

Radiation driven GBM cell migration can be inhibited by treatment with E117/BDP9066. Treatment with 100 nM of E117/BDP9066 was found to fully oppose radiation driven sub confluent migration in two different GBM cells lines (G7 and E2, FIG. 3 C) and ex vivo brain slice invasion (E2, FIG. 3D). Furthermore, treatment of irradiated GBM cells with increasing concentrations of E117/BDP9066 produced a robust dose response in cell speed (FIG. 3E).

Figure 4A:
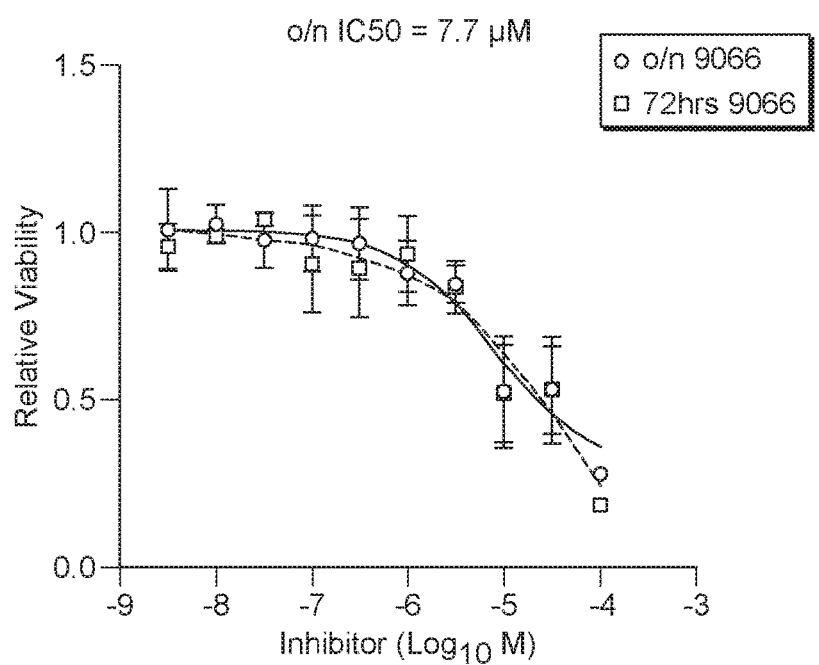
Figure 4B:
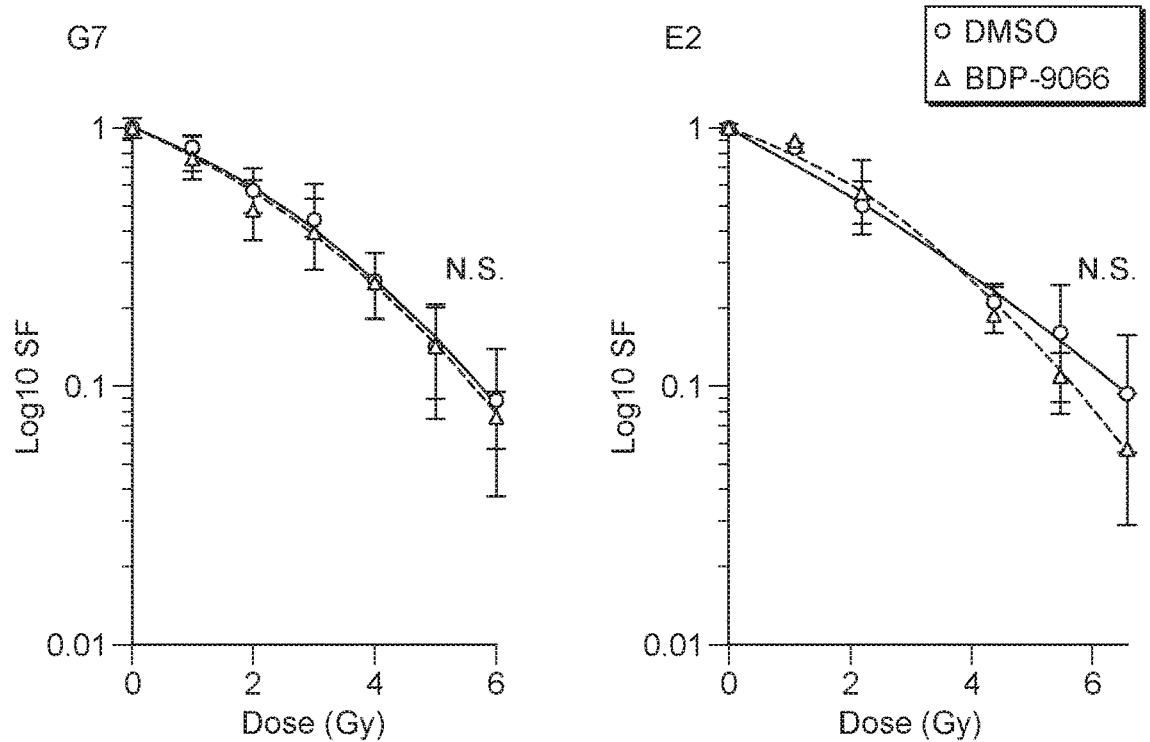
Figure 4C:
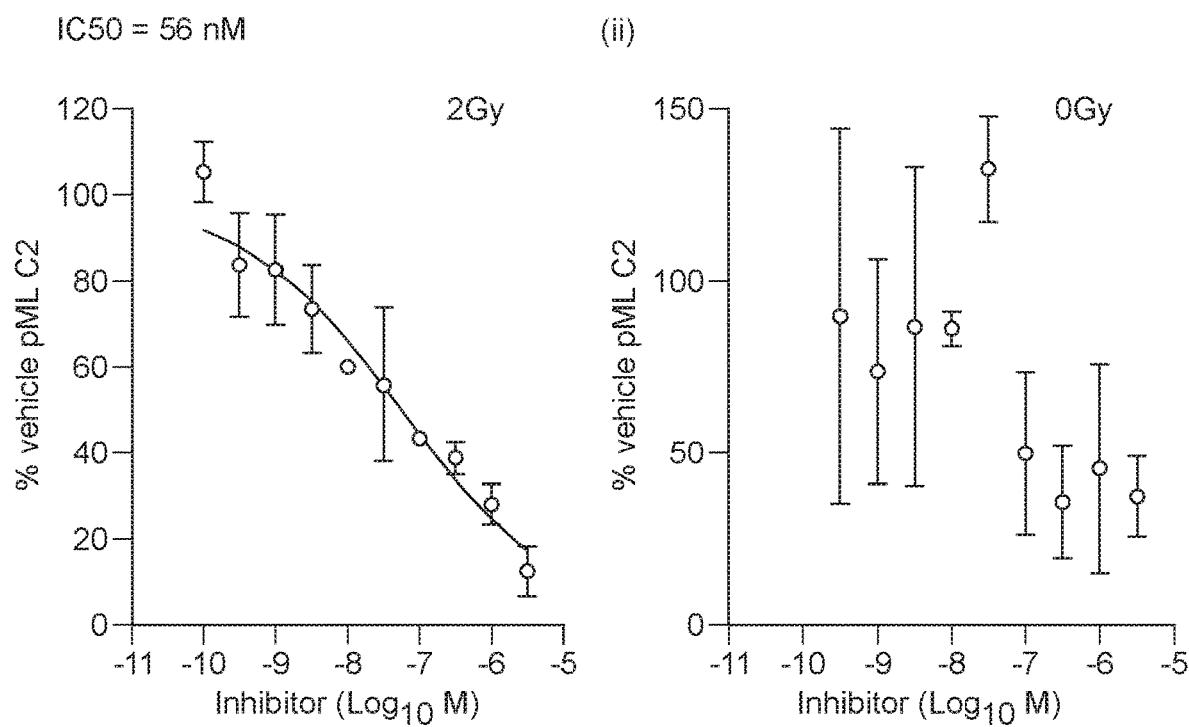
Figure 4D:
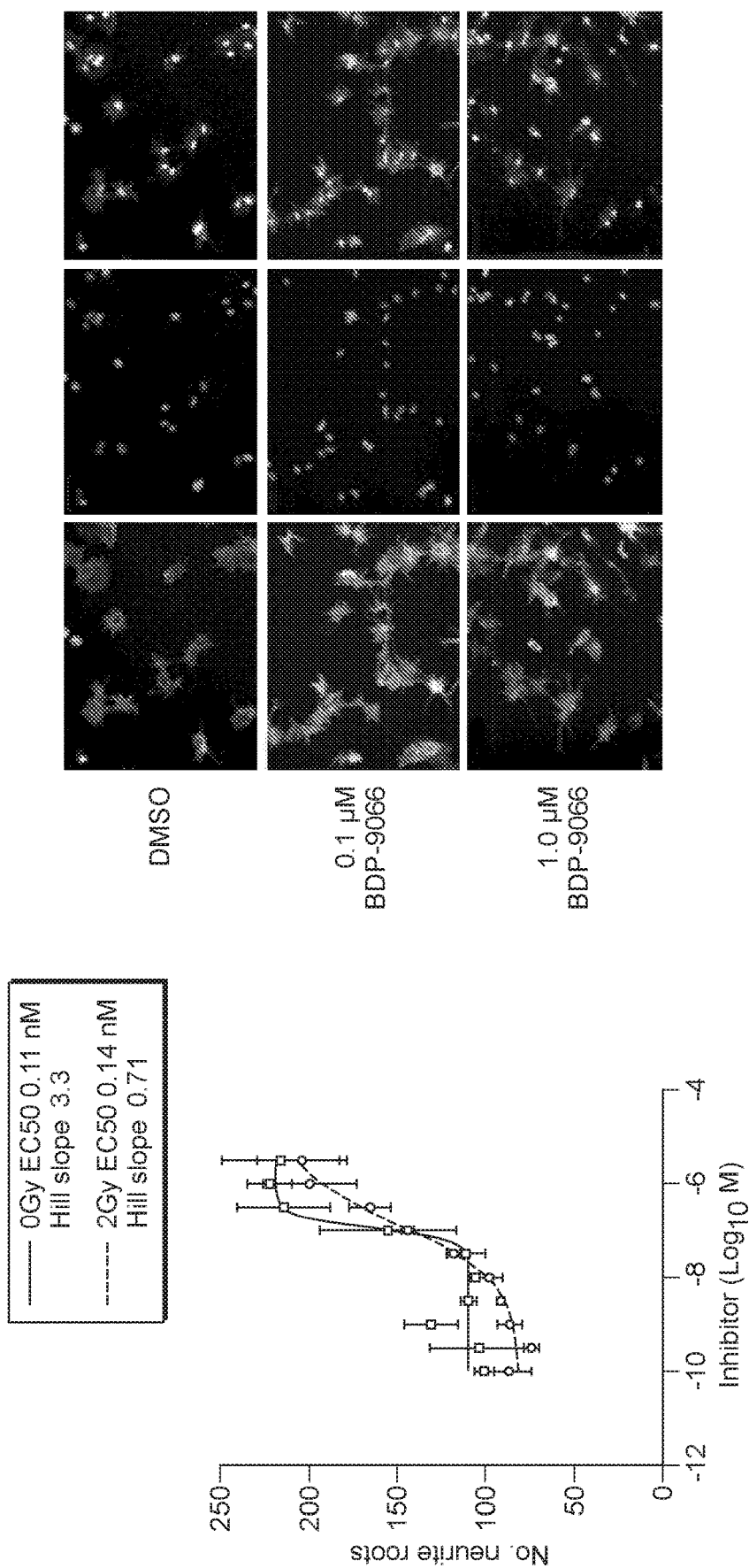

Treatment with E117/BDP-9066 does not affect cell survival but elicits a robust biomarker response at sub-micromolar concentrations. To test whether BDP-9066 had any impact on tumour cell survival either as a single agent or in combination with radiation we performed cell viability and clonogenic survival assays. No effect on viability was observed at sub-micromolar levels of BDP-9066 (FIG. 4A), and 100 nM BDP-9066 had no impact on the radiation sensitivity of G7 or E2 cells as measured by clonogenic survival (FIG. 4B). The loss of cell viability at higher concentrations is likely to represent off target toxicity. In contrast, irradiated G7 and E2 cells displayed a robust dose response to BDP-9066 in terms of biomarker (pMLC2 IC50=56 nM) and aberrant morphological changes as measured by neurite numbers (EC50 0.14, hillslope 0.71; FIG. 4 C-D).

Figure 5A:
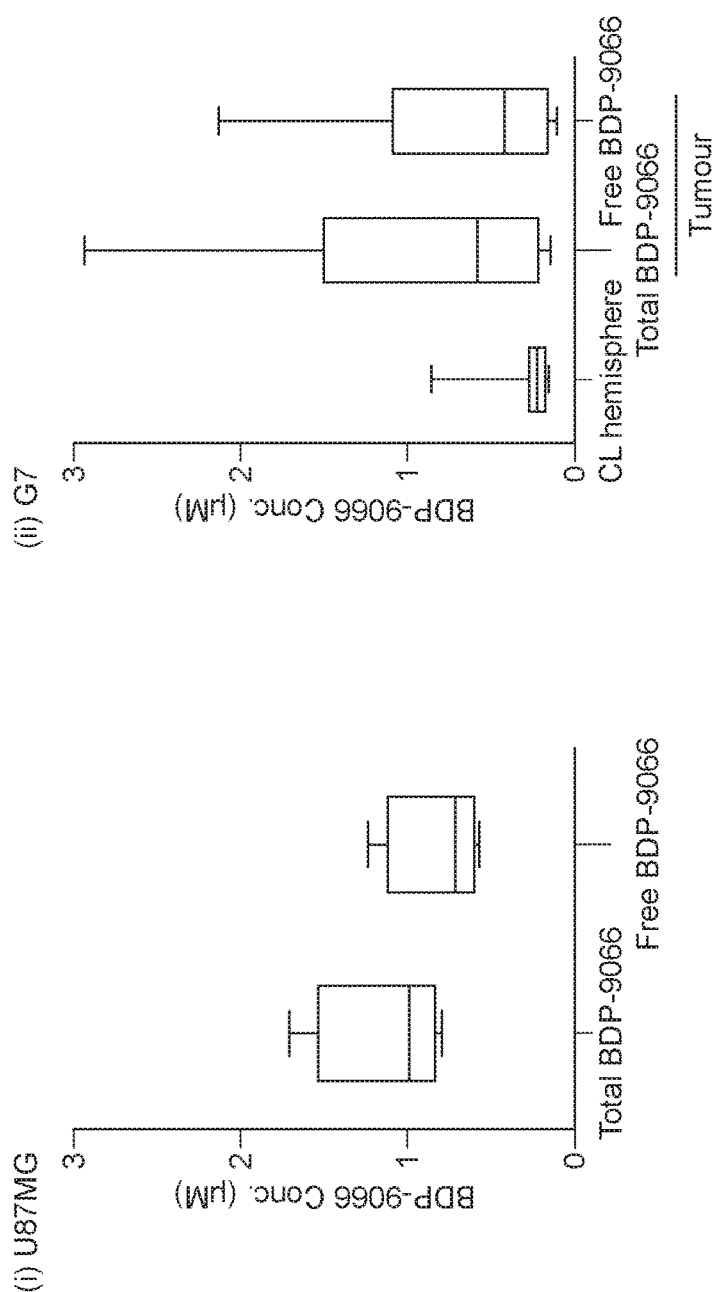
Figure 5B:
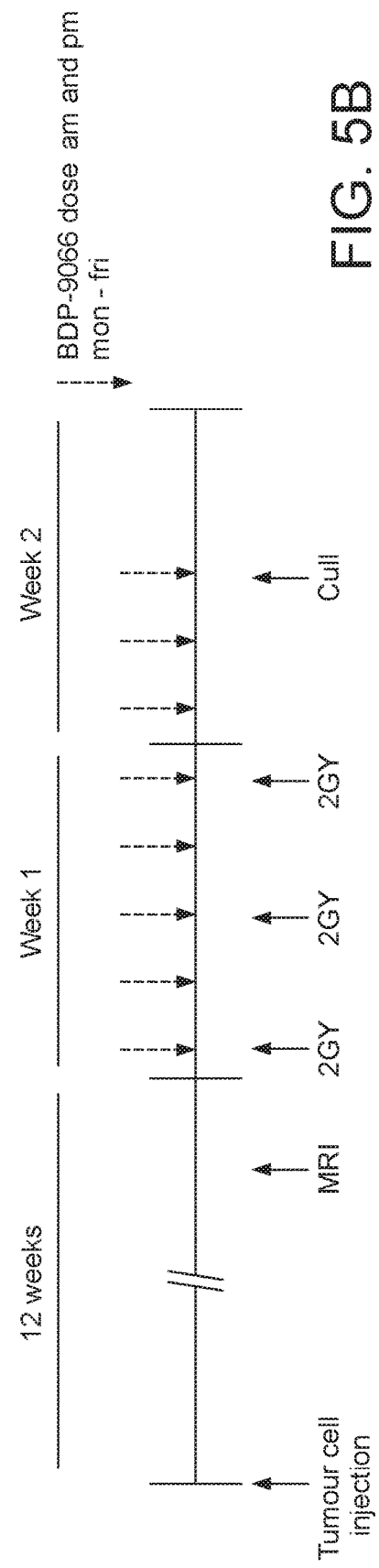

Pharmacological inhibition of MRCK inhibits GBM cell infiltration in vivo. Compound level analysis of sub dissected intracranial U87MG and G7 tumours indicated that BDP-9066 penetrated intracranial tumours at concentrations that would be expected to inhibit of MRCK in vivo, even when adjusted for free drug levels (based on plasma protein binding of 27.3%; FIG. 5A). Samples taken from the contralateral hemisphere indicated that BDP-9066 has very low exposure in the brain in the absence of significant tumour burden, following sub-cutaneous dosing. To test the efficacy of BDP-9066 in inhibiting radiation induced invasion in vivo we established G7 intracranial tumours in four cohorts of mice: vehicle, BDP-9066, RT+vehicle and RT+BDP-9066. Mice underwent T2-weighted magnetic resonance imaging (MRI) to confirm the presence and equivalence of size of tumours 11 weeks after tumour cell injection and treatment was commenced 12 weeks post injection. Mice in the RT cohorts received 3×2 Gy whole brain RT over the course of one week. Twice daily dosing of vehicle or BDP-9066 was initiated at the same time as RT and continued for 10 days before sacrifice of the animals (FIG. 5B). Twice daily dosing was chosen because while the pharmacokinetic (PK) profile of BDP-9066 showed good bioavailability, rapid clearance was also observed (data not shown). The compound was well tolerated and PK analysis of blood taken at the time of culling confirmed its presence at micromolar concentrations.

Figure 5C:
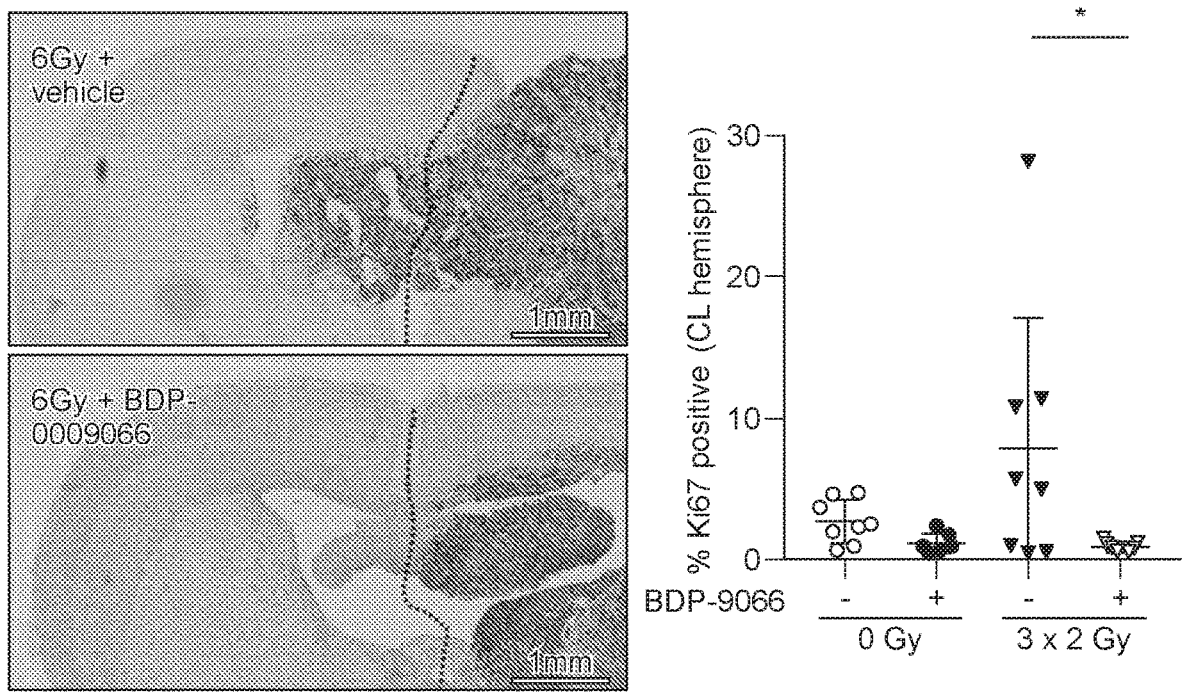
Figure 5D:
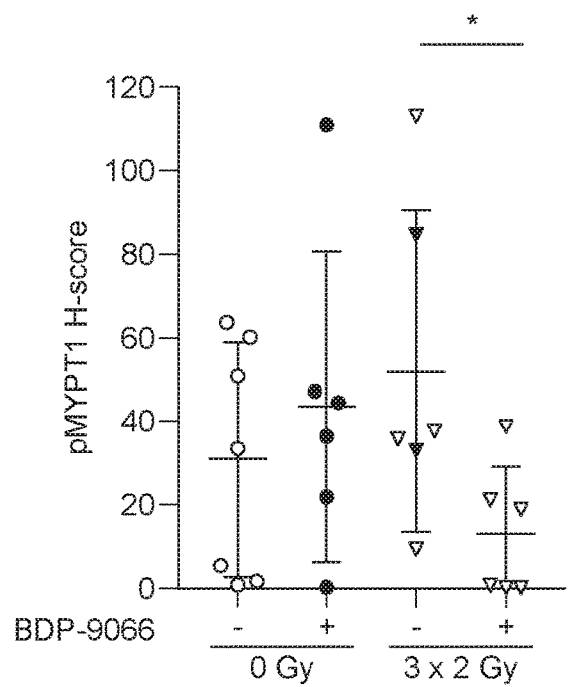

The mouse brains were excised and subjected to immunohistochemical analysis of Ki67 staining. Consistent with our previous experiment, increased numbers of GBM cells were observed in the contralateral hemispheres of mice in the 'irradiated+vehicle' cohort (FIG. 5C). Importantly, irradiated mice that were treated with BDP-9066 showed no increase of tumour cell infiltration to the contralateral hemisphere. In addition, histological analysis of brain section showed that BDP-9066 treatment opposes radiation driven MYPT1 phosphorylation (FIG. 5D).

Pharmacological inhibition of MRCK when combined with radiotherapy confers a significant survival benefit to intracranial GBM tumour bearing mice. G7 intracranial tumours were established in four cohorts of mice: vehicle, BDP-9066, RT+vehicle and RT+BDP-9066 (FIG. 6A) and the 4 week treatment schedule outlined in FIG. 6A was commenced at 10 weeks post tumour cell injection. The experiment was terminated at 104 days after a final T2 MRI on the remaining mice. The results indicate that while there is no significant survival benefit conferred by BDP-9066 alone, when combined with RT there is a highly significant increase in survival compared to the untreated cohort (p=0.0007) which is significantly above that conferred by radiation alone (p=0.0459). These data provide strong proof-of-concept evidence indicating the therapeutic actions of E117/BDP9066 in combination with radiotherapy in GBM.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

1. Hanahan D, Weinberg Robert A: Hallmarks of cancer: the next generation. Cell. 2011, 144: 646-674. 10.1016/j.cell.2011.02.013.
2. Olson M F, Sahai E: The actin cytoskeleton in cancer cell motility. Clin Exp Metastasis. 2009, 26: 273-287. 10.1007/s10585-008-9174-2.
3. Vicente-Manzanares M, Ma X, Adelstein R S, Horwitz A R: Non-muscle myosin II takes centre stage in cell adhesion and migration. Nat Rev Mol Cell Biol. 2009, 10: 778-790. 10.1038/nrm2786.
4. Unbekandt M, Olson M F: The actin-myosin regulatory MRCK kinases: regulation, biological functions and associations with human cancer. J Mol Med (Berl). 2014, 92: 217-225. 10.1007/s00109-014-1133-6.
5. Pearce L R, Komander D, Alessi D R: The nuts and bolts of AGC protein kinases. Nat Rev Mol Cell Biol. 2010, 11: 9-22. 10.1038/nrm2822.
6. Wilkinson S, Paterson H F, Marshall C J: Cdc42-MRCK and Rho-ROCK signalling cooperate in myosin phosphorylation and cell invasion. Nat Cell Biol. 2005, 7: 255-261. 10.1038/ncb1230.
7. Choi S H, Czifra G, Kedei N, Lewin N E, Lazar J, Pu Y, Marquez V E, Blumberg P M: Characterization of the interaction of phorbol esters with the C1 domain of MRCK (myotonic dystrophy kinase-related Cdc42 binding kinase) alpha/beta. J Biol Chem. 2008, 283: 10543-10549. 10.1074/jbc.M707463200.
8. Leung T, Chen X-QQ, Tan I, Manser E, Lim L: Myotonic dystrophy kinase-related Cdc42-binding kinase acts as a Cdc42 effector in promoting cytoskeletal reorganization. Mol Cell Biol. 1998, 18: 130-140.
9. Tan I, Yong J, Dong J M, Lim L, Leung T: A tripartite complex containing MRCK modulates lamellar actomyosin retrograde flow. Cell. 2008, 135: 123-136. 10.1016/j.cell.2008.09.018.
10. Totsukawa G, Wu Y, Sasaki Y, Hartshorne D J, Yamakita Y, Yamashiro S, Matsumura F: Distinct roles of MLCK and ROCK in the regulation of membrane protrusions and focal adhesion dynamics during cell migration of fibroblasts. J Cell Biol. 2004, 164: 427-439. 10.1083/jcb.200306172.
11. Heikkila T, Wheatley E, Crighton D, Schroder E, Boakes A, Kaye S J, Mezna M, Pang L, Rushbrooke M, Turnbull A, Olson M F: Co-crystal structures of inhibitors with MRCKbeta, a key regulator of tumor cell invasion. PLoS One. 2011, 6: e24825-10.1371/journal.pone.0024825.
12. Gaggioli C, Hooper S, Hidalgo-Carcedo C, Grosse R, Marshall J F, Harrington K, Sahai E: Fibroblast-led collective invasion of carcinoma cells with differing roles for RhoGTPases in leading and following cells. Nat Cell Biol. 2007, 9: 1392-1400. 10.1038/ncb1658.
13. Lefort K, Mandinova A, Ostano P, Kolev V, Calpini V, Kolfschoten I, Devgan V, Lieb J, Raffoul W, Hohl D, Neel V, Garlick J, Chiorino G, Dotto G P: Notch1 is a p53 target gene involved in human keratinocyte tumor suppression through negative regulation of ROCK1/2 and MRCK-alpha kinases. Genes Dev. 2007, 21: 562-577. 10.1101/gad.1484707.
14. van't Veer L J, Dai H, van de Vijver M J, He Y D, Hart A A M, Mao M, Peterse H L, van der Kooy K, Marton M J, Witteveen A T, Schreiber G J, Kerkhoven R M, Roberts C, Linsley P S, Bernards R, Friend S H: Gene expression profiling predicts clinical outcome of breast cancer. Nature. 2002, 415: 530-536. 10.1038/415530a.
15. Umbekandt et al., Cell Communication and Signalling 2014, 12:54.
16. Ahmed S U, Carruthers R, Gilmour L, Yildirim S, Watts C, Chalmers A J. Selective Inhibition of Parallel DNA Damage Response Pathways Optimizes Radiosensitization of Glioblastoma Stem-like Cells. Cancer research. 2015; 75:4416-28.
17. Gomez-Roman N, Stevenson K, Gilmour L, Hamilton G, Chalmers A J. A novel 3D human glioblastoma cell culture system for modeling drug and radiation responses. Neuro-oncology. 2017; 19:229

The invention claimed is:
1. A compound of Formula I, or a salt, hydrate or solvate thereof;

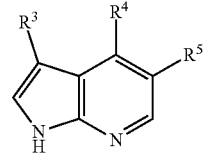

(I)

wherein,
R$^4$ is a group of formula II,

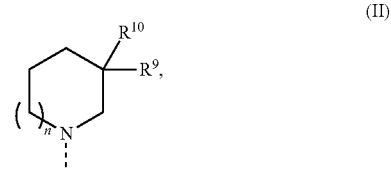

(II)

R$^3$ is selected from 5-15 membered heteroaryl, where said 5-15 membered heteroaryl is optionally substituted by one or more R$^b$;
each R$^b$ is selected from hydrogen, hydroxyl, halogen, CN, C$_{1-6}$ alkyl and O—C$_{1-6}$ alkyl; wherein said C$_{1-6}$ alkyl is optionally substituted with one or more groups selected from hydroxyl, halogen, =O, NR$^c$R$^d$, C$_{1-6}$ alkyl, O—C$_{1-6}$ alkyl, and phenyl;
each R$^c$ is independently selected from hydrogen and C$_{1-6}$ alkyl;
each R$^d$ is independently selected from hydrogen, CN, C$_{1-6}$ haloalkyl, O—C$_{1-6}$ haloalkyl, 3-7 membered heterocycloalkyl, 5-6 membered heteroaryl, C$_{3-6}$cycloalkyl, C$_{1-6}$ alkyl, O—C$_{1-6}$ alkyl and phenyl, wherein said C$_{1-6}$ alkyl, phenyl, 5-6 membered heteroaryl, 3-7 membered heterocycloalkyl and C$_{3-6}$ cycloalkyl are optionally substituted with one or more groups selected from hydroxyl, halogen, CN, NH$_2$, NH(C$_{1-6}$alkyl), N(C$_{1-6}$alkyl)$_2$, C$_{1-6}$ haloalkyl, C$_{3-6}$ cycloalkyl, phenyl, 3-7 membered heterocycloalkyl, C$_{3-10}$alkylheterocycloalkyl, C$_{1-6}$ alkyl and O—C$_{1-6}$ alkyl; or
R$^c$ and R$^d$, when attached to the same atom, together with the atom to which they are attached form a 3-7 membered heterocycloalkyl ring optionally substituted by one or more groups selected from hydroxyl, halogen, CN, NH$_2$, NH(C$_{1-6}$alkyl), N(C$_{1-6}$ alkyl)$_2$, C$_{1-6}$ haloalkyl, O—C$_{1-6}$ haloalkyl, C$_{3-6}$ cycloalkyl, phenyl, 3-7 membered heterocycloalkyl, C$_{1-6}$ alkyl and O—C$_{1-6}$ alkyl;
R$^5$ is selected from hydrogen, halogen, hydroxyl, NH$_2$, NH(C$_{1-6}$ alkyl), N(C$_{1-6}$ alkyl)$_2$, C$_{1-6}$ alkyl, O—C$_{1-6}$ alkyl, C$_{1-6}$ haloalkyl, O—C$_{1-6}$ haloalkyl, C$_{3-6}$ cycloalkyl, phenyl and CN;
R$^9$ and R$^{10}$ are independently selected from hydroxyl, C$_{1-6}$ alkyl, O—C$_{1-6}$ alkyl, C$_{1-6}$ haloalkyl, C$_{1-6}$haloalkoxy, NH$_2$, NH(C$_{1-6}$alkyl), N(C$_{1-6}$alkyl)$_2$, NR$^c$R$^d$, NR$^c$C(=O)R$^d$, C(O)NR$^c$R$^d$, phenyl, and 3-7 membered heterocycloalkyl, where said C$_{1-6}$ alkyl, phenyl and 3-7 membered heterocycloalkyl are optionally substituted with one or more groups selected from halogen, hydroxyl, CN, NH$_2$, NH(C$_{1-6}$alkyl), N(C$_{1-6}$alkyl)$_2$, C$_{1-6}$ alkyl, O—C$_{1-6}$ alkyl, C$_{1-6}$haloalkyl, C$_{1-6}$haloalkoxy, C$_{3-6}$ cycloalkyl and phenyl; or R$^9$ and R$^{10}$ together with the carbon atom to which they are attached form a 4-6 membered heterocycloalkyl ring comprising at least one heteroatom selected from O, N and S, where said heterocycloalkyl ring is optionally substituted with one or more R$^m$;

R$^m$ is selected from hydroxyl, halogen, CN, C$_{1-6}$ alkyl, C$_{3-6}$ cycloalkyl, C$_{1-6}$ haloalkyl, and OR$^a$; where R$^a$ is defined above; and n is a number selected from 0 and 1.

2. The compound according to claim 1, or a salt, hydrate or solvate thereof, wherein R$^4$ is selected from

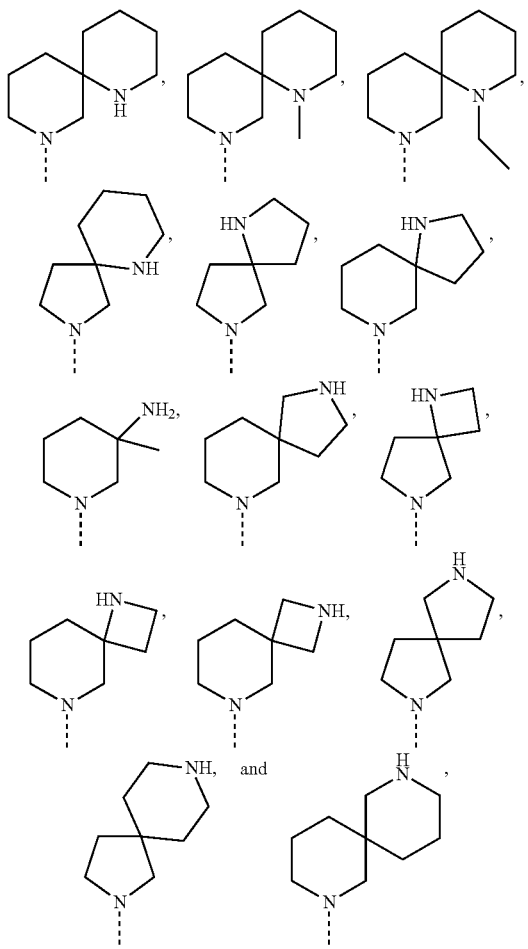

where each is optionally substituted on a carbon atom by one or more R$^i$, wherein R$^j$ is selected from halogen, C$_{1-6}$ alkyl, hydroxyl and O—C$_{1-6}$ alkyl with the proviso that R$^j$ is selected from halogen and C$_{1-6}$ alkyl when bonded to a carbon adjacent to N.

3. The compound according to claim 1, or a salt, hydrate or solvate thereof, wherein R$^9$ and R$^{10}$ are independently selected from hydroxyl, C$_{1-6}$ alkyl, NH$_2$, NH(C$_{1-6}$alkyl), N(C$_{1-6}$alkyl)$_2$, NR$^c$R$^d$, NR$^c$C(=O)R$^d$, C(O)NR$^c$R$^d$, phenyl, and 3-7 membered heterocycloalkyl, where said C$_{1-6}$ alkyl, phenyl and 3-7 membered heterocycloalkyl are optionally substituted with one or more groups selected from halogen, hydroxyl, CN, NH$_2$, NH(C$_{1-6}$alkyl), N(C$_{1-6}$alkyl)$_2$, C$_{1-6}$ alkyl, O—C$_{1-6}$ alkyl, C$_{1-6}$haloalkyl, C$_{1-6}$haloalkoxy, C$_{3-6}$ cycloalkyl and phenyl; or R$^9$ and R$^{10}$ together with the carbon atom to which they are attached form a 4-6 membered heterocycloalkyl ring comprising at least one heteroatom selected from O, N and S, where said heterocycloalkyl ring is optionally substituted with one or more R$^m$.

4. The compound according to any claim 1, or a salt, hydrate or solvate thereof, wherein R$^m$ is selected from C$_{1-3}$ alkyl.

5. The compound according to claim 1, or a salt, hydrate or solvate thereof, wherein R$^3$ is selected from 5-6 membered heteroaryl, where said 5-6 membered heteroaryl is optionally substituted by one or more R$^b$.

6. The compound according to claim 1, or a salt, hydrate or solvate thereof, wherein R$^3$ is a 6 membered heteroaryl optionally substituted by one or more R$^b$.

7. The compound according to claim 1, or a salt, hydrate or solvate thereof, wherein R$^3$ is

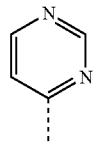

optionally substituted by one or two R$^b$ groups.

8. The compound according to claim 1, or a salt, hydrate or solvate thereof, wherein R$^b$ is selected from hydrogen and C$_{1-3}$ alkyl.

9. The compound according to claim 1, or a salt, hydrate or solvate thereof, wherein R$^5$ is selected from hydrogen, halogen, hydroxyl, C$_{1-6}$ alkyl, O—C$_{1-6}$ alkyl, C$_{1-6}$ haloalkyl, O—C$_{1-6}$ haloalkyl, C$_{3-6}$ cycloalkyl, phenyl and CN.

10. The compound according to claim 1, or a salt, hydrate or solvate thereof, of sub-formula Ic':

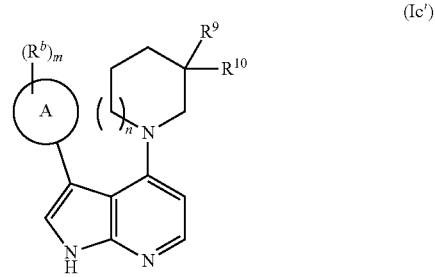

(Ic')

wherein
ring A is a heteroaryl group selected from a pyrimidine, thiazole, thiadiazole, isothiazole, pyridazine, pyridine and pyrazine;
m is a number selected from 0, 1 and 2; and
n, R$^9$ and R$^{10}$ are as defined in claim 1.

11. The compound according to claim 10, or a salt, hydrate or solvate thereof, wherein R$^9$ and R$^{10}$ together with the carbon atom to which they are attached form a 5-6 membered heterocycloalkyl ring comprising one nitrogen atom, where said heterocycloalkyl ring is optionally substituted with one or more R$^m$ as defined in claim 1.

12. The compound according to claim 1, or a salt, hydrate or solvate thereof, selected from:

| | |
|---|---|
| E114 | 4-[4-(1,8-diazaspiro[5.5]undecan-8-yl)-1H-pyrrolo[2,3-b]pyridin-3-yl]isothiazole |
| E115 | 3-[4-[(6R)-1,8-diazaspiro[5.5]undecan-8-yl]-1H-pyrrolo[2,3-b]pyridin-3-yl]-1,2,4-thiadiazole |
| E116 | 3-[4-[(6S)-1,8-diazaspiro[5.5]undecan-8-yl]-1H-pyrrolo[2,3-b]pyridin-3-yl]-1,2,4-thiadiazole |
| E117 | (6S)-8-(3-pyrimidin-4-yl-1H-pyrrolo[2,3-b]pyridin-4-yl)-1,8-diazaspiro[5.5]undecane |
| E118 | (6R)-8-(3-pyrimidin-4-yl-1H-pyrrolo[2,3-b]pyridin-4-yl)-1,8-diazaspiro[5.5]undecane |
| E119 | 3-[4-[(6R)-1,8-diazaspiro[5.5]undecan-8-yl]-1H-pyrrolo[2,3-b]pyridin-3-yl]isothiazole |
| E120 | 3-[4-[(6S)-1,8-diazaspiro[5.5]undecan-8-yl]-1H-pyrrolo[2,3-b]pyridin-3-yl]isothiazole |
| E121 | 3-[4-(1,8-diazaspiro[5.5]undecan-8-yl)-1H-pyrrolo[2,3-b]pyridin-3-yl]isothiazole |
| E122 | (6S)-8-(3-pyrimidin-5-yl-1H-pyrrolo[2,3-b]pyridin-4-yl)-1,8-diazaspiro[5.5]undecane |
| E123 | 4-[(5R)-1,7-diazaspiro[4.4]nonan-7-yl]-3-pyrimidin-5-yl-1H-pyrrolo[2,3-b]pyridine |
| E124 | 4-[(5S)-1,7-diazaspiro[4.4]nonan-7-yl]-3-pyrimidin-5-yl-1H-pyrrolo[2,3-b]pyridine |
| E125 | (5R)-2-(3-pyrimidin-5-yl-1H-pyrrolo[2,3-b]pyridin-4-yl)-2,6-diazaspiro[4.5]decane |
| E126 | (5S)-2-(3-pyrimidin-5-yl-1H-pyrrolo[2,3-b]pyridin-4-yl)-2,6-diazaspiro[4.5]decane |
| E127 | (5R)-2-(3-pyrimidin-4-yl-1H-pyrrolo[2,3-b]pyridin-4-yl)-2,6-diazaspiro[4.5]decane |
| E128 | (5S)-2-(3-pyrimidin-4-yl-1H-pyrrolo[2,3-b]pyridin-4-yl)-2,6-diazaspiro[4.5]decane |
| E129 | 3-[4-(2,6-diazaspiro[4.5]decan-2-yl)-1H-pyrrolo[2,3-b]pyridin-3-yl]-1,2,4-thiadiazole |
| E130 | 2-[4-[(5R)-2,6-diazaspiro[4.5]decan-2-yl]-1H-pyrrolo[2,3-b]pyridin-3-yl]-5-methyl-thiazole |
| E131 | 2-[4-[(5S)-2,6-diazaspiro[4.5]decan-2-yl]-1H-pyrrolo[2,3-b]pyridin-3-yl]-5-methyl-thiazole |
| E132 | 2-[4-[(5R)-2,6-diazaspiro[4.5]decan-2-yl]-1H-pyrrolo[2,3-b]pyridin-3-yl]thiazole |
| E133 | 2-[4-[(5S)-2,6-diazaspiro[4.5]decan-2-yl]-1H-pyrrolo[2,3-b]pyridin-3-yl]thiazole |
| E134 | 2-[4-[(5S)-1,7-diazaspiro[4.4]nonan-7-yl]-1H-pyrrolo[2,3-b]pyridin-3-yl]thiazole |
| E135 | 2-[4-[(5R)-1,7-diazaspiro[4.4]nonan-7-yl]-1H-pyrrolo[2,3-b]pyridin-3-yl]thiazole |
| E136 | 3-[4-(1,7-diazaspiro[4.4]nonan-7-yl)-1H-pyrrolo[2,3-b]pyridin-3-yl]isothiazole |
| E137 | 4-(1,7-diazaspiro[4.4]nonan-7-yl)-3-(2-pyridyl)-1H-pyrrolo[2,3-b]pyridine |
| E138 | 8-[3-(2-pyridyl)-1H-pyrrolo[2,3,b]pyridin-4-yl]-1,8-diazaspiro[5.5]undecane |
| E139 | (6S)-8-[3-(2-pyridyl)-1H-pyrrolo[2,3-b]pyridin-4-yl]-1,8-diazaspiro[5.5]undecane |
| E140 | (6R)-8-[3-(2-pyridyl)-1H-pyrrolo[2,3-b]pyridin-4-yl]-1,8-diazaspiro[5.5]undecane |
| E141 | 2-[3-(2-pyridyl)-1H-pyrrolo[2,3-b]pyridin-4-yl]-2,6-diazaspiro[4.5]decane |
| E142 | 3-[4-(1,8-diazaspiro[5.5]undecan-8-yl)-1H-pyrrolo[2,3-b]pyridin-3-yl]-4-methyl-isothiazole |
| E143 | 2-[4-(1,9-diazaspiro[4.5]decan-9-yl)-1H-pyrrolo[2,3-b]pyridin-3-yl]-5-methyl-thiazole |
| E144 | 2-[4-(2,6-diazaspiro[4.5]decan-2-yl)-1H-pyrrolo[2,3-b]pyridin-3-yl]-5-methyl-thiazole |
| E146 | 2-[4-[(6S)-1,8-diazaspiro[5.5]undecan-8-yl]-1H-pyrrolo[2,3-b]pyridin-3-yl]-5-methyl-thiazole |
| E147 | 2-[4-(1,8-diazaspiro[5.5]undecan-8-yl)-1H-pyrrolo[2,3-b]pyridin-3-yl]-5-methyl-thiazole |
| E148 | 2-[4-[(6R)-1,8-diazaspiro[5.5]undecan-8-yl]-1H-pyrrolo[2,3-b]pyridin-3-yl]-5-methyl-thiazole |
| E149 | 2-[4-(1,8-diazaspiro[5.5]undecan-8-yl)-1H-pyrrolo[2,3-b]pyridin-3-yl]thiazole |
| E150 | 2-[4-[(6S)-1,8-diazaspiro[5.5]undecan-8-yl]-1H-pyrrolo[2,3-b]pyridin-3-yl]thiazole |
| E151 | 2-[4-[(6R)-1,8-diazaspiro[5.5]undecan-8-yl]-1H-pyrrolo[2,3-b]pyridin-3-yl]thiazole |
| E152 | 2-[4-(1,7-diazaspiro[3.4]octan-7-yl)-1H-pyrrolo[2,3-b]pyridin-3-yl]-5-methyl-thiazole |
| E153 | 2-[4-(1,8-diazaspiro[3.5]nonan-8-yl)-1H-pyrrolo[2,3-b]pyridin-3-yl]-5-methyl-thiazole |
| E154 | 2-[4-(1,7-diazaspiro[4.4]nonan-7-yl)-1H-pyrrolo[2,3-b]pyridin-3-yl]thiazole |
| E155 | 2-[4-(2,6-diazaspiro[4.5]decan-2-yl)-1H-pyrrolo[2,3-b]pyridin-3-yl]thiazole |
| E156 | 4-(2,6-diazaspiro[3.5]nonan-6-yl)-3-pyridazin-4-yl-1H-pyrrolo[2,3-b]pyridine |
| E157 | 8-(3-pyrimidin-2-yl-1H-pyrrolo[2,3-b]pyridin-4-yl)-1,8-diazaspiro[5.5]undecane |
| E158 | 2-[4-(1,8-diazaspiro[5.5]undecan-8-yl)-1H-pyrrolo[2,3-b]pyridin-3-yl]-4-methyl-thiazole |
| E159 | 4-[4-(1,8-diazaspiro[5.5]undecan-8-yl)-1H-pyrrolo[2,3-b]pyridin-3-yl]-2-methyl-thiazole |
| E160 | 8-[3-(2-methylpyrimidin-4-yl)-1H-pyrrolo[2,3-b]pyridin-4-yl]-1,8-diazaspiro[5.5]undecane |
| E161 | 4-(1,7-diazaspiro[4.4]nonan-7-yl)-3-pyridazin-4-yl-1H-pyrrolo[2,3-b]pyridine |
| E162 | 2-(3-pyridazin-4-yl-1H-pyrrolo[2,3-b]pyridin-4-yl)-2,6-diazaspiro[4.5]decane |
| E163 | 7-(3-pyridazin-4-yl-1H-pyrrolo[2,3-b]pyridin-4-yl)-2,7-diazaspiro[4.5]decane |
| E164 | 4-(2,7-diazaspiro[4.4]nonan-2-yl)-3-pyridazin-4-yl-1H-pyrrolo[2,3-b]pyridine |
| E166 | 8-[3-(2-methylpyrimidin-5-yl)-1H-pyrrolo[2,3-b]pyridin-4-yl]-1,8-diazaspiro[5.5]undecane |
| E167 | 4-[4-(1,8-diazaspiro[5.5]undecan-8-yl)-1H-pyrrolo[2,3-b]pyridin-3-yl]-3,5-dimethyl-isoxazole |
| E168 | 8-(3-pyrimidin-4-yl-1H-pyrrolo[2,3-b]pyridin-4-yl)-1,8-diazaspiro[5.5]undecane |
| E169 | 8-[3-(3-fluoro-2-pyridyl)-1H-pyrrolo[2,3-b]pyridin-4-yl]-1,8-diazaspiro[5.5]undecane |
| E170 | 8-[3-(5-fluoro-2-pyridyl)-1H-pyrrolo[2,3-b]pyridin-4-yl]-1,8-diazaspiro[5.5]undecane |
| E171 | 8-[3-(5-fluoro-3-pyridyl)-1H-pyrrolo[2,3-b]pyridin-4-yl]-1,8-diazaspiro[5.5]undecane |
| E172 | 8-(3-pyridazin-4-yl-1H-pyrrolo[2,3-b]pyridin-4-yl)-1,8-diazaspiro[5.5]undecane |
| E173 | (6R)-8-(3-pyridazin-4-yl-1H-pyrrolo[2,3-b]pyridin-4-yl)-1,8-diazaspiro[5.5]undecane |
| E174 | (6S)-8-(3-pyridazin-4-yl-1H-pyrrolo[2,3-b]pyridin-4-yl)-1,8-diazaspiro[5.5]undecane |
| E175 | 8-(3-pyridazin-3-yl-1H-pyrrolo[2,3-b]pyridin-4-yl)-1,8-diazaspiro[5.5]undecane |
| E176 | 3-methyl-1-(3-thiazol-2-yl-1H-pyrrolo[2,3-b]pyridin-4-yl)-piperidin-3-amine |
| E177 | 3-ethyl-1-[3-(5-methylthiazol-2-yl)-1H-pyrrolo[2,3-b]pyridin-4-yl]piperidin-3-amine |
| E178 | 3-methyl-1-(3-pyrimidin-5-yl-1H-pyrrolo[2,3-b]pyridin-4-yl)-piperidin-3-amine |
| E188 | 8-[3-(1-methylpyrazol-4-yl)-1H-pyrrolo[2,3-b]pyridin-4-yl]-1,8-diazaspiro[5.5]undecane |
| E189 | 8-(3-pyrazin-2-yl-1H-pyrrolo[2,3-b]pyridin-4-yl)-1,8-diazaspiro[5.5]undecane |
| E191 | 2-(3-pyrimidin-5-yl-1H-pyrrolo[2,3-b]pyridin-4-yl)-2,8-diazaspiro[4.5]decane |
| E192 | (6R)-8-(3-pyrimidin-5-yl-1H-pyrrolo[2,3-b]pyridin-4-yl)-1,8-diazaspiro[5.5]undecane |
| E194 | 2-(3-pyrimidin-5-yl-1H-pyrrolo[2,3-b]pyridin-4-yl)-2,8-diazaspiro[4.5]decane |
| E195 | 9-(3-pyrimidin-5-yl-1H-pyrrolo[2,3-b]pyridin-4-yl)-1,9-diazaspiro[4.5]decane |
| E196 | 8-(3-pyrimidin-5-yl-1H-pyrrolo[2,3-b]pyridin-4-yl)-1,8-diazaspiro[5.5]undecane |
| E206 | (6S)-1-methyl-8-(3-pyrimidin-4-yl-1H-pyrrolo[2,3-b]pyridin-4-yl)-1,8-diazaspiro[5.5]undecane |
| E207 | (6S)-1-ethyl-8-(3-pyrimidin-4-yl-1H-pyrrolo[2,3-b]pyridin-4-yl)-1,8-diazaspiro[5.5]undecane |
| E208 | (6R)-1-ethyl-8-(3-pyrimidin-5-yl-1H-pyrrolo[2,3-b]pyridin-4-yl)-1,8-diazaspiro[5.5]undecane |
| E209 | 2-[4-(1-ethyl-1,8-diazaspiro[5.5]undecan-8-yl)-1H-pyrrolo[2,3-b]pyridin-3-yl]thiazole |
| E210 | 2-[4-(1-ethyl-1,8-diazaspiro[5.5]undecan-8-yl)-1H-pyrrolo[2,3-b]pyridin-3-yl]-5-methyl-thiazole |
| E236 | 3-[4-[1,8-diazaspiro[5.5]undecan-8-yl]-1H-pyrrolo[2,3-b]pyridin-3-yl]-1,2,4-thiadiazole |
| E237 | 2-[4-(1,7-diazaspiro[4.4]nonan-7-yl)-1H-pyrrolo[2,3-b]pyridin-3-yl]-5-methyl-thiazole. |

13. A pharmaceutical composition which comprises a compound according to claim 1, or a pharmaceutically acceptable salt or solvate thereof, and one or more pharmaceutically acceptable excipients.

14. A combination comprising a compound according to claim 1, or a pharmaceutically acceptable salt or solvate thereof.

15. The compound of claim 1, or a salt, hydrate or solvate thereof, selected from:

| | Structure | IUPAC Name |
|---|---|---|
| E116 | 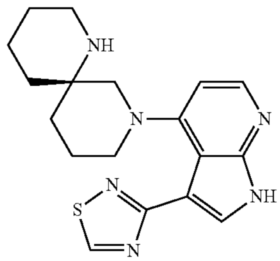 [SMILES: c1cc(N2CCC[C@@]3(CCCCN3)C2)c2c(-c3ncsn3)c[nH]c2n1] | 3-[4-[(6S)-1,8-diazaspiro[5.5]undecan-8-yl]-1H-pyrrolo[2,3-b]pyridin-3-yl]-1,2,4-thiadiazole |
| E120 | 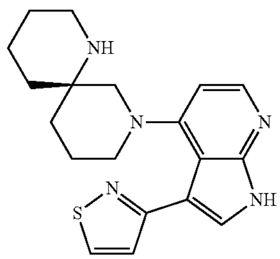 [SMILES: c1cc(N2CCC[C@@]3(CCCCN3)C2)c2c(-c3ccsn3)c[nH]c2n1] | 3-[4-[(6S)-1,8-diazaspiro[5.5]undecan-8-yl]-1H-pyrrolo[2,3-b]pyridin-3-yl]isothiazole |
| E117 | 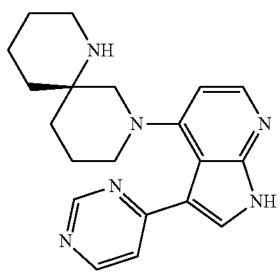 [SMILES: c1cc(-c2c[nH]c3nccc(N4CCC[C@@]5(CCCCN5)C4)c23)ncn1] | (6S)-8-(3-pyrimidin-4-yl-1H-pyrrolo[2,3-b]pyridin-4-yl)-1,8-diazaspiro[5.5]undecane |
| E150 | 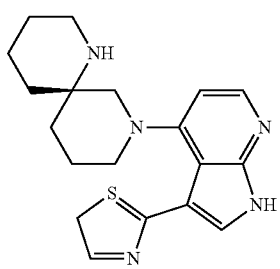 | 2-[4-[(6S)-1,8-diazaspiro[5.5]undecan-8-yl]-1H-pyrrolo[2,3-b]pyridin-3-yl]thiazole |
| E174 | 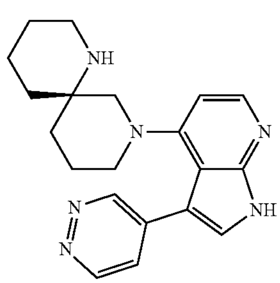 [SMILES: c1cc(-c2c[nH]c3nccc(N4CCC[C@@]5(CCCCN5)C4)c23)cnn1] | (6S)-8-(3-pyridazin-4-yl-1H-pyrrolo[2,3-b]pyridin-4-yl)-1,8-diazaspiro[5.5]undecane |

-continued

| | Structure | IUPAC Name |
|---|---|---|
| E206 | 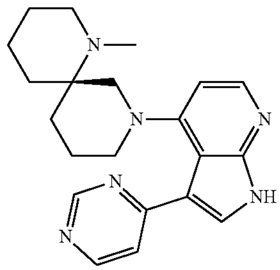 [SMILES: CN1CCCC[C@@]12CCCN(c1ccnc3[nH]cc(-c4ccncn4)c13)C2] | (6S)-1-methyl-8-(3-pyrimidin-4-yl-1H-pyrrolo[2,3-b]pyridin-4-yl)-1,8-diazaspiro[5.5]undecane |
| E133 | 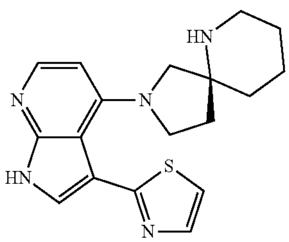 [SMILES: c1csc(-c2c[nH]c3nccc(N4CC[C@@]5(CCCCN5)C4)c23)n1] | 2-[4-[(5S)-2,6-diazaspiro[4.5]decan-2-yl]-1H-pyrrolo[2,3-b]pyridin-3-yl]thiazole |
| E209 | 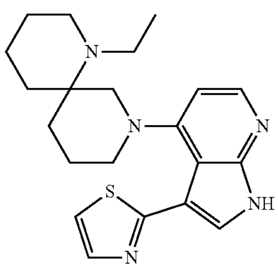 [SMILES: CCN1CCCCC12CCCN(c1ccnc3[nH]cc(-c4nccs4)c13)C2] | 2-[4-(1-ethyl-1,8-diazaspiro[5.5]undecan-8-yl)-1H-pyrrolo[2,3-b]pyridin-3-yl]thiazole |
| E139 | 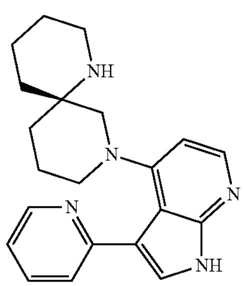 [SMILES: c1ccc(-c2c[nH]c3nccc(N4CCC[C@@]5(CCCCN5)C4)c23)nc1] | (6S)-8-[3-(2-pyridyl)-1H-pyrrolo[2,3-b]pyridin-4-yl]-1,8-diazaspiro[5.5]undecane |
| E207 | 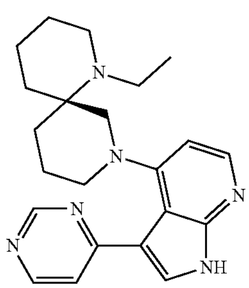 [SMILES: CCN1CCCC[C@@]12CCCN(c1ccnc3[nH]cc(-c4ccncn4)c13)C2] | (6S)-1-ethyl-8-(3-pyrimidin-4-yl-1H-pyrrolo[2,3-b]pyridin-4-yl)-1,8-diazaspiro[5.5]undecane |

-continued

| | Structure | IUPAC Name |
|---|---|---|
| E146 | 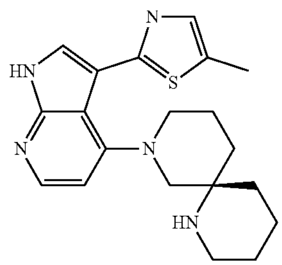 | 2-[4-[(6S)-1,8-diazaspiro[5.5]undecan-8-yl]-1H-pyrrolo[2,3-b]pyridin-3-yl]-5-methyl-thiazole |
| E126 | 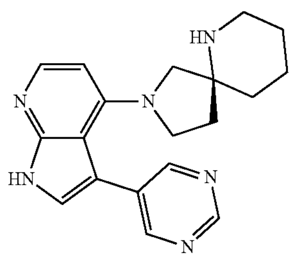 [SMILES: c1ncc(-c2c[nH]c3nccc(N4CC[C@@]5(CCCCN5)C4)c23)cn1] | (5S)-2-(3-pyrimidin-5-yl-1H-pyrrolo[2,3-b]pyridin-4-yl)-2,6-diazaspiro[4.5]decane |
| E131 | 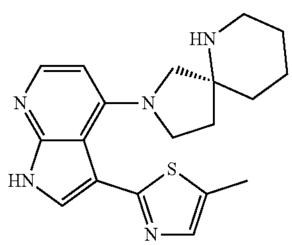 [SMILES: Cc1cnc(-c2c[nH]c3nccc(N4CC[C@@]5(CCCCN5)C4)c23)s1] | 2-[4-[(5S)-2,6-diazaspiro[4.5]decan-2-yl]-1H-pyrrolo[2,3-b]pyridin-3-yl]-5-methyl-thiazole |
| E210 | 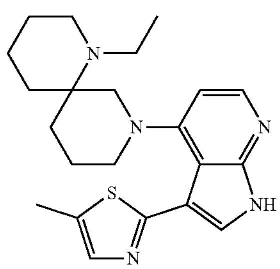 [SMILES: CCN1CCCCC12CCCN(c1ccnc3[nH]cc(-c4ncc(C)s4)c13)C2] | 2-[4-(1-ethyl-1,8-diazaspiro[5.5]undecan-8-yl)-1H-pyrrolo[2,3-b]pyridin-3-yl]-5-methyl-thiazole |
| E171 | 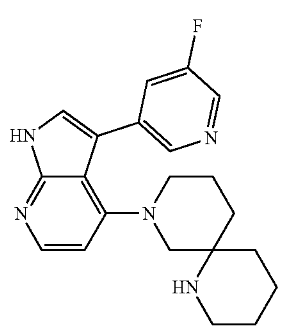 [SMILES: Fc1cncc(-c2c[nH]c3nccc(N4CCCC5(CCCCN5)C4)c23)c1] | 8-[3-(5-fluoro-3-pyridyl)-1H-pyrrolo[2,3-b]pyridin-4-yl]-1,8-diazaspiro[5.5]undecane |

| | Structure | IUPAC Name |
|---|---|---|
| E168 | 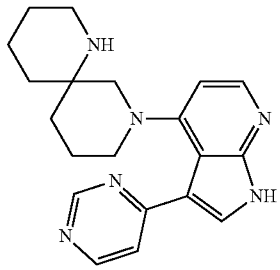 [SMILES: c1cc(-c2c[nH]c3nccc(N4CCCC5(CCCCN5)C4)c23)ncn1] | 8-(3-pyrimidin-4-yl-1H-pyrrolo[2,3-b]pyridin-4-yl)-1,8-diazaspiro[5.5]undecane |
| E128 | 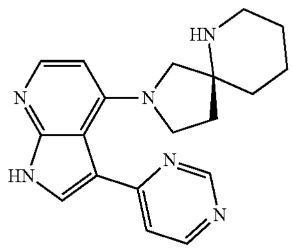 [SMILES: c1cc(-c2c[nH]c3nccc(N4CC[C@@]5(CCCCN5)C4)c23)ncn1] | (5S)-2-(3-pyrimidin-4-yl-1H-pyrrolo[2,3-b]pyridin-4-yl)-2,6-diazaspiro[4.5]decane |
| E114 | 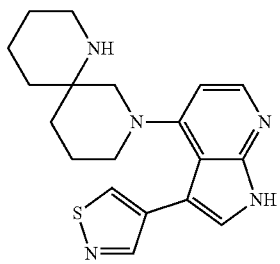 [SMILES: c1cc(N2CCCC3(CCCCN3)C2)c2c(-c3cnsc3)c[nH]c2n1] | 4-[4-(1,8-diazaspiro[5.5]undecan-8-yl)-1H-pyrrolo[2,3-b]pyridin-3-yl]isothiazole |
| E155 | 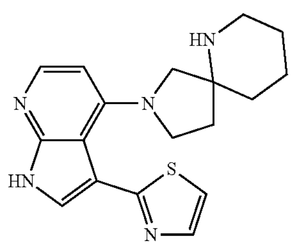 [SMILES: c1csc(-c2c[nH]c3nccc(N4CCC5(CCCCN5)C4)c23)n1] | 2-[4-(2,6-diazaspiro[4.5]decan-2-yl)-1H-pyrrolo[2,3-b]pyridin-3-yl]thiazole |
| E236 | 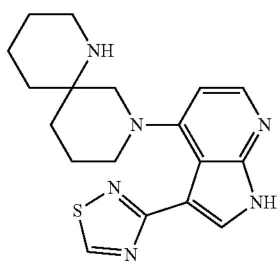 [SMILES: c1cc(N2CCCC3(CCCCN3)C2)c2c(-c3ncsn3)c[nH]c2n1] | 3-[4-[1,8-diazaspiro[5.5]undecan-8-yl]-1H-pyrrolo[2,3-b]pyridin-3-yl]-1,2,4-thiadiazole |
| E176 | 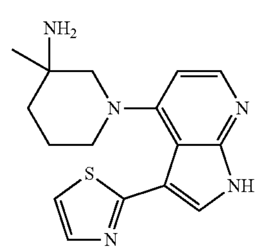 [SMILES: CC1(N)CCCN(c2ccnc3[nH]cc(-c4nccs4)c23)C1] | 3-methyl-1-(3-thiazol-2-yl-1H-pyrrolo[2,3-b]pyridin-4-yl)piperidin-3-amine |

-continued

| | Structure | IUPAC Name |
|---|---|---|
| E170 | 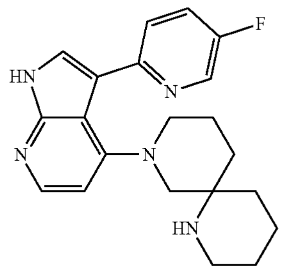 [SMILES: Fc1ccc(-c2c[nH]c3nccc(N4CCCC5(CCCCN5)C4)c23)nc1] | 8-[3-(5-fluoro-2-pyridyl)-1H-pyrrolo[2,3-b]pyridin-4-yl]-1,8-diazaspiro[5.5]undecane |
| E169 | 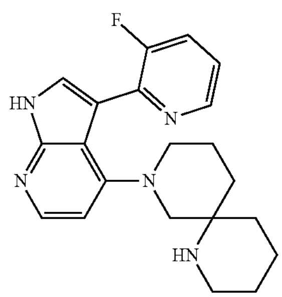 [SMILES: Fc1cccnc1-c1c[nH]c2nccc(N3CCCC4(CCCCN4)C3)c12] | 8-[3-(3-fluoro-2-pyridyl)-1H-pyrrolo[2,3-b]pyridin-4-yl]-1,8-diazaspiro[5.5]undecane |
| E136 | 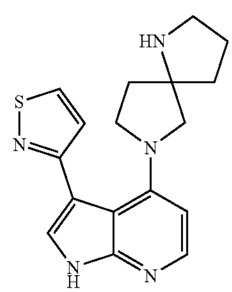 [SMILES: c1cc(N2CCC3(CCCN3)C2)c2c(-c3ccsn3)c[nH]c2n1] | 3-[4-(1,7-diazaspiro[4.4]nonan-7-yl)-1H-pyrrolo[2,3-b]pyridin-3-yl]isothiazole |
| E178 | 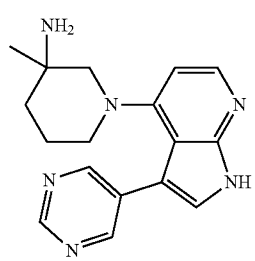 [SMILES: CC1(N)CCCN(c2ccnc3[nH]cc(-c4cncnc4)c23)C1] | 3-methyl-1-(3-pyrimidin-5-yl-1H-pyrrolo[2,3-b]pyridin-4-yl)piperidin-3-amine |
| E142 | 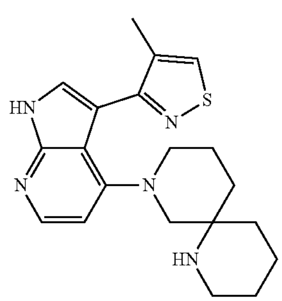 [SMILES: Cc1csnc1-c1c[nH]c2nccc(N3CCCC4(CCCCN4)C3)c12] | 3-[4-(1,8-diazaspiro[5.5]undecan-8-yl)-1H-pyrrolo[2,3-b]pyridin-3-yl]-4-methyl-isothiazole |

-continued
| | Structure | IUPAC Name |
|---|---|---|
| E129 | 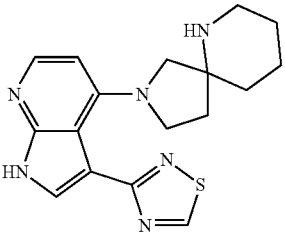 [SMILES: c1cc(N2CCC3(CCCCN3)C2)c2c(-c3ncsn3)c[nH]c2n1] | 3-[4-(2,6-diazaspiro[4.5]decan-2-yl)-1H-pyrrolo[2,3-b]pyridin-3-yl]-1,2,4-thiadiazole |
| E134 | 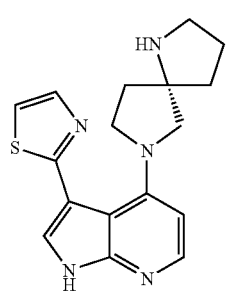 [SMILES: c1csc(-c2c[nH]c3nccc(N4CC[C@@]5(CCCN5)C4)c23)n1] | 2-[4-[(5S)-1,7-diazaspiro[4.4]nonan-7-yl]-1H-pyrrolo[2,3-b]pyridin-3-yl]thiazole |
| E122 | 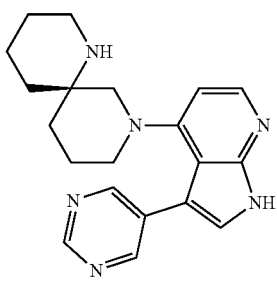 [SMILES: c1ncc(-c2c[nH]c3nccc(N4CCC[C@@]5(CCCCN5)C4)c23)cn1] | (6S)-8-(3-pyrimidin-5-yl-1H-pyrrolo[2,3-b]pyridin-4-yl)-1,8-diazaspiro[5.5]undecane. |
* * * * *